(12) United States Patent
Osterhout et al.

(10) Patent No.: US 11,186,853 B2
(45) Date of Patent: *Nov. 30, 2021

(54) MICROORGANISMS AND METHODS FOR PRODUCTION OF SPECIFIC LENGTH FATTY ALCOHOLS AND RELATED COMPOUNDS

(71) Applicant: Genomatica, Inc., San Diego, CA (US)

(72) Inventors: Robin E. Osterhout, San Diego, CA (US); Anthony P. Burgard, Elizabeth, PA (US)

(73) Assignee: Genomatica, Inc., San Diego, CA (US)

( * ) Notice: Subject to any disclaimer, the term of this patent is extended or adjusted under 35 U.S.C. 154(b) by 65 days.

This patent is subject to a terminal disclaimer.

(21) Appl. No.: 16/682,332

(22) Filed: Nov. 13, 2019

(65) Prior Publication Data

US 2020/0157585 A1 May 21, 2020

Related U.S. Application Data

(63) Continuation of application No. 14/053,381, filed on Oct. 14, 2013, now Pat. No. 10,513,716.
(Continued)

(51) Int. Cl.
*C12P 7/64* (2006.01)
*C12N 15/52* (2006.01)
(Continued)

(52) U.S. Cl.
CPC .............. *C12P 7/64* (2013.01); *C07C 31/207* (2013.01); *C12N 9/001* (2013.01); *C12N 9/0006* (2013.01); *C12N 9/0008* (2013.01); *C12N 9/1025* (2013.01); *C12N 9/1029* (2013.01); *C12N 9/1217* (2013.01); *C12N 9/1294* (2013.01); *C12N 9/13* (2013.01); *C12N 9/16* (2013.01); *C12N 9/88* (2013.01); *C12N 9/93* (2013.01); *C12N 15/52* (2013.01); *C12P 7/04* (2013.01); *C12P 7/24* (2013.01); *C12P 7/6409* (2013.01); *C12Y 101/01035* (2013.01); *C12Y 101/01037* (2013.01); *C12Y 101/05004* (2013.01); *C12Y 101/05006* (2013.01); *C12Y 101/99033* (2013.01); *C12Y 102/01* (2013.01); *C12Y 102/0101* (2013.01); *C12Y 102/01002* (2013.01); *C12Y 102/01003* (2013.01); *C12Y 102/0105* (2013.01); *C12Y 102/01015* (2013.01); *C12Y 102/01018* (2013.01); *C12Y 102/01027* (2013.01); *C12Y 102/01042* (2013.01); *C12Y 102/01076* (2013.01); *C12Y 102/05001* (2013.01); *C12Y 103/01044* (2013.01); *C12Y 103/99012* (2013.01); *C12Y 203/01008* (2013.01); *C12Y 203/01016* (2013.01); *C12Y 203/01054* (2013.01); *C12Y 203/01174* (2013.01); *C12Y 203/03008* (2013.01); *C12Y 207/02001* (2013.01); *C12Y 207/02007* (2013.01); *C12Y 207/09002* (2013.01); *C12Y 208/03003* (2013.01); *C12Y 301/03001* (2013.01); *C12Y 301/03002* (2013.01); *C12Y 301/0302* (2013.01); *C12Y 301/0306* (2013.01); *C12Y 401/01* (2013.01); *C12Y 401/01001* (2013.01); *C12Y 401/01003* (2013.01); *C12Y 401/01007* (2013.01); *C12Y 401/01009* (2013.01); *C12Y 401/01031* (2013.01); *C12Y 401/01032* (2013.01); *C12Y 401/01049* (2013.01); *C12Y 401/01074* (2013.01); *C12Y 401/01082* (2013.01); *C12Y 401/02005* (2013.01); *C12Y 401/03006* (2013.01); *C12Y 401/03034* (2013.01); *C12Y 402/01017* (2013.01);
(Continued)

(58) Field of Classification Search
None
See application file for complete search history.

(56) References Cited

U.S. PATENT DOCUMENTS 6,686,194 B1   2/2004  Mutzel et al.
8,048,624 B1  11/2011  Lynch et al.
(Continued)

FOREIGN PATENT DOCUMENTS

EP       1605048        12/2005
WO   WO 2004/024876      3/2004
(Continued)

OTHER PUBLICATIONS

Abdel-Hamid et al., "Pyruvate oxidase contributes to the aerobic growth efficiency of *Escherichi coli*," Microbiol., 147:1483-1498 (2001).
(Continued)

*Primary Examiner* — Suzanne M Noakes
*Assistant Examiner* — Jae W Lee
(74) *Attorney, Agent, or Firm* — Greenberg Traurig, LLP

(57) ABSTRACT

The invention provides non-naturally occurring microbial organisms containing a fatty alcohol, fatty aldehyde or fatty acid pathway, wherein the microbial organisms selectively produce a fatty alcohol, fatty aldehyde or fatty acid of a specified length. Also provided are non-naturally occurring microbial organisms having a fatty alcohol, fatty aldehyde or fatty acid pathway, wherein the microbial organisms further include an acetyl-CoA pathway. In some aspects, the microbial organisms of the invention have select gene disruptions or enzyme attenuations that increase production of fatty alcohols, fatty aldehydes or fatty acids. The invention additionally provides methods of using the above microbial organisms to produce a fatty alcohol, a fatty aldehyde or a fatty acid.

32 Claims, 8 Drawing Sheets
Specification includes a Sequence Listing.

Related U.S. Application Data

(60) Provisional application No. 61/714,144, filed on Oct. 15, 2012.

(51) Int. Cl.

| | |
|---|---|
| C07C 31/20 | (2006.01) |
| C12N 9/04 | (2006.01) |
| C12N 9/02 | (2006.01) |
| C12N 9/10 | (2006.01) |
| C12N 9/12 | (2006.01) |
| C12N 9/16 | (2006.01) |
| C12N 9/88 | (2006.01) |
| C12N 9/00 | (2006.01) |
| C12P 7/04 | (2006.01) |
| C12P 7/24 | (2006.01) |

(52) U.S. Cl.
CPC .............. C12Y 602/01001 (2013.01); C12Y 602/01013 (2013.01); C12Y 602/01018 (2013.01); C12Y 604/01001 (2013.01)

(56) References Cited

U.S. PATENT DOCUMENTS

| | | |
|---|---|---|
| 10,513,716 B2 | 12/2019 | Osterhout et al. |
| 2009/0047719 A1 | 2/2009 | Burgard et al. |
| 2009/0275097 A1 | 11/2009 | Sun et al. |
| 2010/0298612 A1 | 11/2010 | Behrouzian et al. |
| 2011/0000125 A1 | 1/2011 | McDaniel et al. |
| 2011/0008861 A1 | 1/2011 | Berry et al. |
| 2011/0111470 A1 | 5/2011 | Berry et al. |
| 2011/0124060 A1 | 5/2011 | Anthony et al. |
| 2011/0124606 A1 | 5/2011 | Watanabe et al. |
| 2011/0207203 A1 | 8/2011 | Reppas et al. |
| 2011/0250663 A1 | 10/2011 | Schirmer et al. |
| 2012/0009640 A1 | 1/2012 | Behrouzian et al. |
| 2015/0275242 A1 | 10/2015 | Osterhout et al. |

FOREIGN PATENT DOCUMENTS

| | | |
|---|---|---|
| WO | WO 2007/136762 | 11/2007 |
| WO | WO 2007/141208 | 12/2007 |
| WO | WO 2008/113041 | 9/2008 |
| WO | WO 2009/111672 | 11/2009 |
| WO | WO 2010/068953 | 6/2010 |
| WO | WO 2010/135624 | 11/2010 |
| WO | WO 2012/109176 | 8/2012 |

OTHER PUBLICATIONS

Agnihotri et al., "Enoyl-CoA Hydratase: Reaction, Mechanism, and Inhibition," Bioorg. Med. Chem. 11(1):9-20 (2003).
Alber et al., "Malonyl-coenzyme A reductase in the modified 3-hydroxypropionate cycle for autotrophic carbon fixation in archaeal Metallosphaera and *Sulfolobus* spp.," J. Bacteriol. 188:8551-8559 (2006).
Alber et al., "Study of an alternate glyoxylate cycle for acetate assimilation by Rhodobacter sphaeroides," Mol. Microbiol. 61(2):297-309 (2006).
Alper et al, "Tuning genetic control through promoter engineering," PNAS, 102:12678-12683 (2005).
An et al., "A gene cluster encoding malonyl-CoA decarboxylase (MatA), malonyl-CoA synthetase (MatB) and a putative dicarboxylate carrier protein (MatC) in Rhizobium trifolii—cloning, sequencing, and expression of the enzymes in *Escherichia coli*," Eur. J. Biochem. 257(2):395-402 (1998).
Andreesen and Ljungdahl, "Formate Dehydrogenase of Clostridium thermoaceticum: Incorporation of Selenium-75, and the Effects of Selenite, Molybate, and Tungstate on the Enzyme," J. Bacteriol. 116(2):867-873 (1973).
Aoshima et al., "A novel enzyme, citryl-CoA synthetase, catalysing the first step of the citrate cleavage reaction in Hydrogenobacter thermophilus TK-6," Mol. Microbiol. 52(3):751-761 (2004).
Aoshima, "Novel enzyme reactions related to the tricarboxylic acid cycle: phylogenetic/functional implications and biotechnological applications," Appl. Microbiol. Biotechnol. 75(2):249-255 (2007).
Arent et al, "The multifunctional protein in peroxisomal beta-oxidation: structure and substrate specificity of the *Arabidopsis thaliana* protein MFP2," J Biol Chem 285:24066-24077 (2010).
Arps et al., "Genetics of Serine Pathway Enzymes in Methylobacterium extorquens AM1: Phosphoenolpyruvate Carboxylase and Malyl Coenzyme A Lyase," J. Bacteriol. 175(12):3776-3783 (1993).
Atsumi et al., "Metabolic engineering of *Escherichia coli* for 1-butanol production," Metab. Eng. 10(6):305-311 (2008).
Atteia et al., "Pyruvate formate-lyase and a novel route of eukaryotic ATP synthesis in Chlamydomonas mitochondria," J. Biol. Chem. 281:9909-9918 (2006).
Bakker et al., "Stoichiometry and compartmentation of NADH metabolism in *Saccharomyces cerevisiae*," FEMS Microbiol. Rev. 25:15-37 (2001).
Barrowman et al., "Immunological comparison of microbial TPP-dependent nonoxidative alpha-keto acid decarboxylase," FEMS Microbiology Lett. 34:57-60 (1986).
Baudin et al., "A simple and efficient method for direct gene deletion in *Saccharomyces cerevisiae*," Nucleic Acids Res. 21(14):3329-3330 (1993).
Bekal et al., "Purification of Leuconostoc menteroides Citrate Lyase and Cloning and Characterization of the citCDEFG Gene Clueseter," J. Bacteriol. 180:647-654 (1998).
Benning et al., "New reactions in the crotonase superfamily: Structure of methylmalonyl CoA decarboxylase from *Escherichia coli*," Biochemistry 39:4630-4639 (2000).
Beopoulos et al, "Control of Lipid Accumulation in the Yeast *Yarrowia lipolytica*," AEM 74:7779-7789 (2008).
Berg et al., "A 3-Hydroxypropionate/4-Hydroxybutyrate Autotrophic Carbon Dioxide Assimilation Pathway in Archaea," Science 318:1782-1786 (2007).
Bergquist et al., "Degenerate oligonucleotide gene shuffling (DOGS) and random drift mutagenesis (RNDN): two complementary techniques for enzyme evolution," Biomol. Eng. 22:63-72 (2005).
Bergquist et al., "Degenerate oligonucleotide gene shuffling," Methods Mol. Biol. 352:191-204 (2007).
Bessoule et al, "Fatty acid synthesis in mitochondria from *Saccharomyces cerevisiae*," FEBS Lett 214: 158-162 (1987).
Binstock et al., "Fatty acid oxidation complex from *Escherichia coli*," Methods Enzymol. 71 Pt C:403-411 (1981).
Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," Eur. J. Biochem. 123(3):563-569 (1982).
Bocanegra et al., "Creation of an NADP-dependent pyruvate dehydrogenase multienzyme complex by protein engineering," Biochemistry, 32(11):2737-2740 (1993).
Bock et al., "Purification and characterization of two extremely thermostable enzymes, phosphate acetyltransferase and acetate kinase, from the hyperthermophilic eubacterium Thermotoga maritima," J. Bacteriol. 181:1861-1867 (1999).
Boles et al., "Characterization of a glucose-repressed pyruvate kinase (Pyk2p) in *Saccharomyces cerevisiae* that is catalytically insensitive to fructose-1,6-bisphosphate," J. Bacteriol. 179:2987-2993 (1997).
Bott et al., "Methylmalonyl-CoA decarboxylase from Propionigenium modestum. Cloning and sequencing of the structural genes and purification of the enzyme complex," Eur. J. Biochem. 250:590-599 (1997).
Bott et al., "Klebsiella pneumonia genes for citrate lyase and citrate lyase ligase: localization, sequencing, and expression," Mol. Microbiol. 14:347-356 (1994).
Bott, "Anaerobic citrate metabolism and its regulation in enterobacteria," Arch. Microbiol. 167: 78-88 (1997).
Boubekeur et al, "Participation of acetaldehyde dehydrogenases in ethanol and pyruvate metabolism of the yeast *Saccharomyces cerevisiae*," Eur. J. Biochem. 268:5057-5065 (2001).

(56) References Cited

OTHER PUBLICATIONS

Boynton et al., "Cloning, sequencing, and expression of clustered genes encoding β-hydroxybutyryl-Coenzyme A (CoA) dehydrogenase, crotonase, and butyryl-CoA dehydrogenase from Clostridium acetobutylicum ATCC 824," J. Bacteriol. 178(11):3015-3024 (1996).
Bozzi et al., "Structural and biochemical studies of alcohol dehydrogenase isozymes from Kluyveromyces lactis," Biochim. Biophys. Acta 1339:133-142 (1997).
Brachmann et al., "Designer deletion strains derived from *Saccharomyces cerevisiae* S288C: a useful set of strains and plasmids for PCR-mediated gene disruption and other applications," Yeast 14(2):115-132 (1998).
Bradford et al., "A rapid and sensitive method for the quantitation of microgram quantities of protein utilizing the principle of protein-dye binding," Anal. Biochem. 72:248-254 (1976).
Brasen et al., "Unusual ADP-forming acetyl-coenzyme A synthetases from the mesophilic halophilic eurarchaeon Haloarcula marismortui and from the hyperthermophilic crenarchaeon Pyrobaculum aerophilum," Arch. Microbiol. 182:277-287 (2004).
Bricker et al., "A mitochondrial pyruvate carrier required for pyruvate uptake in yeast, *Drosophila*, and humans," Science 337:96-100 (2012).
Brown et al., "The enzymic interconversion of acetate and acetyl-coenzyme A in *Escherichia coli*," J. Gen. Microbiol. 102:327-336 (1977).
Brugger et al., "Characteristics of fungal phytases from Aspergillus fumigatus and Sartorya fumigate," Appl. Microbiol. Biotech. 63:383-389 (2004).
Buck et al., "Primary Structure of the Succinyl-CoA Synthetase of *Escherichia coli*," Biochemistry 24:6245-6252 (1985).
Burke et al, "The Isolation, Characterization, and Sequence of the Pyruvate Kinase Gene of *Saccharomyces cerevisiae*," J. Biol. Chem. 258(4):2193-2201 (1983).
Buu et al., "Functional Characterization and Localization of Acetyl-CoA Hydrolase, Ach1p, in *Saccharomyces cerevisiae*," J. Biol. Chem. 278(19):17203-17209 (2003).
Cabre et al., "Purification and properties of bovine liver aldehyde oxidase: comparison with xanthine oxidase," Biochem. Soc. Trans. 15:882-883 (1987).
Campbell et al., "A new *Escherichia coli* metabolic competency: growth on fatty acids by a novel anaerobic β-oxidation pathway," Mol. Microbiol. 47(3):793-805 (2003).
Campbell et al., "The enigmatic *Escherichia coli* fadE gene is yafH," J. Bacteriol. 184(13):3759-3764 (2002).
Cary et al., "Cloning and expression of Clostridium acetobutylicum ATCC 824 acetoacetyl-coenzyme A:acetate/butyrate:coenzyme A-transferase in *Escherichia coli*," Appl. Environ. Microbiol. 56(6):1576-1583 (1990).
Chandra Raj et al., "Pyruvate decarboxylase: a key enzyme for the oxidative metabolism of lactic acid by Acetobacter pasteruianus," Arch. Microbiol. 176:443-451 (2001).
Chao et al., "The effects of wall populations on coexistence of bacteria in the liquid phase of chemostat cultures," J. Gen. Microbiol., 131(5):1229-1236 (1985).
Chen et al., "Phosphoenolpyruvate carboxykinase assayed at physiological concentrations of metal ions has a high affinity for CO2," Plant Physiol. 128:160-164 (2002).
Circello et al., "Molecular cloning and heterologous expression of the dehydrophos biosynthetic gene cluster," Chem. Biol. 17:402-411 (2010).
Clark, "Molybdenum cofactor negative mutants of *Escherichia coli* use citrate anaerobically," FEMS Microbiol. Lett. 55:245-249 (1990).
Coco et al., "DNA shuffling method for generating highly recombined genes and evolved enzymes," Nat. Biotechnol. 19(4):354-359 (2001).
Colasante et al., "Mitochondrial carrier family inventory of Trypanosoma brucei brucei: Identification, expression and subcellular localization," Mol. Biochem. Parasit. 167:104-117 (2009).

Colonna et al., "Synthesis and radiocarbon evidence of terephthalate polyesters completely prepared from renewable resources," Green Chem. 13:2543-2548 (2011).
Conrad et al., "D- and L-Isoleucine Metabolism and Regulation of Their Pathways in Pseudomonas Putida," J. Bacteriol. 118(1):103-111 (1974).
Cordente et al., "Mutagenesis of specific amino acids converts carnitine acetyltransferase into carnitine palmitoyltransferase," Biochem. 45:6133-6141 (2006).
Corthesy-Theulaz et al., "Cloning and characterization of Helicobacter pylori succinyl CoA:acetoacetate CoA-transferase, a novel prokaryotic member of the CoA-transferase family," J. Biol. Chem. 272(41):25659-25667 (1997).
Cotelesage et al., "How does an enzyme recognize CO2?," Int. J. Biochem. Cell Biol. 39:1204-1210 (2007).
Cruz et al, "Gene-specific involvement of beta-oxidation in wound-activated responses in *Arabidopsis*," Plant Physiol 135:85-94 (2004).
Currie et al., "Authentication and dating of biomass components of industrial materials; links to sustainable technology," Nuclear Instruments and Methods in Physics Research B, 172:281-287 (2000).
Davie et al., "Expression and Assembly of a Functional E1 Component (α2β2) of Mammalian Branched-Chain α-Ketoacid Dehydrogenase Complex in *Escherichia coli*," J. Biol. Chem. 267:16601-16606 (1992).
Davis et al., "Overproduction of acetyl-CoA carboxylase activity increases the rate of fatty acid biosynthesis in *Escherichia coli*," J. Biol. Chem. 275:28593-28598 (2000).
De Bok et al., "Two W-containing formate dehydrogenases (CO2-reductases) involving syntrophic propionate oxidation by Syntrophobacter fumaroxidans," Eur. J. Biochem. 270:2476-2485 (2003).
De Crecy et al., "Development of a novel continuous culture device for experimental evolution of bacterial populations," Appl. Microbiol. Biotechnol. 77(2): 489-496 (2007).
De Graes et al., "The steady-state internal redox state (NADH/NAD) reflects the external redox state and is correlated with catabolic adaptation in *Escherichia coli*," J. Bacteriol. 181:2351-2357 (1999).
De Smidt et al., "The alcohol dehydrogenases of *Saccharomyces cerevisiae*: a comprehensive review," FEMS Yeast Rev. 7:967-978 (2008).
De Vries et al., "Functional characterization of mitochondrial carnitine palmitoyltransferases I and II expressed in the yeast *Pichia pastoris*," Biochemistry 36(17):5285-5292 (1997).
Deana, "Substrate specificity of a dicarboxyl-CoA: dicarboxylic acid Coenzyme A transferase from rat liver mitochondria," Biochem. Int. 26(4):767-773 (1992).
Dehesh et al, "Two novel thioesterases are key determinants of the bimodal distribution of acyl chain length of Cuphea palustris seed oil," Plant Physiol 110:203-210 (1996).
Dekishima et al, "Extending carbon chain length of 1-butanol pathway for 1-hexanol synthesis from glucose by engineered *Escherichia coli*," J Am Chem Soc 133:11399-11401 (2011).
Denic et al., "A molecular caliper mechanism for determining very long-chain fatty acid length," Cell 130:663-677 (2008).
Di Gennaro et al., "Styrene lower catabolic pathway in Pseudomonas Xuorescens ST: identiWcation and characterization of genes for phenylacetic acid degradation," Arch.Microbiol 188:117-125 (2007).
Dickenson et al, "An investigation of the metabolism of isoleucine to active Amyl alcohol in *Saccharomyces cerevisiae*," J Biol Chem 275:10937-10942 (2000).
Doan et al., "Functional expression of five *Arabidopsis* fatty acyl-CoA reductase genes in *Escherichia*," J. Plant Physiol., 166(8):787-796 (2009).
Doten et al., "Cloning and Genetic Organization of the pca Gene Cluster from Acinetobacter calcoaceticus," J Bacteriol. 169:3168-3174 (1987).
Drake, "Acetogenesis, acetogenic bacteria, and the acetyl-CoA "Wood/Ljungdahl" pathway: past and current perspectives," in Acetogenesis, H. L. Drake, (ed.), Chapman & Hall, New York, p. 3-60 (1994).

(56) References Cited

OTHER PUBLICATIONS

Drewke et al., "Ethanol formation in adh) mutants reveals the existence of a novel acetaldehyde-reducing activity in *Saccharomyces cerevisiae*," J. Bacteriol. 172:3909-3917 (1990).
Du et al, "Lactococcus lactis fabH, encoding beta-ketoacyl-acyl carrier protein synthase, can be functionally replaced by the Plasmodium falciparum congener," AEM 76:3959-3966 (2010).
Duncan et al., "Acetate utilization and butyryl Coenzyme A (CoA):acetate-CoA transferase in butyrate-producing bacteria from the human large intestine," Appl. Environ. Microbiol. 68(10):5186-5190 (2002).
Duran et al., "Characterization of cDNA clones for the 2-methyl branched-chain enoyl-CoA reductase. An enzyme involved in branched-chain fatty acid synthesis in anerobic mitochondria of the parasitic nematode Ascaris suum," J. Biol. Chem. 268(30):22391-22396 (1993).
Durre et al., "Solventogenic enzymes of Clostridium acetobutylicum: catalytic properties, genetic organization, and transcriptional regulation," FEMS Microbiol. Rev.17(3):251-262 (1995).
Dykhuizen, "Chemostats used for studying natural selection and adaptive evolution," Methods. Enzymol. 224:613-631 (1993).
Ehsani et al., "Reversal of Coenzyme Specificity of 2,3-Butanediol Dehydrogenase From *Saccharomyces cerevisae* and In Vivo Functional Analysis," Biotechnol. Bioen., 104(2): 381-389 (2009).
Eikmanns et al., "The phosphoenolpyruvate carboxylase gene of Corynebacterium glutamicum: Molecular cloning, nucleotide sequence, and expression." Mol. Gen. Genet. 218:330-339 (1989).
Eisen et al., "The complete genome sequence of Chlorobium tepidum TLS, a photosynthetic, anaerobic, green-sulfur bacterium," Proc. Natl. Acad. Sci. U.S.A. 99(14): 9509-9514 (2002).
Elgersma et al., "Peroxisomal and mitochondrial carnitine acetyltransferases of *Saccharomyces cerevisiae* are encoded by a single gene," EMBO J. 14:3472-3479 (1995).
Fan et al., "Disruption of a gene encoding glycerol 3-phosphatase from Candida albicans impairs intracellular glycerol accumulation-mediated salt-tolerance," FEMS Microbiol. Lett. 245:107-116 (2005).
Farhi et al., "Harnessing yeast subcellular compartments for the production of plant terpenoids," Met. Eng. 13:474-481 (2011).
Fernandez-Valverde et al., "Purification of Pseudomonas putida Acyl coenzyme a Ligase Active with a Range of Aliphatic and Aromatic Substrates," Appl. Environ. Microbiol. 59:1149-1154 (1993).
Ferrandez et al, "Genetic characterization and expression in heterologous hosts of the 3-(3-hydroxyphenyl)propionate catabolic pathway of *Escherichia coli* K-12," J. Bacteriol. 179:2573-2581 (1997).
Fong et al., "In Silico design and adaptive evolution of *Escherichia coli* for production of lactic acid," Biotechnol. Bioeng. 91(5):643-648 (2005).
Fong et al., "Description and Interpretation of Adaptive Evolution of *Escherichia coli* K-12 MG1655 by Using a Genome-Scale in Silico Metabolic Model," J. Bacteriol. 185:6400-6408 (2003).
Fong et al., "Metabolic gene-deletion strains of *Escherichia coli* evolve to computationally predicted growth phenotypes," Nat. Genet. 36(10):1056-1058 (2004).
Fontaine et al., "Molecular charcterization and transcriptional analysis of adhE2, the gene encoding the NADH-dependent aldehyde/alcohol dehydrogenase responsible for butanol production in alcohologenic cultures of Clostridium acetobutylicum ATCC 824," J. Bacteriol. 184:821-830 (2002).
Ford et al., "Molecular properties of the lyst1+ gene and the regulation of a-aminoadipate reductase in Schizosaccharomyces pombe," Curr. Genet. 28:131-137 (1995).
Fox et al., "Isolation and characterization of homogeneous acetate kinase from *Salmonella typhimurium* and *Escherichia coli*," J. Biol. Chem. 261:13487-13497 (1986).
Fujii et al., "Error-prone rolling circle amplification: the simplest random mutagenesis protocol," Nat. Protoc. 1(5):2493-2497 (2006).
Fujii et al., "One-step random mutagenesis by error-prone rolling circle amplification," Nucleic Acids Res. 32(19):e145 (2004).

Fukao et al., "Succinyl-coA:3-Ketoacid CoA Transferase (SCOT): Cloning of the Human Scot Gene, Tertiary Structural Modeling of the Human SCOT Monomer, and Characterization of Three Pathogenic Mutations," Genomics 68:144-151 (2000).
Fukui et al., "Engineering of Ralstonia eutropha for production of poly(3-hydroxybutyrate-co-3-hydroxyhexanoate) from fructose and solid-state properties of the copolymer," Biomacromolecules 3(3):618-624 (2002).
Furdui et al., "The role of pyruvate ferredoxin oxidoreductase in pyruvate synthesis during autotrophic growth by the Wood-Ljungdahl pathway," J. Biol. Chem. 275(37):28494-28499 (2000).
Furumoto et al., "Isolation and characterization of cDNAs for differentially accumulated transcripts between mesophyll cells and bundle sheath strands of maize leaves," Plant Cell Physiol. 41:1200-1209 (2000).
Garattini et al., "Mammalian aldehyde oxidases: genetics, evolution and biochemistry," Cell Mol. Life Sci. 65:1019-1048 (2008).
Giaever et al., "Functional profiling of the *Saccharomyces cerevisiae* genome," Nature 418:387-391 (2002).
Gibbs et al., "Degenerate oligonucleotide gene shuffling (DOGS): a method for enhancing the frequency of recombination with family shuffling," Gene. 271:13-20 (2001).
Gibson et al., "Physical and genetic interactions of cytosolic malate dehydrogenase with other gluconeogenic enzymes," J. Biol. Chem. 278:25628-25636 (2003).
Gobel et al., "Degradation of Aromatics and Chloroaromatics by *Pseudomonas* sp. Strain B13: Cloning, Characterization, and analysis of Sequences Encoding 3-Oxoadipate:Succinyl-Coenzyme A (CoA) Transferase and 3-oxoaipyl-CoA Thiolase," J. Bacteriol. 184(1):216-223 (2002).
Green et al., "Catabolism of α-Ketoglutarate by a sucA Mutant of Bradyrhizobium japonicum: Evidence for an Alternative Tricarboxylic Acid Cycle," J. Bacteriol. 182(10):2838-2844 (2000).
Gueldener et al., "A second set of loxP marker cassettes for Cre-mediated multiple gene knockouts in budding yeast," Nucleic Acids Res. 30:e23 (2002).
Gulick et al., "The 1.75 A crystal structure of acetyl-CoA synthetase bound to adenosine-5'-propylphosphate and coenzyme A," Biochemistry 42:2866-2873 (2003).
Guo et al., "Posttranslational activation, site-directed mutation and phylogenetic analyses of lysine biosynthesis enzymes alpha-aminoadipate reductase Lys1P (AARO and the phosphopantetheinyl transferase Lys7p (PPTase) from Schizosaccharomyces pombe)," Yeast 21(15):1279-1288 (2004).
Guo et al., "Site-directed mutational analysis of the novel catalytic domains of alpha-aminoadipate reductase (Lys2p) from Candida albicans," Mol. Genet. Genomics 269(2):271-279 (2003).
Hager et al., "Flavoprotein-catalyzed pyruvate oxidation in Lactobacillus delbrueckii," Fed. Proc. 13:734-738 (1954).
Haller et al., "Discovering new enzymes and metabolic pathways: conversion of succinate to propionate by *Escherichia coli*," Biochem. 39(16):4622-4629 (2000).
Hanai et al., "Engineered synthetic pathway for isopropanol production in *Escherichia coli*," Appl. Environ. Microbiol. 73:7814-7818 (2007).
Hansen et al., "De novo biosynthesis of vanillin in fission yeast (*Schizosaccharomyces pombe*) and baker's yeast (*Saccharomyces cerevisiae*)," Appl. Environ. Microbiol. 75(9):2765-2774 (2009).
Harrison et al., "The pimFABCDE operon from Rhodopseudomonas palustris mediates dicarboxylic acid degradation and participates in anaerobic benzoate degradation," Microbiology 151:727-736 (2005).
Hartmanis, M.G., "Butyrate kinase from Clostridium acetobutylicum," J. Biol. Chem. 262:617-621 (1987).
Harwood et al., "Identification of the pcaRKF Gene cluster from Pseudomonas putida: Involvement in Chemotaxis, Biodegradation, and Transport of 4-Hydroxybenzoate," J. Bacteriol. 176(21):6479-6488 (1994).
Hasson et al., "The crystal structure of benzoylformate decarboxylase at 1.6 A resolution: diversity of catalytic residues in thiamin diphosphate-dependent enzymes," Biochemistry 37:9918-9930 (1998).
Hayaishi et al., "Enzymatic decarboxylation of malonic acid," J. Biol. Chem. 215:125-136 (1955).

(56) References Cited

OTHER PUBLICATIONS

Hayaishi et al., "Enzymatic studies on the metabolism of beta-alanine," J. Biol. Chem. 236:781-790 (1961).
Hayes et al., "Combining computational and experimental screening for rapid optimization of protein properties," Proc. Natl. Acad. Sci. USA 99:15926-15931 (2002).
Hayman et al., "Purification and characterization of a tartrate-resistant acid phosphatase from human osteoclastomas," Biochem. J. 261:601-609 (1989).
Haywood et al., "Characterization of two 3-ketothiolases possessing differing substrate specificities in the polyhydroxyalkanoate synthesizing organism Alcaligenes eutrophus," FEMS Microbiol. Lett. 52:91-96 (1988).
He et al., "Molecular cloning, expression in *Escherichia coli*, and characterization of a novel L-3-hydroxyacyl coenzyme a dehydrogenase from pig liver," Biochim. Biophys. Acta, 1392:119-126 (1998).
Heath et al., "A conserved histidine is essential for glycerolipid acyltransferase catalysis," J Bacteriol 180:1425-1430 (1998).
Hemschemeier et al., "Biochemical and physiological characterization of the pyruvate formate-lyase Pfl1 of Chlamydomonas reinhardtii, a typically bacterial enzyme in eukaryotic alga," Eukaryot. Cell 7:518-526 (2008).
Henning et al., "Identification of Novel enzoylformate Decarboxlyases by Growth Selection," App. Environ. Microbiol. 72(12)7510-7517 (2006).
Hermann et al., "Biogenesis of cytochrome oxidase—Sophisticated assembly lines in the mitochondrial inner membrane," Gene 354:43-52 (2005).
Herrmann et al., "Energy Conservation via Electron-Transferring Flavoprotein in Anaerobic Bacteria," J. Bacteriol. 190(3):784-791 (2008).
Herzig et al., "Identification and functional expression of the mitochondrial pyruvate carrier," Science, 337:93-96 (2012).
Hesslinger et al., "Novel keto acid formate-lyase and propionate kinase enzymes are components of an anaerobic pathway in *Escherichia coli* that degrades L-threonine to propionate," Mol. Microbiol 27:477-492 (1998).
Hibbert et al. "Directed evolution of biocatalytic processes," Biomol. Eng. 22:11-19 (2005).
Hidaka et al., "Cloning and nucleotide sequence of fosfomycin biosynthetic genes of Streptomyces wedmorensis," Mol. Gen. Genet. 249:274-280 (1995).
Hijarrubia et al., "Domain Structure characterization of the Multi-functional α-Aminoadipate Reductase from Penicillium chrysogenum by Limited Proteolysis," J. Biol. Chem. 278:8250-8256 (2003).
Hijikata et al, "Rat peroxisomal 3-ketoacyl-CoA thiolase gene. Occurrence of two closely related but differentially regulated genes," J Biol Chem 265, 4600-4606 (1990).
Hillmer et al., "Particulate Nature of Enzymes Involved in the Fermentation of Ethanol and Acetate by Clostridium Kluyveri," FEBS Lett. 21(3):351-354 (1974).
Hillmer et al., "Solubilization and partial characterization of particulate dehydrogenases from Clostridium kluyveri," Biochim. Biophys. Acta 334:12-23 (1974).
Hilpert et al, "Conversion of the chemical energy of methylmalonyl-CoA decarboxylation into a Na+ gradient," Nature 296:584-585 (1982).
Hiltunen et al, "Peroxisomal multifunctional beta-oxidation protein of *Saccharomyces cerevisiae*. Molecular analysis of the fox2 gene and gene product," J Biol Chem 267: 6646-6653 (1992).
Hiser et al., "ERG10 from *Saccharomyces cerevisiae* encodes acetoacetyl-CoA thiolase," J. Biol. Chem. 269:31383-31389 (1994).
Hoffmann et al., "Stereochemistry of the methylmalonyl-CoA decarboxylation reaction," FEBS Lett. 220:121-125 (1987).
Hoffmeister et al., "Mitochondrial trans-2-enoyl-CoA reductase of wax ester fermentation from Euglena gracilis defines a new family of enzymes involved in lipid synthesis," J. Biol. Chem. 280(6):4329-4338 (2005).
Hofvander et al, "A prokaryotic acyl-CoA reductase performing reduction of fatty acyl-CoA to fatty alcohol," FEBS Lett 3538-3543 (2011).
Hohmann et al., "Characterisation of PDC2, a gene necessary for high level expression of pyruvate decarboxylase structural genes in *Saccharomyces cerevisiae*," Mol. Gen. Genet. 241:657-666 (1993).
Horie et al., "Existence of acetyl-CoA-dependent chain elongation system in hepatic peroxisomes of rat: effects of clofibrate and di-(2-ethylhexyl)phthalate on the activity," Arch. Biochem. Biophys., 274: 64-73 (1989).
Huder et al., "Sequence of the sodium ion pump methylmalonyl-CoA decarboxylase from Veillonella parvula," J. Biol. Chem. 268:24564-24571 (1993).
Hugler et al., "Malonyl-coenzyme A reductase from Chloroflexus aurantiacus, a key enzyme of the 3-hydroxypropionate cycle for autotrophic CO(2) fixation," J.Bacteriol. 184:2404-2410 (2002).
Hugler et al., "Autotrophic CO2 fixation via the reductive tricarboxylic acid cycle in different lineages within the phylum Aquificae: evidence for two ways of citrate cleavage," Environ. Microbiol. 9:81-92 (2007).
Huisman et al., "Ch. 30: Enzyme Evolution for Chemical Process Applications," In R N. Patel (ed.), Biocatalysis in the pharmaceutical and biotechnology industries, CRC Press, Boca Raton, FL, p. 717-742 (2007).
Hunaiti et al., "Malonyl-CoA decarboxylase from Streptomyces erythreus: purification, properties, and possible role in the production of erythromycin," Arch. Biochem. Biophys. 229:426-439 (1984).
Hynes et al., "ATP-citrate lyase is required for production of cytosolic acetyl coenzyme A and development in Aspergillus nidulans," Eukaryot. Cell 9(7):1039-1048 (2010).
Hynes et al., "Role of carnitine acetyltransferases in acetyl coenzyme A metabolism in Aspergillus nidulans," Eukaryot. Cell 10:547-555 (2011).
Ibarra et al., "*Escherichia coli* K-12 undergoes adaptive evolution to achieve in silico predicted optimal growth," Nature 420(6912):186-189 (2002).
Ingram-Smith et al., "Amp-forming acetyl-CoA synthetases in Archaea show unexpected diversity in substrate utilization," Archaea 2:95-107 (2007).
Ingram-Smith et al., "Characterization of the acetate binding pocket in the Methanosarcina thermophila acetate kinase," J. Bacteriol. 187:2386-2394 (2005).
Inoue et al, "Purification and characterization of a novel alcohol dehydrogenase from *Leifsonia* sp. strain S749: a promising biocatalyst for an asymmetric hydrogen transfer bioreduction," AEM 71: 3633-3641 (2005).
Inui et al., "Fatty acid synthesis in mitochondria of Euglena gracilis," Euro. J. Biochem. 142(1):121-126 (1984).
Iram et al, "The beta-oxidation systems of *Escherichia coli* and *Salmonella enterica* are not functionally equivalent," J Bacteriol 188:599-608 (2006).
Ishige et al., "Wax ester production from n-alkanes by *Acinetobacter* sp. strain M-1: ultrastructure of cellular inclusions and role of acyl coenzyme A reductase," Appl. Environ. Microbiol. 68(3):1192-1195 (2002).
Ismail et al., "Functional genomics by NMR spectroscopy. Phenylacetate catabolism in *Escherichia coli*," Eur. J. Biochem. 270(14):3047-3054 (2003).
Iwakura et al., "Studies on regulatory functions of malic enzymes. VI. Purification and molecular properties of NADP-linked malic enzyme from *Escherichia coli* W," J. Biochem. 85:1355-1365 (1979).
Jenkins et al., "Genetic and molecular characterization of the genes involved in short-chain fatty acid degradation in *Escherichia coli*: the ato system," J. Bacteriol. 169(1):42-52 (1987).
Jo et al, "Cloning, expression, and characterization of an aldehyde dehydrogenase from *Escherichia coli* K-12 that utilizes 3-Hydroxypropionaldehyde as a substrate," Appl. Microbiol. Biotechnol. 81:51-60 (2008).
Jogl et al., "Crystal structure of yeast acetyl-coenzyme A synthetase in complex with AMP," Biochemistry 43:1425-1431 (2004).
Jones et al., "Acetone-Butanol Fermentation Revisited," 50(4):484-524 (1986).

(56) References Cited

OTHER PUBLICATIONS

Kai et al., "Phosphoenolpyruvate carboxylase: three-dimensional structure and molecular mechanisms," Arch. Biochem. Biophys. 414:170-179 (2003).
Kanao et al., "Kinetic and biochemical analyses on the reaction mechanism of a bacterial ATP-citrate lyase," Eur. J. Biochem. 269:3409-3416 (2002).
Karlen et al., "Absolute determination of the activity of two C14 dating standards," Arkiv Geofysik 4:465-471 (1968).
Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," J. Bacteriol. 184(1):207-215 (2002).
Kather et al., "Another unusual type of citric acid cycle enzyme in Helicobacter pylori: the malate:quinone oxidoreductase," J. Bacteriol. 182:3204-3209 (2000).
Kazahaya et al, "Aerobic Dissimilation of Glucose by Heterolactic Bacteria," J. Gen. Appl. Microbiol. 18(1):43-55 (1972).
Kedishvii et al., "Mammalian methylmalonate-semialdehyde dehydrogenase," Methods Enzymol. 324:207-218 (2000).
Kerscher et al, "A single external enzyme confers alternative NADH:ubiquinone oxidoreductase activity in Yarrowia lipolytica," J. Cell Sci. 112:2347-2354 (1999).
Kessler et al., "Pyruvate-formate-lyase-deactivase and acetyl-CoA reductase activities of *Escherichia coli* reside on a polymeric protein particle encoded by adhE," FEBS. Lett. 281:59-63 (1991).
Khoury et al, "Computational design of Candida boidinii xylose reductase for altered cofactor specificity," Protein Sci. 18(10):2125-2138 (2009).
Kiema et al., "Mutagenic and enzymological studies of the hydratase and isomerase activities of 2-enoyl-CoA hydratase-1," Biochem. 38:2991-2999 (1999).
Killenberg-Jabs et al., "Active oligomeric states of pyruvate decarboxylase and their functional characterization," Eur. J. Biochem. 268:1698-1704 (2001).
Kim et al., "Construction of an *Escherichia coli* K-12 Mutant for Homoethanologenic Fermentation of glucose or Xylose without Foreign Genes, " Appl. Environ. Microbiol. 73:1766-1771 (2007).
Kim et al., "Dihydrolipoamide Dehydrogenase Mutation Alters the NADH Sensitivity of Pyruvate Dehydrogenase Complex of *Escherichi coli* K-12," J. Bacteriol. 190:3851-3858 (2008).
Kim et al., "Both subunits of ATP-citrate lyase from Chlorobium tepidum contribute to catalytic activity," J. Bacteriol. 188:6544-6552 (2006).
Kim et al., "Effect of overexpression of Actinobacillus succinogenes phosphoenolpyruvate carboxykinase on succinate production in *Escherichia coli*," Appl. Environ. Microbiol. 70:1238-1241 (2004).
Kinoshita, "Purification of two alcohol dehydrogenases from Zymomonas mobilis and their properties," Appl. Microbiol. Biotechnol. 22:249-254 (1985).
Kizer et al., "Application of functional genomics to pathway optimization for increased isoprenoid production," Appl. Environ. Microbiol., 74(10):3229-3241 (2008).
Klyosov, "Kinetics and specificity of human liver aldehyde dehydrogenases toward aliphatic, aromatic, and fused polycyclic aldehydes," Biochemistry 35(14):4457-4467 (1996).
Knappe et al., "Post-translational activation introduces a free radical into pyruvate formate-lyase," Proc. Natl. Acad. Sci. U.S.A. 81:1332-1335 (1984).
Knutzon et al, "Isolation and characterization of two safflower oleoyl-acyl carrier protein thioesterase cDNA clones," Plant Physiol 100:1751-1758 (1992).
Kohlwein et al, "Tscl3p is required for fatty acid elongation and localizes to a novel structure at the nuclear-vacuolar interface in *Saccharomyces cerevisiae*," Mol Cell Biol 21:109-125 (2001).
Koland et al., "Proximity of Reactive Cysteine Residue and Flavin in *Escherichia coli* Pyruvate Oxidase As Estimated by Flourescence Energy Transfer," Biochemistry 21:4438-4442 (1982).

Koo et al, "Functional evaluation of the genes involved in malonate decarboxylation by Acinetobacter calcoaceticus," Eur. J. Biochem. 266:683-690 (1999).
Koo et al., "Cloning and characterization of the bifunctional alcohol/acetaldehyde dehydrogenase gene (adhE) in Leuconostoc mesenteroides isolated from kimchi," Biotechnol. Lett. 27(7):505-510 (2005).
Korolev et al., "Autotracing of *Escherichia coli* acetate CoA-transferase α-subunit structure using 3.4 Å MAD and 1.9 Å native data," Acta. Cryst. D58:2116-2121 (2002).
Kosaka et al., "Characterization of the sol operon in butanol-hyperproducing Clostridium saccharoperbutylacetonicum strain N1-4 and its degeneration mechanism," Biosci. Biotechnol. Biochem. 71:58-68 (2007).
Kowalchuk et al., "Contrasting patterns of evolutionary divergence within the Acinetobacter calcoaceticus pca operon," Gene 146:23-30 (1994).
Kretz et al., "Gene site saturation mutagenesis: a comprehensive mutagenesis approach," Methods Enzymol. 388:3-11 (2004).
Krieger et al., "Pyruvate decarboxylase from Kluyveromyces lactis An enzyme with an extraordinary substrate activation behaviour," Eur. J. Biochem. 269:3256-3263 (2002).
Kuznetsova et al., "Enzyme genomics: Application of general enzymatic screens to discover new enzymes," FEMS Microbiol. Rev. 29:263-279 (2005).
Kwon et al., "Influence of gluconeogenic phosphoenolpyruvate carboxykinase (PCK) expression on succinic acid fermentation in *Escherichia coli* under high bicarbonate condition," J. Microbiol. Biotechnol. 16(9):1448-1452 (2006).
Laivenieks et al., "Cloning sequencing, and overexpression of the Anaerobiospirillum succinicproducens phosphoenolpyruvate carboxykinase (pckA) gene," Appl. Environ. Microbiol. 63:2273-2280 (1997).
Lea et al., "Does phosphoenolpyruvate carboxykinase have a role in both amino acid and carbohydrate metabolism?," Amino Acids 20:225-241 (2001).
Leal, "PduP is a coenzyme-a-acylating propionaldehyde dehydrogenase associated with the polyhedral bodies involved in B12-dependent 1,2-propanediol degradation by *Salmonella enterica* serovar Typhimurium LT2,"Arch. Microbiol. 180:353-361 (2003).
Lee et al., "Cloning and Characterization of Mannheimia succiniciproducens MBEL55E Phosphoenolpyruvate Carboxykinase (pckA) Gene," Biotechnol. Bioprocess Eng. 7:95-99 (2002).
Lee et al., "A new approach to directed gene evolution by recombined extension on truncated templates (RETT)," J. Molec. Catalysis 26:119-129 (2003).
Lee et al., "Chaperonin GroESL mediates the protein folding of human liver mitochondrial aldehyde dehydrogenase in *Escherichia coli*," Biochem. Biophys. Res. Commun. 298(2):216-224 (2002).
Lee et al., "Cysteine-286 as the site of acylation of the Lux-specific fatty acyl-CoA reductase," Biochim. Biohys. Acta, 1388:215-222 (1997).
Lehtio et al., "The pyruvate format lyase family: sequences, structures and activation," Protein Eng. Des.Sel. 17:545-552 (2004).
Lehtio et al., "Crystal Structure of a Glycyl Radical Enzyme from Archaeoglobus fulgidus," J Mol.Biol. 357:221-235 (2006).
Lenski et al., "Dynamics of adaptation and diversification: a 10,000-generation experiment with bacterial populations," Proc. Natl. Acad. Sci. U.S.A. 91(15):6808-6814 (1994).
Leppanen et al., "Pyruvate formate lyase is structurally homologous to type I ribonucleotide reductase," Structure 7:733-744 (1999).
Leskovac et al., "The three zinc-containing alcohol dehydrogenases from baker's yeast, *Saccharomyces cerevisiae*," FEMS Yeast Res. 2(4):481-494 (2002).
Li et al., "Effecrts of Substitution of Tryptophan 412 in the Substrate Activation Pathway of Yeast Pyruvate Decarboxylase," Biochemistry 38:10004-10012 (1999).
Li et al., "Properties of Nicotinamide Adenine Dinucleotide Phosphate-Dependent Formate Dehydrogenase from Clostridium thermoaceticum," J. Bacteriol. 92(2):405-412 (1966).
Lin et al., "Fed-batch culture of a metabolically engineered *Escherichia coli* strain designed for high-level succinate production and yield under aerobic conditions," Biotechnol. Bioeng. 90(6):775-779 (2005).

(56) References Cited

OTHER PUBLICATIONS

Lingen et al., "Alteration of the Substrate Specificity of Benzoylformate Decarboxylase from Pseudomonas putida by Directed Evolution," Chembiochem 4:721-726 (2003).

Lingen et al., "Improving the carboligase activity of benzoylformate decarboxylase from Pseudomonas putida by a combination of directed evolution and site-directed mutagenesis," Protein Eng. 15:585-593 (2002).

Liu et al, "Gene cloning, biochemical characterization and physiological role of a thermostable low-specificity L-threonine aldolase from *Escherichia coli*," Eur J Biochem 255:220-226 (1998).

Liu et al, "The GLY1 gene of *Saccharomyces cerevisiae* encodes a low-specific L-threonine aldolase that catalyzes cleavage of L-allothreonine and L-threonine to glycine-expression of the gene in *Escherichia coli* and purification and characterization of the enzyme," Eur J Biochem 245:289-293 (1997).

Liu et al, "Two novel metal-independent long-chain alkyl alcohol dehydrogenases from Geobacillus thermodenitrificans NG80-2," Physiol Biochem 155:2078-2085 (2009).

Liu et al., "Expression and purification of His-tagged rat mitochondrial short-chain 3-hydroxyacyl-CoA dehydrogenase wild-type and Ser137 mutant proteins," Prot. Expr. Purif., 37:344-351 (2004).

Liu et al., "Fatty alcohol production in engineered *E. coli* expressing Marinobacter fatty acyl-CoA reductases," Appl. Microbiol. Biotechnol., 97:7061-7071 (2013).

Lobo et al, "A Streptomyces collinus thiolase with novel acetyl-CoA:acyl carrier protein transacylase activity," Biochem 40:11955-11964 (2001).

Lomakin et al., "The crystal structure of yeast fatty acid synthase, a cellular machine with eight active sites working together," Cell, 129:319-332 (2007).

Longtine et al., "Additional modules for versatile and economical PCR-based gene deletion and modification in *Saccharomyces cerevisiae*," Yeast 14:953-961 (1998).

Lorquet et al., "Characterization and functional analysis of the poxB gene, which encodes pyruvate oxidase in Lactobacillus plantarum," J Bacteriol 186:3749-3759 (2004).

Louis et al., "Restricted Distribution of the Butyrate Kinase Pathway among Butyrate-Producing Bacteria from the Human Colon," J. Bacteriol. 186(7):2099-2106 (2004).

Low et al., "Mimicking somatic hypermutation: affinity maturation of antibodies displayed on baceriophage using a bacterial mutator strain," J. Mol. Biol. 260(3):359-368 (1996).

Lucas et al., "The Aspergillus nidulans carnitine carrier encoded by the acuH gene is exclusively located in the mitochondria," FEMS Microbiol Lett 201:193-198 (2006).

Luo et al, "Purification, identification, and properties of a *Saccharomyces cerevisiae* oleate-activated upstream activating sequence-binding protein that is involved in the activation of POX1," J Biol Chem 271:12068-12075 (1996).

Luo et al., "Identification and characterization of the propanediol utilization protein PduP of Lactobacillus reuteri for 3-hydroxypropionic acid production from glycerol," Appl. Microbiol. Biotech., 89:697-703 (2011).

Lutz et al., "Creating multiple-crossover DNA libraries independent of sequence identity," Proc. Natl. Acad. Sci. U.S.A. 98(20):11248-11253 (2001).

Lutz et al., "Independent and tight regulation of transcriptional units in *Escherichia coli* via the LacR/O, the TetR/O and AraC/I1-I2 regulatory elements," Nucleic Acids Res. 25:1203-1210 (1997).

Lutz et al., "Rapid generation of incremental truncation libraries for protein engineering using α-phosphothioate nucleotides," Nucleic Acids Res. 15:29(4):e16 (2001).

Machado et al., "A selection platform for carbon chain elongation using the CoA-dependent pathway to produce linear higher alcohols," Met. Eng., 14:504-511 (2012).

Machielsen et al, "Cofactor engineering of Lactobacillus brevis alcohol dehydrogenase by computational design," Engineering in Life Sciences, 9(1):38-44 (2009).

Mack et al., "Conversion of glutaconate CoA-transferase from Acidaminococcus fermentas into an acyl-CoA hydrolase by site-directed mutagenesis," FEBS Lett. 405:209-212 (1997).

Maeda et al "Enhanced hydrogen production from glucose by metabolically engineered *Escherichia coli*," Appl. Microbiol. Biotechnol. 77:879-890 (2007).

Makuc et al, "The putative monocarboxylate permeases of the yeast *Saccharomyces cerevisiae* do not transport monocarboxylic acids across the plasma membrane," Yeast 18:1131-1143 (2001).

Mann, Radiocarbon, "An International Reference Material for Radiocarbon Dating," 25(2):519-527 (1983).

Mannaerts et al, "Peroxisomal lipid degradation via beta- and alpha-oxidation in mammals," Cell Biochem Biphys 32:73-87 (2000).

Marolewski et al., "Cloning and characterization of a new purine biosynthetic enzyme: a non-folate glycinamide ribonucleotide transformylase from *E. coli*," Biochemistry 33:2531-2537 (1994).

Martin et al., "Engineering a mevalonate pathway in *Escherichia coli* for production of terpenoids," Nat. Biotechnol. 21:796-802 (2003).

Mattevi et al., "Atomic structure of the cubic core of the pyruvate dehydrogenase multienzyme complex," Science 255:1544-1550 (1992).

Matthies et al., "Reciprocal Isomerization of Butyrate and Isobutyrate by the Strictly Anaerobic Bacterium Strain WoG13 and Methanogenic Isobutyrate Degradation by a Devined Triculture," Appl. Environ. Microbiol. 58(5):1435-1439 (1992).

McAlister-Henn et al., "Isolation and expression of the gene encoding yeast mitochondrial malate dehydrogenase," J. Bacteriol. 169:5157-5166 (1987).

McNeil et al, "Glycine metabolism in Candida albicans: characterization of the serine hydroxymethyltransferase (SHM1, SHM2) and threonine aldolase (GLY1) genes," Yeast 16:167-175 (2000).

Meijer et al., "Gene deletion of cytosolic ATP: citrate lyase leads to altered organic acid production in Aspergillus niger," J. Ind. Microbiol. Biotechnol. 36:1275-1280 (2009).

Melchiorsen et al., "The level of pyruvate-formate lyase controls the shift from homolactic to mixed-acid product formation in Lactoccus lactis," Appl. Microbiol. Biotechnol. 58(3):338-344 (2002).

Mellgren et al., "Mqo, a tricarboxylic acid cycle enzyme, is required for virulence of Pseudomonas syringae pv. tomato strain DC3000 on *Arabidopsis thaliana*," J Bacteriol 191:3132-3142 (2009).

Membrillo et al., "Evolution of the adhE gene product of *Escherichia coli* from a functional reductase to a dehydrogenase. Genetic and biochemical studies of the mutant proteins," J. Biol. Chem. 275(43): 333869-333875 (2000).

Menon et al., "Mechanism of the Clostridium thermoaceticum pyruvate:ferredoxin oxidoreductase: evidence for the common catalytic intermediacy of the hydroxyethylthiamine pyropyrosphate radical," Biochemistry 36(28):8484-8494 (1997).

Menzel et al., "Enzymatic evidence for an involvement of pyruvate dehydrogenase in the anaerobic glycerol metabolism of Klebsiella pneumoniae," J. Biotechnol. 56:135-142 (1997).

Merilainen et al, "The thiolase reaction mechanism: the importance of Asn316 and His348 for stabilizing the enolate intermediate of the Claisen condensation," Biochem 48: 11011-11025 (2009).

Metz et al., "Purification of a jojoba embryo fatty acyl-coenzyme A reductase and expression of its cDNA in high erucic acid rapeseed," Plant Physiol. 122(3):635-644 (2000).

Mikkelsen et al., "Microbial production of indolylglucosinolate through engineering of a multi-gene pathway in a versatile yeast expression platform," Met. Eng., 14:104-111 (2012).

Minard et al., "Isolation, nucleotide sequence analysis, and disruption of the MDH2 gene from Saccharomyces cerevisiae: evidence for three isozymes of yeast malate dehydrogenase," Mol. Cell. Biol. 11:370-380 (1991).

Mitsuhashi et al, "Disruption of malate:quinone oxidoreductase increases L-lysine production by Corynebacterium glutamicum," Biosci Biotechnol Biochem 70:2803-2806 (2006).

Morris et al., "Nucleotide sequence of the LYS2 gene of *Saccharomyces cerevisiae*: homology to Bacillus brevis tyrocidine synthetasel," Gene 98:141-145 (1991).

Mukhopadhyay et al., "Pyruvate carboxylase from Mycobacterium smegmatis: stabilization, rapid purification, moleculare and bio-

(56) References Cited

OTHER PUBLICATIONS chemical characterization and regulation of the cellular level," Biochim. Biophys. Acta 1475(3):191-206 (2000).

Muller et al., "Nucleotide exchange and excision technology (NExT) DNA shuffling: a robust method for DNA fragmentation and directed evolution," Nucleic Acids Res. 33(13):e117 (2005).

Musfeldt et al., "Novel Type of ADP-Forming Acetyl Coenzyme A Synthetase in Hyperthermophilic Archaea: Heterologous Expression and Characterization of Isoenzymes from the Sulfate Reducer Archaeoglobus fulgidus and the Methanogen Methanococcus jannaschii," J. Bacteriol. 184(3):636-644 (2002).

Naesby et al, "Yeast artificial chromosomes employed for random assembly of biosynthetic pathways and production of diverse compounds in Saccharomyces cerevisiae," Microb Cell Fact 8:49-56 (2009).

Nagashima et al., "Long-Chain n-Alkanol Dehydrogenase from Pseudomonas putida," J. Ferment. Bioeng., 82:328-333 (1996).

Naggert et al., "Cloning, Sequencing, and Characterization of Escherichia coli thioesteraseII," J. Biol. Chem. 266(17):11044-11050 (1991).

Nagi et al., "Biochemical properties of short- and long-chain rat liver microsomal trans-2-enoyl coenzyme A reductase," Arch. Biochem. Biophys., 226:50-64 (1983).

Nakahigashi et al., "Nucleotide sequence of the fadA and fadB genes from Escherichia coli," Nucleic Acids Res. 18(16):4937 (1990).

Nakamura et al, "Studies on malonic semialdehyde dehydrogenase from Pseudomonas aeruginosa," Biochim Biophys Acta 50:147-152 (1961).

Nakano et al., "Characterization of Anaerobic Fermentative Growth of Bacillus subtilis: Identification of Fermentation End Products and Genes Required for Growth," J. Bacteriol. 179(21):6749-6755 (1997).

Nakashita et al, "Identification and expression of the gene encoding phosphonopyruvate decarboxylase of Streptomyces hygroscopicus," Biochim Biophys Acta 1490:159-162 (2000).

Navarro-Avino et al, "A proposal for nomenclature of aldehyde dehydrogenases in Saccharomyces cerevisiae and characterization of the stress-inducible ALD2 and ALD3 genes," Yeast 15:829-842 (1999).

Ness et al., "Synthetic shuffling expands functional protein diversity by allowing amino acids to recombine independently," Nat. Biotechnol. 20(12):1251-1255 (2002).

Nie et al., "Identification and characterization of Escherichia coli thioesterase III that functions in fatty acid beta-oxidation," Biochem., 47:7744-7751 (2008).

Nilekani et al., "Purification and properties of citrate lyase from Escherichia coli," Biochemistry 22:4657-4663 (1983).

Nishimaki-Mogami et al., "Involvement of the fatty acid oxidation complex in acetyl-CoA-dependent chain elongation of fatty acids in Escherichia coli," J. Biochem., 102:427-432 (1987).

Nogales et al., "Characterization of the last step of the aerobic phenylacetic acid degradation pathway," Microbiology 153:357-365 (2007).

Nowrousian et al., "The fungal acl1 and acl2 genes encode two polypeptides with homology to the N- and C-terminal parts of the animal ATP citrate lyase polypeptide," Curr. Genet. 37:189-193 (2000).

O'Brien et al, "Regulation by Lipids of Cofactor Binding to a Peripheral Membrane Enzyme: Binding of Thiamin Pyrophosphate to Pyruvate Oxidase," Biochemistry 16(14):3105-3109 (1977).

O'Brien et al., "Studies of the Thiamin Pyrophosphate Binding Site of Escherichia coli Pyruvate Oxidase," J. Biol. Chem. 255(8):3302-3307 (1980).

Oey et al., "dif-1 and colt, both implicated in early embryonic development, encode carnitine acylcarnitine translocaseb," Mol Genet Metab 85:121-124 (2005).

Okamura et al, "Unprecedented acetoacetyl-coenzyme A synthesizing enzyme of the thiolase superfamily involved in the mevalonate pathway," PNAS USA 107:11265-11270 (2010).

Oku et al., "Biosynthesis of Branched-chain Fatty Acids in Bacillis subtilis," J. Biol. Chem. 263:18386-18396 (1988).

Olivera et al., "Molecular characterization of the phenylacetic acid catabolic pathway in Pseudomonas putida U: the phenylacetyl-CoA catabolon," Proc. Natl. Acad. Sci. U.S.A. 95(11):6419-6424 (1998).

Oshima et al., "Regulation of phosphatase synthesis in Saccharomyces cerevisiae—a review," Gene 179:171-177 (1996).

Ostermeier et al., "A combinatorial approach to hybrid enzymes independent of DNA homology," Nat. Biotechnol. 17(12):1205-1209 (1999).

Ostermeier et al., "Combinatorial protein engineering by incremental truncation," Proc. Natl. Acad. Sci. U.S.A. 96(7):3562-3567 (1999).

Overkamp et al., "In vivo analysis of the mechanism for oxidation of cytosolic NADH by Saccharomyces cerevisiae mitochondria," J. Bacteriol. 182:2823-2830 (2000).

Palmieri et al., "Identification of mitochondrial carriers in Saccharomyces cerevisiae by transport assay of reconstituted recombinant proteins," Biochimica et Biophys Acta 1757:1249-1262 (2006).

Palosaari et al., "Purification and properties of the inducible coenzyme A-linked butyraldehyde dehydrogenase from Clostridium acetobutylicum," J. Bacteriol. 170(7):2971-2976 (1988).

Park and Lee, "New FadB homologous enzymes and their use in enhanced biosynthesis of medium-chain-length polyhydroxyalkanoates in FadB mutant Escherichia coli," Biotechnol. Bioeng. 86(6):681-686 (2004).

Park et al., "Biosynthesis of poly(3-hydroxybutyrate- co-3-hydroxyalkanoates) by metabolically engineered Escherichia coli strains," Appl. Biochem. Biotechnol. 113-116:335-346 (2004).

Park et al., "Identification and characterization of a new enoyl Coenzyme A hydratase involved in biosynthesis of medium-chain-length polyhydroxyalkanoates in recombinant Escherichia coli," J. Bacteriol. 185(18):5391-5397 (2003).

Passoth et al, "Molecular cloning of alcohol dehydrogenase genes of the yeast Pichia stipitis and identification of the fermentative ADH," Yeast 14:1311-1323 (1998).

Patel (ed.), "Directed evolution: selecting today's biocatalysts," CRC Press; Otten and Quax. Biomol. Eng 22:1-9 (2005).

Pauli et al., "ato Operon: a Highly Inducible System for Acetoacetate and Butyrate Degradation in Escherichia coli," Eur. J. Biochem. 29:553-562 (1972).

Paxton et al., "Role of branched-chain 2-oxo acid dehydrogenase and pyruvate dehydrogenase in 2-oxobutyrate metabolism," Biochem. J. 234:295-303 (1986).

Perez et al., "Escherichia coli YqhD exhibits aldehyde reductase activity and protects from the harmful effect of lipid peroxidation-derived aldehydes," J. Biol. Chem. 283(12):7346-7353 (2008).

Pierce et al., "The Complete Genome Sequence of Moorella thermoacetia (f. Clostridum thermoaceticum)," Environ. Microbiol. 10(10):2550-2573 (2008).

Pieulle et al., "Isolation and analysis of the gene encoding the pyruvate-ferredoxin oxidoreductase of Desulfovibrio africanus, production of the recombinant enzyme in Escherichia coli, and effect of carboxy-terminal deletions on its stability," J. Bacteriol. 179(18):5684-5692 (1997).

Ploux et al., "The NADPH-linked acetoacetyl-CoA reductase from Zoogloea ramigera, Characterization and mechanistic studies of the cloned enzyme over-produced in Escherichia coli," Eur. J. Biochem. 174:177-182 (1988).

Pohl et al., "Remarkably broad Sustrate Tolerance of Malonyl-CoA Synthetase, an Enzyme Capable of Intracellular Synthesis of Polyketide Precursors," J. Am. Chem. Soc. 123:5822-5823 (2001).

Poletto et al., "Selection of an Escherichia coli host that expresses mutant forms of Mycobacterium tuberculosis 2-trans enoyl-ACP(CoA) reductase and 3-ketoacyl-Acp(CoA) reductase enzymes," Prot. Expr. Purif., 34:118-125 (2004).

Polovnikova et al., "Structural and Kinetic Analysis of Catalysis by a Thiamin Diphosphate-Dependent Enzyme, Benzoylformate Decarboxylase," 42:1820-1830 (2003).

(56) References Cited

OTHER PUBLICATIONS

Popp et al, "Fermentative Production of L-Glycerol 3-Phosphate Utilizing a *Saccharomyces cerevisiae* Strain With an Engineered Glycerol Biosynthetic Pathway," Biotechnol Bioeng 100:497-505 (2008).
Portnoy et al, "Aerobic Fermentation of D-Glucose by an Evolved Cytochrome Oxidase-Deficient *Escherichia coli* Strain," AEM 74:7561-7569 (2008).
Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," J. Bacteriol. 175(2):377-385 (1993).
Prather et al., "De novo biosynthetic pathways: rational design of microbial chemical factories." Curr. Opin. Biotechnol., 19:468-474 (2008).
Prescott et al, "Acyl carrier protein," Adv. Enzymol. Relat. Areas Mol, 36:269-311 (1972).
Priefert et al., "Identification and molecular characterization of the acetyl coenzyme A synthetase gene (acoE) of Alcaligenes eutrophus," J. Bacteriol. 174:6590-6599 (1992).
Pritchard et al., "A general model of error-prone PCR," J. Theor. Biol. 234:497-509 (2005).
Pronk et al., "Pyruvate metabolism in *Saccharomyces cerevisiae*," Yeast 12:1607-1633 (1996).
Quash et al, "Novel competitive irreversible inhibitors of aldehyde dehydrogenase (ALDH1): restoration of chemosensitivity of L1210 cells overexpressing ALDH1 and induction of apoptosis in BAF(3) cells overexpressing bcl(2)," Biochem Pharmacol 64:1279-1292 (2002).
Rado et al., "Phosphotransacetylase from Bacillus subtilis: purification and physiological studies," Biochim. Biophys. Acta 321:114-125 (1973).
Ragsdale, "Pyruvate ferredoxin oxidoreductase and its radical intermediate," Chem. Rev. 103(6):2333-2346 (2003).
Rajpal et al., "A general method for greatly improving the affinity of antibodies by using combinatorial libraries," Proc. Natl. Acad. Sci. U.S.A. 102(24):8466-8471 (2005).
Ramos-Montanez et al., "Polymorphism and regulation of the spxB (pyruvate oxidase) virulence factor gene by a CBS-HotDog domain protein (SpxR) in serotype 2 *Streptococcus pneumonia*," Mol Micro 67:729-746 (2008).
Ramsay et al, "Molecular enzymology of carnitine transfer and transport," Biochim Biophys Acta 1546:21-42 (2001).
Reda et al., "Reversible interconversion of carbon dioxide and formate by an electroactive enzyme," Proc. Natl. Acad. Sci. U.S.A. 105:10654-10658 (2008).
Reetz et al., "Directed Evolution of an Enantioselective Enzyme through Combinatorial Multiple-Cassette Mutagenesis," Agnew. Chem. Int. Ed. Engl. 40:3589-3591 (2001).
Reetz et al., "Iterative saturation mutagenesis (ISM) for rapid directed evolution of functional enzymes," Nat. Protoc. 2(4):891-903 (2007).
Reetz et al., "Iterative Saturation Mutagenesis on the Basis of B Factors as a Strategy for Increasing Protein Thermostability," Agnew. Chem. Int. Ed. Engl. 45:7745-7751 (2006).
Reidhaar-Olson et al., "Combinatorial cassette mutagenesis as a probe of the informational content of protein sequences," Science 241(4861):53-57 (1988).
Reidhaar-Olson et al., "Random mutagenesis of protein sequences using oligonucleotide cassettes," Methods Enzymol. 208:564-586 (1991).
Reiser et al., "Isolation of mutants of Acinetobacter calcoaceticus deficient in wax ester synthesis and complementation of one mutation with a gene encoding a fatty acyl coenzyme A reductase," J. Bacteriol. 179(9):2969-2975 (1997).
Riviere et al., "Acetyl:Succinate CoA-transferase in Procyclic Trypanosoma brucei," J. Biol Chem. 279(44):45337-45346 (2004).
Roberts et al, "The Role of Enoyl-CoA Hydratase in the Metabolism of Isoleucine by Pseudomonas putida," Arch. Microbiol. 117:99-108 (1978).

Robinson et al., "Studies on Rat Brain Acyl-Coenzyme a Hydrolase (Short Chain)," Biochem. Biophys. Res. Commun. 71:959-965 (1976).
Rock et al, "Role of feedback regulation of pantothenate kinase (CoaA) in control of coenzyme A levels in *Escherichia coli*," J Bacteriol 185: 3410-3415 (2003).
Rose et al, "Molecular cloning of the gene for the yeast homolog (ACB) of diazepam binding inhibitor/endozepine/acyl-CoA-binding protein," PNAS USA 89: 11287-11291 (1992).
Sadowski, P. D., "The Flp recombinase of the 2-microns plasmid of *Saccharomyces cerevisiae*," Prog.Nucleic.Acid.Res.Mol.Biol. 51:53-91 (1995).
Salas et al., "Characterization of substrate specificity of plant FatA and FatB acyl-ACP thioesterases," Arch. Biochem. Biophys., 403:25-34 (2002).
Sato et al., "Poly[(R)-3-hydroxybutyrate] formation in *Escherichia coli* from glucose through an enoyl-CoA hydratase-mediated pathway," J. Biosci. Bioeng. 103(1):38-44 (2007).
Schiedel et al., "Cloning, expression, and purification of glyoxysomal 3-oxoacyl-CoA thiolase from sunflower cotyledons," Prot. Expr. Purif., 33:25-33 (2004).
Schirmer et al, "Microbial biosynthesis of alkanes," Science, 329: 559-562 (2010).
Schjerling et al, "Disruption of the gene encoding the acyl-CoA-binding protein (ACB1) perturbs acyl-CoA metabolism in *Saccharomyces cerevisiae*," J Biol Chem 271: 22514-22521 (1996).
Schneider et al., "Biosynthesis of the Prosthetic Group of Citrate Lyase," Biochemistry 39:9438-9450 (2000).
Schreiner et al., "Pyruvate: Quinone Oxidoreductase in Corynebacterium glutamicum: Molecular Analysis of the pqo Gene, Significance of the Enzyme, and Phylogenetic Aspects," J Bacteriol 188:1341-1350 (2006).
Schwartz et al, "Isolation and characterization of the PEP-phosphomutase and the phosphonopyruvate decarboxylase genes from the phosphinothricin tripeptide producer Streptomyces viridochromogenes Tu494," FEMS Microbiol Lett 163:149-157 (1998).
Seedorf et al., "The genome of Clostridium kluyveri, a strict anaerobe with unique metabolic features," Proc. Natl. Acad. Sci. U.S.A. 105(6):2128-2133 (2008).
Sekimoto et al., "Cloning and molecular characterization of plant aldehyde oxidase," J. Biol. Chem. 272(24):15280-15285 (1997).
Sekoguchi et al., "A novel mitochondrial carnitine-acylcarnitine translocase induced by partial hepatectomy and fasting," J Biol Chem 278:38796-38802 (2003).
Selifonova et al., "Rapid evolution of novel traits in microorganisms," Appl. Environ. Microbiol. 67:3645-3649 (2001).
Sen et al., "Developments in directed evolution for improving enzyme functions," Appl. Biochem. Biotechnol. 143(3):212-223 (2007).
Serov et al., "Engineering of coenzyme specificity of formate dehydrogenase from *Saccharomyces cerevisiae*," Biochem J. 1:367(Pt. 3):841-847 (2002).
Shah et al., "Repressible alkaline phosphatase of *Staphylococcus aureus*," J. Bacteriol. 94:780-781 (1967).
Shao et al., "Random-priming in vitro recombination: an effective tool for directed evolution," Nucleic Acids Res. 26(2):681-683 (1998).
Shigeoka et al., "Characterization and molecular properties of 2-oxoglutarate decarboxylase from Euglena gracilis," Arch. Biochem. Biophys. 288:22-28 (1991).
Shimomura et al., "3-Hydroxyisobutyryl-CoA Hydrolase," Meth. Enzymol. 324:229-240 (2000).
Shimomura et al., "Purification and partial characterization of 3-hydroxyisobutyryl-Coenzyme A hydrolase of rat liver," J. Biol. Chem. 269(19):14248-14253 (1994).
Shingler et al., "Nucleotide Sequence and Functional Analysis of the Complete Phenol/3,4-Dimethylphenol Catabolic Pathway of *Pseudomonas* sp. Strain CF600," J. Bacteriol. 174(3):711-724 (1992).
Sieber et al., "Libraries of hybrid proteins from distantly related sequences," Nat. Biotechnol. 19(5):456-460 (2001).

(56) References Cited

OTHER PUBLICATIONS

Siegert et al., "Exchanging the substrate specificities of pyruvate decarboxylase from Zymomonas mobilis and benzoylase from Pseudomonas putida," Protein Eng. Des. Sel. 18:345-357 (2005).
Siew et al., "Localization and characteristics of rat liver mitochondrial aldehyde dehydrogenases," Arch. Biochem. Biophys. 176(2):638-649 (1976).
Sikorski et al., "A system of shuttle vectors and yeast host strains designed for efficient manipulation of DNA in *Saccharomyces cerevisiae*," Genetics 122:19-27 (1989).
Simanshu et al., "Structure and function of enzymes involved in the anaerobic degradation of L-threonine to propionate," J. Biosci. 32(6):1195-1206 (2007).
Simon et al, "cDNA cloning of Brassica napus malonyl-CoA:ACP transacylase (MCAT) (fab D) and complementation of an *E. coli* MCAT mutant," FEBS Lett 435:204-206 (1998).
Skarstedt et al., "*Escherichia coli* Acetate Kinase Mechanism Studied by Net Initial Rate, Equilibriu, and Independent Isotopic Exchange Kinetics," J. Biol. Chem. 251:6775-6783 (1976).
Slater et al., "Multiple β-ketothiolases mediate poly(β-hydroxyalkanoate) copolymer synthesis in Ralstonia eutropha," J. Bacteriol. 180(8):1979-1987 (1998).
Smit et al., "Identification, Cloning, and Characterization of a Lactococcus lactis Branched-Chain α-Keto Acid Decarboxylase Involved in Flavor Formation," Appl. Environ. Microbiol. 71:303-311 (2005).
Sohling et al., "Molecular analysis of the anaerobic succinate degradation pathway in Clostridium kluyveri.," J. Bacteriol. 178(3):871-880 (1996).
Soini et al., "High cell density media for *Escherichia coli* are generally designed for aerobic cultivations—consequences for large-scale bioprocesses and shake flask cultures," Microb. Cell. Fact. 7:26 (2008).
Song et al., "Structure, Function, and Mechanism of the Phenylacetate Pathway Hot Dog-fold Thioesterase PaaI," J. Biol. Chem. 281(16):11028-11038 (2006).
Spellerberg et al., "Pyruvate oxidase, as a determinant of virulence in *Streptococcus pneumonia*," Mol Micro 19:803-813 (1996).
Sramek et al., "Purification and properties of *Escherichia coli* Coenzyme A-transferase," Arch. Biochem. Biophys. 171(1):14-26 (1975).
St. Maurice et al., "Flavodoxin:quinone reductase (FqrB): a redox partner of pyruvate:ferredoxin oxidoreductase that reversibly couples pyruvate oxidation to NADPH production in Helicobacter pylori and Campylobacter jejuni," J. Bacteriol. 189:4764-4773 (2007).
Stadtman, "[98] Phosphotransacetylase from Clostridium kluyveri: Ae~P+CoA ⇆ Ac~SCoA+Pi," Methods Enzymol. 1:596-599 (1955).
Steffan et al., "Isolation and characterization of the yeast gene encoding the MDH3 isozyme of malate dehydrogenase," J. Biol. Chem. 267:24708-24715 (1992).
Steinbüchel et al., "Nad-linked L(+)-lactate dehydrogenase from the strict aerobe alcaligenes eutrophus. 2. Kinetic properties and inhibition by oxaloacetate," Eur. J. Biochem. 130(2):329-334 (1983).
Stemmer, "DNA Shuffling by random fragmentation and reassembly: in vitro recombination for molecular evolution," Proc. Natl. Acad. Sci. U.S.A. 91(22):10747-10751 (1994).
Stemmer, "Rapid evolution of a protein in vitro by DNA shuffling," Nature 370:389-391 (1994).
Stines-Chaumeil et al, "Mechanistic characterization of the MSDH (methylmalonate semialdehyde dehydrogenase) from Bacillus subtilis," Biochem J 395:107-115 (2006).
Stols et al., "Expression of Ascaris suum malic enzyme in a mutant *Escherichia coli* allows production of succinic acid from glucose," Appl. Biochem. Biotechnol. 63-65: 153-158 (1997).
Stols et al., "New vectors for co-expression of proteins: Structure of Bacillus subtilis ScoAB obtained by high-throughput protocols," Protein Expr. Purif. 53:396-403 (2007).
Stols et al., "Production of succinic acid through overexpression of NAD+-dependent malic enzyme in an *Escherichia coli* mutant," Appl. Environ. Microbiol. 63(7):2695-2701 (1997).
Strejbis et al., "Enzymology of the carnitine biosynthesis pathway," IUBMB Life 62:357-362 (2010).
Strijbis et al., "Contributions of carnitine acetyltransferases to intracellular acetyl unit transport in Candida albicans," J Biol Chem 285:24335-24346 (2010).
Strijbis et al., "Identification and characterization of a complete carnitine biosynthesis pathway in Candida albicans," FASEB J 23:2349-2359 (2009).
Stuible et al, "A novel phosphopantetheine:protein transferase activating yeast mitochondrial acyl carrier protein," J Biol Chem: 273: 22334-22339 (1998).
Sulzenbacher et al., "Crystal structure of *E. coli* alcohol dehydrogenase YqhD: evidence of a covalently modified NADP coenzyme," J. Mol. Biol. 342(2):489-502 (2004).
Sumper et al, "Acetyl-CoA Carboxylase from Yeast," Methods Enzym 71:34-37 (1981).
Suzuki et al., "GriC and GriD Constitute a carboxylic acid reductase involved in grixazone biosynthesis in Streptomyces griseus," J. Antibiot. 60(6):380-387 (2007).
Suzuki, "Phosphotransacetylase of *Escherichia coli* B, activation by pyruvate and inhibition by NADH and certain nucleotides," Biochim. Biophys. Acta 191(3):559-569 (1969).
Takacs et al., "Formate hydrogenlyase in the hyperthermophilic archaeon, Thermococcus litoralis," Bmc Microbiol. 8:88 (2008).
Takahashi et al., "Metabolic Pathways for Cytoxic End Product Formation from Glutamate- and Aspartate-Containing Peptides by Porphyromonas gingivalis," J. Bacteriol. 182(17):4704-4710 (2000).
Takahashi-Abbe et al., "Biochemical and functional properties of a pyruvate formate-lyase (PFL)-activating system in *Streptococcus mutans*," Oral Microbiol. Immunol. 18(5)293-297 (2003).
Takamura et al, "Purification and Some Properties of Malonate Decarboxylase From Pseudomonas ovalis: An Oligomeric Enzyme With Bifunctional Properties," Biochem Int 3:483-491 (1981).
Takeo, "Existence and properties of two malic enzymes in *Escherichia coli* especially of NAD-linked enzyme," J. Biochem. 66:379-387 (1969).
Tanaka et al., "Cloning and characterization of a human orthologue of testis-specific succinyl CoA:3-oxo acid CoA transferase (Scot-t) cDNA," Mol. Hum. Reprod. 8:16-23 (2001).
Tani et al., "Thermostable NADP(+)-dependent medium-chain alcohol dehydrogenase from *Acinetobacter* sp strain M-1: Purification and characterization and gene expression in *Escherichia coli*," Appl. Environ. Microbiol. 66:5231-5235 (2000).
Ter Schure et al., "Pyruvate Decarboxylase Catalyzes Decarboxylation of Branched-Chaing 2-Oxo Acids but Is Not Essential for Fusel Alcohol Production by *Saccharomyces cerevisiae*," Appl. Environ. Microbiol. 64(4):1303-1307 (1998).
Thauer, "Microbiology. A fifth pathway of carbon fixation," Science 318:1732-1733 (2007).
Tian et al., "Variant tricarboxylic acid cycle in Mycobacterium tuberculosis: identification of alpha-ketoglutarate decarboxylase," Proc. Natl. Acad. Sci. U.S.A. 102(30):10670-10675 (2005).
Todd et al, "Molecular dissection of bacterial acrylate catabolism—unexpected links with dimethylsulfoniopropionate catabolism and dimethyl sulfide production," Environ Microbiol 12:237-243 (2010).
Todisco et al, "Identification of the mitochondrial NAD+ transporter in *Saccharomyces cerevisiae*," J Biol Chem 281:1524-1531 (2006).
Tokunaga et al, "Separation and properties of the NAD-linked and NADP-linked isozymes of succinic semialdehyde dehydrogenase in Euglena gracilis z," Biochem Biophys Act 429:55-62 (1976).
Toth et al., "The ald gene, encoding a coenzyme A-acylating aldehyde dehydrogenase, distinguishes Clostridium beijerinckii and two other solvent-producing clostridia from Clostridium acetobutylicum," Appl. Environ. Microbiol. 65(11):4973-4980 (1999).
Tucci et al., "A novel prokaryotic trans-2-enoyl-CoA reductase from the spirochete Treponema denticola," FEBS Lett. 581(8):1561-1566 (2007).
Valdes-Hevia et al., "Isolation and characterization of the gene encoding phosphoenolpyruvate carboxykinase from *Saccharomyces cerevisiae*," FEBS Lett. 258(2):313-316 (1989).
Van Grinsven et al., "Acetate:Succinate CoA-transferase in the Hydrogenosomes of Trichomonas vaginalis," J. Biol. Chem. 283:1411-1418 (2008).

(56) References Cited

OTHER PUBLICATIONS

Van Maris et al, "Overproduction of threonine aldolase circumvents the biosynthetic role of pyruvate decarboxylase in glucose-limited chemostat cultures of *Saccharomyces cerevisiae*," AEM 69:2094-2099 (2003).
Van Mourik et al., "Functional analysis of a Campylobacter jejuni alkaline phosphatase secreted via the Tat export machinery," Microbiol. 154:584-592 (2008).
Van Mullen et al., "Construction of a set of *Saccharomyces cerevisiae* vectors designed for recombinational cloning," Yeast 20:739-746 (2003).
Van Roermund et al., "The human peroxisomal ABC half transporter ALDP functions as a homodimer and accepts acyl-CoA esters," FASEB J 22:4201-4208 (2008).
Van Roermund et al., "The membrane of peroxisomes in *Saccharomyces cerevisiae* is impermeable to NAD(H) and acetyl-CoA under in vivo conditions," EMBO J 14:3480-3486 (1995).
Vanderwinkel et al., "Growth of *Escherichia coli* on fatty acids: requirement for Coenzyme A transferase activity," Biochem. Biophys. Res. Commun. 33(6):902-908 (1968).
Vardar-Schara et al., "Metabolically engineered bacteria for producing hydrogen via fermentation," Microbio. Biotechnol._1:107-125 (2008).
Vazquez et al., "Phosphotransbutyrylase Expression in Bacillus megaterium," Curr. Microbiol. 42:345-349 (2001).
Vellanki et al., "Expression of hepatitis B surface antigen in *Saccharomyces cerevisiae* utilizing glyceraldehyde-3-phosphate dehydrogenase promoter of Pichia pastoris," Biotechnol. Lett. 29(2):313-318 (2007).
Venkitasubramanian et al. Biocatalysis in the Pharmaceutical and Biotechnology Industries, ed. R.N. Patel, Chapter 15, pp. 425-440, CRC Press LLC, Boca Raton, Fl. (2007).
Venkitasubramanian et al., "Reduction of Carboxylic Acids by Nocardia Aldehyde Oxidoreductase Requires a Phosphopantetheinylated Enzyme," J. Biol Chem. 282:478-485 (2007).
Verleur et al., "Transport of activated fatty acids by the peroxisomal ATP-binding-cassette transporter Pxa2 in a semi-intact yeast cell system," Eur J Biochem 249: 657-661 (1997).
Verwoert et al, "Cloning, nucleotide sequence, and expression of the *Escherichia coli* fabD gene, encoding malonyl coenzyme A-acyl carrier protein transacylase," J Bacteriol, 174:2851-2857 (1992).
Volkov et al., "Random chimeragenesis by heteroduplex recombination," Methods Enzymol. 328:456-463 (2000).
Volkov et al., "Recombination and chimeragenesis by in vitro heteroduplex formation and in vivo repair," Nucleic Acids Res. 27(18):e18 (1999).
Wakil et al., "Studies on the Fatty Acid Oxidizing System of Animal Tissues," J. Biol. Chem. 207:631-638 (1954).
Walker et al., "Yeast pyruvate carboxylase: identification of two genes encoding isoenzymes," Biochem. Biophys. Res. Commun. 176:1210-1217 (2007).
Walter et al., "Sequence and arrangement of two genes of the butyrate-synthesis pathway of Clostridium acetobutylicum ATCC 824," Gene 134:107-111 (1993).
Walter et al., "Molecular characterization of two Clostridium acetobutylicum ATCC 824 butanol dehydrogenase isozyme genes," J. Bacteriol. 174(22):7149-7158 (1992).
Wang et al, "Molecular cloning, characterization, and potential roles of cytosolic and mitochondrial aldehyde dehydrogenases in ethanol metabolism in *Saccharomyces cerevisiae*," J Bacteriol 180:822-830 (1998).
Wang et al., "Identification of a Type III Thioesterase Reveals the Function of an Operon Crucial for MTB Virulence," Chem.Biol. 14:543-551 (2007).
Weidner et al., "Molecular Characterization of the Genes Encoding Pyruvate Formate-Lyase and Its Activating Enzyme of Clostridium pasteruianum," J. Bacteriol. 178(8):2440-2444 (1996).
Welch et al., "Purification and characterization of the NADH-dependent butanol dehydrogenase from Clostridium acetobutylicum (ATCC 824)," Arch. Biochem. Biophys. 273(2):309-318 (1989).
Werther et al, "Amino acids allosterically regulate the thiamine diphosphate-dependent alpha-keto acid decarboxylase from Mycobacterium tuberculosis," J Biol Chem 283:5344-5354 (2008).
Westin et al., "The Identification of Succinyl-CoA Thioesterase Suggests a Novel Pathway for Succinate Production in Peroxisomes," J. Biol. Chem. 280(46):38125-38132 (2005).
Wiesenborn et al., "Coenzyme A Transferase from Clostridium acetobutylicum ATC 824 and Its Role in the Uptake of Acids," Appl. Environ. Microbiol. 55:323-329 (1989).
Wiesenborn et al., "Phosphotransbutyrylase from clostridium acetobutylicum ATCC 824 and its role in acidogenesis," Appl. Environ. Microbiol. 55:317-322 (1989).
Willis et al., "Characterization of a Fatty Acyl-CoA Reductase from Marinobacter aquaeolei VTB: A Bacterial Enzyme Catalyzing the Reduction of Fatty Acyl-CoA to Fatty Alcohol," Biochem., 50:10550-10558 (2011).
Winkler et al., "A New Type of a Multifunctional β-Oxidation Enzyme in Euglena," Plant Physiology 131:753-762 (2003).
Winzeler et al., "Functional characterization of the *S. cerevisiae* genome by gene deletion and parallel analysis," Science 285:901-906 (1999).
Winzer et al., "Differential regulation of two thiolase genes from Clostridium acetobutylicum DSM 792," J. Mol. Microbiol. Biotechnol. 2:531-541 (2000).
Winzer et al., "Acetate kinase from Clostridium acetobutylicum: a highly specific enzyme that is actively transcribed during acidogenesis and solventogenesis," Microbioloy 143 (Pt 10):3279-3286 (1997).
Wong et al., "Molecular Properties of Pyruvate Formate-Lyase Activating Enzyme," Biochemistry 32:14102-14110 (1993).
Wong et al., "Sequence satruation mutagenesis with tunable mutation frequencies," Anal. Biochem. 341:187-189 (2005).
Wong et al., "Sequence saturation mutagenesis (SeSaM): a novel method for directed evolution," Nucleic Acids Res. 32(3):e26 (2004).
Wong et al., "Transversion-enriched sequence saturation mutagenesis (SeSaM-Tv+): a random Mutagenesis method with consecutive nucleotide exchanges that complements the bias of error-prone PCR," Biotechnol. J. 3:74-82 (2008).
Wrensford et al., "An acyl-coenzyme a chain length dependent assay for 3-oxoacyl-coenzyme A thiolases employing acetyldithio-coenzyme A," Anal. Biochem., 192:49-54 (1991).
Wu et al., "Life in hot carbon monoxide: the complete genome sequence of Carboxydothermus hydrogenoformans Z-2901," PLoS Genet. 1(5):e65 (2005).
Wu et al., "Site-saturation mutagenesis of formate dehydrogenase from Candida bodinii creating effective NADP+-dependent FDH enzymes," J. Mol. Catalysis B Enzym., 61(3-4):157-161 (2009).
Wynn et al., "Chaperonins GroEL and GroES Promote Assembly of Heterotramers (α2β2) of Mammalian Mitochondrial Branched-chain α-Keto Acid Decarboxylase in *Escherichia coli*," J. Biol. Chem. 267(18):12400-12403 (1992).
Wynn et al., "Cloning and Expression in *Escherichia coli* of a Mature E1β Subunit of Bovine Mitochondrial Branched-chain α-Keto Acid Dehydrogenase Complex," J. Biol Chem. 267(3):1881-1887 (1992).
Yabutani et al., "Analysis of β-ketothiolase and acetoacetyl-CoA reductase genes of a methylotrophic bacterium, Paracoccus denitrificans, and their expression in *Escherichia coli*," FEMS Microbiol. Lett. 133:85-90 (1995).
Yamamoto et al., "Purification and Properties of NADP-dependent Formate Dehydrogenase from Clostridium thermoaceticum, a tungsten-Selenium-Iron Protein," J. Biol. Chem. 258(3):1826-1832 (1983).
Yang et al., "Nucleotide sequence of the fadA gene. Primary structure of 3-ketoacyl-Coenzyme A thiolase from *Escherichia coli* and the structural organization of the fadAB operon," J. Biol. Chem. 265(18):10424-10429 (1990).
Yang et al., "Nucleotide sequence of the promoter and fadB gene of the fadBA operon and primary Structure of the multifunctional fatty acid oxidation protein from *Escherichia coli*," Biochem. 30(27):6788-6795 (1991).
Yang, "Location of the fadBA operon on the physical map of *Escherichia coli*," J. Bacteriol. 173(23):7405-7406 (1991).

(56) References Cited

OTHER PUBLICATIONS

Yebra et al, "Identification of a gene cluster enabling Lactobacillus casei BL23 to utilize myo-inositol," AEM 73:3850-3858 (2007).

Ylianttila et al., "Crystal Structure of Yeast Peroxisomal Multifunctional Enzyme: Structural Basis for Substrate Specificity of (3R)-hydroxyacyl-CoA Dehydrogenase Units," J. Mol. Biol. 258:1286-1295 (2006).

Ylianttila et al., "Site-directed mutagenesis to enable and improve crystallizability of candida tropicalis (3R)-hydroxyacyl-CoA dehydrogenase," Biochem. Biophys. Res. Commun. 324:25-30 (2004).

Youngleson et al., "Homology between hydroxybutyryl and hydroxyacyl coenzyme A dehydrogenase enzymes from Clostridium acetobutylicum fermentation and vertebrate fatty acid beta-oxidation pathways," J. Bacteriol. 171(12):6800-6807 (1989).

Yu et al, "Enzymatic functions of wild tomato methylketone synthases 1 and 2," Plant Physiol 154:67-77 (2010).

Zeiher et al., "Identification and Characterization of Mitochondrial Acetyl-Coenzyme A Hydrolase from Pisum sativum L. Seedlings," Plant Physiol. 94:20-27 (1990).

Zeng et al., "Expression and purification of His-tagged rat mitochondrial 3-ketoacyl-CoA thiolase wild-type and His352 mutant proteins," Prot. Expr. Purif., 35:320-326 (2004).

Zhang et al, "The phosphonopyruvate decarboxylase from Bacteroides fragilis," J Biol Chem 278:41302-41308 (2003).

Zhang et al., "The tricarboxylic acid cycle in cyanobacteria," Science 334:1551-1553 (2011).

Zhao et al., "Molecular evolution by staggered extension process (StEP) in vitro recombination," Nat. Biotechnol. 16(3):258-261 (1998).

Zheng et al., "Optimization of fatty alcohol biosynthesis pathway for selectively enhanced production of C12/14 and C16/18 fatty alcohols in engineered *Escherichia coli*," Microb. Cell Fact., 11:65 (2012).

Zhou et al, "Expression, purification, and characterization of human malonyl-CoA decarboxylase," Prot Expr Pur 34:261-269 (2004).

Zhou et al., "Engineering a native homoethanol pathway in *Escherichia coli* B for ethanol production," Biotechnol. Lett. 30:335-342 (2008).

Zhou et al., "The remarkable structural and functional organization of the eukaryotic pyruvate dehydrogenase complexes," Proc. Natl. Acad. Sci. U.S.A. 98:14802-14807 (2001).

Zhu et al., "Cleavage-dependent ligation by the FLP recombinase. Characterization of a mutant FLP protein with an alteration in a catalytic amino acid," J.Biol.Chem. 270:23044-23054 (1995).

Kim et al., "Synthesis of medium-chain length (C6-C10) fuels and chemicals via β-oxidation reversal in *Escherichia coli*," J. Ind. Microbiol. Biotechnol., 42:465-475 (2015).

U.S. Appl. No. 14/053,381, filed Oct. 14, 2013, U.S. Pat. No. 10,513,716 (Dec. 24, 2019), 2014/0127765 (May 8, 2014), Microorganisms and Methods for Production of Specific Length Fatty Alcohols and Related Compounds, Issued.

U.S. Appl. No. 14/435,723, filed Apr. 14, 2015, 2015/0275242 (Oct. 1, 2015), Microorganisms and Methods for Production of Specific Length Fatty Alcohols and Related Compounds, Pending.

MICROORGANISMS AND METHODS FOR PRODUCTION OF SPECIFIC LENGTH FATTY ALCOHOLS AND RELATED COMPOUNDS

This application is a continuation of U.S. patent application Ser. No. 14/053,381, filed Oct. 14, 2013, which claims the benefit of priority to U.S. Provisional Application No. 61/714,144, filed Oct. 15, 2012, the entire contents of each of which is incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 5, 2019, is named 12956-491-999_Sequence_Listing.txt and is 18,493 bytes in size.

BACKGROUND OF THE INVENTION

The present invention relates generally to biosynthetic processes, and more specifically to organisms having specific length fatty alcohol, fatty aldehyde or fatty acid biosynthetic capacity.

Primary alcohols are a product class of compounds having a variety of industrial applications which include a variety of biofuels and specialty chemicals. Primary alcohols also can be used to make a large number of additional industrial products including polymers and surfactants. For example, higher primary alcohols, also known as fatty alcohols ($C_4$-$C_{24}$) and their ethoxylates are used as surfactants in many consumer detergents, cleaning products and personal care products worldwide such as laundry powders and liquids, dishwashing liquid and hard surface cleaners. They are also used in the manufacture of a variety of industrial chemicals and in lubricating oil additives. Specific length fatty alcohols, such as octanol and hexanol, have useful organoleptic properties and have long been employed as fragrance and flavor materials. Smaller chain length $C_4$-$C_8$ alcohols (e.g., butanol) are used as chemical intermediates for production of derivatives such as acrylates used in paints, coatings, and adhesives applications.

Fatty alcohols are currently produced from, for example, hydrogenation of fatty acids, hydroformylation of terminal olefins, partial oxidation of n-paraffins and the Al-catalyzed polymerization of ethylene. Unfortunately, it is not commercially viable to produce fatty alcohols directly from the oxidation of petroleum-based linear hydrocarbons (n-paraffins). This impracticality is because the oxidation of n-paraffins produces primarily secondary alcohols, tertiary alcohols or ketones, or a mixture of these compounds, but does not produce high yields of fatty alcohols. Additionally, currently known methods for producing fatty alcohols suffer from the disadvantage that they are restricted to feedstock which is relatively expensive, notably ethylene, which is produced via the thermal cracking of petroleum. In addition, current methods require several steps, and several catalyst types.

Fatty alcohol production by microorganisms involves fatty acid synthesis followed by acyl-reduction steps. The universal fatty acid biosynthesis pathway found in most cells has been investigated for production of fatty alcohols and other fatty acid derivatives. There is currently a great deal of improvement that can be achieved to provide more efficient biosynthesis pathways for fatty alcohol production with significantly higher theoretical product and energy yields.

Thus, there exists a need for alternative means for effectively producing commercial quantities of fatty alcohols. The present invention satisfies this need and provides related advantages as well.

SUMMARY OF INVENTION

The invention provides non-naturally occurring microbial organisms containing fatty alcohol, fatty aldehyde or fatty acid pathways. In some embodiments, the non-naturally occurring microbial organism of the invention has a malonyl-CoA independent fatty acyl-CoA elongation (MI-FAE) cycle and a termination pathway as depicted in FIGS. 1, 6 and 7, wherein an enzyme of the MI-FAE cycle or termination pathway is encoded by at least one exogenous nucleic acid and is expressed in a sufficient amount to produce a fatty alcohol, fatty aldehyde or fatty acid of Formula (I):

(I)

wherein $R_1$ is $C_{1\text{-}24}$ linear alkyl; $R_2$ is $CH_2OH$, CHO, or COOH; $R_3$ is H, OH, or oxo (=O); and ------ represents a single or double bond with the proviso that the valency of the carbon atom to which $R_3$ is attached is four, wherein the substrate of each of said enzymes of the MI-FAE cycle and the termination pathway are independently selected from a compound of Formula (II), propionyl-CoA or acetyl-CoA:

(II)

wherein $R_1$ is $C_{1\text{-}24}$ linear alkyl; $R_3$ is H, OH, or oxo (=O); $R_4$ is S-CoA, ACP, OH or H; and ------ represents a single or double bond with the proviso that the valency of the carbon atom to which $R_3$ is attached is four; wherein said one or more enzymes of the MI-FAE cycle are each selective for a compound of Formula (II) having a number of carbon atoms at $R_1$ that is no greater than the number of carbon atoms at $R_1$ of said compound of Formula (I), and wherein said one or more enzymes of the termination pathway are each selective for a compound of Formula (II) having a number of carbon atoms at $R_1$ that is no less than the number of carbon atoms at $R_1$ of said compound of Formula (I).

In some embodiments, the invention provides a non-naturally occurring microbial organism having a fatty alcohol, fatty aldehyde or fatty acid pathway, wherein the microbial organism further includes an acetyl-CoA pathway and at least one exogenous nucleic acid encoding an acetyl-CoA pathway enzyme expressed in a sufficient amount to produce acetyl-CoA, wherein the acetyl-CoA pathway includes a pathway shown in FIG. 2, 3, 4 or 5.

In some embodiments, the invention provides a non-naturally occurring microbial organism having a fatty alcohol, fatty aldehyde or fatty acid pathway, wherein the microbial organism has one or more gene disruptions, wherein the one or more gene disruptions occur in endogenous genes encoding proteins or enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by the microbial organism, the one or more gene disruptions confer increased production of a fatty alcohol, fatty aldehyde or fatty acid in the microbial organism.

In some embodiments, the invention provides a non-naturally occurring microbial organism having a fatty alcohol, fatty aldehyde or fatty acid pathway, wherein one or more enzymes of the MI-FAE cycle or the termination pathway preferentially react with an NADH cofactor or have reduced preference for reacting with an NAD(P)H cofactor.

In some embodiments, the invention provides a non-naturally occurring microbial organism having a fatty alcohol, fatty aldehyde or fatty acid pathway, wherein the microbial organism has one or more gene disruptions in genes encoding proteins or enzymes that result in an increased ratio of NAD(P)H to NAD(P) present in the cytosol of the microbial organism following the disruptions.

In some embodiments, the non-naturally occurring microbial organism of the invention is Crabtree positive and is in culture medium comprising excess glucose. In such conditions, as described herein, the microbial organism can result in increasing the ratio of NAD(P)H to NAD(P) present in the cytosol of the microbial organism.

In some embodiments, the invention provides a non-naturally occurring microbial organism having a fatty alcohol, fatty aldehyde or fatty acid pathway, wherein the microbial organism has at least one exogenous nucleic acid encoding an extracellular transporter or an extracellular transport system for a fatty alcohol, fatty aldehyde or fatty acid of the invention.

In some embodiments, the invention provides a non-naturally occurring microbial organism having a fatty alcohol, fatty aldehyde or fatty acid pathway, wherein the microbial organism one or more endogenous enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, has attenuated enzyme activity or expression levels.

In some embodiments, the invention provides a non-naturally occurring microbial organism having a fatty alcohol, fatty aldehyde or fatty acid pathway, wherein the microbial organism has attenuated enzyme activity or expression levels for one or more endogenous enzymes involved in the oxidation of NAD(P)H or NADH.

The invention additionally provides methods of using the above microbial organisms to produce a fatty alcohol, a fatty aldehyde or a fatty acid by culturing a non-naturally occurring microbial organism containing a fatty alcohol, fatty aldehyde or fatty acid pathway under conditions and for a sufficient period of time to produce a fatty alcohol, fatty aldehyde or fatty acid.

DETAILED DESCRIPTION OF THE INVENTION

Figure 1:
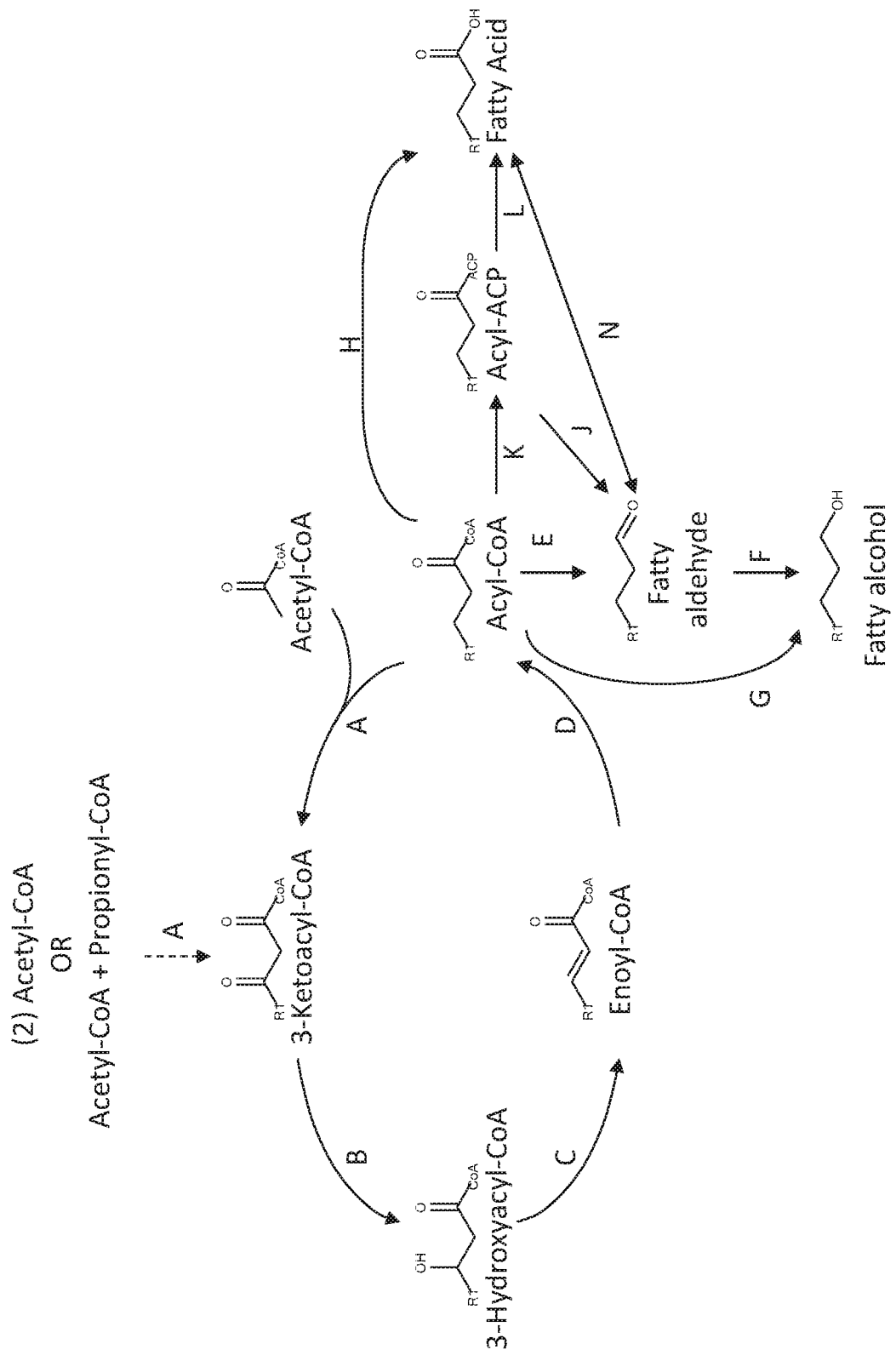
FIG. 1 shows an exemplary MI-FAE cycle in combination with termination pathways for production of fatty alcohols, aldehydes, or acids from the acyl-CoA intermediate of the MI-FAE cycle. Enzymes are: A. Thiolase; B. 3-Oxoacyl-CoA reductase; C. 3-Hydroxyacyl-CoA dehydratase; D. Enoyl-CoA reductase; E. Acyl-CoA reductase (aldehyde forming); F. Alcohol dehydrogenase; G. Acyl-CoA reductase (alcohol forming); H. acyl-CoA hydrolase, transferase or synthase; J. Acyl-ACP reductase; K. Acyl-CoA:ACP acyltransferase; L. Thioesterase; and N. Aldehyde dehydrogenase (acid forming) or carboxylic acid reductase.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a fatty alcohol, fatty aldehyde or fatty alcohol biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "ACP" or "acyl carrier protein" refers to any of the relatively small acidic proteins that are associated with the fatty acid synthase system of many organisms, from bacteria to plants. ACPs can contain one 4'-phosphopantetheine prosthetic group bound covalently by a phosphate ester bond to the hydroxyl group of a serine residue. The sulfhydryl group of the 4'-phosphopantetheine moiety serves as an anchor to which acyl intermediates are (thio)esterified during fatty-acid synthesis. An example of an ACP is *Escherichia coli* ACP, a separate single protein, containing 77 amino-acid residues (8.85 kDa), wherein the phosphopantetheine group is linked to serine 36.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions in the non-naturally occurring microorganisms of the invention. The phenotypic effect of a gene disruption can be a null mutation, which can arise from many types of mutations including inactivating point mutations, entire gene deletions, and deletions of chromosomal segments or entire chromosomes. Specific enzyme inhibitors, such as antibiotics, can also produce null mutant phenotype, therefore being equivalent to gene disruption.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given pathway to function. However, the attenuation of the activity or amount of an enzyme or protein that mimics complete disruption for one pathway, can still be sufficient for a separate pathway to continue to function. For example, attenuation of an endogenous enzyme or protein can be sufficient to mimic the complete disruption of the same enzyme or protein for production of a fatty alcohol, fatty aldehyde or fatty acid product of the invention, but the remaining activity or amount of enzyme or protein can still be sufficient to maintain other pathways, such as a pathway that is critical for the host microbial organism to survive, reproduce or grow. Attenuation of an enzyme or protein can also be weakening, reducing or diminishing the activity or amount of the enzyme or protein in an amount that is sufficient to increase yield of a fatty alcohol, fatty aldehyde or fatty acid product of the invention, but does not necessarily mimic complete disruption of the enzyme or protein.

The term "fatty alcohol," as used herein, is intended to mean an aliphatic compound that contains one or more hydroxyl groups and contains a chain of 4 or more carbon atoms. The fatty alcohol possesses the group —$CH_2OH$ that can be oxidized so as to form a corresponding aldehyde or acid having the same number of carbon atoms. A fatty alcohol can also be a saturated fatty alcohol, an unsaturated fatty alcohol, a 1,3-diol, or a 3-oxo-alkan-1-ol. Exemplary fatty alcohols include a compound of Formula (III)-(VI):

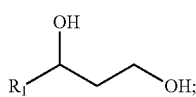

(III)

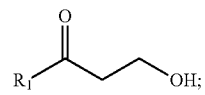

(IV)

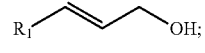

(V)

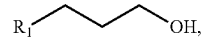

(VI)

wherein $R_1$ is a $C_{1-24}$ linear alkyl.

The term "fatty aldehyde," as used herein, is intended to mean an aliphatic compound that contains an aldehyde (CHO) group and contains a chain of 4 or more carbon atoms. The fatty aldehyde can be reduced to form the corresponding alcohol or oxidized to form the carboxylic acid having the same number of carbon atoms. A fatty aldehyde can also be a saturated fatty aldehyde, an unsaturated fatty aldehyde, a 3-hydroxyaldehyde or 3-oxoaldehyde. Exemplary fatty aldehydes include a compound of Formula (VII)-(X):

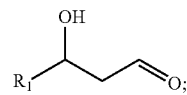

(VII)

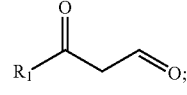

(VIII)

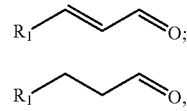

(IX)

(X)

wherein $R_1$ is a $C_{1-24}$ linear alkyl.

The term "fatty acid," as used herein, is intended to mean an aliphatic compound that contains a carboxylic acid group and contains a chain of 4 or more carbon atoms. The fatty acid can be reduced to form the corresponding alcohol or aldehyde having the same number of carbon atoms. A fatty acid can also be a saturated fatty acid, an unsaturated fatty acid, a 3-hydroxyacid or a 3-oxoacids. Exemplary fatty acids include a compound of Formula (XI)-(XIV):

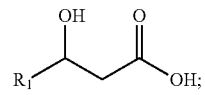

(XI)

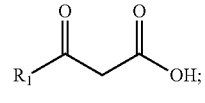

(XII)

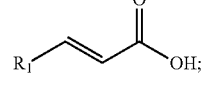

(XIII)

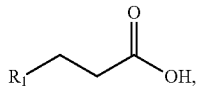

(XIV)

wherein $R_1$ is a $C_{1-24}$ linear alkyl.

The term "alkyl" refers to a linear saturated monovalent hydrocarbon. The alkyl can be a linear saturated monovalent hydrocarbon that has 1 to 24 ($C_{1-24}$), 1 to 17 ($C_{1-17}$), or 9 to 13 ($C_{9-13}$) carbon atoms. Examples of alkyl groups include, but are not limited to, methyl, ethyl, propyl, butyl, pentyl, hexyl, heptyl, octyl, nonyl, decyl, undecyl and dodecyl. For example, $C_{9-13}$ alkyl refers to a linear saturated monovalent hydrocarbon of 9 to 13 carbon atoms.

The invention disclosed herein is based, at least in part, on recombinant microorganisms capable of synthesizing fatty alcohols, fatty aldehydes, or fatty acids using a malonyl-CoA-independent fatty acid elongation (MI-FAE) cycle and a termination pathway. In some embodiments, the microorganisms of the invention can utilize a heterologous MI-FAE cycle coupled with an acyl-CoA termination pathway to form fatty alcohols, fatty aldehydes, or fatty acids. The MI-FAE cycle can include a thiolase, a 3-oxoacyl-CoA reductase, a 3-hydroxyacyl-CoA dehydratase and an enoyl-CoA reductase. Each passage through the MI-FAE cycle results in the formation of an acyl-CoA elongated by a single two carbon unit compared to the acyl-CoA substrate entering the elongation cycle. Products can be even or odd chain length, depending on the initial substrate entering the acyl-CoA elongation pathway, i.e. two acety-CoA substrates or one acetyl-CoA substrate combined with a propionyl-CoA substrate. Elongation of the two acetyl-CoA substrates produces an even chain length product, whereas elongation with the propionyl-CoA substrate produces an odd chain length product. A termination pathway catalyzes the conversion of a MI-FAE intermediate, such as the acyl-CoA, to its corresponding fatty alcohol, fatty aldehyde, or fatty acid product. MI-FAE cycle and termination pathway enzymes can be expressed in one or more compartments of the microorganism. For example, in one embodiment, all MI-FAE cycle and termination pathway enzymes are expressed in the cytosol. Additionally, the microorganisms of the invention can be engineered to optionally secret the desired product into the culture media or fermentation broth for further manipulation or isolation.

Products of the invention include fatty alcohols, fatty aldehydes, or fatty acids derived from intermediates of the MI-FAE elongation cycle. For example, alcohol products can include saturated fatty alcohols, unsaturated fatty alcohols, 1,3-diols, and 3-oxo-alkan-1-ols. Aldehyde products can include saturated fatty aldehydes, unsaturated fatty aldehydes, 3-hydroxyaldehydes and 3-oxoaldehydes. Acid products can include saturated fatty acids, unsaturated fatty acids, 3-hydroxyacids and 3-oxoacids. These products can further be converted to derivatives such as fatty esters, either by chemical or enzymatic means. Methods for converting fatty alcohols to esters are well known in the art.

The invention also encompasses fatty alcohol, fatty aldehyde, and fatty acid chain-length control strategies in conjunction with host strain engineering strategies, such that the non-naturally occurring microorganism of the invention efficiently directs carbon and reducing equivalents toward fermentation products of a specific chain length.

Recombinant microorganisms of the invention can produce commercial quantities of a fatty alcohol, fatty aldehyde, or fatty acid ranging in chain length from four carbon atoms ($C_4$) to twenty-four carbon atoms ($C_{24}$) or more carbon atoms. The microorganism of the invention can produce a desired product that is at least 50%, 60%, 70%, 75%, 85%, 90%, 95% or more selective for a particular chain length. The carbon chain-length of the product is controlled by one or more enzymes of the MI-FAE cycle (steps A/B/C/D of FIG. 6) in combination with one or more termination pathway enzymes (steps E-N of FIG. 7). Chain length can be capped during the elongation cycle by one or more MI-FAE cycle enzymes (thiolase, 3-oxoacyl-CoA reductase, 3-hydroxyacyl-CoA dehydratase and/or enoyl-CoA reductase) exhibiting selectivity for MI-FAE cycle substrates having a number of carbon atoms that are no greater than the desired product size. Chain length can be further constrained by one or more enzymes catalyzing the conversion of the MI-FAE cycle intermediate to the fatty alcohol, fatty aldehyde or fatty acid product such that the one or more termination enzymes only reacts with substrates having a number of carbon atoms that are no less than the desired fatty alcohol, fatty aldehyde or fatty acid product.

The termination pathway enzymes catalyzing conversion of a MI-FAE-CoA intermediate to a fatty alcohol can include combinations of a fatty acyl-CoA reductase (alcohol or aldehyde forming), a fatty aldehyde reductase, an acyl-ACP reductase, an acyl-CoA:ACP acyltransferase, a thioesterase, an acyl-CoA hydrolase and/or a carboxylic acid reductase (pathways G; E/F; K/J/F; H/N/F; or K/L/N/F of FIG. 7). Termination pathway enzymes for converting a MI-FAE-CoA intermediate to a fatty acid can include combinations of a thioesterase, a CoA hydrolase, an acyl-CoA:ACP acyltransferase, an aldehyde dehydrogenase and/or an acyl-ACP reductase (pathways H; K/L; E/N; K/J/N of FIG. 7). For production of a fatty aldehyde, the termination pathway enzymes can include combinations of a fatty acyl-CoA reductase (aldehyde forming), an acyl-ACP reductase, an acyl-CoA:ACP acyltransferase, a thioesterase, an acyl-CoA hydrolase and/or a carboxylic acid reductase (pathways E; K/J; H/N; or K/L/N of FIG. 7).

The non-naturally occurring microbial organisms of the invention can also efficiently direct cellular resources, including carbon, energy and reducing equivalents, to the production of fatty alcohols, fatty aldehydes and fatty acids, thereby resulting in improved yield, productivity and/or titer relative to a naturally occurring organism. In one embodiment, the microorganism is modified to increase cytosolic acetyl-CoA levels. In another embodiment, the microorganism is modified to efficiently direct cytosolic acyl-CoA into fatty alcohols, fatty aldehydes or fatty acids rather than other byproducts or cellular processes. Enzymes or pathways that lead to the formation of byproducts can be attenuated or deleted. Exemplary byproducts include, but are not limited to, ethanol, glycerol, lactate, acetate, esters and carbon dioxide. Additional byproducts can include fatty-acyl-CoA derivatives such as alcohols, alkenes, alkanes, esters, acids and aldehydes. Accordingly, a byproduct can include any fermentation product diverting carbon and/or reducing equivalents from the product of interest.

In another embodiment, the availability of reducing equivalents or redox ratio is increased. In yet another embodiment, the cofactor requirements of the microorganism are balanced such that the same reduced cofactors generated during carbon assimilation and central metabolism are utilized by MI-FAE cycle and/or termination pathway enzymes. In yet another embodiment, the fatty alcohol, fatty aldehyde or fatty acid producing organism expresses a transporter which exports the fatty alcohol, fatty aldehyde or fatty acid from the cell.

Microbial organisms capable of fatty alcohol production are exemplified herein with reference to the *Saccharomyces cerevisaie* genetic background. However, with the complete genome sequence available now for thousands of species (with more than half of these available on public databases such as the NCBI), the identification of an alternate species homolog for one or more genes, including for example, orthologs, paralogs and nonorthologous gene displacements, and the interchange of genetic alterations between eukaryotic organisms is routine and well known in the art. Accordingly, the metabolic alterations enabling production of fatty alcohols described herein with reference to a particular organism such as *Saccharomyces cerevisiae* can be readily applied to other microorganisms. Given the teachings and guidance provided herein, those skilled in the art understand that a metabolic alteration exemplified in one organism can be applied equally to other organisms.

The methods of the invention are applicable to various prokaryotic and eukaryotic organisms such as bacteria, yeast and fungus. For example, the yeast can include *Saccharomyces cerevisiae* and *Rhizopus arrhizus*. Exemplary eukaryotic organisms can also include Crabtree positive and negative yeasts, and yeasts in the genera *Saccharomyces, Kluyveromyces, Candida* or *Pichia*. Further exemplary eukaryotic species include those selected from *Schizosaccharomyces pombe, Kluyveromyces lactis, Kluyveromyces marxianus, Aspergillus terreus, Aspergillus niger, Rhizopus arrhizus, Rhizopus oryzae, Candida albicans, Candida boidinii, Candida sonorensis, Candida tropicalis, Yarrowia lipolytica* and *Pichia pastoris*. Additionally, select cells from larger eukaryotic organisms are also applicable to methods of the present invention. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*.

In some aspects of the invention, production of fatty alcohols, fatty aldehydes and fatty acids through the modified pathways disclosed herein are particularly useful because the pathways result in higher product and ATP yields than through naturally occurring biosynthetic pathways such as the well-known malonyl-CoA dependent fatty acid synthesis pathway. Using acetyl-CoA as a $C_2$ extension unit instead of malonyl-acyl carrier protein (malonyl-ACP) saves one ATP molecule per unit flux of acetyl-CoA entering the MI-FAE cycle. The MI-FAE cycle results in acyl-CoA instead of acyl-ACP, and can preclude the need of the ATP-consuming acyl-CoA synthase reactions for the production of octanol and other fatty alcohols, fatty aldehydes or fatty acids. The fatty alcohol, fatty aldehyde and fatty acid producing organisms of the invention can additionally allow the use of biosynthetic processes to convert low cost renewable feedstock for the manufacture of chemical products.

The eukaryotic organism of the invention can be further engineered to metabolize and/or co-utilize a variety of feedstocks including glucose, xylose, fructose, syngas, methanol, and the like.

Chain length control can be achieved using a combination of highly active enzymes with suitable substrate ranges appropriate for biosynthesis of the desired fatty alcohol, fatty aldehyde, or fatty acid. Chain length of the product can be controlled using one or more enzymes of MI-FAE cycle or termination pathway. As described herein, chain length can be capped during the MI-FAE cycle by one or more MI-FAE cycle enzymes (thiolase, 3-oxoacyl-CoA reductase, 3-hydroxyacyl-CoA dehydratase and/or enoyl-CoA reductase) exhibiting selectivity for MI-FAE cycle substrates having a number of carbon atoms that are no greater than the desired product size. Since enzymes are reversible, any of the elongation pathway enzymes can serve in this capacity. Selecting enzymes with broad substrate ranges but defined chain-length boundaries enables the use of a single enzyme to catalyze multiple cycles of elongation, while conferring product specificity. To further hone specificity and prevent the accumulation of shorter byproducts, selectivity is further constrained by product-forming termination enzymes, such that one or more enzymes are selective for acyl-CoA or other termination pathway substrates having a number of carbon atoms that are no less than the desired chain length. The deletion or attenuation of endogenous pathway enzymes that produce different chain length products can further hone product specificity.

Using the approaches outlined herein, one skilled in the art can select enzymes from the literature with characterized substrate ranges that selectively produce a fatty alcohol, fatty aldehyde or fatty acid product of a specific chain length. To selectively produce fatty alcohols, fatty aldehydes or fatty acids of a desired length, one can utilize combinations of known enzymes in the literature with different selectivity ranges as described above. For example, a non-naturally occurring microbial organism that produces $C_{16}$ fatty alcohol can express enzymes such as the *Rattus norvegicus* Acaala thiolase and the enoyl-CoA reducatse of *Mycobacterium smegmatis*, which only accept substrates up to length $C_{16}$. Coupling one or both chain elongation enzymes with a $C_{16}$-$C_{18}$ fatty acyl-CoA reductase (alcohol or aldehyde forming) such as FAR of *Simmondsia chinensis* further increases product specificity by reducing the synthesis of shorter alcohol products. As another example, a non-naturally occurring microbial organism of the invention can selectively produce alcohols of length $C_{14}$ by combining the 3-hydroxyacyl-CoA dehydratase of *Arabidopsis thaliana* with the acyl-CoA reductase Acrl of *Acinetobacter* sp. Strain M-1. To produce 3-oxoacids of length $C_{14}$, one can, for example, combine the rat thiolase with the 3-oxoacyl-CoA hydrolase of *Solanum lycopersicum*. As still a further example, to produce $C_{18}$ fatty acids, one can combine the *Salmonella enterica* fadE enoyl-CoA reductase with the tesB thioesterase of *E. coli*. In yet another example, selective production of $C_6$ alcohols are formed by combining the paaH1 thiolase from *Ralstonia eutropha* with the *Leifsonia* sp. S749 alcohol dehydrogenase lsadh.

Exemplary MI-FAE cycle and termination pathway enzymes are described in detail in Example I. The biosynthetic enzymes described herein exhibit varying degrees of substrate specificity. Exemplary substrate ranges of enzymes characterized in the literature are shown in the table below and described in further detail in Example I.

| Pathway step | Chain length | Gene | Organism |
|---|---|---|---|
| 1A | C4 | atoB | *Escherichia coli* |
| 1A | C6 | phaD | *Pseudomonas putida* |
| 1A | C6-C8 | bktB | *Ralstonia eutropha* |
| 1A | C10-C16 | Acaa1a | *Rattus norvegicus* |
| 1B | C4 | hbd | *Clostridium acetobutylicum* |
| 1B | C4-C6 | paaH1 | *Ralstonia eutropha* |
| 1B | C4-C10 | HADH | *Sus scrofa* |
| 1B | C4-C18 | fadB | *Escherichia coli* |
| 1C | C4-C6 | crt | *Clostridium acetobutylicum* |
| 1C | C4-C7 | pimF | *Rhodopseudomonas palustris* |
| 1C | C4-C14 | MFP2 | *Arabidopsis thaliana* |
| 1D | C4-C6 | ECR1 | *Euglena gracilis* |
| 1D | C6-C8 | ECR3 | *Euglena gracilis* |
| 1D | C8-10 | ECR2 | *Euglena gracilis* |
| 1D | C8-C16 | ECR | *Rattus norvegicus* |
| 1D | C10-C16 | ECR | *Mycobacterium smegmatis* |
| 1D | C2-C18 | fadE | *Salmonella enterica* |
| 1E | C2-C4 | bphG | *Pseudomonas* sp |
| 1E | C4 | Bld | *Clostridium saccharoperbutylacetonicum* |
| 1E | C12-C20 | ACR | *Acinetobacter calcoaceticus* |
| 1E | C14-C18 | Acr1 | *Acinetobacter* sp. Strain M-1 |
| 1E | C16-C18 | Rv1543, Rv3391 | *Mycobacterium tuberculosis* |
| 1F | C6-C7 | lsadh | *Leifsonia* sp. S749 |
| 1F | C2-C8 | yqhD | *Escherichia coli* |
| 1F | C3-C10 | Adh | *Pseudomonas putida* |
| 1F | C2-C14 | alrA | *Acinetobacter* sp. strain M-1 |
| 1F | C2-C30 | ADH1 | *Geobacillus thermodenitrificans* |
| 1G | C2 | adhE | *Escherichia coli* |
| 1G | C2-C8 | adhe2 | *Clostridium acetobutylicum* |
| 1G | C14-C16 | At3g11980 | *Arabidopsis thaliana* |
| 1G | C16 | At3g44560 | *Arabidopsis thaliana* |
| 1G | C16-C18 | FAR | *Simmondsia chinensis* |
| 1H | C4 | Cat2 | *Clostridium kluyveri* |
| 1H | C4-C6 | Acot12 | *Rattus norvegicus* |
| 1H | C14 | MKS2 | *Solanum lycopersicum* |
| 1L | C8-C10 | fatB2 | *Cuphea hookeriana* |
| 1L | C12 | fatB | *Umbellularia california* |
| 1L | C14-C16 | fatB3 | *Cuphea hookeriana* |
| 1L | C18 | tesA | *Escherichia coli* |
| 1N | C12-C18 | Car | *Nocardia iowensis* |
| 1N | C12-C16 | Car | *Mycobacterium* sp. (strain JLS) |

Figure 6:
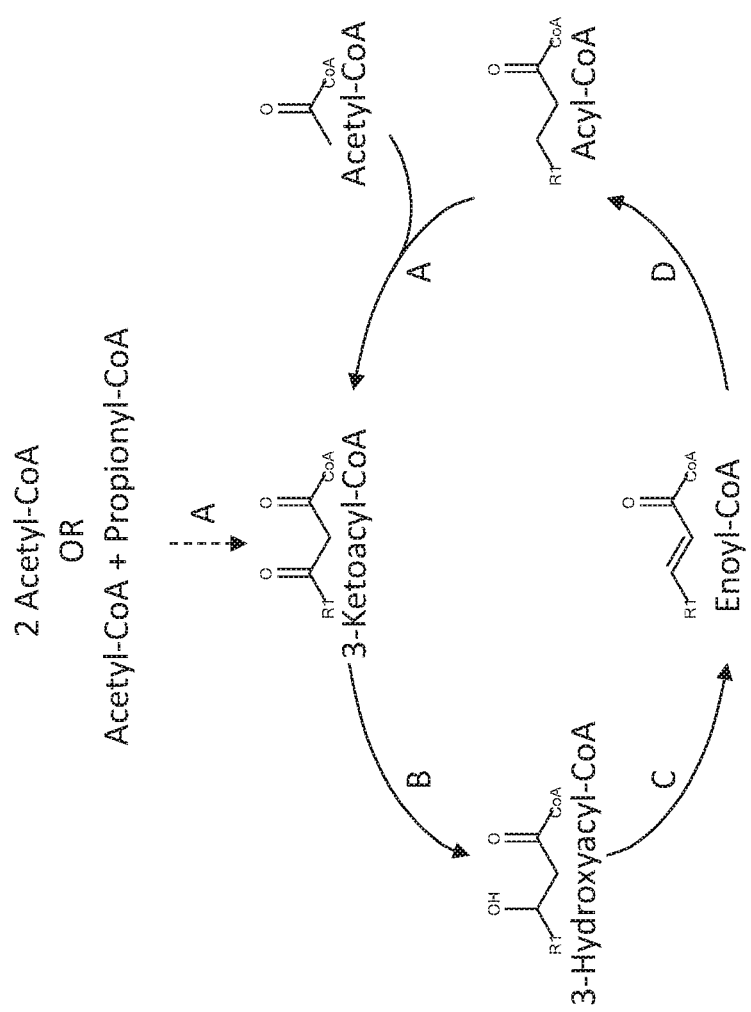
FIG. 6 shows an exemplary MI-FAE cycle for elongating the linear alkyl of $R_1$. Enzymes are: A. Thiolase; B. 3-Ketoacyl-CoA reductase; C. 3-Hydroxyacyl-CoA dehydratase; and D. Enoyl-CoA reductase.

Taking into account the differences in chain-length specificities of each enzyme in the MI-FAE cycle, one skilled in the art can select one or more enzymes for catalyzing each elongation cycle reaction step (steps A-D of FIG. 6). For example, for the thiolase step of the MI-FAE cycle, some thiolase enzymes such as bktB of *Ralstonia eutropha* catalyze the elongation of short- and medium-chain acyl-CoA intermediates ($C_6$-$C_8$), whereas others such as Acaa1a of *R. norvegicus* are active on longer-chain substrates ($C_{10}$-$C_{16}$). Thus, an microbial organism producing a fatty alcohol, fatty aldehyde or fatty acid can comprise one, two, three, four or more variants of a thiolase, 3-oxoacyl-CoA reductase, 3-hydroxyacyl-CoA dehydratase and/or enoyl-CoA reductase.

Chain length specificity of enzymes can be assayed by methods well known in the art (eg. Wrensford et al, *Anal Biochem* 192:49-54 (1991)). The substrate ranges of fatty alcohol, fatty aldehyde, or fatty acid producing enzymes can be further extended or narrowed by methods well known in the art. Variants of biologically-occurring enzymes can be generated, for example, by rational and directed evolution, mutagenesis and enzyme shuffling as described herein. As one example, a rational engineering approach for altering chain length specificity was taken by Denic and Weissman (Denic and Weissman, *Cell* 130:663-77 (2008)). Denic and Weissman mapped the region of the yeast elongase protein ELOp responsible for chain length, and introduced mutations to vary the length of fatty acid products. In this instance, the geometry of the hydrophobic substrate pocket set an upper boundary on chain length. A similar approach can be useful for altering the chain length specificities of enzymes of the MI-FAE cycle and/or termination pathways.

Enzyme mutagenesis, expression in a host, and screening for fatty alcohol production is another useful approach for generating enzyme variants with improved properties for the desired application. For example, US patent application 2012/0009640 lists hundreds of variants of *Marinobacter algicola* and *Marinobacter aquaeolei* FAR enzymes with improved activity over the wild type enzyme, and varying product profiles.

Enzyme mutagenesis (random or directed) in conjunction with a selection platform is another useful approach. For example, Machado and coworkers developed a selection platform aimed at increasing the activity of acyl-CoA elongation cycle enzymes on longer chain length substrates (Machado et al., Met Eng in press (2012)). Machado et al. identified the chain-length limiting step of their pathway (a 3-hydroxyacyl-CoA dehydrogenase) and evolved it for improved activity on $C_6$-$C_8$ substrates using an anaerobic growth rescue platform. Additional variants of enzymes useful for producing fatty alcohols are listed in the table below.

| Enzyme | Protein/GenBankID/ GI number | Organism | Variant(s) | Reference |
| --- | --- | --- | --- | --- |
| 3-Ketoacyl-CoA thiolase | Acaa2 NP_569117.1 GI:18426866 | Rattus norvegicus | H352A, H352E, H352K, H352Y | Zeng et al., Prot. Expr. Purif. 35: 320-326 (2004) |
| 3-Hydroxyacyl-CoA dehydrogenase | Hadh NP_476534.1 GI:17105336 | Rattus norvegicus | S137A, S137C, S137T | Liu et al., Prot. Expr. Purif. 37: 344-351 (2004). |
| Enoyl-CoA hydratase | Ech1 NP_072116.1 GI:12018256 | Rattus norvegicus | E144A, E144A/Q162L, E164A, Q162A, Q162L, Q162M | Kiema et al., Biochem. 38: 2991-2999 (1999) |
| Enoyl-CoA reductase | InhA AAY54545.1 GI:66737267 | Mycobacterium tuberculosis | K165A, K165Q, Y158F | Poletto, S. et al., Prot. Expr. Purif. 34: 118-125 (2004). |
| Acyl-CoA reductase | LuxC AAT00788.1 GI:46561111 | Photobacterium phosphoreum | C171S, C279S, C286S | Lee, C. et al., Biochim. Biophys. Acta. 1338: 215-222 (1997). |
| Alcohol dehydrogenase | YADH-1 P00330.4 GI:1168350 | Saccharomyces cerevisiae | D223G, D49N, E68Q, G204A, G224I, H47R, H51E, L203A | Leskovac et al., FEMS Yeast Res. 2(4): 481-94 (2002). |
| Fatty alcohol forming acyl-CoA reductase (FAR) | AdhE NP_415757.1 GI:16129202 | Escherichia coli | A267T/E568K, A267T | Membrillo et al., J. Biol. Chem. 275(43): 333869-75 (2000). |

Those skilled in the art will understand that the genetic alterations, including metabolic modifications exemplified herein, are described with reference to a suitable host organism such as E. coli or S. cerevisiae and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having fatty alcohol, fatty aldehyde or fatty acid biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes. Similarly for a gene disruption, evolutionally related genes can also be disrupted or deleted in a host microbial organism to reduce or eliminate functional redundancy of enzymatic activities targeted for disruption.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

Figure 7:
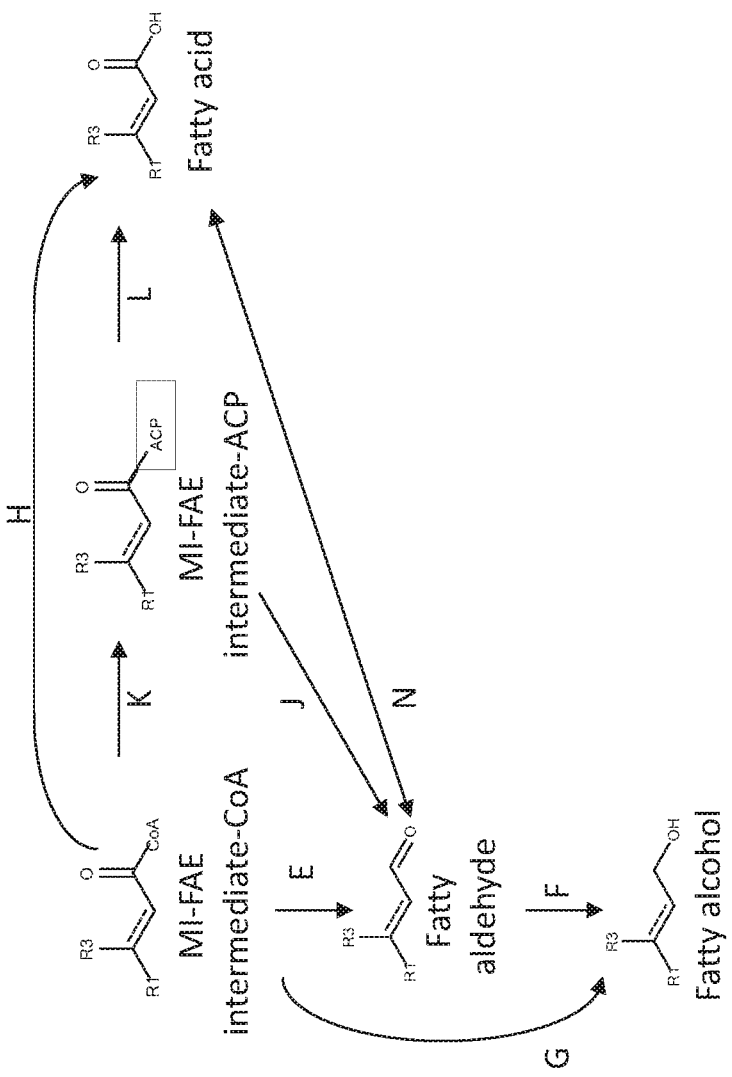
FIG. 7 shows an exemplary termination cycle for generating a fatty alcohol, fatty aldehyde or fatty acid from any of the MI-FAE cycle intermediates of FIG. 6. Enzymes are: E. MI-FAE intermediate-CoA reductase (aldehyde forming); F. Alcohol dehydrogenase; G. MI-FAE intermediate-CoA reductase (alcohol forming); H. MI-FAE intermediate-CoA hydrolase, transferase or synthase; J. MI-FAE intermediate-ACP reductase; K. MI-FAE intermediate-CoA:ACP acyltransferase; L. Thioesterase; and N. Aldehyde dehydrogenase (acid forming) or carboxylic acid reductase. $R_1$ is $C_{1-24}$ linear alkyl; $R_3$ is H, OH, or oxo (=O) and ====== represents a single or double bond with the proviso that the valency of the carbon atom to which $R_3$ is attached is four.
Figure 8:
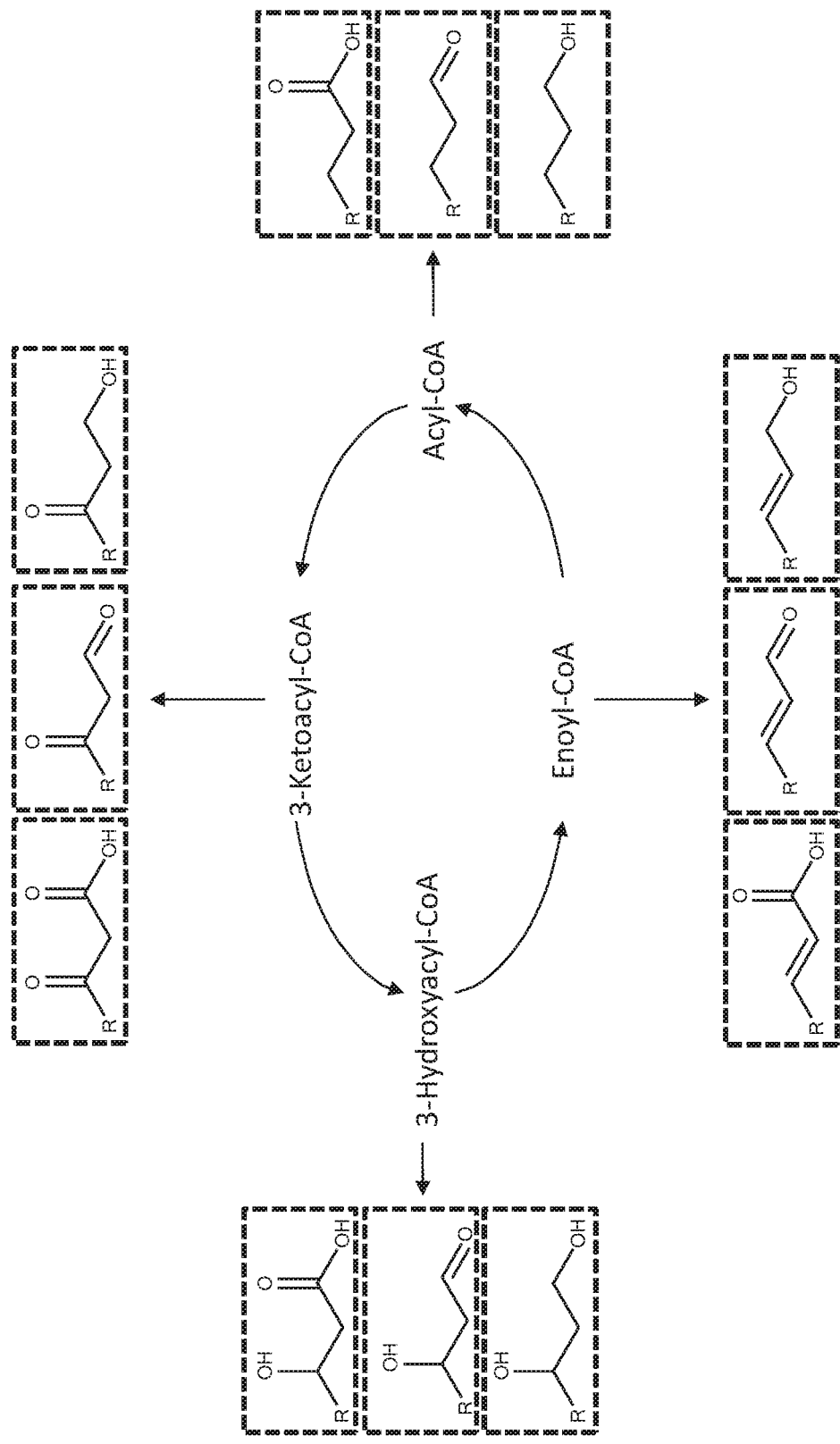
FIG. 8 shows exemplary compounds that can be produced from the four MI-FAE cycle intermediates using the cycle depicted in FIG. 6 and the termination pathways depicted in FIG. 7. R is $C_{1-24}$ linear alkyl.

In some embodiments, the invention provides a non-naturally occurring microbial organism having a MI-FAE cycle and a termination pathway, wherein the MI-FAE cycle includes one or more thiolase, one or more 3-oxoacyl-CoA reductase, one or more 3-hydroxyacyl-CoA dehydratase, and one or more enoyl-CoA reductase, wherein the termination pathway includes a pathway shown in FIG. 1, 6 or 7 selected from: (1) 1H; (2) 1K and 1L; (3) 1E and 1N; (4) 1K, 1J, and 1N; (5) 1E; (6) 1K and 1J; (7) 1H and 1N; (8) 1K, 1L, and 1N; (9) 1E and 1F; (10) 1K, 1J, and 1F; (11) 1H, 1N, and 1F; (12) 1K, 1L, 1N, and 1F; and (13) 1G, wherein 1E is an acyl-CoA reductase (aldehyde forming), wherein 1F is an alcohol dehydrogenase, wherein 1G is an acyl-CoA reductase (alcohol forming), wherein 1H is an acyl-CoA hydrolase, acyl-CoA transferase or acyl-CoA synthase, wherein 1J is an acyl-ACP reductase, wherein 1K is an acyl-CoA:ACP acyltransferase, wherein 1L is a thioesterase, wherein 1N is an aldehyde dehydrogenase (acid forming) or a carboxylic acid reductase, wherein an enzyme of the MI-FAE cycle or termination pathway is encoded by at least one exogenous nucleic acid and is expressed in a sufficient amount to produce a compound of Formula (I):

(I)

wherein $R_1$ is $C_{1-24}$ linear alkyl; $R_2$ is $CH_2OH$, CHO, or COOH; $R_3$ is H, OH, or oxo (=O); and ===== represents a single or double bond with the proviso that the valency of the carbon atom to which $R_3$ is attached is four, wherein the substrate of each of said enzymes of the MI-FAE cycle and the termination pathway are independently selected from a compound of Formula (II), propionyl-CoA or acetyl-CoA:

(II)

wherein $R_1$ is $C_{1-24}$ linear alkyl; $R_3$ is H, OH, or oxo (=O); $R_4$ is S-CoA, ACP, OH or H; and ===== represents a single or double bond with the proviso that the valency of the carbon atom to which $R_3$ is attached is four; wherein said one or more enzymes of the MI-FAE cycle are each selective for a compound of Formula (II) having a number of carbon atoms at $R_1$ that is no greater than the number of carbon atoms at $R_1$ of said compound of Formula (I), and wherein said one or more enzymes of the termination pathway are each selective for a compound of Formula (II) having a number of carbon atoms at $R_1$ that is no less than the number of carbon atoms at $R_1$ of said compound of Formula (I).

In some aspects of the invention, non-naturally occurring microbial organism of the invention can produce a compound of Formula (I) wherein $R_1$ is $C_{1-17}$ linear alkyl. In another aspect of the invention, the $R_1$ of the compound of Formula (I) is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some aspects of the invention, the microbial organism microbial organism includes two, three, or four exogenous nucleic acids each encoding an enzyme of the MI-FAE cycle. In some aspects of the invention, the microbial organism includes two, three, or four exogenous nucleic acids each encoding an enzyme of the termination pathway. In some aspects of the invention, the microbial organism includes exogenous nucleic acids encoding each of the enzymes of at least one of the pathways selected from (1)-(13). In some aspects, the at least one exogenous nucleic acid is a heterologous nucleic acid. In some aspects, the non-naturally occurring microbial organism is in a substantially anaerobic culture medium.

In some embodiments, the invention provides a non naturally occurring microbial organism, wherein the one or more enzymes of the MI-FAE cycle or termination pathway is expressed in a sufficient amount to produce a fatty alcohol selected from the Formulas (III)-(VI):

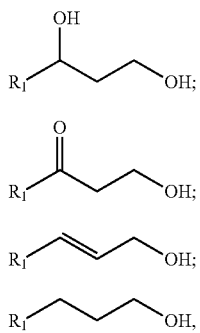

wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, Cis linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a non naturally occurring microbial organism, wherein the one or more enzymes of the MI-FAE cycle or termination pathway is expressed in a sufficient amount to produce a fatty aldehyde selected from the Formula (VII)-(X):

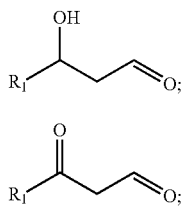
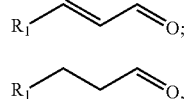
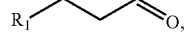

wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, Cis linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a non naturally occurring microbial organism, wherein the one or more enzymes of the MI-FAE cycle or termination pathway is expressed in a sufficient amount to produce a fatty acid selected from the Formula (XI)-(XIV):

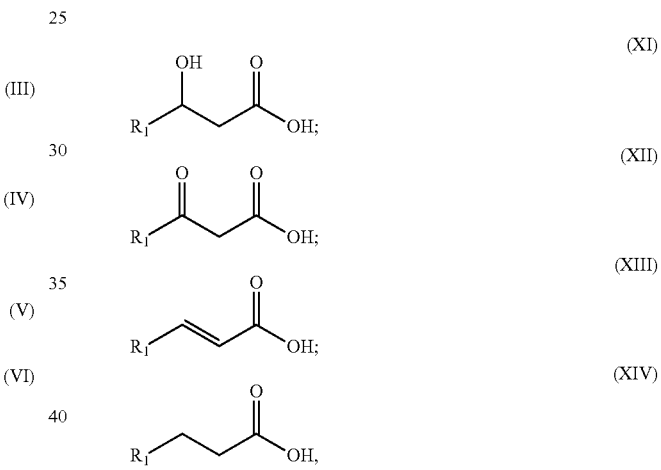

wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, Cis linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a non-naturally occurring microbial organism as described herein, wherein the microbial organism further includes an acetyl-CoA pathway and at least one exogenous nucleic acid encoding an acetyl-CoA pathway enzyme expressed in a sufficient amount to produce acetyl-CoA, wherein the acetyl-CoA pathway includes a pathway shown in FIG. 2, 3, 4 or 5 selected from: (1) 2A and 2B; (2) 2A, 2C, and 2D; (3) 2H; (4) 2G and 2D; (5) 2E, 2F and 2B; (6) 2E and 2I; (7) 2J, 2F and 2B; (8) 2J and 2I; (9) 3A, 3B, and 3C; (10) 3A, 3B, 3J, 3K, and 3D; (11) 3A, 3B, 3G, and 3D; (12) 3A, 3F, and 3D; (13) 3N, 3H, 3B and 3C; (14) 3N, 3H, 3B, 3J, 3K, and 3D; (15) 3N, 3H, 3B, 3G, and 3D; (16) 3N, 3H, 3F, and 3D; (17) 3L, 3M, 3B and 3C; (18) 3L, 3M, 3B, 3J, 3K, and 3D;

(19) 3L, 3M, 3B, 3G, and 3D; (20) 3L, 3M, 3F, and 3D; (21) 4A, 4B, 4D, 4H, 4I, and 4J; (22) 4A, 4B, 4E, 4F, 4H, 4I, and 4J; (23) 4A, 4B, 4E, 4K, 4L, 4H, 4I, and 4J; (24) 4A, 4C, 4D, 4H, and 4J; (25) 4A, 4C, 4E, 4F, 4H, and 4J; (26) 4A, 4C, 4E, 4K, 4L, 4H, and 4J; (27) 5A, 5B, 5D, and 5G; (28) 5A, 5B, 5E, 5F, and 5G; (29) 5A, 5B, 5E, 5K, 5L, and 5G; (30) 5A, 5C, and 5D; (31) 5A, 5C, 5E, and 5F; and (32) 5A, 5C, 5E, 5K, and 5L, wherein 2A is a pyruvate oxidase (acetate-forming), wherein 2B is an acetyl-CoA synthetase, an acetyl-CoA ligase or an acetyl-CoA transferase, wherein 2C is an acetate kinase, wherein 2D is a phosphotransacetylase, wherein 2E is a pyruvate decarboxylase, wherein 2F is an acetaldehyde dehydrogenase, wherein 2G is a pyruvate oxidase (acetyl-phosphate forming), wherein 2H is a pyruvate dehydrogenase, a pyruvate:ferredoxin oxidoreductase, a pyruvate:NAD(P)H oxidoreductase or a pyruvate formate lyase, wherein 2I is an acetaldehyde dehydrogenase (acylating), wherein 2J is a threonine aldolase, wherein 3A is a phosphoenolpyruvate (PEP) carboxylase or a PEP carboxykinase, wherein 3B is an oxaloacetate decarboxylase, wherein 3C is a malonate semialdehyde dehydrogenase (acetylating), wherein 3D is an acetyl-CoA carboxylase or a malonyl-CoA decarboxylase, wherein 3F is an oxaloacetate dehydrogenase or an oxaloacetate oxidoreductase, wherein 3G is a malonate semialdehyde dehydrogenase (acylating), wherein 3H is a pyruvate carboxylase, wherein 3J is a malonate semialdehyde dehydrogenase, wherein 3K is a malonyl-CoA synthetase or a malonyl-CoA transferase, wherein 3L is a malic enzyme, wherein 3M is a malate dehydrogenase or a malate oxidoreductase, wherein 3N is a pyruvate kinase or a PEP phosphatase, wherein 4A is a citrate synthase, wherein 4B is a citrate transporter, wherein 4C is a citrate/malate transporter, wherein 4D is an ATP citrate lyase, wherein 4E is a citrate lyase, wherein 4F is an acetyl-CoA synthetase or an acetyl-CoA transferase, wherein 4H is a cytosolic malate dehydrogenase, wherein 4I is a malate transporter, wherein 4J is a mitochondrial malate dehydrogenase, wherein 4K is an acetate kinase, wherein 4L is a phosphotransacetylase, wherein 5A is a citrate synthase, wherein 5B is a citrate transporter, wherein 5C is a citrate/oxaloacetate transporter, wherein 5D is an ATP citrate lyase, wherein 5E is a citrate lyase, wherein 5F is an acetyl-CoA synthetase or an acetyl-CoA transferase, wherein 5G is an oxaloacetate transporter, wherein 5K is an acetate kinase, and wherein 5L is a phosphotransacetylase.

In some aspects, the microbial organism of the invention can include two, three, four, five, six, seven or eight exogenous nucleic acids each encoding an acetyl-CoA pathway enzyme. In some aspects, the microbial organism includes exogenous nucleic acids encoding each of the acetyl-CoA pathway enzymes of at least one of the pathways selected from (1)-(32).

In an additional embodiment, the invention provides a non-naturally occurring microbial organism having a fatty alcohol, fatty aldehyde or fatty acid pathway, wherein the non-naturally occurring microbial organism comprises at least one exogenous nucleic acid encoding an enzyme or protein that converts a substrate to a product selected from the group consisting of two acetyl-CoA molecules to a 3-ketoacyl-CoA, acetyl-CoA plus propionyl-CoA to a ketoacyl-CoA, a 3-ketoacyl-CoA to a 3-hydroxyacyl-CoA, a 3-hydroxyacyl-CoA to an enoyl-CoA, an enoyl-CoA to an acyl-CoA, an acyl-CoA plus an acetyl-CoA to a 3-ketoacyl-CoA, an acyl-CoA to a fatty aldehyde, a fatty aldehyde to a fatty alcohol, an acyl-CoA to a fatty alcohol, an acyl-CoA to an acyl-ACP, an acyl-ACP to a fatty acid, an acyl-CoA to a fatty acid, an acyl-ACP to a fatty aldehyde, a fatty acid to a fatty aldehyde, a fatty aldehyde to a fatty acid, pyruvate to acetate, acetate to acetyl-CoA, pyruvate to acetyl-CoA, pyruvate to acetaldehyde, threonin to acetaldehyde, acetaldehyde to acetate, acetaldehyde to acetyl-CoA, pyruvate to acetyl-phosphate, acetate to acetyl-phosphate, acetyl-phosphate to acetyl-CoA, phosphoenolpyruvate (PEP) to pyruvate, pyruvate to malate, malate to oxaloacetate, pyruvate to oxaloacetate, PEP to oxaloacetate, oxaloacetate to malonate semialdehyde, oxaloacetate to malonyl-CoA, malonate semialdehyde to malonate, malonate to malonyl-CoA, malonate semialdehyde to malonyl-CoA, malonyl-CoA to acetyl-CoA, malonate semialdehyde to acetyl-CoA, oxaloacetate plus acetyl-CoA to citrate, citrate to oxaloacetate plus acetyl-CoA, citrate to oxaloacetate plus acetate, and oxaloacetate to malate. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a fatty alcohol, fatty aldehyde or fatty acid pathway, such as that shown in FIG. 1-8.

While generally described herein as a microbial organism that contains a fatty alcohol, fatty aldehyde or fatty acid pathway, it is understood that the invention additionally provides a non-naturally occurring microbial organism comprising at least one exogenous nucleic acid encoding a fatty alcohol, fatty aldehyde or fatty acid pathway enzyme or protein expressed in a sufficient amount to produce an intermediate of a fatty alcohol, fatty aldehyde or fatty acid pathway. For example, as disclosed herein, a fatty alcohol, fatty aldehyde or fatty acid pathway is exemplified in FIGS. 1-7. Therefore, in addition to a microbial organism containing a fatty alcohol, fatty aldehyde or fatty acid pathway that produces fatty alcohol, fatty aldehyde or fatty acid, the invention additionally provides a non-naturally occurring microbial organism comprising at least one exogenous nucleic acid encoding a fatty alcohol, fatty aldehyde or fatty acid pathway enzyme, where the microbial organism produces a fatty alcohol, fatty aldehyde or fatty acid pathway intermediate, for example, a 3-ketoacyl-CoA, a 3-hydroxyacyl-CoA, an enoyl-CoA, an acyl-CoA, an acyl-ACP, acetate, acetaldehyde, acetyl-phosphate, oxaloacetate, matate, malonate semialdehyde, malonate, malonyl-CoA, acetyl-CoA, or citrate.

It is understood that any of the pathways disclosed herein, as described in the Examples and exemplified in the Figures, including the pathways of FIGS. 1-7, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a fatty alcohol, fatty aldehyde or fatty acid pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention can be produced by introducing expressible nucleic acids encoding one or more of the enzymes or proteins participating in one or more fatty alcohol, fatty aldehyde or fatty acid biosynthetic pathways. Depending on the host microbial organism chosen for biosynthesis, nucleic acids for some or all of a particular fatty alcohol, fatty aldehyde or fatty acid biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve fatty alcohol, fatty aldehyde or fatty acid biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as fatty alcohol, fatty aldehyde or fatty acid.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae* and *Yarrowia lipolytica*. It is understood that any suitable microbial host organism can be used to introduce metabolic and/or genetic modifications to produce a desired product.

Depending on the fatty alcohol, fatty aldehyde or fatty acid biosynthetic pathway constituents of a selected host microbial organism, the non-naturally occurring microbial organisms of the invention will include at least one exogenously expressed fatty alcohol, fatty aldehyde or fatty acid pathway-encoding nucleic acid and up to all encoding nucleic acids for one or more fatty alcohol, fatty aldehyde or fatty acid biosynthetic pathways. For example, fatty alcohol, fatty aldehyde or fatty acid biosynthesis can be established in a host deficient in a pathway enzyme or protein through exogenous expression of the corresponding encoding nucleic acid. In a host deficient in all enzymes or proteins of a fatty alcohol, fatty aldehyde or fatty acid pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of fatty alcohol, fatty aldehyde or fatty acid can be included, such as a thiolase, a 3-oxoacyl-CoA reductase, a 3-hydroxyacyl-CoA dehydratase, an enoyl-CoA redutase, an acyl-CoA reductase (aldehyde forming) and an alcohol dehydrogenase, for production of a fatty alcohol.

Given the teachings and guidance provided herein, those skilled in the art will understand that the number of encoding nucleic acids to introduce in an expressible form will, at least, parallel the fatty alcohol, fatty aldehyde or fatty acid pathway deficiencies of the selected host microbial organism. Therefore, a non-naturally occurring microbial organism of the invention can have one, two, three, four, five, six, seven or eight up to all nucleic acids encoding the enzymes or proteins constituting a fatty alcohol, fatty aldehyde or fatty acid biosynthetic pathway disclosed herein. In some embodiments, the non-naturally occurring microbial organisms also can include other genetic modifications that facilitate or optimize fatty alcohol, fatty aldehyde or fatty acid biosynthesis or that confer other useful functions onto the host microbial organism. One such other functionality can include, for example, augmentation of the synthesis of one or more of the fatty alcohol, fatty aldehyde or fatty acid pathway precursors such as acetyl-CoA or propionyl-CoA.

Generally, a host microbial organism is selected such that it produces the precursor of a fatty alcohol, fatty aldehyde or fatty acid pathway, either as a naturally produced molecule or as an engineered product that either provides de novo production of a desired precursor or increased production of a precursor naturally produced by the host microbial organism. For example, acetyl-CoA is produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a fatty alcohol, fatty aldehyde or fatty acid pathway.

In some embodiments, a non-naturally occurring microbial organism of the invention is generated from a host that contains the enzymatic capability to synthesize fatty alcohol, fatty aldehyde or fatty acid. In this specific embodiment it can be useful to increase the synthesis or accumulation of a fatty alcohol, fatty aldehyde or fatty acid pathway product to, for example, drive fatty alcohol, fatty aldehyde or fatty acid pathway reactions toward fatty alcohol, fatty aldehyde or fatty acid production. Increased synthesis or accumulation can be accomplished by, for example, overexpression of nucleic acids encoding one or more of the above-described fatty alcohol, fatty aldehyde or fatty acid pathway enzymes or proteins. Overexpression of the enzyme or enzymes and/or protein or proteins of the fatty alcohol, fatty aldehyde or fatty acid pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing fatty alcohol, fatty aldehyde or fatty acid, through overexpression of one, two, three, four, five, six, seven, or eight, that is, up to all nucleic acids encoding fatty alcohol, fatty aldehyde or fatty acid biosynthetic pathway enzymes or proteins. In addition, a non-naturally occurring organism can be generated by mutagenesis of an endogenous gene that results in an increase in activity of an enzyme in the fatty alcohol, fatty aldehyde or fatty acid biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a fatty alcohol, fatty aldehyde or fatty acid biosynthetic pathway onto the microbial organism. Alternatively, encoding nucleic acids can be introduced to produce an intermediate microbial organism having the biosynthetic capability to catalyze some of the required reactions to confer fatty alcohol, fatty aldehyde or fatty acid biosynthetic capability. For example, a non-naturally occurring microbial organism having a fatty alcohol, fatty aldehyde or fatty acid biosynthetic pathway can comprise at least two exogenous nucleic acids encoding desired enzymes or proteins, such as the combination of a thiolase and an acyl-CoA reductase (alcohol forming), or alternatively a 2-oxoacyl-CoA reductase and an acyl-CoA hydrolase, or alternatively a enoyl-CoA reductase and an acyl-CoA reductase (aldehyde forming), and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, a thiolase, an enoyl-CoA reductase and a aldehyde dehydrogenase (acid forming), or alternatively a 3-hydroxyacyl-coA dehydratase, an acyl-CoA:ACP acyltransferase and a thioesterase, or alternatively a 3-oxoacyl-CoA reductase, an acyl-CoA hydrolase and a carboxylic acid reductase, and so forth, as desired, so long as the combination of enzymes and/or proteins of the desired biosynthetic pathway results in production of the corresponding desired product. Similarly, any combination of four, five, six, seven, eight or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of fatty alcohol, fatty aldehyde or fatty acid as described herein, the non-naturally occurring microbial organisms and methods of the invention also can be utilized in various combinations with each other and/or with other microbial organisms and methods well known in the art to achieve product biosynthesis by other routes. For example, one alternative to produce fatty alcohol, fatty aldehyde or fatty acid other than use of the fatty alcohol, fatty aldehyde or fatty acid producers is through addition of another microbial organism capable of converting a fatty alcohol, fatty aldehyde or fatty acid pathway intermediate to fatty alcohol, fatty aldehyde or fatty acid. One such procedure includes, for example, the fermentation of a microbial organism that produces a fatty alcohol, fatty aldehyde or fatty acid pathway intermediate. The fatty alcohol, fatty aldehyde or fatty acid pathway intermediate can then be used as a substrate for a second microbial organism that converts the fatty alcohol, fatty aldehyde or fatty acid pathway intermediate to fatty alcohol, fatty aldehyde or fatty acid. The fatty alcohol, fatty aldehyde or fatty acid pathway intermediate can be added directly to another culture of the second organism or the original culture of the fatty alcohol, fatty aldehyde or fatty acid pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, fatty alcohol, fatty aldehyde or fatty acid. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of fatty alcohol, fatty aldehyde or fatty acid can be accomplished by constructing a microbial organism that contains biosynthetic pathways for conversion of one pathway intermediate to another pathway intermediate or the product. Alternatively, fatty alcohol, fatty aldehyde or fatty acid also can be biosynthetically produced from microbial organisms through co-culture or co-fermentation using two organisms in the same vessel, where the first microbial organism produces a fatty alcohol, fatty aldehyde or fatty acid intermediate and the second microbial organism converts the intermediate to fatty alcohol, fatty aldehyde or fatty acid.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce fatty alcohol, fatty aldehyde or fatty acid.

Similarly, it is understood by those skilled in the art that a host organism can be selected based on desired characteristics for introduction of one or more gene disruptions to increase production of fatty alcohol, fatty aldehyde or fatty acid. Thus, it is understood that, if a genetic modification is to be introduced into a host organism to disrupt a gene, any homologs, orthologs or paralogs that catalyze similar, yet non-identical metabolic reactions can similarly be disrupted to ensure that a desired metabolic reaction is sufficiently disrupted. Because certain differences exist among metabolic networks between different organisms, those skilled in the art will understand that the actual genes disrupted in a given organism may differ between organisms. However, given the teachings and guidance provided herein, those skilled in the art also will understand that the methods of the invention can be applied to any suitable host microorganism to identify the cognate metabolic alterations needed to construct an organism in a species of interest that will increase fatty alcohol, fatty aldehyde or fatty acid biosynthesis. In a particular embodiment, the increased production couples biosynthesis of fatty alcohol, fatty aldehyde or fatty acid to growth of the organism, and can obligatorily couple production of fatty alcohol, fatty aldehyde or fatty acid to growth of the organism if desired and as disclosed herein.

Sources of encoding nucleic acids for a fatty alcohol, fatty aldehyde or fatty acid pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, 255956237 *Penicillium chrysogenum* Wisconsin 54-1255, *Acetobacter pasteurians, Acidaminococcus fermentans, Acinetobacter baylyi, Acinetobacter calcoaceticus, Acinetobacter* sp. ADP—1, *Acinetobacter* sp. Strain M-1, *Actinobacillus succinogenes, Aedes aegypti, Agrobacterium tumefaciens, Alkaliphilus metalliredigens* QYMF, *Alkaliphilus oremlandii* OhILAs, *Anabaena variabilis* ATCC 29413, *Anaerobiospirillum succiniciproducens, Anopheles gambiae* str. PEST, *Apis mellifera, Aquifex aeolicus, Arabidopsis thaliana, Archaeoglobus fulgidus, Archaeoglobus fulgidus* DSM 4304, *Ascaris suum, Aspergillus fumigatus, Aspergillus nidulans, Aspergillus niger, Aspergillus niger* CBS 513.88, *Aspergillus terreus* NIH2624, *Azotobacter vinelandii* DJ, *Bacillus cereus, Bacillus megaterium, Bacillus methanolicus* MGA3, *Bacillus methanolicus* PB1, *Bacillus* sp. SG-1, *Bacillus subtilis, Bacillus weihenstephanensis* KBAB4, *Bacteroides fragilis, Bombyx mori, Bos taurus, Bradyrhizobium japonicum, Bradyrhizobium japonicum* USDA110, *Brassica napsus, Burkholderia ambifaria* AMMD, *Burkholderia multivorans* ATCC 17616, *Burkholderia phymatum, Burkholderia stabilis,* butyrate-producing bacterium L2-50, *Caenorhabditis briggsae* AF16, *Caenorhabditis elegans, Campylobacter jejuni, Candida albicans, Candida boidinii, Candida methylica, Candida parapsilosis, Candida tropicalis, Candida tropicalis* MYA-3404, *Candidatus Protochlamydia amoebophila, Canis lupus familiaris* (dog), *Carboxydothermus hydrogenoformans, Carthamus tinctorius, Chlamydomonas reinhardtii, Chlorobium limicola, Chlorobium tepidum, Chloroflexus aurantiacus, Citrus junos, Clostridium acetobutylicum, Clostridium aminobutyricum, Clostridium beijerinckii, Clostridium beijerinckii* NCIMB 8052, *Clostridium carboxidivorans* P7, *Clostridium kluyveri, Clostridium kluyveri* DSM 555, *Clostridium pasteurianum, Clostridium saccharoperbutylacetonicum, Clostridium symbiosum, Clostridium tetani* E88, *Colwellia psychrerythraea* 34H, *Corynebacterium glutamicum, Cryptococcus neoformans* var, *Cryptosporidium parvum* Iowa II, *Cuphea hookeriana, Cuphea palustris, Cupriavidus necator, Cupriavidus taiwanensis, Cyanobium* PCC7001, *Cyanothece* sp. PCC 7425, *Danio rerio, Desulfatibacillum alkenivorans* AK-01, *Desulfococcus oleovorans* Hxd3, *Desulfovibrio africanus, Dictyostelium discoideum, Dictyostelium discoideum* AX4, *Drosophila melanogaster, Erythrobacter* sp. NAP1, *Escherichia coli* K-12 MG1655, *Euglena gracilis, Flavobacteria bacterium* BAL38, *Fusobacterium nucleatum, Geobacillus thermodenitrificans, Haemophilus* influenza, *Haloarcula marismortui, Haloarcula marismortui* ATCC 43049, *Halomonas* sp. HTNK1, *Helianthus annuus, Helicobacter pylori, Helicobacterpylori* 26695, *Homo sapiens, Hydrogenobacter thermophilus, Klebsiella pneumoniae, Kluyveromyces lactis, Kluyveromyces lactis* NRRL Y-1140, *Lactobacillus casei, Lactobacillus plantarum, Lactobacillus reuteri, Lactococcus lactis, Leifsonia* sp. S749, *Leuconostoc mesenteroides, Lyngbya* sp. PCC 8106, *Macaca mulatta, Magnetospirillum magneticum* AMB-1, *Mannheimia succiniciproducens,* marine gamma proteobacterium HTCC2080, *Marinobacter aquaeolei, Marinobacter aquaeolei* VT8, *Megathyrsus maximus, Mesorhizobium loti, Metallosphaera sedula, Methanosarcina thermophila, Methanothermobacter thermautotrophicus, Methylobacterium extorquens, Monosiga brevicollis* MX1, *Moorella thermoacetica, Moorella thermoacetica* A TCC 39073, *Mus musculus, Mycobacterium avium* subsp. *paratuberculosis* K-10, *Mycobacterium bovis* BCG, *Mycobacterium marinum* M, *Mycobacterium smegmatis, Mycobacterium smegmatis* MC2 155, *Mycobacterium* sp. (strain JLS), *Mycobacterium* sp. MCS, *Mycobacterium* sp. strain JLS, *Mycobacterium tuberculosis, Myxococcus xanthus* DK 1622, *Nematostella vectensis, Neurospora crassa* OR74A, *Nicotiana tabacum, Nocardia brasiliensis, Nocardia farcinica* IFM 10152, *Nocardia iowensis, Nodularia spumigena* CCY9414, *Nostoc azollae, Nostoc* sp. PCC 7120, *Opitutaceae bacterium* TAV2, *Paracoccus denitrificans, Penicillium chrysogenum, Perkinsus marinus* ATCC 50983, *Photobacterium phosphoreum, Photobacterium* sp. SKA34, *Picea sitchensis, Pichia pastoris, Pichia pastoris* GS 15, *Plasmodium falciparum, Porphyromonas gingivalis, Porphyromonas gingivalis* W83, *Prochlorococcus marinus* MIT 9312, *Propionigenium modestum, Pseudomonas aeruginosa, Pseudomonas aeruginosa* PAO1, *Pseudomonas fluorescens, Pseudomonas fluorescens* Pf0-1, *Pseudomonas knackmussii, Pseudomonas knackmussii* (B13), *Pseudomonas putida, Pseudomonas putida* GB-1, *Pseudomonas* sp, *Pseudomonas* sp. CF600, *Pseudomonas stutzeri, Pseudomonas stutzeri* A1501, *Pseudomonas syringae, Pyrobaculum aerophilum* str. IM2, *Ralstonia eutropha, Ralstonia metallidurans, Rattus norvegicus, Reinekea* sp. MED297, *Rhizobium etli* CFN 42, *Rhizobium leguminosarum, Rhodobacter sphaeroides, Rhodococcus erythropolis, Rhodococcus* sp., *Rhodopseudomonas palustris, Roseiflexus castenholzii, Roseovarius* sp. HTCC2601, *Saccharomyces cerevisiae, Saccharomyces cerevisiae* s288c, *Salmonella* enteric, *Salmonella enterica* subsp. *enterica serovar Typhimurium* str. LT2, *Salmonella typhimurium, Salmonella typhimurium* LT2, *Scheffersomyces stipitis, Schizosaccharomyces pombe, Shigella dysenteriae, Shigella sonnei, Simmondsia chinensis, Solanum lycopersicum, Sordaria macrospora, Staphylococcus aureus, Stenotrophomonas maltophilia, Streptococcus mutans, Streptococcus pneumoniae, Streptococcus sanguinis, Streptomyces anulatus, Streptomyces avermitillis, Streptomyces cinnamonensis, Streptomyces coelicolor, Streptomyces griseus* subsp. *griseus* NBRC 13350, *Streptomyces luridus,*

*Streptomyces* sp CL190, *Streptomyces* sp. KO-3988, *Streptomyces viridochromogenes, Streptomyces wedmorensis, Strongylocentrotus purpuratus, Sulfolobus acidocaldarius, Sulfolobus solfataricus, Sulfolobus tokodaii, Sulfurihydrogenibium subterraneum, Sulfurimonas denitrificans, Sus scrofa, Synechococcus elongatus* PCC 6301, *Synechococcus elongatus* PCC 7942, *Synechococcus* sp. PCC 7002, *Syntrophobacter fumaroxidans, Syntrophus aciditrophicus, Tetraodon nigroviridis, Thermoanaerobacter ethanolicus* JW 200, *Thermoanaerobacter pseudethanolicus* A TCC 33223, *Thermococcus litoralis, Thermoproteus neutrophilus, Thermotoga maritime, Treponema denticola, Tribolium castaneum, Trichomonas vaginalis* G3, *Triticum aestivum, Trypanosoma brucei, Trypanosoma cruzi* strain CL Brener, *Tsukamurella paurometabola* DSM 20162, *Umbellularia California, Veillonella parvula, Vibrio cholerae* V51, *Xenopus tropicalis, Yarrowia lipolytica, Zea mays, Zoogloea ramiger, Zymomonas mobilis, Zymomonas mobilis* subsp. *mobilis* ZM4, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite fatty alcohol, fatty aldehyde or fatty acid biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of fatty alcohol, fatty aldehyde or fatty acid described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative fatty alcohol, fatty aldehyde or fatty acid biosynthetic pathway exists in an unrelated species, fatty alcohol, fatty aldehyde or fatty acid biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize fatty alcohol, fatty aldehyde or fatty acid.

Methods for constructing and testing the expression levels of a non-naturally occurring fatty alcohol, fatty aldehyde or fatty acid-producing host can be performed, for example, by recombinant and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

Exogenous nucleic acid sequences involved in a pathway for production of fatty alcohol, fatty aldehyde or fatty acid can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more fatty alcohol, fatty aldehyde or fatty acid biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the invention provides a method for producing a compound of Formula (I):

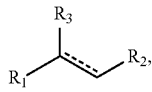
(I)

wherein $R_1$ is $C_{1-24}$ linear alkyl; $R_2$ is $CH_2OH$, CHO, or COOH; $R_3$ is H, OH, or oxo (=O); and ----- represents a single or double bond with the proviso that the valency of the carbon atom to which $R_3$ is attached is four, comprising culturing a non-naturally occurring microbial organism of under conditions and for a sufficient period of time to produce the compound of Formula (I), wherein the non-naturally occurring microbial organism has a MI-FAE cycle and a termination pathway, wherein the MI-FAE cycle includes one or more thiolase, one or more 3-oxoacyl-CoA reductase, one or more 3-hydroxyacyl-CoA dehydratase, and one or more enoyl-CoA reductase, wherein the termination pathway includes a pathway shown in FIG. 1, 6 or 7 selected from: (1) 1H; (2) 1K and 1L; (3) 1E and 1N; (4) 1K, 1J, and 1N; (5) 1E; (6) 1K and 1J; (7) 1H and 1N; (8) 1K, 1L, and 1N; (9) 1E and 1F; (10) 1K, 1J, and 1F; (11) 1H, 1N, and 1F; (12) 1K, 1L, 1N, and 1F; and (13) 1G, wherein 1E is an acyl-CoA reductase (aldehyde forming), wherein 1F is an alcohol dehydrogenase, wherein 1G is an acyl-CoA reductase (alcohol forming), wherein 1H is an acyl-CoA hydrolase, acyl-CoA transferase or acyl-CoA synthase, wherein 1J is an acyl-ACP reductase, wherein 1K is an acyl-CoA:ACP acyltransferase, wherein 1L is a thioesterase, wherein 1N is an aldehyde dehydrogenase (acid forming) or a carboxylic acid reductase, wherein an enzyme of the MI-FAE cycle or termination pathway is encoded by at least one exogenous nucleic acid and is expressed in a sufficient amount to produce the compound of Formula (I), wherein the substrate of each of said enzymes of the MI-FAE cycle and the termination pathway are independently selected from a compound of Formula (II), propionyl-CoA or acetyl-CoA:

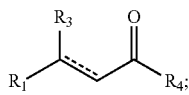
(II)

wherein $R_1$ is $C_{1-24}$ linear alkyl; $R_3$ is H, OH, or oxo (=O); $R_4$ is S-CoA, ACP, OH or H; and ----- represents a single or double bond with the proviso that the valency of the carbon atom to which $R_3$ is attached is four; wherein said one or more enzymes of the MI-FAE cycle are each selective for a compound of Formula (II) having a number of carbon atoms at $R_1$ that is no greater than the number of carbon atoms at $R_1$ of said compound of Formula (I), and wherein said one or more enzymes of the termination pathway are each selective for a compound of Formula (II) having a number of carbon atoms at $R_1$ that is no less than the number of carbon atoms at $R_1$ of said compound of Formula (I).

In some embodiments, the invention provides a method for producing a compound of Formula (I) wherein $R_1$ is $C_{1-17}$ linear alkyl. In another aspect of the invention, the $R_1$ of the compound of Formula (I) is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, Cis linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some aspects of the invention, the microbial organism microbial organism used in the method of the invention includes two, three, or four exogenous nucleic acids each encoding an enzyme of the MI-FAE cycle. In some aspects of the invention, the microbial organism used in the method of the invention includes two, three, or four exogenous nucleic acids each encoding an enzyme of the termination pathway. In some aspects of the invention, the microbial organism used in the method of the invention includes exogenous nucleic acids encoding each of the enzymes of at least one of the pathways selected from (1)-(13). In some aspects, the at least one exogenous nucleic acid is a heterologous nucleic acid. In some aspects, the non-naturally occurring microbial organism used in the method of the invention is in a substantially anaerobic culture medium.

In some embodiments, the invention provides a method for producing a fatty alcohol selected from the Formulas (III)-(VI):

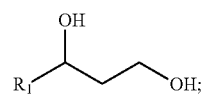
(III)

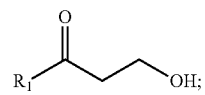
(IV)

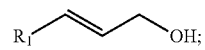
(V)

(VI)

wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, Cis linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a method for producing a fatty aldehyde selected from the Formulas (VII)-(X):

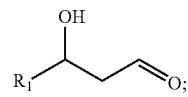
(VII)

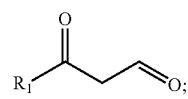
(VIII)

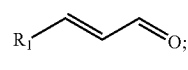
(IX)

-continued

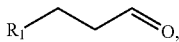
(X)

Wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, Cis linear alkyl, $C_{16}$ linear alkyl, $C_{17}$ linear alkyl, Cis linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a method for producing a fatty acid selected from the Formulas (XI)-(XIV):

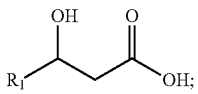
(XI)

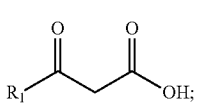
(XII)

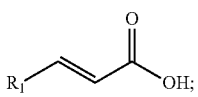
(XIII)

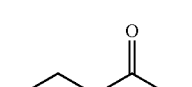
(XIV)

wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, Cis linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the method for producing a fatty alcohol, fatty aldehyde or fatty acid described herein includes using a non-naturally occurring microbial organism that has an acetyl-CoA pathway and at least one exogenous nucleic acid encoding an acetyl-CoA pathway enzyme expressed in a sufficient amount to produce acetyl-CoA, wherein the acetyl-CoA pathway includes a pathway shown in FIG. 2, 3, 4 or 5 selected from: (1) 2A and 2B; (2) 2A, 2C, and 2D; (3) 2H; (4) 2G and 2D; (5) 2E, 2F and 2B; (6) 2E and 2I; (7) 2J, 2F and 2B; (8) 2J and 2I; (9) 3A, 3B, and 3C; (10) 3A, 3B, 3J, 3K, and 3D; (11) 3A, 3B, 3G, and 3D; (12) 3A, 3F, and 3D; (13) 3N, 3H, 3B and 3C; (14) 3N, 3H, 3B, 3J, 3K, and 3D; (15) 3N, 3H, 3B, 3G, and 3D; (16) 3N, 3H, 3F, and 3D; (17) 3L, 3M, 3B and 3C; (18) 3L, 3M, 3B, 3J, 3K, and 3D; (19) 3L, 3M, 3B, 3G, and 3D; (20) 3L, 3M, 3F, and 3D; (21) 4A, 4B, 4D, 4H, 4I, and 4J; (22) 4A, 4B, 4E, 4F, 4H, 4I, and 4J; (23) 4A, 4B, 4E, 4K, 4L, 4H, 4I, and 4J; (24) 4A, 4C, 4D, 4H, and 4J; (25) 4A, 4C, 4E, 4F, 4H, and 4J; (26) 4A, 4C, 4E, 4K, 4L, 4H, and 4J; (27) 5A, 5B, 5D, and 5G; (28) 5A, 5B, 5E, 5F, and 5G; (29) 5A, 5B, 5E, 5K, 5L, and 5G; (30) 5A, 5C, and 5D; (31) 5A, 5C, 5E, and 5F; and (32) 5A, 5C, 5E, 5K, and 5G, wherein 2A is a pyruvate oxidase (acetate-forming), wherein 2B is an acetyl-CoA synthetase, an acetyl-CoA ligase or an acetyl-CoA transferase, wherein 2C is an acetate kinase, wherein 2D is a phosphotransacetylase, wherein 2E is a pyruvate decarboxylase, wherein 2F is an acetaldehyde dehydrogenase, wherein 2G is a pyruvate oxidase (acetyl-phosphate forming), wherein 2H is a pyruvate dehydrogenase, a pyruvate:ferredoxin oxidoreductase, a pyruvate:NAD(P)H oxidoreductase or a pyruvate formate lyase, wherein 2I is an acetaldehyde dehydrogenase (acylating), wherein 2J is a threonine aldolase, wherein 3A is a phosphoenolpyruvate (PEP) carboxylase or a PEP carboxykinase, wherein 3B is an oxaloacetate decarboxylase, wherein 3C is a malonate semialdehyde dehydrogenase (acetylating), wherein 3D is an acetyl-CoA carboxylase or a malonyl-CoA decarboxylase, wherein 3F is an oxaloacetate dehydrogenase or an oxaloacetate oxidoreductase, wherein 3G is a malonate semialdehyde dehydrogenase (acylating), wherein 3H is a pyruvate carboxylase, wherein 3J is a malonate semialdehyde dehydrogenase, wherein 3K is a malonyl-CoA synthetase or a malonyl-CoA transferase, wherein 3L is a malic enzyme, wherein 3M is a malate dehydrogenase or a malate oxidoreductase, wherein 3N is a pyruvate kinase or a PEP phosphatase, wherein 4A is a citrate synthase, wherein 4B is a citrate transporter, wherein 4C is a citrate/malate transporter, wherein 4D is an ATP citrate lyase, wherein 4E is a citrate lyase, wherein 4F is an acetyl-CoA synthetase or an acetyl-CoA transferase, wherein 4H is a cytosolic malate dehydrogenase, wherein 4I is a malate transporter, wherein 4J is a mitochondrial malate dehydrogenase, wherein 4K is an acetate kinase, wherein 4L is a phosphotransacetylase, wherein 5A is a citrate synthase, wherein 5B is a citrate transporter, wherein 5C is a citrate/ oxaloacetate transporter, wherein 5D is an ATP citrate lyase, wherein 5E is a citrate lyase, wherein 5F is an acetyl-CoA synthetase or an acetyl-CoA transferase, wherein 5G is an oxaloacetate transporter, wherein 5K is an acetate kinase, and wherein 5L is a phosphotransacetylase.

In some aspects, the microbial organism used in the method of the invention includes two, three, four, five, six, seven or eight exogenous nucleic acids each encoding an acetyl-CoA pathway enzyme. In some aspects, the microbial organism used in the method of the invention includes exogenous nucleic acids encoding each of the acetyl-CoA pathway enzymes of at least one of the pathways selected from (1)-(32).

Suitable purification and/or assays to test for the production of fatty alcohol, fatty aldehyde or fatty acid can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The fatty alcohol, fatty aldehyde or fatty acid can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the fatty alcohol, fatty aldehyde or fatty acid producers can be cultured for the biosynthetic production of fatty alcohol, fatty aldehyde or fatty acid.

For the production of fatty alcohol, fatty aldehyde or fatty acid, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high fatty alcohol, fatty aldehyde or fatty acid yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of fatty alcohol, fatty aldehyde or fatty acid.

In addition to renewable feedstocks such as those exemplified above, the fatty alcohol, fatty aldehyde or fatty acid microbial organisms of the invention also can be modified for growth on syngas as its source of carbon. In this specific embodiment, one or more proteins or enzymes are expressed in the fatty alcohol, fatty aldehyde or fatty acid producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a fatty alcohol, fatty aldehyde or fatty acid pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the fatty alcohol, fatty aldehyde or fatty acid precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a fatty alcohol, fatty aldehyde or fatty acid pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains a reductive TCA pathway can confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, fatty alcohol, fatty aldehyde or fatty acid and any of the intermediate metabolites in the fatty alcohol, fatty aldehyde or fatty acid pathway. All that is required is to engineer in one or more of the required enzyme or protein activities to achieve biosynthesis of the desired compound or intermediate including, for example, inclusion of some or all of the fatty alcohol, fatty aldehyde or fatty acid biosynthetic pathways. Accordingly, the invention provides a non-naturally occurring microbial organism that produces and/or secretes fatty alcohol, fatty aldehyde or fatty acid when grown on a carbohydrate or other carbon source and produces and/or secretes any of the intermediate metabolites shown in the fatty alcohol, fatty aldehyde or fatty acid pathway when grown on a carbohydrate or other carbon source. The fatty alcohol, fatty aldehyde or fatty acid producing microbial organisms of the invention can initiate synthesis from an intermediate, for example, a 3-ketoacyl-CoA, a 3-hydroxyacyl-CoA, an enoyl-CoA, an acyl-CoA, an acyl-ACP, acetate, acetaldehyde, acetyl-phosphate, oxaloacetate, matate, malonate semialdehyde, malonate, malonyl-CoA, acetyl-CoA, or citrate.

The non-naturally occurring microbial organisms of the invention are constructed using methods well known in the art as exemplified herein to exogenously express at least one nucleic acid encoding a fatty alcohol, fatty aldehyde or fatty acid pathway enzyme or protein in sufficient amounts to produce fatty alcohol, fatty aldehyde or fatty acid. It is understood that the microbial organisms of the invention are cultured under conditions sufficient to produce fatty alcohol, fatty aldehyde or fatty acid. Following the teachings and guidance provided herein, the non-naturally occurring microbial organisms of the invention can achieve biosynthesis of fatty alcohol, fatty aldehyde or fatty acid resulting in intracellular concentrations between about 0.1-200 mM or more. Generally, the intracellular concentration of fatty alcohol, fatty aldehyde or fatty acid is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the fatty alcohol, fatty aldehyde or fatty acid producers can synthesize fatty alcohol, fatty aldehyde or fatty acid at intracellular concentrations of 5-10 mM or more as well as all other concentrations exemplified herein. It is understood that, even though the above description refers to intracellular concentrations, fatty alcohol, fatty aldehyde or fatty acid producing microbial organisms can produce fatty alcohol, fatty aldehyde or fatty acid intracellularly and/or secrete the product into the culture medium.

In addition to the culturing and fermentation conditions disclosed herein, growth condition for achieving biosynthesis of fatty alcohol, fatty aldehyde or fatty acid can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylpropionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in fatty alcohol, fatty aldehyde or fatty acid or any fatty alcohol, fatty aldehyde or fatty acid pathway intermediate. The various carbon feedstock and other uptake sources enumerated above will be referred to herein, collectively, as "uptake sources." Uptake sources can provide isotopic enrichment for any atom present in the product fatty alcohol, fatty aldehyde or fatty acid or fatty alcohol, fatty aldehyde or fatty acid pathway intermediate, or for side products generated in reactions diverging away from a fatty alcohol, fatty aldehyde or fatty acid pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950) $^{14}C/^{12}C$ ratio of $1.176\pm0.010\times10^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mille. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides fatty alcohol, fatty aldehyde or fatty acid or a fatty alcohol, fatty aldehyde or fatty acid pathway intermediate that has a carbon-12, carbon-13, and carbon-14 ratio that reflects an atmospheric carbon, also referred to as environmental carbon, uptake source. For example, in some aspects the fatty alcohol, fatty aldehyde or fatty acid or a fatty alcohol, fatty aldehyde or fatty acid pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides fatty alcohol, fatty aldehyde or fatty acid or a fatty alcohol, fatty aldehyde or fatty acid pathway intermediate that has a carbon-12, carbon-13, and carbon-14 ratio that reflects petroleum-based carbon uptake source. In this aspect, the fatty alcohol, fatty aldehyde or fatty acid or a fatty alcohol, fatty aldehyde or fatty acid pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides fatty alcohol, fatty aldehyde or fatty acid or a fatty alcohol, fatty aldehyde or fatty acid pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced fatty alcohol, fatty aldehyde or fatty acid or fatty alcohol, fatty aldehyde or fatty acid pathway intermediate as disclosed herein, and to the products derived therefrom, wherein the fatty alcohol, fatty aldehyde or fatty acid or a fatty alcohol, fatty aldehyde or fatty acid pathway intermediate has a carbon-12, carbon-13, and carbon-14 isotope ratio of about the same value as the $CO_2$ that occurs in the environment. For example, in some aspects the invention provides bioderived fatty alcohol, fatty aldehyde or fatty acid or a bioderived fatty alcohol, fatty aldehyde or fatty acid intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived fatty alcohol, fatty aldehyde or fatty acid or a bioderived fatty alcohol, fatty aldehyde or fatty acid pathway intermediate as disclosed herein, wherein the bioderived product is chemically modified to generate a final product. Methods of chemically modifying a bioderived product of fatty alcohol, fatty aldehyde or fatty acid, or an intermediate thereof, to generate a desired product are well known to those skilled in the art, as described herein. The invention further provides biofuels, chemicals, polymers, surfactants, soaps, detergents, shampoos, lubricating oil additives, fragrances, flavor materials or acrylates having a carbon-12 versus carbon-13 versus carbon-14 isotope ratio of about the same value as the $CO_2$ that occurs in the environment, wherein the biofuels, chemicals, polymers, surfactants, soaps, detergents, shampoos, lubricating oil additives, fragrances, flavor materials or acrylates are generated directly from or in combination with bioderived fatty alcohol, fatty aldehyde or fatty acid or a bioderived fatty alcohol, fatty aldehyde or fatty acid pathway intermediate as disclosed herein.

Fatty alcohol, fatty aldehyde or fatty acid is a chemical used in commercial and industrial applications. Non-limiting examples of such applications include production of biofuels, chemicals, polymers, surfactants, soaps, detergents, shampoos, lubricating oil additives, fragrances, flavor materials and acrylates. Accordingly, in some embodiments, the invention provides biobased biofuels, chemicals, polymers, surfactants, soaps, detergents, shampoos, lubricating oil additives, fragrances, flavor materials and acrylates comprising one or more bioderived fatty alcohol, fatty aldehyde or fatty acid or bioderived fatty alcohol, fatty aldehyde or fatty acid pathway intermediate produced by a non-naturally occurring microorganism of the invention or produced using a method disclosed herein.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides a biofuel, chemical, polymer, surfactant, soap, detergent, shampoo, lubricating oil additive, fragrance, flavor material or acrylate comprising bioderived fatty alcohol, fatty aldehyde or fatty acid or bioderived fatty alcohol, fatty aldehyde or fatty acid pathway intermediate, wherein the bioderived fatty alcohol, fatty aldehyde or fatty acid or bioderived fatty alcohol, fatty aldehyde or fatty acid pathway intermediate includes all or part of the fatty alcohol, fatty aldehyde or fatty acid or fatty alcohol, fatty aldehyde or fatty acid pathway intermediate used in the production of a biofuel, chemical, polymer, surfactant, soap, detergent, shampoo, lubricating oil additive, fragrance, flavor material or acrylate. Thus, in some aspects, the invention provides a biobased biofuel, chemical, polymer, surfactant, soap, detergent, shampoo, lubricating oil additive, fragrance, flavor material or acrylate comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived fatty alcohol, fatty aldehyde or fatty acid or bioderived fatty alcohol, fatty aldehyde or fatty acid pathway intermediate as disclosed herein. Additionally, in some aspects, the invention provides a biobased biofuel, chemical, polymer, surfactant, soap, detergent, shampoo, lubricating oil additive, fragrance, flavor material or acrylate wherein the fatty alcohol, fatty aldehyde or fatty acid or fatty alcohol, fatty aldehyde or fatty acid pathway intermediate used in its production is a combination of bioderived and petroleum derived fatty alcohol, fatty aldehyde or fatty acid or fatty alcohol, fatty aldehyde or fatty acid pathway intermediate. For example, a biobased a biofuel, chemical, polymer, surfactant, soap, detergent, shampoo, lubricating oil additive, fragrance, flavor material or acrylate can be produced using 50% bioderived fatty alcohol, fatty aldehyde or fatty acid and 50% petroleum derived fatty alcohol, fatty aldehyde or fatty acid or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing a biofuel, chemical, polymer, surfactant, soap, detergent, shampoo, lubricating oil additive, fragrance, flavor material or acrylate using the bioderived fatty alcohol, fatty aldehyde or fatty acid or bioderived fatty alcohol, fatty aldehyde or fatty acid pathway intermediate of the invention are well known in the art.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of fatty alcohol, fatty aldehyde or fatty acid includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of fatty alcohol, fatty aldehyde or fatty acid. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of fatty alcohol, fatty aldehyde or fatty acid. Generally, and as with non-continuous culture procedures, the continuous and/or near-continuous production of fatty alcohol, fatty aldehyde or fatty acid will include culturing a non-naturally occurring fatty alcohol, fatty aldehyde or fatty acid producing organism of the invention in sufficient nutrients and medium to sustain and/or nearly sustain growth in an exponential phase. Continuous culture under such conditions can include, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of fatty alcohol, fatty aldehyde or fatty acid can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the fatty alcohol, fatty aldehyde or fatty acid producers of the invention for continuous production of substantial quantities of fatty alcohol, fatty aldehyde or fatty acid, the fatty alcohol, fatty aldehyde or fatty acid producers also can be, for example, simultaneously subjected to chemical synthesis procedures to convert the product to other compounds or the product can be separated from the fermentation culture and sequentially subjected to chemical or enzymatic conversion to convert the product to other compounds, if desired.

In addition to active and selective enzymes producing fatty alcohols, fatty aldehydes, or fatty acids at high yield, titer and productivity, a robust host organism that can efficiently direct carbon and reducing equivalents to fatty alcohol, fatty aldehyde and fatty acid biosynthesis can be beneficial. Host modifications described herein are particularly useful in combination with selective enzymes described herein that favor formation of the desired fatty alcohol, fatty aldehyde, or fatty acid product. Several host modifications described herein entail introducing heterologous enzyme activities into the host organism. Other modifications involve overexpressing or elevating enzyme activity relative to wild type levels. Yet other modifications include disrupting endogenous genes or attenuating endogenous enzyme activities.

In one embodiment of the invention, the microbial organisms efficiently directs carbon and energy sources into production of acetyl-CoA, which is used as both a primer and extension unit in the MI-FAE cycle. In unmodified microbial organism, fatty alcohol, fatty aldehyde and fatty acid production in the cytosol relies on the native cell machinery to provide the necessary precursors. Thus, high concentrations of cytosolic acetyl-CoA are desirable for facilitating deployment of a cytosolic fatty alcohol, fatty aldehyde or fatty acid production pathway that originates from acetyl-CoA. Metabolic engineering strategies for increasing cytosolic acetyl-CoA are disclosed herein.

Since many eukaryotic organisms synthesize most of their acetyl-CoA in the mitochondria during growth on glucose, increasing the availability of acetyl-CoA in the cytosol can be obtained by introduction of a cytosolic acetyl-CoA biosynthesis pathway. Accordingly, acetyl-CoA biosynthesis pathways are described herein. In one embodiment, utilizing the pathways shown in FIG. 2, acetyl-CoA can be synthesized in the cytosol from a pyruvate or threonine precursor. In other embodiments, acetyl-CoA can be synthesized in the cytosol from phosphoenolpyruvate (PEP) or pyruvate (FIG. 3). In yet another embodiment acetyl-CoA can be synthesized in cellular compartments and transported to the cytosol. For example, one mechanism involves converting mitochondrial acetyl-CoA to a metabolic intermediate such as citrate or citramalate, transporting those intermediates to the cytosol, and then regenerating the acetyl-CoA (see FIGS. 4 and 5). Exemplary acetyl-CoA pathways and corresponding enzymes are further described in Examples II-IV.

In another embodiment, increasing cytosolic acetyl-CoA availability for fatty alcohol, fatty aldehyde, or fatty acid biosynthesis is to disrupt or attenuate competing enzymes and pathways that utilize acetyl-CoA or its precursors. Exemplary competing enzyme activities include, but are not limited to, pyruvate decarboxylase, lactate dehydrogenase, short-chain aldehyde and alcohol dehydrogenases, acetate kinase, phosphotransacetylase, glyceraldehyde-3-phosphate dehydrogenases, pyruvate oxidase and acetyl-CoA carboxylase. Exemplary acetyl-CoA consuming pathways whose disruption or attenuation can improve fatty alcohol, fatty aldehyde, or fatty acid production include the mitochondrial TCA cycle, fatty acid biosynthesis, ethanol production and amino acid biosynthesis. These enzymes and pathways are further described herein.

Yet another strategy for increasing cytosolic acetyl-CoA production is to increase the pool of CoA available in the cytoplasm. This can be accomplished by overexpression of CoA biosynthetic enzymes in the cytosol. In particular, expression of pantothenate kinase (EC 2.7.1.33) can be used. This enzyme catalyzes the first step and rate-limiting enzyme of CoA biosynthesis. Exemplary pantothenate kinase variants resistant to feedback inhibition by CoA are well known in the art (Rock et al, *J Bacteriol* 185: 3410-5 (2003)) and are described in the below table.

| Protein | Accession # | GI number | Organism |
|---|---|---|---|
| coaA | AAC76952 | 1790409 | *Escherichia coli* |
| CAB1 | NP_010820.3 | 398366683 | *Saccharomyces cerevisiae* |
| KLLA0C00869g | XP_452233.1 | 50304555 | *Kluyveromyces lactis* |
| YALI0D25476g | XP_503275.1 | 50551601 | *Yarrowia lipolytica* |
| ANI_1_3272024 | XP_001400486.2 | 317028058 | *Aspergillus niger* |

Competing enzymes and pathways that divert acyl-CoA substrates from production of fatty alcohols, fatty aldehydes or fatty acids of the invention can also be attenuated or disrupted. Exemplary enzymes for attenuation include acyltransferases, carnitine shuttle enzymes and negative regulators of MI-FAE cycle or termination pathway enzymes.

Disruption or attenuation of acyltransferases that transfer acyl moieties from CoA to other acceptors such as ACP, glycerol, ethanol and others, can increase the availability of acyl-CoA for fatty alcohol, fatty aldehyde or fatty acid production. For example, Acyl-CoA:ACP transacylase (EC 2.3.1.38; 2.3.1.39) enzymes such asfabH (KASIII) of *E. coli* transfer acyl moieties from CoA to ACP. FabH is active on acetyl-CoA and butyryl-CoA (Prescott et al, *Adv. Enzymol. Relat. AreasMol,* 36:269-311 (1972)). Acetyl-CoA:ACP transacylase enzymes from *Plasmodium falciparum* and *Streptomyces avermitillis* have been heterologously expressed in *E. coli* (Lobo et al, *Biochem* 40:11955-64 (2001)). A synthetic KASIII (FabH) from *P. falciparum* expressed in a fabH-deficient *Lactococcus lactis* host was able to complement the native fadH activity (Du et al, AEM 76:3959-66 (2010)). The acetyl-CoA:ACP transacylase enzyme from *Spinacia oleracea* accepts other acyl-ACP molecules as substrates, including butyryl-ACP (Shimakata et al, *Methods Enzym* 122:53-9 (1986)). Malonyl-CoA:ACP transacylase enzymes include FabD of *E. coli* and *Brassica napsus* (Verwoert et al, *J Bacteriol,* 174:2851-7 (1992); Simon et al, *FEBS Lett* 435:204-6 (1998)). FabD of *B. napsus* was able to complementfabD-deficient *E. coli*. The multifunctional eukaryotic fatty acid synthase enzyme complexes (described herein) also catalyze this activity. Other exemplary acyltransferases include diacylglycerol acyltransferases such as LRO1 and DGA1 of *S. cerevisiae* and DGA1 and DGA2 of *Yarrowia lipolytica*, glycerolipid acyltransferase enzymes such as plsB of *E. coli* (GenBank: AAC77011.2, GI:87082362; Heath and Rock, *J Bacteriol* 180:1425-30 (1998)), sterol acyltransferases such as ARE1 and ARE2 of *S. cerevisiae*, ethanol acyltransferases (EEB 1, EHT1), putative acyltransferases (YMR210W) and others.

| Protein | GenBank ID | GI Number | Organism |
| --- | --- | --- | --- |
| fabH | AAC74175.1 | 1787333 | Escherichia coli |
| fadA | NP_824032.1 | 29829398 | Streptomyces avermitillis |
| fabH | AAC63960.1 | 3746429 | Plasmodium falciparum |
| Synthetic construct | ACX34097.1 | 260178848 | Plasmodium falciparum |
| fabH | CAL98359.1 | 124493385 | Lactococcus lactis |
| fabD | AAC74176.1 | 1787334 | Escherichia coli |
| fabD | CAB45522.1 | 5139348 | Brassica napsus |
| LRO1 | NP_014405.1 | 6324335 | Saccharomyces cerevisiae |
| DGA1 | NP_014888.1 | 6324819 | Saccharomyces cerevisiae |
| DGA1 | CAG79269.1 | 49649549 | Yarrowia lipolytica |
| DGA2 | XP_504700.1 | 50554583 | Yarrowia lipolytica |
| ARE1 | NP_009978.1 | 6319896 | Saccharomyces cerevisiae |
| ARE2 | NP_014416.1 | 6324346 | Saccharomyces cerevisiae |
| EEB1 | NP_015230.1 | 6325162 | Saccharomyces cerevisiae |
| EHT1 | NP_009736.3 | 398365307 | Saccharomyces cerevisiae |
| YMR210W | NP_013937.1 | 6323866 | Saccharomyces cerevisiae |
| ALE1 | NP_014818.1 | 6324749 | Saccharomyces cerevisiae |

Increasing production of fatty alcohols, fatty aldehydes or fatty acids may necessitate disruption or attenuation of enzymes involved in the trafficking of acetyl-CoA and acyl-CoA molecules from the cytosol to other compartments of the organism such as mitochondria, endoplasmic reticulum, proteoliposomes and peroxisomes. In these compartments, the acyl-CoA intermediate can be degraded or used as building blocks to synthesize fatty acids, cofactors and other byproducts.

Acetyl-CoA and acyl-CoA molecules localized in the cytosol can be transported into other cellular compartments with the aid of the carrier molecule carnitine via carnitine shuttles (van Roermund et al., EMBO J 14:3480-86 (1995)). Acyl-carnitine shuttles between cellular compartments have been characterized in yeasts such as Candida albicans (Strijbis et al, J Biol Chem 285:24335-46 (2010)). In these shuttles, the acyl moiety of acyl-CoA is reversibly transferred to carnitine by acylcarnitine transferase enzymes. Acetylcarnitine can then be transported across the membrane by organelle-specific acylcarnitine/carnitine translocase enzymes. After translocation, the acyl-CoA is regenerated by acetylcarnitine transferase. Enzymes suitable for disruption or attenuation include carnitine acyltransferase enzymes, acylcarnitine translocases, acylcarnitine carrier proteins and enzymes involved in carnitine biosynthesis.

Carnitine acetyltransferase (CAT, EC 2.3.1.7) reversibly links acetyl units from acetyl-CoA to the carrier molecule, carnitine. Candida albicans encodes three CAT isozymes: Cat2, Yat1 and Yat2 (Strijbis et al., J Biol Chem 285:24335-46 (2010)). Cat2 is expressed in both the mitochondrion and the peroxisomes, whereas Yat1 and Yat2 are cytosolic. The Cat2 transcript contains two start codons that are regulated under different carbon source conditions. The longer transcript contains a mitochondrial targeting sequence whereas the shorter transcript is targeted to peroxisomes. Cat2 of Saccharomyces cerevisiae and AcuJ of Aspergillus nidulans employ similar mechanisms of dual localization (Elgersma et al., EMBO J 14:3472-9 (1995); Hynes et al., Euk Cell 10:547-55 (2011)). The cytosolic CAT of A. nidulans is encoded byfacC. Other exemplary CAT enzymes are found in Rattus norvegicus and Homo sapiens (Cordente et al., Biochem 45:6133-41 (2006)). Exemplary carnitine acyltransferase enzymes (EC 2.3.1.21) are the Cpt1 and Cpt2 gene products of Rattus norvegicus (de Vries et al., Biochem 36:5285-92 (1997)).

| Protein | Accession # | GI number | Organism |
| --- | --- | --- | --- |
| Cat2 | AAN31660.1 | 23394954 | Candida albicans |
| Yat1 | AAN31659.1 | 23394952 | Candida albicans |
| Yat2 | XP_711005.1 | 68490355 | Candida albicans |
| Cat2 | CAA88327.1 | 683665 | Saccharomyces cerevisiae |
| Yat1 | AAC09495.1 | 456138 | Saccharomyces cerevisiae |
| Yat2 | NP_010941.1 | 6320862 | Saccharomyces cerevisiae |
| AcuJ | CBF69795.1 | 259479509 | Aspergillus nidulans |
| FacC | AAC82487.1 | 2511761 | Aspergillus nidulans |
| Crat | AAH83616.1 | 53733439 | Rattus norvegicus |
| Crat | P43155.5 | 215274265 | Homo sapiens |
| Cpt1 | AAB48046.1 | 1850590 | Rattus norvegicus |
| Cpt2 | AAB02339.1 | 1374784 | Rattus norvegicus |

Carnitine-acylcarnitine translocases can catalyze the bidirectional transport of carnitine and carnitine-fatty acid complexes. The Cact gene product provides a mechanism for transporting acyl-carnitine substrates across the mitochondrial membrane (Ramsay et al Biochim Biophys Acta 1546: 21-42 (2001)). A similar protein has been studied in humans (Sekoguchi et al., J Biol Chem 278:38796-38802 (2003)). The Saccharomyces cerevisiae mitochondrial carnitine carrier is Crc1 (van Roermund et al., supra; Palmieri et al., Biochimica et Biophys Acta 1757:1249-62 (2006)). The human carnitine translocase was able to complement a Crc1-deficient strain of S. cerevisiae (van Roermund et al., supra). Two additional carnitine translocases found in Drosophila melanogaster and Caenorhabditis elegans were also able to complement Crc1-deficient yeast (Oey et al., Mol Genet Metab 85:121-24 (2005)). Four mitochondrial carnitine/acetylcarnitine carriers were identified in Trypanosoma brucei based on sequence homology to the yeast and human transporters (Colasante et al., Mol Biochem Parasit 167: 104-117 (2009)). The carnitine transporter of Candida albicans was also identified by sequence homology. An additional mitochondrial carnitine transporter is the acuH gene product of Aspergillus nidulans, which is exclusively localized to the mitochondrial membrane (Lucas et al., FEMS Microbiol Lett 201:193-8 (2006)).

| Protein | GenBank ID | GI Number | Organism |
| --- | --- | --- | --- |
| Cact | P97521.1 | 2497984 | Rattus norvegicus |
| Cacl | NP_001034444.1 | 86198310 | Homo sapiens |
| CaO19.2851 | XP_715782.1 | 68480576 | Candida albicans |
| Crc1 | NP_014743.1 | 6324674 | Saccharomyces cerevisiae |
| Dif-1 | CAA88283.1 | 829102 | Caenorhabditis elegans |
| colt | CAA73099.1 | 1944534 | Drosophila melanogaster |
| Tb11.02.2960 | EAN79492.1 | 70833990 | Trypanosoma brucei |
| Tb11.03.0870 | EAN79007.1 | 70833505 | Trypanosoma brucei |
| Tb11.01.5040 | EAN80288.1 | 70834786 | Trypanosoma brucei |
| Tb927.8.5810 | AAX69329.1 | 62175181 | Trypanosoma brucei |
| acuH | CAB44434.1 | 5019305 | Aspergillus nidulans |

Transport of carnitine and acylcarnitine across the peroxisomal membrane has not been well-characterized. Specific peroxisomal acylcarnitine carrier proteins in yeasts have not been identified to date. However, mitochonidrial camitine translocases can also function in the peroxisomal transport of camitine and acetylcarnitine. Experimental evidence suggests that the OCTN3 protein of *Mus musculus* is a peroxisomal camitine/acylcarnitine translocase.

Yet another possibility is that acyl-CoA or acyl-camitine are transported across the peroxisomal or mitochondrial membranes by an acyl-CoA transporter such as the Pxa1 and Pxa2 ABC transporter of *Saccharomyces cerevisiae* or the ALDP ABC transporter of *Homo sapiens* (van Roermund et al., *FASEB J* 22:4201-8 (2008)). Pxa1 and Pxa2 (Pat1 and Pat2) form a heterodimeric complex in the peroxisomal membrane and catalyze the ATP-dependent transport of fatty acyl-CoA esters into the peroxisome (Verleur et al., *Eur J Biochem* 249: 657-61 (1997)). The mutant phenotype of a pxa1/pxa2 deficient yeast can be rescued by heterologous expression of ALDP, which was shown to transport a range of acyl-CoA substrates (van Roermund et al., *FASEB J* 22:4201-8 (2008)). Deletion of the Pxa12 transport system, in tandem with deletion of the peroxisomal fatty acyl-CoA synthetase (Faa2) abolished peroxisomal beta-oxidation in *S. cerevisiae*. Yet another strategy for reducing transport of pathway intermediates or products into the peroxisome is to attenuate or eliminate peroxisomal function, by interfering with systems involved in peroxisomal biogenesis. An exemplary target is Pex10 of *Yarrowia lipolytica* and homologs.

| Protein | Accession # | GI number | Organism |
| --- | --- | --- | --- |
| OCTN3 | BAA78343.1 | 4996131 | Mus musculus |
| Pxa1 | AAC49009.1 | 619668 | Saccharomyces cerevisiae |
| Pxa2 | AAB51597.1 | 1931633 | Saccharomyces cerevisiae |
| Faa2 | NP_010931.3 | 398364331 | Saccharomyces cerevisiae |
| ALDP | NP_000024.2 | 7262393 | Homo sapiens |
| Pex10 | BAA99413.1 | 9049374 | Yarrowia lipolytica |

Carnitine biosynthetic pathway enzymes are also suitable candidates for disruption or attenuation. In *Candida albicans*, for example, carnitine is synthesized from trimethyl-L-lysine in four enzymatic steps (Strijbis et al., *FASEB J* 23:2349-59 (2009)). The carnitine pathway precursor, trimethyllysine (TML), is produced during protein degradation. TML dioxygenase (CaO13.4316) hydroxylates TML to form 3-hydroxy-6-N-trimethylly sine. A pyridoxal-5'-phoshpate dependent aldolase (CaO19.6305) then cleaves HTML into 4-trimethylaminobutyraldehyde. The 4-trimethylaminobutyraldehyde is subsequently oxidized to 4-trimethylaminobutyrate by a dehydrogenase (CaO19.6306). In the final step, 4-trimethylaminobutyrate is hydroxylated to form carnitine by the gene product of CaO19.7131. Flux through the carnitine biosynthesis pathway is limited by the availability of the pathway substrate and very low levels of carnitine seem to be sufficient for normal carnitine shuttle activity (Strejbis et al., *IUBMB Life* 62:357-62 (2010)).

| Protein | Accession # | GI number | Organism |
| --- | --- | --- | --- |
| CaO19.4316 | XP_720623.1 | 68470755 | Candida albicans |
| CaO19.6305 | XP_711090.1 | 68490151 | Candida albicans |
| CaO19.6306 | XP_711091.1 | 68490153 | Candida albicans |
| CaO19.7131 | XP_715182.1 | 68481628 | Candida albicans |

Carbon flux towards production of fatty alcohols, fatty aldehydes or fatty acids can be improved by deleting or attenuating competing pathways. Typical fermentation products of yeast include ethanol, glycerol and $CO_2$. The elimination or reduction of these byproducts can be accomplished by approaches described herein. For example, carbon loss due to respiration can be reduced. Other potential byproducts include lactate, acetate, formate, fatty acids and amino acids.

The conversion of acetyl-CoA into ethanol can be detrimental to the production of fatty alcohols, fatty aldehyes or fatty acids because the conversion process can draw away both carbon and reducing equivalents from the MI-FAE cycle and termination pathway. Ethanol can be formed from pyruvate in two enzymatic steps catalyzed by pyruvate decarboxylase and ethanol dehydrogenase. *Saccharomyces cerevisiae* has three pyruvate decarboxylases (PDC1, PDC5 and PDC6). PDC1 is the major isozyme and is strongly expressed in actively fermenting cells. PDC5 also functions during glycolytic fermentation, but is expressed only in the absence of PDC1 or under thiamine limiting conditions. PDC6 functions during growth on nonfermentable carbon sources. Deleting PDC1 and PDC5 can reduce ethanol production significantly; however these deletions can lead to mutants with increased PDC6 expression. Deletion of all three eliminates ethanol formation completely but also can cause a growth defect because of inability of the cells to form sufficient acetyl-CoA for biomass formation. This, however, can be overcome by evolving cells in the presence of reducing amounts of $C_2$ carbon source (ethanol or acetate) (van Maris et al, *AEM* 69:2094-9 (2003)). It has also been reported that deletion of the positive regulator PDC2 of pyruvate decarboxylases PDC1 and PDC5, reduced ethanol formation to ~10% of that made by wild-type (Hohmann et al, *Mol Gen Genet* 241:657-66 (1993)). Protein sequences and identifiers of PDC enzymes are listed in Example II.

Alternatively, alcohol dehydrogenases that convert acetaldehyde into ethanol and/or other short chain alcohol dehydrogenases can be disrupted or attenuated to provide carbon and reducing equivalents for the MI-FAE cycle or termination pathway. To date, seven alcohol dehydrogenases, ADHI-ADHVII, have been reported in *S. cerevisiae* (de Smidt et al, *FEMS Yeast Res* 8:967-78 (2008)). ADH1 (GI: 1419926) is the key enzyme responsible for reducing acetaldehyde to ethanol in the cytosol under anaerobic conditions. It has been reported that a yeast strain deficient in ADH1 cannot grow anaerobically because an active respiratory chain is the only alternative path to regenerate NADH and lead to a net gain of ATP (Drewke et al, *J Bacteriol* 172:3909-17 (1990)). This enzyme is an ideal candidate for downregulation to limit ethanol production. ADH2 is severely repressed in the presence of glucose. In *K. lactis*, two NAD-dependent cytosolic alcohol dehydrogenases have been identified and characterized. These genes also show activity for other aliphatic alcohols. The genes ADH1 (GI: 113358) and ADHII (GI:51704293) are preferentially expressed in glucose-grown cells (Bozzi et al, *Biochim Biophys Acta* 1339:133-142 (1997)). Cytosolic alcohol dehydrogenases are encoded by ADH1 (GI:608690) in *C. albicans*, ADH1 (GI:3810864) in *S. pombe*, ADH1 (GI:5802617) in *Y. lipolytica*, ADH1 (GI:2114038) and ADHII (GI:2143328) in *Pichia stipitis* or *Scheffersomyces stipitis* (Passoth et al, *Yeast* 14:1311-23 (1998)). Candidate alcohol dehydrogenases are shown the table below.

| Protein | GenBank ID | GI number | Organism |
|---|---|---|---|
| SADH | BAA24528.1 | 2815409 | *Candida parapsilosis* |
| ADH1 | NP_014555.1 | 6324486 | *Saccharomyces cerevisiae* s288c |
| ADH2 | NP_014032.1 | 6323961 | *Saccharomyces cerevisiae* s288c |
| ADH3 | NP_013800.1 | 6323729 | *Saccharomyces cerevisiae* s288c |
| ADH4 | NP_011258.2 | 269970305 | *Saccharomyces cerevisiae* s288c |
| ADH5 (SFA1) | NP_010113.1 | 6320033 | *Saccharomyces cerevisiae* s288c |
| ADH6 | NP_014051.1 | 6323980 | *Saccharomyces cerevisiae* s288c |
| ADH7 | NP_010030.1 | 6319949 | *Saccharomyces cerevisiae* s288c |
| adhP | CAA44614.1 | 2810 | *Kluyveromyces lactis* |
| ADH1 | P20369.1 | 113358 | *Kluyveromyces lactis* |
| ADH2 | CAA45739.1 | 2833 | *Kluyveromyces lactis* |
| ADH3 | P49384.2 | 51704294 | *Kluyveromyces lactis* |
| ADH1 | CAA57342.1 | 608690 | *Candida albicans* |
| ADH2 | CAA21988.1 | 3859714 | *Candida albicans* |
| SAD | XP_712899.1 | 68486457 | *Candida albicans* |
| ADH1 | CAA21782.1 | 3810864 | *Schizosaccharomyces pombe* |
| ADH1 | AAD51737.1 | 5802617 | *Yarrowia lipolytica* |
| ADH2 | AAD51738.1 | 5802619 | *Yarrowia lipolytica* |
| ADH3 | AAD51739.1 | 5802621 | *Yarrowia lipolytica* |
| AlcB | AAX53105.1 | 61696864 | *Aspergillus niger* |
| ANI_1_282024 | XP_001399347.1 | 145231748 | *Aspergillus niger* |
| ANI_1_126164 | XP_001398574.2 | 317037131 | *Aspergillus niger* |
| ANI_1_1756104 | XP_001395505.2 | 317033815 | *Aspergillus niger* |
| ADH2 | CAA73827.1 | 2143328 | *Scheffersomyces stipitis* |

Attenuation or disruption of one or more glycerol-3-phosphatase or glycerol-3-phosphate (G3P) dehydrogenase enzymes can eliminate or reduce the formation of glycerol, and thereby conserving carbon and reducing equivalents for production of fatty alcohols, fatty aldehydes or fatty acids.

G3P phosphatase catalyzes the hydrolysis of G3P to glycerol. Enzymes with this activity include the glycerol-1-phosphatase (EC 3.1.3.21) enzymes of *Saccharomyces cerevisiae* (GPP1 and GPP2), *Candida albicans* and *Dunaleilla parva* (Popp et al, *Biotechnol Bioeng* 100:497-505 (2008); Fan et al, *FEMS Microbiol Lett* 245:107-16 (2005)). The *D. parva* gene has not been identified to date. These and additional G3P phosphatase enzymes are shown in the table below.

| Protein | GenBank ID | GI Number | Organism |
|---|---|---|---|
| GPP1 | DAA08494.1 | 285812595 | *Saccharomyces cerevisiae* |
| GPP2 | NP_010984.1 | 6320905 | *Saccharomyces cerevisiae* |
| GPP1 | XP_717809.1 | 68476319 | *Candida albicans* |

-continued

| Protein | GenBank ID | GI Number | Organism |
|---|---|---|---|
| KLLA0C08217g | XP_452565.1 | 50305213 | *Kluyveromyces lactis* |
| KLLA0C11143g | XP_452697.1 | 50305475 | *Kluyveromyces lactis* |
| ANI_1_380074 | XP_001392369.1 | 145239445 | *Aspergillus niger* |
| ANI_1_444054 | XP_001390913.2 | 317029125 | *Aspergillus niger* |

*S. cerevisiae* has three G3P dehydrogenase enzymes encoded by GPD1 and GDP2 in the cytosol and GUT2 in the mitochondrion. GPD2 is known to encode the enzyme responsible for the majority of the glycerol formation and is responsible for maintaining the redox balance under anaerobic conditions. GPD1 is primarily responsible for adaptation of *S. cerevisiae* to osmotic stress (Bakker et al., *FEMS Microbiol Rev* 24:15-37 (2001)). Attenuation of GPD1, GPD2 and/or GUT2 will reduce glycerol formation. GPD1 and GUT2 encode G3P dehydrogenases in *Yarrowia lipolytica* (Beopoulos et al, *AEM* 74:7779-89 (2008)). GPD1 and GPD2 encode for G3P dehydrogenases in *S. pombe*. Similarly, G3P dehydrogenase is encoded by CTRG_02011 in *Candida tropicalis* and a gene represented by GI:20522022 in *Candida albicans*.

| Protein | GenBank ID | GI number | Organism |
|---|---|---|---|
| GPD1 | CAA98582.1 | 1430995 | *Saccharomyces cerevisiae* |
| GPD2 | NP_014582.1 | 6324513 | *Saccharomyces cerevisiae* |

-continued

| Protein | GenBank ID | GI number | Organism |
|---|---|---|---|
| GUT2 | NP_012111.1 | 6322036 | *Saccharomyces cerevisiae* |
| GPD1 | CAA22119.1 | 6066826 | *Yarrowia lipolytica* |
| GUT2 | CAG83113.1 | 49646728 | *Yarrowia lipolytica* |
| GPD1 | CAA22119.1 | 3873542 | *Schizosaccharomyces pombe* |
| GPD2 | CAA91239.1 | 1039342 | *Schizosaccharomyces pombe* |
| ANI_1_786014 | XP_001389035.2 | 317025419 | *Aspergillus niger* |
| ANI_1_1768134 | XP_001397265.1 | 145251503 | *Aspergillus niger* |
| KLLA0C04004g | XP_452375.1 | 50304839 | *Kluyveromyces lactis* |
| CTRG_02011 | XP_002547704.1 | 255725550 | *Candida tropicalis* |
| GPD1 | XP_714362.1 | 68483412 | *Candida albicans* |
| GPD2 | XP_713824.1 | 68484586 | *Candida albicans* |

Enzymes that form acid byproducts such as acetate, formate and lactate can also be attenuated or disrupted. Such enzymes include acetate kinase, phosphotransacetylase and pyruvate oxidase. Disruption or attenuation of pyruvate formate lyase and formate dehydrogenase could limit formation of formate and carbon dioxide. These enzymes are described in further detail in Example II.

Alcohol dehydrogenases that convert pyruvate to lactate are also candidates for disruption or attenuation. Lactate dehydrogenase enzymes include ldhA of *E. coli* and ldh from *Ralstonia eutropha* (Steinbuchel and Schlegel, *Eur. J Biochem.* 130:329-334 (1983)). Other alcohol dehydrogenases listed above may also exhibit LDH activity.

| Protein | GenBank ID | GI number | Organism |
|---|---|---|---|
| ldhA | NP_415898.1 | 16129341 | *Escherichia coli* |
| Ldh | YP_725182.1 | 113866693 | *Ralstonia eutropha* |

Tuning down activity of the mitochondrial pyruvate dehydrogenase complex will limit flux into the mitochondrial TCA cycle. Under anaerobic conditions and in conditions where glucose concentrations are high in the medium, the capacity of this mitochondrial enzyme is very limited and there is no significant flux through it. However, in some embodiments, this enzyme can be disrupted or attenuated to increase fatty alcohol, fatty aldehyde or fatty acid production. Exemplary pyruvate dehydrogenase genes include PDB 1, PDA1, LAT1 and LPD1. Accession numbers and homologs are listed in Example II.

Another strategy for reducing flux into the TCA cycle is to limit transport of pyruvate into the mitochondria by tuning down or deleting the mitochondrial pyruvate carrier. Transport of pyruvate into the mitochondria in *S. cerevisiae* is catalyzed by a heterocomplex encoded by MPC1 and MPC2 (Herzig et al, *Science* 337:93-6 (2012); Bricker et al, *Science* 337:96-100 (2012)). *S. cerevisiae* encodes five other putative monocarboxylate transporters (MCH1-5), several of which may be localized to the mitochondrial membrane (Makuc et al, *Yeast* 18:1131-43 (2001)). NDT1 is another putative pyruvate transporter, although the role of this protein is disputed in the literature (Todisco et al, *J Biol Chem* 20:1524-31 (2006)). Exemplary pyruvate and monocarboxylate transporters are shown in the table below:

| Protein | GenBank ID | GI number | Organism |
|---|---|---|---|
| MPC1 | NP_011435.1 | 6321358 | *Saccharomyces cerevisiae* |
| MPC2 | NP_012032.1 | 6321956 | *Saccharomyces cerevisiae* |
| MPC1 | XP_504811.1 | 50554805 | *Yarrowia lipolytica* |
| MPC2 | XP_501390.1 | 50547841 | *Yarrowia lipolytica* |
| MPC1 | XP_719951.1 | 68471816 | *Candida albicans* |
| MPC2 | XP_716190.1 | 68479656 | *Candida albicans* |
| MCH1 | NP_010229.1 | 6320149 | *Saccharomyces cerevisiae* |
| MCH2 | NP_012701.2 | 330443640 | *Saccharomyces cerevisiae* |
| MCH3 | NP_014274.1 | 6324204 | *Saccharomyces cerevisiae* |
| MCH5 | NP_014951.2 | 330443742 | *Saccharomyces cerevisiae* |
| NDT1 | NP_012260.1 | 6322185 | *Saccharomyces cerevisiae* |
| ANI_1_1592184 | XP_001401484.2 | 317038471 | *Aspergillus niger* |
| CaJ7_0216 | XP_888808.1 | 77022728 | *Candida albicans* |
| YALI0E16478g | XP_504023.1 | 50553226 | *Yarrowia lipolytica* |
| KLLA0D14036g | XP_453688.1 | 50307419 | *Kluyveromyces lactis* |

Disruption or attenuation of enzymes that synthesize malonyl-CoA and fatty acids can increase the supply of carbon available for fatty alcohol, fatty aldehyde or fatty acid biosynthesis from acetyl-CoA. Exemplary enzymes for disruption or attenuation include fatty acid synthase, acetyl-CoA carboxylase, biotin:apoenzyme ligase, acyl carrier protein, thioesterase, acyltransferases, ACP malonyltransferase, fatty acid elongase, acyl-CoA synthetase, acyl-CoA transferase and acyl-CoA hydrolase.

Another strategy to reduce fatty acid biosynthesis is expression or overexpression of regulatory proteins which repress fatty acid forming genes. Acetyl-CoA carboxylase (EC 6.4.1.2) catalyzes the first step of fatty acid biosynthesis in many organisms: the ATP-dependent carboxylation of acetyl-CoA to malonyl-CoA. This enzyme utilizes biotin as a cofactor. Exemplary ACC enzymes are encoded by accABCD of E. coli (Davis et al, J Biol Chem 275:28593-8 (2000)), ACC1 of Saccharomyces cerevisiae and homologs (Sumper et al, Methods Enzym 71:34-7 (1981)). The mitochondrial acetyl-CoA carboxylase of S. cerevisiae is encoded by HFA1. Acetyl-CoA carboxylase holoenzyme formation requires attachment of biotin by a biotin:apoprotein ligase such as BPL1 of S. cerevisiae.

| Protein | GenBank ID | GI Number | Organism |
|---|---|---|---|
| ACC1 | CAA96294.1 | 1302498 | Saccharomyces cerevisiae |
| KLLA0F06072g | XP_455355.1 | 50310667 | Kluyveromyces lactis |
| ACC1 | XP_718624.1 | 68474502 | Candida albicans |
| YALI0C11407p | XP_501721.1 | 50548503 | Yarrowia lipolytica |
| ANI_1_1724104 | XP_001395476.1 | 145246454 | Aspergillus niger |
| accA | AAC73296.1 | 1786382 | Escherichia coli |
| accB | AAC76287.1 | 1789653 | Escherichia coli |
| accC | AAC76288.1 | 1789654 | Escherichia coli |
| accD | AAC75376.1 | 1788655 | Escherichia coli |
| HFA1 | NP_013934.1 | 6323863 | Saccharomyces cerevisiae |
| BPL1 | NP_010140.1 | 6320060 | Saccharomyces cerevisiae |

Proteins participating in the synthesis of fatty acids are shown below. The fatty acid synthase enzyme complex of yeast is composed of two multifunctional subunits, FAS1 and FAS2, which together catalyze the net conversion of acetyl-CoA and malonyl-CoA to fatty acids (Lomakin et al, Cell 129: 319-32 (2007)). Additional proteins associated with mitochondrial fatty acid synthesis include OAR1, Mct1, ETR1, ACP1 and PPT2. ACP1 is the mitochondrial acyl carrier protein and PPT2 encodes a phosphopantetheine transferase, which pantetheinylates mitochondrial ACP and is required for fatty acid biosynthesis in the mitochondria (Stuible et al, J Biol Chem: 273: 22334-9 (1998)). A non-genetic strategy for reducing activity of fatty acid synthases is to add an inhibitor such as cerulenin. Global regulators of lipid biosynthesis can also be altered to tune down endogenous fatty acid biosynthesis pathways during production of long chain alcohols or related products. An exemplary global regulator is SNF1 of Yarrowia lipolytica and Saccharomyces cerevisiae.

| Protein | GenBank ID | GI Number | Organism |
|---|---|---|---|
| FAS1 | NP_012739.1 | 6322666 | Saccharomyces cerevisiae |
| FAS2 | NP_015093.1 | 6325025 | Saccharomyces cerevisiae |
| FAS1 | XP_451653.1 | 50303423 | Kluyveromyces lactis |
| FAS2 | XP_452914.1 | 50305907 | Kluyveromyces lactis |
| FAS1 | XP_716817.1 | 68478392 | Candida albicans |
| FAS2 | XP_723014.1 | 68465892 | Candida albicans |
| FAS1 | XP_500912.1 | 50546885 | Yarrowia lipolytica |
| FAS2 | XP_501096.1 | 50547253 | Yarrowia lipolytica |
| FAS1 | XP_001393490.2 | 317031809 | Aspergillus niger |
| FAS2 | XP_001388458.1 | 145228299 | Aspergillus niger |
| OAR1 | NP_012868.1 | 6322795 | Saccharomyces cerevisiae |
| MCT1 | NP_014864.4 | 398365823 | Saccharomyces cerevisiae |
| ETR1 | NP_009582.1 | 6319500 | Saccharomyces cerevisiae |
| ACP1 | NP_012729.1 | 6322656 | Saccharomyces cerevisiae |
| PPT2 | NP_015177.2 | 37362701 | Saccharomyces cerevisiae |
| SNF1 | CAG80498.1 | 49648180 | Yarrowia lipolytica |
| SNF1 | P06782.1 | 134588 | Saccharomyces cerevisiae |

Disruption or attenuation of elongase enzymes which convert acyl-CoA substrates to longer-chain length fatty acids can also be used to increase fatty alcohol, fatty aldehyde or fatty acid production. Elongase enzymes are found in compartments such as the mitochondria, endoplasmic reticulum, proteoliposomes and peroxisomes. For example, some yeast such as S. cerevisiae are able to synthesize long-chain fatty acids of chain length C16 and higher via a mitochondrial elongase which accepts exogenous or endogenous acyl-CoA substrates (Bessoule et al, FEBS Lett 214: 158-162 (1987)). This system requires ATP for activity. The endoplasmic reticulum also has an elongase system for synthesizing very long chain fatty acids (C18+) from acyl-CoA substrates of varying lengths (Kohlwein et al, Mol Cell Biol 21:109-25 (2001)). Genes involved in this system include TSC13, ELO2 and ELO3. ELO1 catalyzes the elongation of C12 acyl-CoAs to C16-C18 fatty acids.

| Protein | Accession # | GI number | Organism |
|---|---|---|---|
| ELO2 | NP_009963.1 | 6319882 | Saccharomyces cerevisiae |
| ELO3 | NP_013476.3 | 398366027 | Saccharomyces cerevisiae |
| TSC13 | NP_010269.1 | 6320189 | Saccharomyces cerevisiae |
| ELO1 | NP_012339.1 | 6322265 | Saccharomyces cerevisiae |

Native enzymes converting acyl-CoA pathway intermediates to acid byproducts can also reduce fatty alcohol, fatty aldehyde or fatty acid yield. For example, CoA hydrolases, transferases and synthetases can act on acyl-CoA intermediates to form short-, medium- or long chain acids. Disruption or attenuation of endogenous CoA hydrolases, CoA transerases and/or reversible CoA synthetases can be used to increase fatty alcohol, fatty aldehyde or fatty acid yield. Exemplary enzymes are shown in the table below.

| Protein | GenBank ID | GI number | Organism |
|---|---|---|---|
| Tes1 | NP_012553.1 | 6322480 | Saccharomyces cerevisiae s288c |
| ACH1 | NP_009538.1 | 6319456 | Saccharomyces cerevisiae s288c |
| EHD3 | NP_010321.1 | 6320241 | Saccharomyces cerevisiae s288c |
| YALI0F14729p | XP_505426.1 | 50556036 | Yarrowia lipolytica |
| YALI0E30965p | XP_504613.1 | 50554409 | Yarrowia lipolytica |
| KLLA0E16523g | XP_454694.1 | 50309373 | Kluyveromyces lactis |
| KLLA0E10561g | XP_454427.1 | 50308845 | Kluyveromyces lactis |
| ACH1 | P83773.2 | 229462795 | Candida albicans |
| CaO19.10681 | XP_714720.1 | 68482646 | Candida albicans |
| ANI_1_318184 | XP_001401512.1 | 145256774 | Aspergillus niger |
| ANI_1_1594124 | XP_001401252.2 | 317035188 | Aspergillus niger |
| tesB | NP_414986.1 | 16128437 | Escherichia coli |
| tesB | NP_355686.2 | 159185364 | Agrobacterium tumefaciens |
| atoA | 2492994 | P76459.1 | Escherichia coli |
| atoD | 2492990 | P76458.1 | Escherichia coli |

Enzymes that favor the degradation of products or MI-FAE cycle or termination pathway intermediates can also be disrupted or attenuated. Examples include aldehyde dehydrogenases, aldehyde decarbonylases, oxidative alcohol dehydrogenases, and irreversible fatty acyl-CoA degrading enzymes.

For production of fatty alcohols, fatty aldehydes or fatty acids of the invention, deletion or attenuation of non-specific aldehyde dehydrogenases can improve yield. For production of fatty acids, expression of such an enzyme may improve product formation. Such enzymes can, for example, convert acetyl-CoA into acetaldehyde, fatty aldehydes to fatty acids, or fatty alcohols to fatty acids. Acylating aldehyde dehydrogenase enzymes are described in Example I. Acid-forming aldehyde dehydrogenase are described in Examples III and IX.

The pathway enzymes that favor the reverse direction can also be disrupted or attenuated, if they are detrimental to fatty alcohol, fatty aldehyde or fatty acid production. An example is long chain alcohol dehydrogenases (EC 1.1.1.192) that favor the oxidative direction. Exemplary long chain alcohol dehydrogenases are ADH1 and ADH2 of Geobacillus thermodenitrificans, which oxidize alcohols up to a chain length of C30 (Liu et al, Physiol Biochem 155:2078-85 (2009)). These and other exemplary fatty alcohol dehydrogenase enzymes are listed in Examples I and II. If an alcohol-forming acyl-CoA reductase is utilized for fatty alcohol, fatty aldehyde or fatty acid biosynthesis, deletion of endogenous fatty alcohol dehydrogenases will substantially reduce backflux.

Beta-oxidation enzymes may be reversible and operate in the direction of acyl-CoA synthesis. However, if they are irreversible or strongly favored in the degradation direction they are candidates for disruption or attenuation. An enzyme that fall into this category includes FOX2 of S. cerevisiae, a multifunctional enzyme with 3-hydroxyacyl-CoA dehydrogenase and enoyl-CoA hydratase activity (Hiltunen et al, J Biol Chem 267: 6646-6653 (1992)). Additional genes include degradative thiolases such as POT1 and acyl-CoA dehydrogenases that utilize cofactors other than NAD(P)H (EG. EC 1.3.8.-) such as fadE of E. coli.

| Protein | GenBank ID | GI Number | Organism |
|---|---|---|---|
| POT1 | NP_012106.1 | 6322031 | Saccharomyces cerevisiae |
| FOX2 | NP_012934.1 | 6322861 | Saccharomyces cerevisiae |
| fadE | AAC73325.2 | 87081702 | Escherichia coli |

Fatty acyl-CoA oxidase enzymes such as POX1 of S. cerevisiae catalyze the oxygen-dependent oxidation of fatty acyl-CoA substrates. Enzymes with this activity can be disrupted or attenuated, if they are expressed under fatty alcohol, fatty aldehyde or fatty acid producing conditions. POX1 (EC 1.3.3.6) genes and homologs are shown in the table below. POX1 is subject to regulation by OAF 1, which also activates genes involved in peroxisomal beta-oxidation, organization and biogenesis (Luo et al, J Biol Chem 271: 12068-75 (1996)). Regulators with functions similar to OAF 1, and peroxisomal fatty acid transporters PXA1 and PXA2 are also candidates for deletion.

| Protein | GenBank ID | GI Number | Organism |
|---|---|---|---|
| POX1 | NP_011310.1 | 6321233 | Saccharomyces cerevisiae |
| OAF1 | NP_009349.3 | 330443370 | Saccharomyces cerevisiae |
| PXA1 | NP_015178.1 | 6325110 | Saccharomyces cerevisiae |
| PXA2 | NP_012733.1 | 6322660 | Saccharomyces cerevisiae |
| YALI0F10857g | XP_505264.1 | 50555712 | Yarrowia lipolytica |
| YALI0D24750p | XP_503244.1 | 50551539 | Yarrowia lipolytica |
| YALI0E32835p | XP_504703.1 | 50554589 | Yarrowia lipolytica |
| YALI0E06567p | XP_503632.1 | 50552444 | Yarrowia lipolytica |
| YALI0E27654p | XP_504475.1 | 50554133 | Yarrowia lipolytica |
| YALI0C23859p | XP_502199.1 | 50549457 | Yarrowia lipolytica |
| POX | XP_455532.1 | 50311017 | Kluyveromyces lactis |
| POX104 | XP_721610.1 | 68468582 | Candida albicans |
| POX105 | XP_717995.1 | 68475844 | Candida albicans |
| POX102 | XP_721613.1 | 68468588 | Candida albicans |

Another candidate for disruption or attenuation is an acyl-CoA binding protein. The acyl binding protein ACB1 of *S. cerevisiae*, for example, binds acyl-CoA esters and shuttles them to acyl-CoA utilizing processes (Schjerling et al, J Biol Chem 271: 22514-21 (1996)). Deletion of this protein did not impact growth rate and lead to increased accumulation of longer-chain acyl-CoA molecules. Acyl-CoA esters are involved in diverse cellular processes including lipid biosynthesis and homeostatis, signal transduction, growth regulation and cell differentiation (Rose et al, PNAS USA 89: 11287-11291 (1992)).

| Protein | GenBank ID | GI Number | Organism |
|---|---|---|---|
| ACB1 | P31787.3 | 398991 | Saccharomyces cerevisiae |
| KLLA0B05643g | XP_451787.2 | 302309983 | Kluyveromyces lactis |
| YALI0E23185g | XP_002143080.1 | 210076210 | Yarrowia lipolytica |
| ANI_1_1084034 | XP_001390082.1 | 145234867 | Aspergillus niger |

To achieve high yields of fatty alcohols, fatty aldehydes or fatty acids, it is desirable that the host organism can supply the cofactors required by the MI-FAE cycle and/or the termination pathway in sufficient quantities. In several organisms, in particular eukaryotic organisms, such as several *Saccharomyces, Kluyveromyces, Candida, Aspergillus*, and *Yarrowia* species, NADH is more abundant than NADPH in the cytosol as it is produced in large quantities by glycolysis. NADH can be made even more abundant by converting pyruvate to acetyl-CoA by means of heterologous or native NAD-dependant enzymes such as NAD-dependant pyruvate dehydrogenase, NAD-dependant formate dehydrogenase, NADH:ferredoxin oxidoreductase, or NAD-dependant acylating acetylaldehyde dehydrogenase in the cytosol. Given the abundance of NADH in the cytosol of most organisms, it can be beneficial for all reduction steps of the MI-FAE cycle and/or terminatio pathway to accept NADH as the reducing agent preferentially over other reducing agents such as NADPH. High yields of fatty alcohols, fatty aldehydes or fatty acids can thus be accomplished by, for example: 1) identifying and implementing endogenous or exogenous MI-FAE cycle and/or termination pathway enzymes with a stronger preference for NADH than other reducing equivalents such as NADPH; 2) attenuating one or more endogenous MI-FAE cycle or termination pathway enzymes that contribute NADPH-dependant reduction activity; 3) altering the cofactor specificity of endogenous or exogenous MI-FAE cycle or termination pathway enzymes so that they have a stronger preference for NADH than their natural versions; or 4) altering the cofactor specificity of endogenous or exogenous MI-FAE cycle or termination pathway enzymes so that they have a weaker preference for NADPH than their natural versions.

Strategies for engineering NADH-favoring MI-FAE cycle and/or termination pathways are described in further detail in Example V. Methods for changing the cofactor specificity of an enzyme are well known in the art, and an example is described in Example VI.

If one or more of the MI-FAE cycle and/or termination pathway enzymes utilizes NADPH as the cofactor, it can be beneficial to increase the production of NADPH in the host organism. In particular, if the MI-FAE cycle and/or termination pathway is present in the cytosol of the host organism, methods for increasing NADPH production in the cytosol can be beneficial. Several approaches for increasing cytosolic production of NADPH can be implemented including channeling an increased amount of flux through the oxidative branch of the pentose phosphate pathway relative to wild-type, channeling an increased amount of flux through the Entner Doudoroff pathway relative to wild-type, introducing a soluble or membrane-bound transhydrogenase to convert NADH to NADPH, or employing NADP-dependant versions of the following enzymes: phosphorylating or non-phosphorylating glyceraldehyde-3-phosphate dehydrogenase, pyruvate dehydrogenase, formate dehydrogenase, or acylating acetylaldehyde dehydrogenase. These activities can be augmented by disrupting or attenuating native NAD-dependant enzymes including glyceraldehyde-3-phosphate dehydrogenase, pyruvate dehydrogenase, formate dehydrogenase, or acylating acetylaldehyde dehydrogenase. Strategies for engineering increased NADPH availability are described in Example VII.

Synthesis of fatty alcohols, fatty aldehyes or fattyc acids in the cytosol can be dependent upon the availability of sufficient carbon and reducing equivalents. Therefore, without being bound to any particular theory of operation, increasing the redox ratio of NAD(P)H to NAD(P) can help drive the MI-FAE cycle and/or termination pathway in the forward direction. Methods for increasing the redox ratio of NAD(P)H to NAD(P) include limiting respiration, attenuating or disrupting competing pathways that produce reduced byproducts such as ethanol and glycerol, attenuating or eliminating the use of NADH by NADH dehydrogenases, and attenuating or eliminating redox shuttles between compartments.

One exemplary method to provide an increased number of reducing equivalents, such as NAD(P)H, for enabling the formation of fatty alcohols, fatty aldehydes or fatty acids is to constrain the use of such reducing equivalents during respiration. Respiration can be limited by: reducing the availability of oxygen, attenuating NADH dehydrogenases and/or cytochrome oxidase activity, attenuating G3P dehydrogenase, and/or providing excess glucose to Crabtree positive organisms.

Restricting oxygen availability by culturing the non-naturally occurring eukaryotic organisms in a fermenter is one example for limiting respiration and thereby increasing the ratio of NAD(P)H to NAD(P). The ratio of NAD(P)H/NAD(P) increases as culture conditions become more anaerobic, with completely anaerobic conditions providing the highest ratios of the reduced cofactors to the oxidized ones. For example, it has been reported that the ratio of NADH/NAD=0.02 in aerobic conditions and 0.75 in anaerobic conditions in *E. coli* (de Graes et al, J Bacteriol 181: 2351-57 (1999)).

Respiration can also be limited by reducing expression or activity of NADH dehydrogenases and/or cytochrome oxidases in the cell under aerobic conditions. In this case, respiration can be limited by the capacity of the electron transport chain. Such an approach has been used to enable anaerobic metabolism of *E. coli* under completely aerobic conditions (Portnoy et al, *AEM* 74:7561-9 (2008)). *S. cerevisiae* can oxidize cytosolic NADH directly using external NADH dehydrogenases, encoded by NDE1 and NDE2. One such NADH dehydrogenase in *Yarrowia lipolytica* is encoded by NDH2 (Kerscher et al, *J Cell Sci* 112:2347-54 (1999)). These and other NADH dehydrogenase enzymes are listed in the table below.

| Protein | GenBank ID | GI number | Organism |
| --- | --- | --- | --- |
| NDE1 | NP_013865.1 | 6323794 | Saccharomyces cerevisiae s288c |
| NDE2 | NP_010198.1 | 6320118 | Saccharomyces cerevisiae s288c |
| NDH2 | AJ006852.1 | 3718004 | Yarrowia lipolytica |
| ANI_1_610074 | XP_001392541.2 | 317030427 | Aspergillus niger |
| ANI_1_2462094 | XP_001394893.2 | 317033119 | Aspergillus niger |
| KLLA0E21891g | XP_454942.1 | 50309857 | Kluyveromyces lactis |
| KLLA0C06336g | XP_452480.1 | 50305045 | Kluyveromyces lactis |
| NDE1 | XP_720034.1 | 68471982 | Candida albicans |
| NDE2 | XP_717986.1 | 68475826 | Candida albicans |

Cytochrome oxidases of *Saccharomyces cerevisiae* include the COX gene products. COX1-3 are the three core subunits encoded by the mitochondrial genome, whereas COX4-13 are encoded by nuclear genes. Attenuation or disruption of any of the cytochrome genes results in a decrease or block in respiratory growth (Hermann and Funes, Gene 354:43-52 (2005)). Cytochrome oxidase genes in other organisms can be inferred by sequence homology.

| Protein | GenBank ID | GI number | Organism |
| --- | --- | --- | --- |
| COX1 | CAA09824.1 | 4160366 | Saccharomyces cerevisiae s288c |
| COX2 | CAA09845.1 | 4160387 | Saccharomyces cerevisiae s288c |
| COX3 | CAA09846.1 | 4160389 | Saccharomyces cerevisiae s288c |
| COX4 | NP_011328.1 | 6321251 | Saccharomyces cerevisiae s288c |
| COX5A | NP_014346.1 | 6324276 | Saccharomyces cerevisiae s288c |
| COX5B | NP_012155.1 | 6322080 | Saccharomyces cerevisiae s288c |
| COX6 | NP_011918.1 | 6321842 | Saccharomyces cerevisiae s288c |
| COX7 | NP_013983.1 | 6323912 | Saccharomyces cerevisiae s288c |
| COX8 | NP_013499.1 | 6323427 | Saccharomyces cerevisiae s288c |
| COX9 | NP_010216.1 | 6320136 | Saccharomyces cerevisiae s288c |
| COX12 | NP_013139.1 | 6323067 | Saccharomyces cerevisiae s288c |
| COX13 | NP_011324.1 | 6321247 | Saccharomyces cerevisiae s288c |

Cytosolic NADH can also be oxidized by the respiratory chain via the G3P dehydrogenase shuttle, consisting of cytosolic NADH-linked G3P dehydrogenase and a membrane-bound G3P:ubiquinone oxidoreductase. The deletion or attenuation of G3P dehydrogenase enzymes will also prevent the oxidation of NADH for respiration. Enzyme candidates encoding these enzymes are described herein.

Additionally, in Crabtree positive organisms, fermentative metabolism can be achieved in the presence of excess of glucose. For example, *S. cerevisiae* makes ethanol even under aerobic conditions. The formation of ethanol and glycerol can be reduced/eliminated and replaced by the production of fatty alcohol, fatty aldehyde or fatty acid in a Crabtree positive organism by feeding excess glucose to the Crabtree positive organism. In another aspect, provided herein is a method for producing fatty alcohols, fatty aldehydes or fatty acids, comprising culturing a non-naturally occurring eukaryotic organism under conditions and for a sufficient period of time to produce fatty alcohol, fatty aldehyde or fatty acid, wherein the eukaryotic organism is a Crabtree positive organism that comprises at least one exogenous nucleic acid encoding a MI-FAE cycle and/or termination pathway enzyme and wherein eukaryotic organism is in a culture medium comprising excess glucose.

Preventing formation of reduced fermentation byproducts will increase the availability of both carbon and reducing equivalents for fatty alcohol, fatty aldehyde or fatty acid production. The two key reduced byproducts under anaerobic and microaerobic conditions are ethanol and glycerol. Ethanol is typically formed from pyruvate in two enzymatic steps catalyzed by pyruvate decarboxylase and ethanol dehydrogenase. Glycerol is formed from the glycolytic intermediate dihydroxyacetone phosphate by the enzymes glycerol-3-phsophate dehydrogenase and glycerol-3-phosphate phosphatase. Attenuation of one or more of these enzyme activities will increase the yield of fatty alcohols, fatty aldehydes or fatty acids. Strain engineering strategies for reducing or eliminating ethanol and glycerol formation are described herein.

Yeast such as *S. cerevisiae* can produce glycerol to allow for regeneration of NAD(P) under anaerobic conditions. Another way to reduce or eliminate glycerol production is by oxygen-limited cultivation (Bakker et al, supra). Glycerol formation only sets in when the specific oxygen uptake rates of the cells decrease below the rate that is required to reoxidize the NADH formed in biosynthesis.

In addition to the redox sinks listed above, malate dehydrogenase can potentially draw away reducing equivalents when it functions in the reductive direction. Several redox shuttles believed to be functional in *S. cerevisiae* utilize this enzyme to transfer reducing equivalents between the cytosol and the mitochondria. This transfer of redox can be prevented by attenuating malate dehydrogenase and/or malic enzyme activity. The redox shuttles that can be blocked by the attenuation of mdh include (i) malate-asparate shuttle, (ii) malate-oxaloacetate shuttle, and (iii) malate-pyruvate shuttle. Genes encoding malate dehydrogenase and malic enzymes are listed in the table below.

| Protein | GenBank ID | GI Number | Organism |
| --- | --- | --- | --- |
| MDH1 | NP_012838.1 | 6322765 | Saccharomyces cerevisiae |
| MDH2 | NP_014515.2 | 116006499 | Saccharomyces cerevisiae |
| MDH3 | NP_010205.1 | 6320125 | Saccharomyces cerevisiae |
| MAE1 | NP_012896.1 | 6322823 | Saccharomyces cerevisiae |
| MDH1 | XP_722674.1 | 68466384 | Candida albicans |
| MDH2 | XP_718638.1 | 68474530 | Candida albicans |
| MAE1 | XP_716669.1 | 68478574 | Candida albicans |
| KLLA0F25960g | XP_456236.1 | 50312405 | Kluyveromyces lactis |
| KLLA0E18635g | XP_454793.1 | 50309563 | Kluyveromyces lactis |
| KLLA0E07525g | XP_454288.1 | 50308571 | Kluyveromyces lactis |
| YALI0D16753p | XP_502909.1 | 50550873 | Yarrowia lipolytica |
| YALI0E18634p | XP_504112.1 | 50553402 | Yarrowia lipolytica |
| ANI_1_268064 | XP_001391302.1 | 145237310 | Aspergillus niger |
| ANI_1_12134 | XP_001396546.1 | 145250065 | Aspergillus niger |
| ANI_1_22104 | XP_001395105.2 | 317033225 | Aspergillus niger |

Overall, disruption or attenuation of the aforementioned sinks for redox either individually or in combination with the other redox sinks can eliminate or lower the use of reducing power for respiration or byproduct formation. It has been reported that the deletion of the external NADH dehydrogenases (NDE1 and NDE2) and the mitochondrial G3P dehydrogenase (GUT2) almost completely eliminates cytosolic NAD+ regeneration in S. cerevisiae (Overkamp et al, J Bacteriol 182:2823-30 (2000)).

Microorganisms of the invention produce fatty alcohols, fatty aldehydes or fatty acids and optionally secrete the fatty alcohols, fatty aldehydes or fatty acis into the culture medium. S. cerevisiae, Yarrowia lipolytica and E. coli harboring heterologous fatty alcohol forming activities acculated fatty alcohols intracellularly; however fatty alcohols were not detected in the culture medium (Behrouzian et al, United States Patent Application 20100298612). The introduction of fatty acyl-CoA reductase enzymes with improved activity resulted in higher levels of fatty alcohol secreted into the culture media. Alternately, introduction of a fatty alcohol, fatty aldehyde or fatty acid transporter or transport system can improve extracellular accumulation of fatty alcohols, fatty aldehydes or fatty acids. Exemplary transporters are listed in the table below.

| Protein | GenBank ID | GI Number | Organism |
| --- | --- | --- | --- |
| Fatp | NP_524723.2 | 24583463 | Drosophila melanogaster |
| AY161280.1:45 . . . 1757 | AAN73268.1 | 34776949 | Rhodococcus erythropolis |
| acrA | CAF23274.1 | 46399825 | Candidatus Protochlamydia amoebophila |
| acrB | CAF23275.1 | 46399826 | Candidatus Protochlamydia amoebophila |
| CER5 | AY734542.1 | 52354013 | Arabidopsis thaliana |
| AmiS2 | JC5491 | 7449112 | Rhodococcus sp. |
| ANI_1_1160064 | XP_001391993.1 | 145238692 | Aspergillus niger |
| YALI0E16016g | XP_504004.1 | 50553188 | Yarrowia lipolytica |

Thus, in some embodiments, the invention provides a non-naturally occurring microbial organism as disclosed herein having one or more gene disruptions, wherein the one or more gene disruptions occurr in endogenous genes encoding proteins or enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by the microbial organism, the one or more gene disruptions confer increased production of a fatty alcohol, fatty aldehyde or fatty acid in the microbial organism. Accordingly, the protein or enzyme can be a fatty acid synthase, an acetyl-CoA carboxylase, a biotin:apoenzyme ligase, an acyl carrier protein, a thioesterase, an acyltransferase, an ACP malonyltransferase, a fatty acid elongase, an acyl-CoA synthetase, an acyl-CoA transferase, an acyl-CoA hydrolase, a pyruvate decarboxylase, a lactate dehydrogenase, an alcohol dehydrogenase, an acid-forming aldehyde dehydrogenases, an acetate kinase, a phosphotransacetylase, a pyruvate oxidase, a glycerol-3-phosphate dehydrogenase, a glycerol-3-phosphate phosphatase, a mitochondrial pyruvate carrier, a peroxisomal fatty acid transporter, a peroxisomal acyl-CoA transporter, a peroxisomal carnitine/acylcarnitine transferase, an acyl-CoA oxidase, or an acyl-CoA binding protein. In some aspects, the one or more gene disruptions include a deletion of the one or more genes.

In some embodiments, the invention provides a non-naturally occurring microbial organism as described herein, wherein one or more enzymes of the MI-FAE cycle or the termination pathway preferentially react with an NADH cofactor or have reduced preference for reacting with an NAD(P)H cofactor. For example, the one or more enzymes of the MI-FAE cycle can be a 3-ketoacyl-CoA reductase or an enoyl-CoA reductase. For the termination pathway, the one or more enzymes can be an acyl-CoA reductase (aldehyde forming), an alcohol dehydrogenase, an acyl-CoA reductase (alcohol forming), an aldehyde decarbonylase, an acyl-ACP reductase, an aldehyde dehydrogenase (acid forming) or a carboxylic acid reductase.

In some embodiments, the invention provides a non-naturally occurring microbial organism as described herein having one or more gene disruptions in genes encoding proteins or enzymes that result in an increased ratio of NAD(P)H to NAD(P) present in the cytosol of the microbial organism following the disruptions. Accordingly, the gene encoding a protein or enzyme that results in an increased ratio of NAD(P)H to NAD(P) present in the cytosol of the microbial organism following the disruptions can be an NADH dehydrogenase, a cytochrome oxidase, a G3P dehydrogenase, G3P phosphatase, an alcohol dehydrogenase, a pyruvate decarboxylase, an aldehyde dehydrogenase (acid forming), a lactate dehydrogenase, a glycerol-3-phosphate dehydrogenase, a glycerol-3-phosphate:quinone oxidoreductase, a malic enzyme and a malate dehydrogenase. In some aspects, the one or more gene disruptions include a deletion of the one or more genes.

In some embodiments, the non-naturally occurring microbial organism of the invention is Crabtree positive and is in culture medium comprising excess glucose. In such conditions, as described herein, the microbial organism can result in increasing the ratio of NAD(P)H to NAD(P) present in the cytosol of the microbial organism.

In some embodiments, the invention provides a non-naturally occurring microbial organism as described herein having at least one exogenous nucleic acid encoding an extracellular transporter or an extracellular transport system for a fatty alcohol, fatty aldehyde or fatty acid of the invention.

In some embodiments, the invention provides a non-naturally occurring microbial organism as described herein, wherein one or more endogenous enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, has attenuated enzyme activity or expression levels. Accordingly, the endogenous enzyme can be a fatty acid synthase, an acetyl-CoA carboxylase, a biotin:apoenzyme ligase, an acyl carrier protein, a thioesterase, an acyltransferase, an ACP malonyltransferase, a fatty acid elongase, an acyl-CoA synthetase, an acyl-CoA transferase, an acyl-CoA hydrolase, a pyruvate decarboxylase, a lactate dehydrogenase, an alcohol dehydrogenase, an acid-forming aldehyde dehydrogenases, an acetate kinase, a phosphotransacetylase, a pyruvate oxidase, a glycerol-3-phosphate dehydrogenase, a glycerol-3-phosphate phosphatase, a mitochondrial pyruvate carrier, a peroxisomal fatty acid transporter, a peroxisomal acyl-CoA transporter, a peroxisomal carnitine/acylcarnitine transferase, an acyl-CoA oxidase, or an acyl-CoA binding protein.

In some embodiments, the invention provides a non-naturally occurring microbial organism as described herein, wherein one or more endogenous enzymes involved in the oxidation of NAD(P)H or NADH, has attenuated enzyme activity or expression levels. Accordingly, the one or more endogenous enzymes can be a NADH dehydrogenase, a cytochrome oxidase, a G3P dehydrogenase, G3P phosphatase, an alcohol dehydrogenase, a pyruvate decarboxylase, an aldehyde dehydrogenase (acid forming), a lactate dehydrogenase, a glycerol-3-phosphate dehydrogenase, a glycerol-3-phosphate:quinone oxidoreductase, a malic enzyme and a malate dehydrogenase.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Also provided is a method of producing a non-naturally occurring microbial organisms having stable growth-coupled production of fatty alcohol, fatty aldehyde or fatty acid. The method can include identifying in silico a set of metabolic modifications that increase production of fatty alcohol, fatty aldehyde or fatty acid, for example, increase production during exponential growth; genetically modifying an organism to contain the set of metabolic modifications that increase production of fatty alcohol, fatty aldehyde or fatty acid, and culturing the genetically modified organism. If desired, culturing can include adaptively evolving the genetically modified organism under conditions requiring production of fatty alcohol, fatty aldehyde or fatty acid. The methods of the invention are applicable to bacterium, yeast and fungus as well as a variety of other cells and microorganism, as disclosed herein.

Thus, the invention provides a non-naturally occurring microbial organism comprising one or more gene disruptions that confer increased production of fatty alcohol, fatty aldehyde or fatty acid. In one embodiment, the one or more gene disruptions confer growth-coupled production of fatty alcohol, fatty aldehyde or fatty acid, and can, for example, confer stable growth-coupled production of fatty alcohol, fatty aldehyde or fatty acid. In another embodiment, the one or more gene disruptions can confer obligatory coupling of fatty alcohol, fatty aldehyde or fatty acid production to growth of the microbial organism. Such one or more gene disruptions reduce the activity of the respective one or more encoded enzymes.

The non-naturally occurring microbial organism can have one or more gene disruptions included in a gene encoding a enzyme or protein disclosed herein. As disclosed herein, the one or more gene disruptions can be a deletion. Such non-naturally occurring microbial organisms of the invention include bacteria, yeast, fungus, or any of a variety of other microorganisms applicable to fermentation processes, as disclosed herein.

Thus, the invention provides a non-naturally occurring microbial organism, comprising one or more gene disruptions, where the one or more gene disruptions occur in genes encoding proteins or enzymes where the one or more gene disruptions confer increased production of fatty alcohol, fatty aldehyde or fatty acid in the organism. The production of fatty alcohol, fatty aldehyde or fatty acid can be growth-coupled or not growth-coupled. In a particular embodiment, the production of fatty alcohol, fatty aldehyde or fatty acid can be obligatorily coupled to growth of the organism, as disclosed herein.

The invention provides non naturally occurring microbial organisms having genetic alterations such as gene disruptions that increase production of fatty alcohol, fatty aldehyde or fatty acid, for example, growth-coupled production of fatty alcohol, fatty aldehyde or fatty acid. Product production can be, for example, obligatorily linked to the exponential growth phase of the microorganism by genetically altering the metabolic pathways of the cell, as disclosed herein. The genetic alterations can increase the production of the desired product or even make the desired product an obligatory product during the growth phase. Metabolic alterations or transformations that result in increased production and elevated levels of fatty alcohol, fatty aldehyde or fatty acid biosynthesis are exemplified herein. Each alteration corresponds to the requisite metabolic reaction that should be functionally disrupted. Functional disruption of all reactions within one or more of the pathways can result in the increased production of fatty alcohol, fatty aldehyde or fatty acid by the engineered strain during the growth phase.

Each of these non-naturally occurring alterations result in increased production and an enhanced level of fatty alcohol, fatty aldehyde or fatty acid production, for example, during the exponential growth phase of the microbial organism, compared to a strain that does not contain such metabolic alterations, under appropriate culture conditions. Appropriate conditions include, for example, those disclosed herein, including conditions such as particular carbon sources or reactant availabilities and/or adaptive evolution.

Given the teachings and guidance provided herein, those skilled in the art will understand that to introduce a metabolic alteration such as attenuation of an enzyme, it can be necessary to disrupt the catalytic activity of the one or more enzymes involved in the reaction. Alternatively, a metabolic alteration can include disrupting expression of a regulatory protein or cofactor necessary for enzyme activity or maximal activity. Furthermore, genetic loss of a cofactor necessary for an enzymatic reaction can also have the same effect as a disruption of the gene encoding the enzyme. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is reduced or eliminated.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods of the invention and incorporated into the non-naturally occurring microbial organisms of the invention in order to achieve the increased production of fatty alcohol, fatty aldehyde or fatty acid or growth-coupled product production.

Given the teachings and guidance provided herein, those skilled in the art also will understand that enzymatic activity or expression can be attenuated using well known methods. Reduction of the activity or amount of an enzyme can mimic complete disruption if the reduction causes activity of the enzyme to fall below a critical level that is normally required for the pathway to function. Reduction of enzymatic activity by various techniques rather than disruption can be important for an organism's viability. Methods of reducing enzymatic activity that result in similar or identical effects of a gene disruption include, but are not limited to: reducing gene transcription or translation; destabilizing mRNA, protein or catalytic RNA; and mutating a gene that affects enzyme kinetics. Natural or imposed regulatory controls can also accomplish enzyme attenuation including: promoter replacement; loss or alteration of transcription factors; introduction of inhibitory RNAs or peptides such as siRNA, antisense RNA, RNA or peptide/small-molecule binding aptamers, ribozymes, aptazymes and riboswitches; and addition of drugs and other chemicals that reduce or disrupt enzymatic activity such as gene splicing.

One of ordinary skill in the art will also recognize that attenuation of an enzyme can be done at various levels. For example, at the gene level, mutations causing a partial or complete null phenotype or epistatic genetic effects that mask the activity of a gene product can be used to attenuate an enzyme. At the gene expression level, methods for attenuation include: coupling transcription to an endogenous or exogenous inducer such as IPTG, then adding low or 0 levels of inducer during the production phase; introducing or modifying positive or negative regulators; modify histone acetylation/deacetylation in region where gene is integrated; introducing a transposition to disrupt a promoter or a regulatory gene; flipping of a transposable element or promoter region; deleting one allele resulting in loss of heterozygosity in a diploid organism; introducing nucleic acids that increase RNA degradation; or in bacteria, for example, introduction of a tmRNA tag, which can lead to RNA degradation and ribosomal stalling. At the translational level, attenuation can include: introducing rare codons to limit translation; introducing RNA interference molecules that block translation; modifying regions outside the coding sequence, such as introducing secondary structure into UTR regions to block translation or reduce efficiency of translation; adding RNAase sites for rapid transcript degradation; introducing antisense RNA oligomers or antisense transcripts; introducing RNA or peptide aptamers, ribozymes, aptazymes, riboswitches; or introducing translational regulatory elements involving RNA structure that can prevent or reduce translation that can be controlled by the presence or absence of small molecules. At the level of enzyme localization and/or longevity, enzyme attenuation can include: adding a degradation tag for faster protein turnover; or adding a localization tag that results in the enzyme being localized to a compartment where it would not be able to react normally. At the level of post-translational regulation, enzyme attenuation can include: increasing intracellular concentration of known inhibitors; or modifying post-translational modified sites. At the level of enzyme activity, enzyme attenuation can include: adding endogenous or exogenous inhibitor, such as a target-specific drug, to reduce enzyme activity; limiting availability of essential cofactors, such as B12, for an enzyme that require it; chelating a metal ion that is required for activity; or introducing a dominant negative mutation.

In some embodiments, microaerobic designs can be used based on the growth-coupled formation of the desired product. To examine this, production cones can be constructed for each strategy by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs are given a low priority.

The fatty alcohol, fatty aldehyde or fatty acid-production strategies identified in the various tables disclosed herein can be disrupted to increase production of fatty alcohol, fatty aldehyde or fatty acid. Accordingly, the invention also provides a non-naturally occurring microbial organism having metabolic modifications coupling fatty alcohol, fatty aldehyde or fatty acid production to growth of the organism, where the metabolic modifications includes disruption of one or more genes selected from the genes encoding proteins and/or enzymes shown in the various tables disclosed herein.

Each of the strains can be supplemented with additional deletions if it is determined that the strain designs do not sufficiently increase the production of fatty alcohol, fatty aldehyde or fatty acid and/or couple the formation of the product with biomass formation. Alternatively, some other enzymes not known to possess significant activity under the growth conditions can become active due to adaptive evolution or random mutagenesis. Such activities can also be knocked out. However, the list of gene deletion disclosed herein allows the construction of strains exhibiting high-yield production of fatty alcohol, fatty aldehyde or fatty acid, including growth-coupled production of fatty alcohol, fatty aldehyde or fatty acid.

In some embodiments, the invention provides a method for producing a compound of Formula (I):

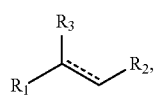

(I)

wherein $R_1$ is $C_{1-24}$ linear alkyl; $R_2$ is $CH_2OH$, CHO, or COOH; $R_3$ is H, OH, or oxo (=O); and ===== represents a single or double bond with the proviso that the valency of the carbon atom to which $R_3$ is attached is four, comprising culturing a non-naturally occurring microbial organism described herein under conditions and for a sufficient period of time to produce the compound of Formula (I), wherein the non-naturally occurring microbial organism has one or more gene disruptions, wherein the one or more gene disruptions occurr in endogenous genes encoding proteins or enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by the microbial organism, the one or more gene disruptions confer increased production of a fatty alcohol, fatty aldehyde or fatty acid in the microbial organism. Accordingly, the protein or enzyme can be a fatty acid synthase, an acetyl-CoA carboxylase, a biotin:apoenzyme ligase, an acyl carrier protein, a thioesterase, an acyltransferases, an ACP malonyltransferase, a fatty acid elongase, an acyl-CoA synthetase, an acyl-CoA transferase, an acyl-CoA hydrolase, a pyruvate decarboxylase, a lactate dehydrogenase, an alcohol dehydrogenase, an acid-forming aldehyde dehydrogenases, an acetate kinase, a phosphotransacetylase, a pyruvate oxidase, a glycerol-3-phosphate dehydrogenase, a glycerol-3-phosphate phosphatase, a mitochondrial pyruvate carrier, a peroxisomal fatty acid transporters, a peroxisomal acyl-CoA transporters, a peroxisomal carnitine/acylcarnitine transferases, an acyl-CoA oxidase, or an acyl-CoA binding protein. In some aspects, the one or more gene disruptions include a deletion of the one or more genes.

In some embodiments, the invention provides a method for producing a fatty alcohol, fatty aldehyde or fatty acid using a non-naturally occurring microbial organism as described herein, wherein one or more enzymes of the MI-FAE cycle or the termination pathway preferentially react with an NADH cofactor or have reduced preference for reacting with an NAD(P)H cofactor. For example, the one or more enzymes of the MI-FAE cycle can be a 3-ketoacyl-CoA reductase or an enoyl-CoA reductase. For the termination pathway, the one or more enzymes can be an acyl-CoA reductase (aldehyde forming), an alcohol dehydrogenase, an acyl-CoA reductase (alcohol forming), an aldehyde decarbonylase, an acyl-ACP reductase, an aldehyde dehydrogenase (acid forming) or a carboxylic acid reductase.

In some embodiments, the invention provides a method for producing a fatty alcohol, fatty aldehyde or fatty acid using a non-naturally occurring microbial organism as described herein having one or more gene disruptions in genes encoding proteins or enzymes that result in an increased ratio of NAD(P)H to NAD(P) present in the cytosol of the microbial organism following the disruptions. Accordingly, the gene encoding a protein or enzyme that results in an increased ratio of NAD(P)H to NAD(P) present in the cytosol of the microbial organism following the disruptions can be an NADH dehydrogenase, a cytochrome oxidase, a glycerol-3-phosphate (G3P) dehydrogenase, a glycerol-3-phosphate (G3P) phosphatase, an alcohol dehydrogenase, a pyruvate decarboxylase, an aldehyde dehydrogenase (acid forming), a lactate dehydrogenase, a glycerol-3-phosphate dehydrogenase, a glycerol-3-phosphate:quinone oxidoreductase, a malic enzyme and a malate dehydrogenase. In some aspects, the one or more gene disruptions include a deletion of the one or more genes.

In some embodiments, the invention provides a method for producing a fatty alcohol, fatty aldehyde or fatty acid using a non-naturally occurring microbial organism of the invention that is Crabtree positive and is in culture medium comprising excess glucose. In such conditions, as described herein, the microbial organism can result in increasing the ratio of NAD(P)H to NAD(P) present in the cytosol of the microbial organism.

In some embodiments, the invention provides a method for producing a fatty alcohol, fatty aldehyde or fatty acid using a non-naturally occurring microbial organism as described herein having at least one exogenous nucleic acid encoding an extracellular transporter or an extracellular transport system for a fatty alcohol, fatty aldehyde or fatty acid of the invention.

In some embodiments, the invention provides a method for producing a fatty alcohol, fatty aldehyde or fatty acid using a non-naturally occurring microbial organism as described herein, wherein one or more endogenous enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, has attenuated enzyme activity or expression levels. Accordingly, the endogenous enzyme can be a fatty acid synthase, an acetyl-CoA carboxylase, a biotin:apoenzyme ligase, an acyl carrier protein, a thioesterase, an acyltransferase, an ACP malonyltransferase, a fatty acid elongase, an acyl-CoA synthetase, an acyl-CoA transferase, an acyl-CoA hydrolase, a pyruvate decarboxylase, a lactate dehydrogenase, an alcohol dehydrogenase, an acid-forming aldehyde dehydrogenases, an acetate kinase, a phosphotransacetylase, a pyruvate oxidase, a glycerol-3-phosphate dehydrogenase, a glycerol-3-phosphate phosphatase, a mitochondrial pyruvate carrier, a peroxisomal fatty acid transporter, a peroxisomal acyl-CoA transporter, a peroxisomal carnitine/acylcarnitine transferase, an acyl-CoA oxidase, and an acyl-CoA binding protein.

In some embodiments, the invention provides a method for producing a fatty alcohol, fatty aldehyde or fatty acid using a non-naturally occurring microbial organism as described herein, wherein one or more endogenous enzymes involved in the oxidation of NAD(P)H or NADH, has attenuated enzyme activity or expression levels. Accordingly, the one or more endogenous enzymes can be NADH dehydrogenase, a cytochrome oxidase, a glycerol-3-phosphate dehydrogenase, glycerol-3-phosphate phosphatase, an alcohol dehydrogenase, a pyruvate decarboxylase, an aldehyde dehydrogenase (acid forming), a lactate dehydrogenase, a glycerol-3-phosphate dehydrogenase, a glycerol-3-phosphate:quinone oxidoreductase, a malic enzyme and a malate dehydrogenase.

A fatty alcohol, fatty aldehyde or fatty acid can be harvested or isolated at any time point during the culturing of the microbial organism, for example, in a continuous and/or near-continuous culture period, as disclosed herein. Generally, the longer the microorganisms are maintained in a continuous and/or near-continuous growth phase, the proportionally greater amount of fatty alcohol, fatty aldehyde or fatty acid can be produced.

Therefore, the invention additionally provides a method for producing fatty alcohol, fatty aldehyde or fatty acid that includes culturing a non-naturally occurring microbial organism having one or more gene disruptions, as disclosed herein. The disruptions can occur in one or more genes encoding an enzyme that increases production of fatty alcohol, fatty aldehyde or fatty acid, including optionally coupling fatty alcohol, fatty aldehyde or fatty acid production to growth of the microorganism when the gene disruption reduces or eliminates an activity of the enzyme. For example, the disruptions can confer stable growth-coupled production of fatty alcohol, fatty aldehyde or fatty acid onto the non-naturally microbial organism.

In some embodiments, the gene disruption can include a complete gene deletion. In some embodiments other methods to disrupt a gene include, for example, frameshifting by omission or addition of oligonucleotides or by mutations that render the gene inoperable. One skilled in the art will recognize the advantages of gene deletions, however, because of the stability it confers to the non-naturally occurring organism from reverting to a parental phenotype in which the gene disruption has not occurred. In particular, the gene disruptions are selected from the gene sets as disclosed herein.

Once computational predictions are made of gene sets for disruption to increase production of fatty alcohol, fatty aldehyde or fatty acid, the strains can be constructed, evolved, and tested. Gene disruptions, including gene deletions, are introduced into host organism by methods well known in the art. A particularly useful method for gene disruption is by homologous recombination, as disclosed herein.

The engineered strains can be characterized by measuring the growth rate, the substrate uptake rate, and/or the product/byproduct secretion rate. Cultures can be grown and used as inoculum for a fresh batch culture for which measurements are taken during exponential growth. The growth rate can be determined by measuring optical density using a spectrophotometer (A600). Concentrations of glucose and other organic acid byproducts in the culture supernatant can be determined by well known methods such as HPLC, GC-MS or other well known analytical methods suitable for the analysis of the desired product, as disclosed herein, and used to calculate uptake and secretion rates.

Strains containing gene disruptions can exhibit suboptimal growth rates until their metabolic networks have adjusted to their missing functionalities. To assist in this adjustment, the strains can be adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model (Fong and Palsson, *Nat. Genet.* 36:1056-1058 (2004)). The growth improvements brought about by adaptive evolution can be accompanied by enhanced rates of fatty alcohol, fatty aldehyde or fatty acid production. The strains are generally adaptively evolved in replicate, running in parallel, to account for differences in the evolutionary patterns that can be exhibited by a host organism (Fong and Palsson, *Nat. Genet.* 36:1056-1058 (2004); Fong et al., *J. Bacteriol.* 185:6400-6408 (2003); Ibarra et al., *Nature* 420:186-189 (2002)) that could potentially result in one strain having superior production qualities over the others. Evolutions can be run for a period of time, typically 2-6 weeks, depending upon the rate of growth improvement attained. In general, evolutions are stopped once a stable phenotype is obtained.

Following the adaptive evolution process, the new strains are characterized again by measuring the growth rate, the substrate uptake rate, and the product/byproduct secretion rate. These results are compared to the theoretical predictions by plotting actual growth and production yields along side the production envelopes from metabolic modeling. The most successful design/evolution combinations are chosen to pursue further, and are characterized in lab-scale batch and continuous fermentations. The growth-coupled biochemical production concept behind the methods disclosed herein such as OptKnock approach should also result in the generation of genetically stable overproducers. Thus, the cultures are maintained in continuous mode for an extended period of time, for example, one month or more, to evaluate long-term stability. Periodic samples can be taken to ensure that yield and productivity are maintained.

Adaptive evolution is a powerful technique that can be used to increase growth rates of mutant or engineered microbial strains, or of wild-type strains growing under unnatural environmental conditions. It is especially useful for strains designed via methods such as OptKnock, which results in growth-coupled product formation. Therefore, evolution toward optimal growing strains will indirectly optimize production as well. Unique strains of *E. coli* K-12 MG1655 were created through gene knockouts and adaptive evolution. (Fong and Palsson, *Nat. Genet.* 36:1056-1058 (2004)). In this work, all adaptive evolutionary cultures were maintained in prolonged exponential growth by serial passage of batch cultures into fresh medium before the stationary phase was reached, thus rendering growth rate as the primary selection pressure. Knockout strains were constructed and evolved on minimal medium supplemented with different carbon substrates (four for each knockout strain). Evolution cultures were carried out in duplicate or triplicate, giving a total of 50 evolution knockout strains. The evolution cultures were maintained in exponential growth until a stable growth rate was reached. The computational predictions were accurate (within 10%) at predicting the post-evolution growth rate of the knockout strains in 38 out of the 50 cases examined. Furthermore, a combination of OptKnock design with adaptive evolution has led to improved lactic acid production strains. (Fong et al., *Biotechnol. Bioeng.* 91:643-648 (2005)). Similar methods can be applied to the strains disclosed herein and applied to various host strains.

There are a number of developed technologies for carrying out adaptive evolution. Exemplary methods are disclosed herein. In some embodiments, optimization of a non-naturally occurring organism of the present invention includes utilizing adaptive evolution techniques to increase fatty alcohol, fatty aldehyde or fatty acid production and/or stability of the producing strain.

Serial culture involves repetitive transfer of a small volume of grown culture to a much larger vessel containing fresh growth medium. When the cultured organisms have grown to saturation in the new vessel, the process is repeated. This method has been used to achieve the longest demonstrations of sustained culture in the literature (Lenski and Travisano, *Proc. Natl. Acad. Sci. USA* 91:6808-6814 (1994)) in experiments which clearly demonstrated consistent improvement in reproductive rate over a period of years. Typically, transfer of cultures is usually performed during exponential phase, so each day the transfer volume is precisely calculated to maintain exponential growth through the next 24 hour period. Manual serial dilution is inexpensive and easy to parallelize.

In continuous culture the growth of cells in a chemostat represents an extreme case of dilution in which a very high fraction of the cell population remains. As a culture grows and becomes saturated, a small proportion of the grown culture is replaced with fresh media, allowing the culture to continually grow at close to its maximum population size. Chemostats have been used to demonstrate short periods of rapid improvement in reproductive rate (Dykhuizen, *Methods Enzymol.* 613-631 (1993)). The potential usefulness of these devices was recognized, but traditional chemostats were unable to sustain long periods of selection for increased reproduction rate, due to the unintended selection of dilution-resistant (static) variants. These variants are able to resist dilution by adhering to the surface of the chemostat, and by doing so, outcompete less adherent individuals, including those that have higher reproductive rates, thus obviating the intended purpose of the device (Chao and Ramsdell, *J. Gen. Microbiol* 20:132-138 (1985)). One possible way to overcome this drawback is the implementation of a device with two growth chambers, which periodically undergo transient phases of sterilization, as described previously (Marliere and Mutzel, U.S. Pat. No. 6,686,194).

Evolugator™ is a continuous culture device developed by Evolugate, LLC (Gainesville, Fla.) and exhibits significant time and effort savings over traditional evolution techniques (de Crecy et al., *Appl. Microbiol. Biotechnol.* 77:489-496 (2007)). The cells are maintained in prolonged exponential growth by the serial passage of batch cultures into fresh medium before the stationary phase is attained. By automating optical density measurement and liquid handling, the Evolugator™ can perform serial transfer at high rates using large culture volumes, thus approaching the efficiency of a chemostat in evolution of cell fitness. For example, a mutant of *Acinetobacter* sp ADP1 deficient in a component of the translation apparatus, and having severely hampered growth, was evolved in 200 generations to 80% of the wild-type growth rate. However, in contrast to the chemostat which maintains cells in a single vessel, the machine operates by moving from one "reactor" to the next in subdivided regions of a spool of tubing, thus eliminating any selection for wall-growth. The transfer volume is adjustable, and normally set to about 50%. A drawback to this device is that it is large and costly, thus running large numbers of evolutions in parallel is not practical. Furthermore, gas addition is not well regulated, and strict anaerobic conditions are not maintained with the current device configuration. Nevertheless, this is an alternative method to adaptively evolve a production strain.

As disclosed herein, a nucleic acid encoding a desired activity of a fatty alcohol, fatty aldehyde or fatty acid pathway can be introduced into a host organism. In some cases, it can be desirable to modify an activity of a fatty alcohol, fatty aldehyde or fatty acid pathway enzyme or protein to increase production of fatty alcohol, fatty aldehyde or fatty acid. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, $>10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding (Km), including broadening substrate binding to include non-natural substrates; inhibition (Ki), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

Described below in more detail are exemplary methods that have been developed for the mutagenesis and diversification of genes to target desired properties of specific enzymes. Such methods are well known to those skilled in the art. Any of these can be used to alter and/or optimize the activity of a fatty alcohol, fatty aldehyde or fatty acid pathway enzyme or protein.

EpPCR (Pritchard et al., *J Theor. Biol.* 234:497-509 (2005)) introduces random point mutations by reducing the fidelity of DNA polymerase in PCR reactions by the addition of Mn²⁺ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful to screen a larger number of potential variants having a desired activity. A high number of mutants can be generated by EpPCR, so a high-throughput screening assay or a selection method, for example, using robotics, is useful to identify those with desirable characteristics.

Error-prone Rolling Circle Amplification (epRCA) (Fujii et al., *Nucleic Acids Res.* 32:e145 (2004); and Fujii et al., *Nat. Protoc.* 1:2493-2497 (2006)) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the Mn²⁺ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a commercially available kit.

DNA or Family Shuffling (Stemmer, *Proc Natl Acad Sci USA* 91:10747-10751 (1994)); and Stemmer, *Nature* 370:389-391 (1994)) typically involves digestion of two or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious, random and neutral mutations.

Staggered Extension (StEP) (Zhao et al., *Nat. Biotechnol.* 16:258-261 (1998)) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template (Shao et al., *Nucleic Acids Res* 26:681-683 (1998)). Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)). The mismatch repair step is at least somewhat mutagenic. Heteroduplexes transform more efficiently than linear homoduplexes. This method is suitable for large genes and whole operons.

Random Chimeragenesis on Transient Templates (RA-CHITT) (Coco et al., *Nat. Biotechnol.* 19:354-359 (2001)) employs Dnase I fragmentation and size fractionation of single stranded DNA (ssDNA). Homologous fragments are hybridized in the absence of polymerase to a complementary ssDNA scaffold. Any overlapping unhybridized fragment ends are trimmed down by an exonuclease. Gaps between fragments are filled in and then ligated to give a pool of full-length diverse strands hybridized to the scaffold, which contains U to preclude amplification. The scaffold then is destroyed and is replaced by a new strand complementary to the diverse strand by PCR amplification. The method involves one strand (scaffold) that is from only one parent while the priming fragments derive from other genes, and the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates (Lee et al., *J. Molec. Catalysis* 26:119-129 (2003)). No DNA endonucleases are used. Unidirectional ssDNA is made by DNA polymerase with random primers or serial deletion with exonuclease. Unidirectional ssDNA are only templates and not primers. Random priming and exonucleases do not introduce sequence bias as true of enzymatic cleavage of DNA shuffling/RACHITT. RETT can be easier to optimize than StEP because it uses normal PCR conditions instead of very short extensions. Recombination occurs as a component of the PCR steps, that is, no direct shuffling. This method can also be more random than StEP due to the absence of pauses.

In Degenerate Oligonucleotide Gene Shuffling (DOGS) degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)). Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is similar to ITCHY except that phosphothioate dNTPs are used to generate truncations (Lutz et al., *Nucleic Acids Res* 29:E16 (2001)). Relative to ITCHY, THIO-ITCHY can be easier to optimize, provide more reproducibility, and adjustability.

SCRATCHY combines two methods for recombining genes, ITCHY and DNA shuffling (Lutz et al., *Proc. Natl. Acad. Sci. USA* 98:11248-11253 (2001)). SCRATCHY combines the best features of ITCHY and DNA shuffling. First, ITCHY is used to create a comprehensive set of fusions between fragments of genes in a DNA homology-independent fashion. This artificial family is then subjected to a DNA-shuffling step to augment the number of crossovers. Computational predictions can be used in optimization. SCRATCHY is more effective than DNA shuffling when sequence identity is below 80%.

In Random Drift Mutagenesis (RNDM) mutations are made via epPCR followed by screening/selection for those retaining usable activity (Bergquist et al., *Biomol. Eng.* 22:63-72 (2005)). Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates a pool of random length fragments using random incorporation of a phosphothioate nucleotide and cleavage; this pool is used as a template to 2) extend in the presence of "universal" bases such as inosine; 3) replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)). Using this technique it can be possible to generate a large library of mutants within 2 to 3 days using simple methods. This technique is non-directed in comparison to the mutational bias of DNA polymerases. Differences in this approach makes this technique complementary (or an alternative) to epPCR.

In Synthetic Shuffling, overlapping oligonucleotides are designed to encode "all genetic diversity in targets" and allow a very high diversity for the shuffled progeny (Ness et al., *Nat. Biotechnol.* 20:1251-1255 (2002)). In this technique, one can design the fragments to be shuffled. This aids in increasing the resulting diversity of the progeny. One can design sequence/codon biases to make more distantly related sequences recombine at rates approaching those observed with more closely related sequences. Additionally, the technique does not require physically possessing the template genes.

Nucleotide Exchange and Excision Technology NexT exploits a combination of dUTP incorporation followed by treatment with uracil DNA glycosylase and then piperidine to perform endpoint DNA fragmentation (Muller et al., *Nucleic Acids Res.* 33:e117 (2005)). The gene is reassembled using internal PCR primer extension with proofreading polymerase. The sizes for shuffling are directly controllable using varying dUPT::dTTP ratios. This is an end point reaction using simple methods for uracil incorporation and cleavage. Other nucleotide analogs, such as 8-oxo-guanine, can be used with this method. Additionally, the technique works well with very short fragments (86 bp) and has a low error rate. The chemical cleavage of DNA used in this technique results in very few unshuffled clones.

In Sequence Homology-Independent Protein Recombination (SHIPREC), a linker is used to facilitate fusion between two distantly related or unrelated genes. Nuclease treatment is used to generate a range of chimeras between the two genes. These fusions result in libraries of single-crossover hybrids (Sieber et al., *Nat. Biotechnol.* 19:456-460 (2001)). This produces a limited type of shuffling and a separate process is required for mutagenesis. In addition, since no homology is needed, this technique can create a library of chimeras with varying fractions of each of the two unrelated parent genes. SHIPREC was tested with a heme-binding domain of a bacterial CP450 fused to N-terminal regions of a mammalian CP450; this produced mammalian activity in a more soluble enzyme.

In Gene Site Saturation Mutagenesis™ (GSSM™) the starting materials are a supercoiled dsDNA plasmid containing an insert and two primers which are degenerate at the desired site of mutations (Kretz et al., *Methods Enzymol.* 388:3-11 (2004)). Primers carrying the mutation of interest, anneal to the same sequence on opposite strands of DNA. The mutation is typically in the middle of the primer and flanked on each side by approximately 20 nucleotides of correct sequence. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (that is, one codon). The technique facilitates the generation of all possible replacements at a single-site with no nonsense codons and results in equal to near-equal representation of most possible alleles. This technique does not require prior knowledge of the structure, mechanism, or domains of the target enzyme. If followed by shuffling or Gene Reassembly, this technology creates a diverse library of recombinants containing all possible combinations of single-site up-mutations. The usefulness of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)). Simultaneous substitutions at two or three sites are possible using this technique. Additionally, the method tests a large multiplicity of possible sequence changes at a limited range of sites. This technique has been used to explore the information content of the lambda repressor DNA-binding domain.

Combinatorial Multiple Cassette Mutagenesis (CMCM) is essentially similar to CCM except it is employed as part of a larger program: 1) use of epPCR at high mutation rate to 2) identify hot spots and hot regions and then 3) extension by CMCM to cover a defined region of protein sequence space (Reetz et al., *Angew. Chem. Int. EdEngl.* 40:3589-3591 (2001)). As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique, conditional ts mutator plasmids allow increases of 20 to 4000-X in random and natural mutation frequency during selection and block accumulation of deleterious mutations when selection is not required (Selifonova et al., *Appl. Environ. Microbiol.* 67:3645-3649 (2001)). This technology is based on a plasmid-derived mutD5 gene, which encodes a mutant subunit of DNA polymerase III. This subunit binds to endogenous DNA polymerase III and compromises the proofreading ability of polymerase III in any strain that harbors the plasmid. A broad-spectrum of base substitutions and frame-shift mutations occur. In order for effective use, the mutator plasmid should be removed once the desired phenotype is achieved; this is accomplished through a temperature sensitive (ts) origin of replication, which allows for plasmid curing at 41° C. It should be noted that mutator strains have been explored for quite some time (see Low et al., *J. Mol. Biol.* 260:359-3680 (1996)). In this technique, very high spontaneous mutation rates are observed. The conditional property minimizes non-desired background mutations. This technology could be combined with adaptive evolution to enhance mutagenesis rates and more rapidly achieve desired phenotypes.

Look-Through Mutagenesis (LTM) is a multidimensional mutagenesis method that assesses and optimizes combinatorial mutations of selected amino acids (Rajpal et al., *Proc. Natl. Acad. Sci. USA* 102:8466-8471 (2005)). Rather than saturating each site with all possible amino acid changes, a set of nine is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and can increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to create a large library of chimeras (multiple mutations) of a single gene (Tunable GeneReassembly™ (TGR™) Technology supplied by Verenium Corporation). Typically this technology is used in combination with ultra-high-throughput screening to query the represented sequence space for desired improvements. This technique allows multiple gene recombination independent of homology. The exact number and position of cross-over events can be predetermined using fragments designed via bioinformatic analysis. This technology leads to a very high level of diversity with virtually no parental gene reformation and a low level of inactive genes. Combined with GSSM™, a large range of mutations can be tested for improved activity. The method allows "blending" and "fine tuning" of DNA shuffling, for example, codon usage can be optimized.

In Silico Protein Design Automation (PDA) is an optimization algorithm that anchors the structurally defined protein backbone possessing a particular fold, and searches sequence space for amino acid substitutions that can stabilize the fold and overall protein energetics (Hayes et al., *Proc. Natl. Acad. Sci. USA* 99:15926-15931 (2002)). This technology uses in silico structure-based entropy predictions in order to search for structural tolerance toward protein amino acid variations. Statistical mechanics is applied to calculate coupling interactions at each position. Structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants ($10^{50}$). The choice of sequence variants to test is related to predictions based on the most favorable thermodynamics. Ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves: 1) using knowledge of structure/function to choose a likely site for enzyme improvement; 2) performing saturation mutagenesis at chosen site using a mutagenesis method such as Stratagene QuikChange (Stratagene; San Diego Calif.); 3) screening/selecting for desired properties; and 4) using improved clone(s), start over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)). This is a proven methodology, which assures all possible replacements at a given position are made for screening/selection.

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

Example I

Production of Fatty Alcohols and Fatty Aldehydes by MI-FAE Cycle and Acyl-CoA Termination Pathways Encoding nucleic acids and species that can be used as sources for conferring fatty alcohol and fatty aldehyde production capability onto a host microbial organism are exemplified further below.

Multienzyme Complexes

In one exemplary embodiment, the genes fadA and fadB encode a multienzyme complex that exhibits three constituent activities of the malonyl-CoA independent FAS pathway, namely, ketoacyl-CoA thiolase, 3-hydroxyacyl-CoA dehydrogenase, and enoyl-CoA hydratase activities (Nakahigashi, K. and H. Inokuchi, *Nucleic Acids Research* 18:4937 (1990); Yang et al., *Journal of Bacteriology* 173:7405-7406 (1991); Yang et al, *Journal of Biological Chemistry* 265: 10424-10429 (1990); Yang et al., *Biochemistry* 30:6788-6795 (1990)). The fadI and fadJ genes encode similar activities which can substitute for the above malonyl-CoA independent FAS conferring genes fadA and fadB. The acyl-Coa dehydrogenase of *E. coli* is encoded by fadE (Campbell et al, *J Bacteriol* 184: 3759-64)). This enzyme catalyzes the rate-limiting step of beta-oxidation (O'Brien et al, *J Bacteriol* 132:532-40 (1977)). The nucleic acid sequences for each of the above fad genes are well known in the art and can be accessed in the public databases such as Genbank using the following accession numbers.

| Protein | GenBank ID | GI Number | Organism |
|---|---|---|---|
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |
| fadE | AAC73325.2 | 87081702 | *Escherichia coli* |

Step A. Thiolase

Thiolase enzymes, also know as beta-keto thiolase, acyl-CoA C-acetyltransferase, acyl-CoA:acetyl-CoA C-acyltransferase, 3-oxoacyl-CoA thiolase, 3-ketoacyl-CoA thiolase, beta-ketoacyl-CoA thiolase, and acyl-CoA thiolase, that are suitable for fatty alcohol, fatty aldehyde or fatty acid production are described herein (FIGS. 1A and 6A). Exemplary acetoacetyl-CoA thiolase enzymes include the gene products of atoB and homolog yqeF from *E. coli* (Martin et al., *Nat. Biotechnol* 21:796-802 (2003)), thlA and thlB from *C. acetobutylicum* (Hanai et al., *Appl Environ Microbiol* 73:7814-7818 (2007); Winzer et al., *J. Mol. Microbiol Biotechnol* 2:531-541 (2000)), and ERG10 from *S. cerevisiae* (Hiser et al., *J. Biol. Chem.* 269:31383-31389 (1994)). A degradative thiolase of *S. cerevisiae* is encoded by POT1. Another candidate thiolase is the phaA gene product of *R. eutropha* (Jenkins et al, *Journal of Bacteriology* 169:42-52 (1987)). The acetoacetyl-CoA thiolase from *Zoogloea ramigera* is irreversible in the biosynthetic direction and a crystal structure is available (Merilainen et al, *Biochem* 48: 11011-25 (2009)). Accession numbers for these thiolases and homologs are included in the table below.

| Protein | GenBank ID | GI Number | Organism |
|---|---|---|---|
| atoB | NP_416728 | 16130161 | *Escherichia coli* |
| yqeF | NP_417321.2 | 90111494 | *Escherichia coli* |
| thlA | NP_349476.1 | 15896127 | *Clostridium acetobutylicum* |
| thlB | NP_149242.1 | 15004782 | *Clostridium acetobutylicum* |
| ERG10 | NP_015297 | 6325229 | *Saccharomyces cerevisiae* |
| POT1 | NP_012106.1 | 6322031 | *Saccharomyces cerevisiae* |
| phaA | YP_725941 | 113867452 | *Ralstonia eutropha* |
| phbA | P07097.4 | 135759 | *Zoogloea ramigera* |
| h16_A1713 | YP_726205.1 | 113867716 | *Ralstonia eutropha* |

| Protein | GenBank ID | GI Number | Organism |
|---|---|---|---|
| pcaF | YP_728366.1 | 116694155 | *Ralstonia eutropha* |
| h16_B1369 | YP_840888.1 | 116695312 | *Ralstonia eutropha* |
| h16_A0170 | YP_724690.1 | 113866201 | *Ralstonia eutropha* |
| h16_A0462 | YP_724980.1 | 113866491 | *Ralstonia eutropha* |
| h16_A1528 | YP_726028.1 | 113867539 | *Ralstonia eutropha* |
| h16_B0381 | YP_728545.1 | 116694334 | *Ralstonia eutropha* |
| h16_B0662 | YP_728824.1 | 116694613 | *Ralstonia eutropha* |
| h16_B0759 | YP_728921.1 | 116694710 | *Ralstonia eutropha* |
| h16_B0668 | YP_728830.1 | 116694619 | *Ralstonia eutropha* |
| h16_A1720 | YP_726212.1 | 113867723 | *Ralstonia eutropha* |
| h16_A1887 | YP_726356.1 | 113867867 | *Ralstonia eutropha* |
| bktB | YP_002005382.1 | 194289475 | *Cupriavidus taiwanensis* |
| Rmet_1362 | YP_583514.1 | 94310304 | *Ralstonia metallidurans* |
| Bphy_0975 | YP_001857210.1 | 186475740 | *Burkholderia phymatum* |

Many thiolase enzymes catalyze the formation of longer-chain acyl-CoA products. Exemplary thiolases include, for example, 3-oxoadipyl-CoA thiolase (EC 2.3.1.174) and acyl-CoA thiolase (EC 2.3.1.16). 3-Oxoadipyl-CoA thiolase converts succinyl-CoA and acetyl-CoA to 3-oxoadipyl-CoA, and is a key enzyme of the beta-ketoadipate pathway for aromatic compound degradation. The enzyme is widespread in soil bacteria and fungi including *Pseudomonas putida* (Harwood et al., *J Bacteriol.* 176:6479-6488 (1994)) and *Acinetobacter calcoaceticus* (Doten et al., *J Bacteriol.* 169: 3168-3174 (1987)). The gene products encoded by pcaF in *Pseudomonas* strain B13 (Kaschabek et al., *J Bacteriol.* 184:207-215 (2002)), phaD in *Pseudomonas putida* U (Olivera et al., *Proc. Natl. Acad. Sci U.S.A* 95:6419-6424 (1998)), paaE in *Pseudomonas fluorescens* ST (Di et al., *Arch. Microbiol* 188:117-125 (2007)), and paaJ from *E. coli* (Nogales et al., *Microbiology* 153:357-365 (2007)) also catalyze this transformation. Several beta-ketothiolases exhibit significant and selective activities in the oxoadipyl-CoA forming direction including bkt from *Pseudomonas putida*, pcaF and bkt from *Pseudomonas aeruginosa* PAO1, bkt from *Burkholderia ambifaria* AMMD, paaJ from *E. coli*, and phaD from *P. putida*. Two gene products of *Ralstonia eutropha* (formerly known as *Alcaligenes eutrophus*), encoded by genes bktB and bktC, catalyze the formation of 3-oxopimeloyl-CoA (Slater et al., *J. Bacteriol.* 180:1979-1987 (1998); Haywood et al., *FEMS Microbiology Letters* 52:91-96 (1988)). The sequence of the BktB protein is known; however, the sequence of the BktC protein has not been reported. BktB is also active on substrates of length C6 and C8 (Machado et al, *Met Eng* in press (2012)). The pim operon of Rhodopseudomonaspalustris also encodes a beta-ketothiolase, encoded by pimB, predicted to catalyze this transformation in the degradative direction during benzoyl-CoA degradation (Harrison et al., *Microbiology* 151:727-736 (2005)). A beta-ketothiolase enzyme candidate in *S. aciditrophicus* was identified by sequence homology to bktB (43% identity, evalue=1e-93).

| Gene name | GI# | GenBank Accession # | Organism |
|---|---|---|---|
| paaJ | 16129358 | NP_415915.1 | *Escherichia coli* |
| pcaF | 17736947 | AAL02407 | *Pseudomonas knackmussii* (B13) |
| phaD | 3253200 | AAC24332.1 | *Pseudomonas putida* |
| pcaF | 506695 | AAA85138.1 | *Pseudomonas putida* |
| pcaF | 141777 | AAC37148.1 | *Acinetobacter calcoaceticus* |
| paaE | 106636097 | ABF82237.1 | *Pseudomonas fluorescens* |
| bkt | 115360515 | YP_777652.1 | *Burkholderia ambifaria* AMMD |
| bkt | 9949744 | AAG06977.1 | *Pseudomonas aeruginosa* PAO1 |
| pcaF | 9946065 | AAG03617.1 | *Pseudomonas aeruginosa* PAO1 |
| bktB | YP_725948 | 11386745 | *Ralstonia eutropha* |
| pimB | CAE29156 | 39650633 | *Rhodopseudomonas palustris* |
| syn_02642 | YP_462685.1 | 85860483 | *Syntrophus aciditrophicus* |

Acyl-CoA thiolase (EC 2.3.1.16) enzymes involved in the beta-oxidation cycle of fatty acid degradation exhibit activity on a broad range of acyl-CoA substrates of varying chain length. Exemplary acyl-CoA thiolases are found in *Arabidopsis thaliana* (Cruz et al, *Plant Physiol* 135:85-94 (2004)), *Homo sapiens* (Mannaerts et al, Cell Biochem Biphys 32:73-87 (2000)), *Helianthus annuus* (Schiedel et al, Prot Expr Purif 33:25-33 (2004)). The chain length specificity of thiolase enzymes can be assayed by methods well known in the art (Wrensford et al, *Anal Biochem* 192:49-54 (1991)). A peroxisomal thiolase found in rat liver catalyze the acetyl-CoA dependent formation of longer chain acyl-CoA products from octanoyl-CoA (Horie et al, *Arch Biochem Biophys* 274: 64-73 (1989); Hijikata et al, *J Biol Chem* 265, 4600-4606 (1990)).

| Protein | GenBank ID | GI Number | Organism |
|---|---|---|---|
| AY308827.1:1...1350 | AAQ77242.1 | 34597334 | *Helianthus annuus* |
| KAT2 | Q56WD9.2 | 73919871 | *Arabidopsis thaliana* |
| KAT1 | Q8LF48.2 | 73919870 | *Arabidopsis thaliana* |
| KAT5 | Q570C8.2 | 73919872 | *Arabidopsis thaliana* |
| ACAA1 | P09110.2 | 135751 | *Homo sapiens* |
| LCTHIO | AAF04612.1 | 6165556 | *Sus scrofa* |
| Acaa1a | NP_036621.1 | 6978429 | *Rattus norvegicus* |
| Acaa1b | NP_001035108.1 | 90968642 | *Rattus norvegicus* |
| Acaa2 | NP_569117.1 | 18426866 | *Rattus norvegicus* |

Acetoacetyl-CoA can also be synthesized from acetyl-CoA and malonyl-CoA by acetoacetyl-CoA synthase (EC 2.3.1.194). This enzyme (FhsA) has been characterized in the soil bacterium *Streptomyces* sp. CL190 where it participates in mevalonate biosynthesis (Okamura et al, *PNAS USA* 107:11265-70 (2010)). As this enzyme catalyzes an essentially irreversible reaction, it is particularly useful for metabolic engineering applications for overproducing metabolites, fuels or chemicals derived from acetoacetyl-CoA such as long chain alcohols. Other acetoacetyl-CoA synthase genes can be identified by sequence homology to JhsA. Acyl-CoA synthase enzymes such as fhsA and homologs can be engineered or evolved to accept longer acyl-CoA substrates by methods known in the art.

Chain length selectivity of selected thiolase enzymes described above is summarized in the table below.

| Chain length | Gene | Organism |
|---|---|---|
| C4 | atoB | *Escherichia coli* |
| C6 | phaD | *Pseudomonas putida* |
| C6-C8 | bktB | *Ralstonia eutropha* |
| C10-C16 | Acaa1a | *Rattus norvegicus* |

Step B. 3-Oxoacyl-CoA Reductase

3-Oxoacyl-CoA reductases (also known as 3-hydroxyacyl-CoA dehydrogenases, 3-ketoacyl-CoA reductases, beta-ketoacyl-CoA reductases, beta-hydroxyacyl-CoA dehydrogenases, hydroxyacyl-CoA dehydrogenases, and ketoacyl-CoA reductases) catalyze the reduction of 3-oxoacyl-CoA substrates to 3-hydroxyacyl-CoA products (FIG. 1B and FIG. 6B). These enzymes are often involved in fatty acid beta-oxidation and aromatic degradation pathways. For example, subunits of two fatty acid oxidation complexes in *E. coli*, encoded by fadB and fad, function as 3-hydroxyacyl-CoA dehydrogenases (Binstock et al., *Methods Enzymol.* 71 Pt C:403-411 (1981)). Knocking out a negative regulator encoded by fadR can be utilized to activate the fadB gene product (Sato et al., *J Biosci. Bioeng* 103:38-44 (2007)). Another 3-hydroxyacyl-CoA dehydrogenase from *E. coli* is paaH (Ismail et al., *European Journal of Biochemistry* 270:3047-3054 (2003)). Additional 3-oxoacyl-CoA enzymes include the gene products of phaC in *Pseudomonas putida* (Olivera et al., *Proc. Natl. Acad. Sci U.S.A* 95:6419-6424 (1998)) and paaC in *Pseudomonas fluorescens* (Di et al., 188:117-125 (2007)). These enzymes catalyze the reversible oxidation of 3-hydroxyadipyl-CoA to 3-oxoadipyl-CoA during the catabolism of phenylacetate or styrene. Other suitable enzyme candidates include AAO72312.1 from *E. gracilis* (Winkler et al., *Plant Physiology* 131:753-762 (2003)) and paaC from *Pseudomonas putida* (Olivera et al., *PNAS USA* 95:6419-6424 (1998)). Enzymes catalyzing the reduction of acetoacetyl-CoA to 3-hydroxybutyryl-CoA include hbd of *Clostridium acetobutylicum* (Youngleson et al., *J Bacteriol.* 171:6800-6807 (1989)), phbB from *Zoo-*

| Protein | GenBank ID | GI Number | Organism |
|---|---|---|---|
| fhsA | BAJ83474.1 | 325302227 | *Streptomyces* sp CL190 |
| AB183750.1:11991...12971 | BAD86806.1 | 57753876 | *Streptomyces* sp. KO-3988 |
| epzT | ADQ43379.1 | 312190954 | *Streptomyces cinnamonensis* |
| ppzT | CAX48662.1 | 238623523 | *Streptomyces anulatus* |
| O3I_22085 | ZP_09840373.1 | 378817444 | *Nocardia brasiliensis* | gloea ramigera (Ploux et al., *Eur. J Biochem.* 174:177-182 (1988)), phaB from *Rhodobacter sphaeroides* (Alber et al., *Mol. Microbiol* 61:297-309 (2006)) and paaH1 of *Ralstonia eutropha* (Machado et al, *Met Eng*, In Press (2012)). The *Z. ramigera* enzyme is NADPH-dependent and also accepts 3-oxopropionyl-CoA as a substrate (Ploux et al., *Eur. J Biochem.* 174:177-182 (1988)). Additional genes include phaB in *Paracoccus denitrificans*, Hbd1 (C-terminal domain) and Hbd2 (N-terminal domain) in *Clostridium kluyveri* (Hillmer and Gottschalk, *Biochim. Biophys. Acta* 3334:12-23 (1974)) and HSD17B10 in *Bos taurus* (Wakil et al., *J Biol. Chem.* 207:631-638 (1954)). The enzyme from *Paracoccus denitrificans* has been functionally expressed and characterized in *E. coli* (Yabutani et al., *FEMS Microbiol Lett.* 133:85-90 (1995)). A number of similar enzymes have been found in other species of Clostridia and in *Metallosphaera sedula* (Berg et al., *Science.* 318:1782-1786 (2007)). The enzyme from *Candida tropicalis* is a component of the peroxisomal fatty acid beta-oxidation multifunctional enzyme type 2 (MFE-2). The dehydrogenase B domain of this protein is catalytically active on acetoacetyl-CoA. The domain has been functionally expressed in *E. coli*, a crystal structure is available, and the catalytic mechanism is well-understood (Ylianttila et al., *Biochem Biophys Res Commun* 324:25-30 (2004); Ylianttila et al., *J Mol Biol* 358:1286-1295 (2006)). 3-Hydroxyacyl-CoA dehydrogenases that accept longer acyl-CoA substrates (eg. EC 1.1.1.35) are typically involved in beta-oxidation. An example is HSD17B10 in *Bos taurus* (Wakil et al., *J Biol. Chem.* 207:631-638 (1954)). The pig liver enzyme is preferentially active on short and medium chain acyl-CoA substrates whereas the heart enzyme is less selective (He et al, *Biochim Biophys Acta* 1392:119-26 (1998)). The *S. cerevisiae* enzyme FOX2 is active in beta-degradation pathways and also has enoyl-CoA hydratase activity (Hiltunen et al, *J Biol Chem* 267: 6646-6653 (1992)).

| Protein | Genbank ID | GI number | Organism |
|---|---|---|---|
| fadB | P21177.2 | 119811 | *Escherichia coli* |
| fadJ | P77399.1 | 3334437 | *Escherichia coli* |
| paaH | NP_415913.1 | 16129356 | *Escherichia coli* |
| Hbd2 | EDK34807.1 | 146348271 | *Clostridium kluyveri* |
| Hbd1 | EDK32512.1 | 146345976 | *Clostridium kluyveri* |
| phaC | NP_745425.1 | 26990000 | *Pseudomonas putida* |
| paaC | ABF82235.1 | 106636095 | *Pseudomonas fluorescens* |
| HSD17B10 | O02691.3 | 3183024 | *Bos taurus* |
| phbB | P23238.1 | 130017 | *Zoogloea ramigera* |
| phaB | YP_353825.1 | 77464321 | *Rhodobacter sphaeroides* |
| paaH1 | CAJ91433.1 | 113525088 | *Ralstonia eutropha* |
| phaB | BAA08358 | 675524 | *Paracoccus denitrificans* |
| Hbd | NP_349314.1 | 15895965 | *Clostridium acetobutylicum* |
| Hbd | AAM14586.1 | 20162442 | *Clostridium beijerinckii* |
| Msed_1423 | YP_001191505 | 146304189 | *Metallosphaera sedula* |
| Msed_0399 | YP_001190500 | 146303184 | *Metallosphaera sedula* |
| Msed_0389 | YP_001190490 | 146303174 | *Metallosphaera sedula* |
| Msed_1993 | YP_001192057 | 146304741 | *Metallosphaera sedula* |
| Fox2 | Q02207 | 399508 | *Candida tropicalis* |
| HSD17B10 | O02691.3 | 3183024 | *Bos taurus* |
| HADH | NP_999496.1 | 47523722 | *Bos taurus* |
| 3HCDH | AAO72312.1 | 29293591 | *Euglena gracilis* |
| FOX2 | NP_012934.1 | 6322861 | *Saccharomyces cerevisiae* |

Chain length specificity of selected hydroxyacyl-CoA dehydrogenase enzymes is shown below. Directed evolution can enhance selectivity of enzymes for longer-chain substrates. For example, Machado and coworkers developed a selection platform for directed evolution of chain elongation enzymes that favor longer acyl-CoA substrates. This group evolved paaH1 of *Ralstonia eutropha* for improved activity on 3-oxo-hexanoyl-CoA (Machado et al, *Met Eng*, In Press (2012)).

| Chain length | Gene | Organism |
|---|---|---|
| C4 | hbd | *Clostridium acetobutylicum* |
| C5 | phbB | *Zoogloea ramigera* |
| C4-C6 | paaH1 | *Ralstonia eutropha* |
| C4-C10 | HADH | *Sus scrofa* |
| C4-C18 | fadB | *Escherichia coli* |

Step C. 3-Hydroxyacyl-CoA Dehydratase

3-Hydroxyacyl-CoA dehydratases (eg. EC 4.2.1.17, also known as enoyl-CoA hydratases) catalyze the dehydration of a range of 3-hydroxyacyl-CoA substrates (Roberts et al., *Arch. Microbiol* 117:99-108 (1978); Agnihotri et al., *Bioorg. Med. Chem.* 11:9-20 (2003); Conrad et al., *J Bacteriol.* 118:103-111 (1974)) and can be used in the conversion of 3-hydroxyacyl-CoA to enoyl-CoA (FIGS. 1C and 6C). The ech gene product of *Pseudomonas putida* catalyzes the conversion of 3-hydroxybutyryl-CoA to crotonyl-CoA (Roberts et al., *Arch. Microbiol* 117:99-108 (1978)). This transformation is also catalyzed by the crt gene product of *Clostridium acetobutylicum*, the crt1 gene product of *C. kluyveri*, and other clostridial organisms Atsumi et al., *Metab Eng* 10:305-311 (2008); Boynton et al., *J Bacteriol.* 178:3015-3024 (1996); Hillmer et al., *FEBS Lett.* 21:351-354 (1972)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). The gene product of pimF in *Rhodopseudomonas palustris* is predicted to encode an enoyl-CoA hydratase that participates in pimeloyl-CoA degradation (Harrison et al., *Microbiology* 151:727-736 (2005)). Lastly, a number of *Escherichia coli* genes have been shown to demonstrate enoyl-CoA hydratase functionality including maoC (Park et al., *J Bacteriol.* 185:5391-5397 (2003)), paaF (Ismail et al., *Eur. J Biochem.* 270:3047-3054 (2003); Park et al., *Appl. Biochem. Biotechnol* 113-116:335-346 (2004); Park et al., *Biotechnol Bioeng* 86:681-686 (2004)) and paaG (Ismail et al., *Eur. J Biochem.* 270:3047-3054 (2003); Park and Lee, *Appl. Biochem. Biotechnol* 113-116:335-346 (2004); Park and Yup, *Biotechnol Bioeng* 86:681-686 (2004)). Enzymes with 3-hydroxyacyl-CoA dehydratase activity in *S. cerevisiae* include PHS1 and FOX2.

| Gene | GenBank Accession No. | GI No. | Organism |
|---|---|---|---|
| ech | NP_745498.1 | 26990073 | *Pseudomonas putida* |
| crt | NP_349318.1 | 15895969 | *Clostridium acetobutylicum* |
| crt1 | YP_001393856 | 153953091 | *Clostridium kluyveri* |
| phaA | ABF82233.1 | 26990002 | *Pseudomonas putida* |
| phaB | ABF82234.1 | 26990001 | *Pseudomonas putida* |
| paaA | NP_745427.1 | 106636093 | *Pseudomonas fluorescens* |
| paaB | NP_745426.1 | 106636094 | *Pseudomonas fluorescens* |
| pimF | CAE29158.1 | 39650635 | *Rhodopseudomonas palustris* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |
| FOX2 | NP_012934.1 | 6322861 | *Saccharomyces cerevisiae* |
| PHS1 | NP_012438.1 | 6322364 | *Saccharomyces cerevisiae* |

Enoyl-CoA hydratases involved in beta-oxidation can also be used in an fatty alcohol, fatty aldehyde and fatty acid biosynthetic pathway. For example, the multifunctional MFP2 gene product of Arabidopsis thaliana exhibits an enoyl-CoA reductase activity selective for chain lengths less than or equal to $C_{14}$ (Arent et al, *J Biol Chem* 285:24066-77 (2010)). Alternatively, the *E. coli* gene products of fadA and fadB encode a multienzyme complex involved in fatty acid oxidation that exhibits enoyl-CoA hydratase activity (Yang et al., *Biochemistry* 30:6788-6795 (1991); Yang, *J Bacteriol.* 173:7405-7406 (1991); Nakahigashi et al., *Nucleic Acids Res.* 18:4937 (1990)). The fadI and fadJ genes encode similar functions and are naturally expressed under anaerobic conditions (Campbell et al., *Mol. Microbiol* 47:793-805 (2003)).

| Protein | GenBank ID | GI Number | Organism |
| --- | --- | --- | --- |
| MFP2 | AAD18042.1 | 4337027 | Arabidopsis thaliana |
| fadA | YP_026272.1 | 49176430 | Escherichia coli |
| fadB | NP_418288.1 | 16131692 | Escherichia coli |
| fadI | NP_416844.1 | 16130275 | Escherichia coli |
| fadJ | NP_416843.1 | 16130274 | Escherichia coli |
| fadR | NP_415705.1 | 16129150 | Escherichia coli |

Chain length specificity of selected 3-hydroxyacyl-CoA dehydratase enzymes is shown below.

| Chain length | Gene | Organism |
| --- | --- | --- |
| C4-C6 | crt | Clostridium acetobutylicum |
| C4-C7 | pimF | Rhodopseudomonas palustris |
| C4-C14 | MFP2 | Arabidopsis thaliana |

Step D. Enoyl-CoA Reductase

Enoyl-CoA reductases (also known as acyl-CoA dehydrogenases, trans-2-enoyl-CoA reductases, or acyl-CoA oxidoreductases) catalyze the conversion of an enoyl-CoA to an acyl-CoA (step D of FIGS. 1 and 6). Exemplary acyl-CoA dehydrogenase or enoyl-CoA reductase (ECR) enzymes are the gene products of fadE of *E. coli* and *Salmonella enterica* (Iram et al, *J Bacteriol* 188:599-608 (2006)). The bcd gene product from *Clostridium acetobutylicum* (Atsumi et al., 10:305-311 (2008); Boynton et al., *J Bacteriol.* 178:3015-3024 (1996)) catalyzes the reduction of crotonyl-CoA to butyryl-CoA (EC 1.3.99.2). This enzyme participates in the acetyl-CoA fermentation pathway to butyrate in Clostridial species (Jones et al., *Microbiol Rev.* 50:484-524 (1986)). Activity of butyryl-CoA reductase can be enhanced by expressing bcd in conjunction with expression of the *C. acetobutylicum* etfAB genes, which encode an electron transfer flavoprotein. An additional candidate for the enoyl-CoA reductase step is the enoyl-CoA reductase (EC 1.3.1.44) TER from *E. gracilis* (Hoffmeister et al., *J Biol. Chem* 280:4329-4338 (2005)). A construct derived from this sequence following the removal of its mitochondrial targeting leader sequence was cloned in *E. coli* resulting in an active enzyme. A close homolog of the ECR protein from the prokaryote *Treponema denticola*, encoded by TDE0597, has also been cloned and expressed in *E. coli* (Tucci et al., FEBS Lett, 581:1561-1566 (2007)). Six genes in *Syntrophus aciditrophicus* were identified by sequence homology to the *C. acetobutylicum* bcd gene product. The *S. aciditrophicus* genes syn_02637 and syn_02636 bear high sequence homology to the etfAB genes of *C. acetobutylicum*, and are predicted to encode the alpha and beta subunits of an electron transfer flavoprotein.

| Protein | GenBank ID | GI Number | Organism |
| --- | --- | --- | --- |
| fadE | AAC73325.2 | 87081702 | Escherichia coli |
| fadE | YP_005241256.1 | 379699528 | Salmonella enterica |
| bcd | NP_349317.1 | 15895968 | Clostridium acetobutylicum |
| etfA | NP_349315.1 | 15895966 | Clostridium acetobutylicum |
| etfB | NP_349316.1 | 15895967 | Clostridium acetobutylicum |
| TER | Q5EU90.1 | 62287512 | Euglena gracilis |
| TER | NP_612558.1 | 19924091 | Rattus norvegicus |
| TDE0597 | NP_971211.1 | 42526113 | Treponema denticola |
| syn_02587 | ABC76101 | 85721158 | Syntrophus aciditrophicus |
| syn_02586 | ABC76100 | 85721157 | Syntrophus aciditrophicus |
| syn_01146 | ABC76260 | 85721317 | Syntrophus aciditrophicus |
| syn_00480 | ABC77899 | 85722956 | Syntrophus aciditrophicus |
| syn_02128 | ABC76949 | 85722006 | Syntrophus aciditrophicus |
| syn_01699 | ABC78863 | 85723920 | Syntrophus aciditrophicus |
| syn_02637 | ABC78522.1 | 85723579 | Syntrophus aciditrophicus |
| syn_02636 | ABC78523.1 | 85723580 | Syntrophus aciditrophicus |

Additional enoyl-CoA reductase enzyme candidates are found in organisms that degrade aromatic compounds. *Rhodopseudomonas palustris*, a model organism for benzoate degradation, has the enzymatic capability to degrade pimelate via beta-oxidation of pimeloyl-CoA. Adjacent genes in the pim operon, pimC and pimD, bear sequence homology to *C. acetobutylicum* bcd and are predicted to encode a flavin-containing pimeloyl-CoA dehydrogenase (Harrison et al., 151:727-736 (2005)). The genome of nitrogen-fixing soybean symbiont *Bradyrhizobium japonicum* also contains a pim operon composed of genes with high sequence similarity to pimC and pimD of *R. palustris* (Harrison and Harwood, *Microbiology* 151:727-736 (2005)).

| Protein | GenBank ID | GI Number | Organism |
| --- | --- | --- | --- |
| pimC | CAE29155 | 39650632 | Rhodopseudomonas palustris |
| pimD | CAE29154 | 39650631 | Rhodopseudomonas palustris |
| pimC | BAC53083 | 27356102 | Bradyrhizobium japonicum |
| pimD | BAC53082 | 27356101 | Bradyrhizobium japonicum |

An additional candidate is 2-methyl-branched chain enoyl-CoA reductase (EC 1.3.1.52 and EC 1.3.99.12), an enzyme catalyzing the reduction of sterically hindered trans-enoyl-CoA substrates. This enzyme participates in branched-chain fatty acid synthesis in the nematode *Ascaris suum* and is capable of reducing a variety of linear and branched chain substrates including 2-methylvaleryl-CoA, 2-methylbutanoyl-CoA, 2-methylpentanoyl-CoA, octanoyl-CoA and pentanoyl-CoA (Duran et al., 268:22391-22396 (1993)). Two isoforms of the enzyme, encoded by genes acad1 and acad, have been characterized.

| Protein | GenBank ID | GI Number | Organism |
|---|---|---|---|
| acad1 | AAC48316.1 | 2407655 | *Ascaris suum* |
| acad | AAA16096.1 | 347404 | *Ascaris suum* |

At least three mitochondrial enoyl-CoA reductase enzymes exist in *E. gracilis* and are applicable for use in the invention. Three mitochondrial enoyl-CoA reductase enzymes of *E. gracilis* (ECR1-3) exhibit different chain length preferences (Inui et al., *European Journal of Biochemistry* 142:121-126 (1984)), which is particularly useful for dictating the chain length of the desired fatty alcohol, fatty aldehyde or fatty acid products. EST's ELL00002199, ELL00002335, and ELL00002648, which are all annotated as mitochondrial trans-2-enoyl-CoA reductases, can be used to isolate these additional enoyl-CoA reductase genes by methods known in the art. Two ECR enzymes from rat liver microsomes also exhibit different substrate specificities (Nagi et al, *Arch Biochem Biophys* 226:50-64 (1983)). The sequences of these enzymes have not been identified to date. The *Mycobacterium smegmatis* enoyl-CoA reductase accepts acyl-CoA substrates of chain lengths between C10-C16 (Shimakata et al, *J Biochem* 89:1075-80 (1981)).

Enoyl-CoA reductases and their chain length specificities are shown in the table below.

| Chain length | Gene | Organism |
|---|---|---|
| C4-C6 | ECR1 | *Euglena gracilis* |
| C6-C8 | ECR3 | *Euglena gracilis* |
| C8-10 | ECR2 | *Euglena gracilis* |
| C8-C16 | Long chain ECR | *Rattus norvegicus* |
| C10-C16 | ECR | *Mycobacterium smegmatis* |
| C2-C18 | fadE | *Salmonella enterica* |

Step E. Acyl-CoA Reductase (Aldehyde Forming)

Reduction of an acyl-CoA to a fatty alcohol is catalyzed by either a single enzyme or pair of enzymes that exhibit acyl-CoA reductase and alcohol dehydrogenase activities. Acyl-CoA dehydrogenases that reduce an acyl-CoA to its corresponding aldehyde include fatty acyl-CoA reductase (EC 1.2.1.42, 1.2.1.50), succinyl-CoA reductase (EC 1.2.1.76), acetyl-CoA reductase, butyryl-CoA reductase and propionyl-CoA reductase (EC 1.2.1.3). Aldehyde forming acyl-CoA reductase enzymes with demonstrated activity on acyl-CoA, 3-hydroxyacyl-CoA and 3-oxoacyl-CoA substrates are known in the literature. Several acyl-CoA reductase enzymes are active on 3-hydroxyacyl-CoA substrates. For example, some butyryl-CoA reductases from *Clostridial* organisms, are active on 3-hydroxybutyryl-CoA and propionyl-CoA reductase of *L. reuteri* is active on 3-hydroxypropionyl-CoA. An enzyme for converting 3-oxoacyl-CoA substrates to their corresponding aldehydes is malonyl-CoA reductase. Enzymes in this class that demonstrate activity on enoyl-CoA substrates have not been identified to date. Specificity for a particular substrate can be refined using evolution or enzyme engineering methods known in the art.

Exemplary fatty acyl-CoA reductases enzymes are encoded by acr1 of *Acinetobacter calcoaceticus* (Reiser, *Journal of Bacteriology* 179:2969-2975 (1997)) and *Acinetobacter* sp. M-1 (Ishige et al., *Appl. Environ. Microbiol.* 68:1192-1195 (2002)). Two gene products from *Mycobacterium tuberculosis* accept longer chain fatty acyl-CoA substrates of length C16-C18 (Harminder Singh, U. Central Florida (2007)). Yet another fatty acyl-CoA reductase is LuxC of *Photobacterium phosphoreum* (Lee et al, *Biochim Biohys Acta* 1388:215-22 (1997)). Enzymes with succinyl-CoA reductase activity are encoded by sucD of *Clostridium kluyveri* (Sohling, *J. Bacteriol.* 178:871-880 (1996)) and sucD of *P. gingivalis* (Takahashi, *J. Bacteriol* 182:4704-4710 (2000)). Additional succinyl-CoA reductase enzymes participate in the 3-hydroxypropionate/4-hydroxybutyrate cycle of thermophilic archaea including *Metallosphaera sedula* (Berg et al., *Science* 318:1782-1786 (2007)) and *Thermoproteus neutrophilus* (Ramos-Vera et al., *J Bacteriol,* 191:4286-4297 (2009)). The *M. sedula* enzyme, encoded by Msed_0709, is strictly NADPH-dependent and also has malonyl-CoA reductase activity. The *T. neutrophilus* enzyme is active with both NADPH and NADH. The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski, *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, *J. Gen. Appl. Microbiol.* 18:43-55 (1972); and Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci BiotechnolBiochem.,* 71:58-68 (2007)). Exemplary propionyl-CoA reductase enzymes include pduP of *Salmonella typhimurium* LT2 (Leal, *Arch. Microbiol.* 180:353-361 (2003)) and eutE from *E. coli* (Skraly, WO Patent No. 2004/024876). The propionyl-CoA reductase of *Salmonella typhimurium* LT2, which naturally converts propionyl-CoA to propionaldehyde, also catalyzes the reduction of 5-hydroxyvaleryl-CoA to 5-hydroxypentanal (WO 2010/068953A2). The propionaldehyde dehydrogenase of *Lactobacillus reuteri*, PduP, has a broad substrate range that includes butyraldehyde, valeraldehyde and 3-hydroxypropionaldehyde (Luo et al, *Appl Microbiol Biotech,* 89: 697-703 (2011). Additionally, some acyl-ACP reductase enzymes such as the orf1594 gene product of *Synechococcus elongatus* PCC7942 also exhibit aldehyde-forming acyl-CoA reductase activity (Schirmer et al, *Science,* 329: 559-62 (2010)). Acyl-ACP reductase enzymes and homologs are described in further detail in Example IX.

| Protein | GenBank ID | GI Number | Organism |
|---|---|---|---|
| acr1 | YP_047869.1 | 50086359 | Acinetobacter calcoaceticus |
| acr1 | AAC45217 | 1684886 | Acinetobacter baylyi |
| acr1 | BAB85476.1 | 18857901 | Acinetobacter sp. Strain M-1 |
| Rv1543 | NP_216059.1 | 15608681 | Mycobacterium tuberculosis |
| Rv3391 | NP_217908.1 | 15610527 | Mycobacterium tuberculosis |
| LuxC | AAT00788.1 | 46561111 | Photobacterium phosphoreum |
| Msed_0709 | YP_001190808.1 | 146303492 | Metallosphaera sedula |
| Tneu_0421 | ACB39369.1 | 170934108 | Thermoproteus neutrophilus |
| sucD | P38947.1 | 172046062 | Clostridium kluyveri |
| sucD | NP_904963.1 | 34540484 | Porphyromonas gingivalis |
| bphG | BAA03892.1 | 425213 | Pseudomonas sp |
| adhE | AAV66076.1 | 55818563 | Leuconostoc mesenteroides |
| bld | AAP42563.1 | 31075383 | Clostridium saccharoperbutylacetonicum |
| pduP | NP_460996 | 16765381 | Salmonella typhimurium LT2 |
| eutE | NP_416950 | 16130380 | Escherichia coli |
| pduP | CCC03595.1 | 337728491 | Lactobacillus reuteri |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg, Science 318:1782-1786 (2007); and Thauer, Science 318:1732-1733 (2007)). The enzyme utilizes NADPH as a cofactor and has been characterized in Metallosphaera and Sulfolobus sp. (Alber et al., J. Bacteriol. 188:8551-8559 (2006); and Hugler, J. Bacteriol. 184:2404-2410 (2002)). The enzyme is encoded by Msed_0709 in Metallosphaera sedula (Alber et al., J. Bacteriol. 188:8551-8559 (2006); and Berg, Science 318:1782-1786 (2007)). A gene encoding a malonyl-CoA reductase from Sulfolobus tokodaii was cloned and heterologously expressed in E. coli (Alber et al., J. Bacteriol 188:8551-8559 (2006). This enzyme has also been shown to catalyze the conversion of methylmalonyl-CoA to its corresponding aldehyde (WO2007141208 (2007)). Although the aldehyde dehydrogenase functionality of these enzymes is similar to the bifunctional dehydrogenase from Chloroflexus aurantiacus, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including Sulfolobus solfataricus and Sulfolobus acidocaldarius and have been listed below. Yet another candidate for CoA-acylating aldehyde dehydrogenase is the aid gene from Clostridium beijerinckii (Toth, Appl. Environ. Microbiol. 65:4973-4980 (1999). This enzyme has been reported to reduce acetyl-CoA and butyryl-CoA to their corresponding aldehydes. This gene is very similar to eutE that encodes acetaldehyde dehydrogenase of Salmonella typhimurium and E. coli (Toth, Appl. Environ. Microbiol. 65:4973-4980 (1999).

| Gene | GenBank ID | GI Number | Organism |
|---|---|---|---|
| Msed_0709 | YP_001190808.1 | 146303492 | Metallosphaera sedula |
| mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 49473535 | Clostridium beijerinckii |
| eutE | AAA80209 | 687645 | Salmonella typhimurium |
| eutE | NP_416950 | 16130380 | Escherichia coli |

Chain length specificity ranges of selected aldehyde-forming acyl-CoA reductase enzymes are show in the table below.

| Chain length | Gene | Organism |
|---|---|---|
| C2-C4 | bphG | *Pseudomonas* sp |
| C4 | Bld | *Clostridium saccharoperbutylacetonicum* |
| C12-C20 | ACR | *Acinetobacter calcoaceticus* |
| C14-C18 | Acr1 | *Acinetobacter* sp. Strain M-1 |
| C16-C18 | Rv1543, Rv3391 | *Mycobacterium tuberculosis* |

Step G. Acyl-CoA Reductase (Alcohol Forming)

Bifunctional alcohol-forming acyl-CoA reductase enzymes catalyze step G (i.e. step E and F) of FIGS. 1 and 6. Enzymes with this activity include adhE of *E. coli* (Kessler et al., *FEBS. Lett.* 281:59-63 (1991))) and adhE2 of *Clostridium acetobutylicum* (Fontaine et al., *J. Bacteriol.* 184:821-830 (2002))). The *E. coli* enzyme is active on $C_2$ substrates, whereas the *C. acetobutylicum* enzyme has a broad substrate range that spans C2-C8 (Dekishima et al, *J Am Chem Soc* 133:11399-11401 (2011)). The *C. acetobutylicum* enzymes encoded by bdh I and bdh II (Walter, et al., *J. Bacteriol.* 174:7149-7158 (1992)), reduce acetyl-CoA and butyryl-CoA to ethanol and butanol, respectively. The adhE gene produce from *Leuconostoc mesenteroides* is active on acetyl-CoA and isobutyryl-CoA (Kazahaya et al., *J. Gen. Appl. Microbiol.* 18:43-55 (1972); Koo et al., *Biotechnol Lett,* 27:505-510 (2005)). Enzyme candidates in other organisms including *Roseiflexus castenholzii, Erythrobacter* sp. NAP1 and marine gamma proteobacterium HTCC2080 can be inferred by sequence similarity. Longer chain acyl-CoA molecules can be reduced to their corresponding alcohols by enzymes such as the jojoba (*Simmondsia chinensis*) FAR which encodes an alcohol-forming fatty acyl-CoA reductase. Its overexpression in *E. coli* resulted in FAR activity and the accumulation of C16-C18 fatty alcohols (Metz et al., *Plant Physiol,* 122:635-644 (2000)). FAR enzymes in *Arabidopsis thaliana* include the gene products of At3g11980 and At3g44560 (Doan et al, *J Plant Physiol* 166 (2006)). Bifunctional prokaryotic FAR enzymes are found in *Marinobacter aquaeolei* VT8 (Hofvander et al, FEBS Lett 3538-43 (2011)), *Marinobacter algicola* and *Oceanobacter* strain RED65 (US Pat Appl 20110000125). Other suitable enzymes include bfar from *Bombyx mori*, mfar1 and mfar2 from *Mus musculus*; mfar2 from *Mus musculus*; acrM1 from *Acinetobacter* sp. M1; and hfar from *H. sapiens*.

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| bdh I | NP_349892.1 | 15896543 | *Clostridium acetobutylicum* |
| bdh II | NP_349891.1 | 15896542 | *Clostridium acetobutylicum* |
| adhE | AAV66076.1 | 55818563 | *Leuconostoc mesenteroides* |
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |
| FAR | AAD38039.1 | 5020215 | *Simmondsia chinensis* |
| At3g11980 | NP_191229.1 | 15228993 | *Arabidopsis thaliana* |
| At3g44560 | NP_190042.2 | 145339120 | *Arabidopsis thaliana* |
| FAR | YP_959486.1 | 120555135 | *Marinobacter aquaeolei* |
| bfar | Q8R079 | 81901336 | *Bombyx mori* |

Chain length specificity ranges of selected alcohol-forming acyl-CoA reductase enzymes are show in the table below.

| Chain length | Gene | Organism |
| --- | --- | --- |
| C2 | adhE | Escherichia coli |
| C2-C8 | adhe2 | Clostridium acetobutylicum |
| C14-C16 | At3g11980 | Arabidopsis thaliana |
| C16 | At3g44560 | Arabidopsis thaliana |
| C16-C18 | FAR | Simmondsia chinensis |
| C14-C18 | FAR | Marinobacter aquaeolei |

Step F. Fatty Aldehyde Reductase

Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.* 66:5231-5235 (2000)), yqhD and fucO from *E. coli* (Sulzenbacher et al., 342:489-502 (2004)), and bdh I and bdh II from *C. acetobutylicum* which converts butyryaldehyde into butanol (Walter et al., *J Bacteriol* 174:7149-7158 (1992)). The alrA gene product showed no activity on aldehydes longer than C14, and favored the reductive direction (Tani et al, supra). YqhD catalyzes the reduction of a wide range of aldehydes using NADPH as the cofactor, with a preference for chain lengths longer than C(3) (Sulzenbacher et al, *J Mol Biol* 342:489-502 (2004); Perez et al., *J Biol. Chem.* 283:7346-7353 (2008)). The adhA gene product from *Zymomonas mobilis* has been demonstrated to have activity on a number of aldehydes including formaldehyde, acetaldehyde, propionaldehyde, butyraldehyde, and acrolein (Kinoshita et al., *Appl Microbiol Biotechnol* 22:249-254 (1985)). Additional aldehyde reductase candidates are encoded by bdh in *C. saccharoperbutylacetonicum* and Cbei_1722, Cbei_2181 and Cbei_2421 in *C. beijerinckii*. The alcohol dehydrogenase from *Leifsonia* sp. S749 shows maximal activity on medium chain-length substrates of length C6-C7 (Inoue et al, *AEM* 71: 3633-3641 (2005). The adh gene product of *Pseudomonas putida* is active on substrates of length C3-C10 (Nagashima et al, *J Ferment Bioeng* 82:328-33 (1996)). The alcohol dehydrogenase enzymes ADH1 and ADH2 of *Geobacillus thermodenitrificans* oxidize alcohols up to a chain length of C30 (Liu et al, *Physiol Biochem* 155:2078-85 (2009)).

| Protein | GenBank ID | GI Number | Organism |
| --- | --- | --- | --- |
| alrA | BAB12273.1 | 9967138 | Acinetobacter sp. strain M-1 |
| ADH2 | NP_014032.1 | 6323961 | Saccharomyces cerevisiae |
| yqhD | NP_417484.1 | 16130909 | Escherichia coli |
| fucO | NP_417279.1 | 16130706 | Escherichia coli |
| bdh I | NP_349892.1 | 15896543 | Clostridium acetobutylicum |
| bdh II | NP_349891.1 | 15896542 | Clostridium acetobutylicum |
| adhA | YP_162971.1 | 56552132 | Zymomonas mobilis |
| bdh | BAF45463.1 | 124221917 | Clostridium saccharoperbutylacetonicum |
| Cbei_1722 | YP_001308850 | 150016596 | Clostridium beijerinckii |
| Cbei_2181 | YP_001309304 | 150017050 | Clostridium beijerinckii |
| Cbei_2421 | YP_001309535 | 150017281 | Clostridium beijerinckii |
| lsadh | BAD99642.1 | 67625613 | Leifsonia sp. S749 |
| adh | | | Pseudomonas putida |

Native alcohol dehydrogenases also convert aldehyde substrates to alcohol products. To date, seven alcohol dehydrogenases, ADHI-ADHVII, have been reported in *S. cerevisiae* (de Smidt et al, *FEMS Yeast Res* 8:967-78 (2008)). ADH1 (GI: 1419926) is the key enzyme responsible for reducing acetaldehyde to ethanol in the cytosol under anaerobic conditions. In *K. lactis*, two NAD-dependent cytosolic alcohol dehydrogenases have been identified and characterized. These genes also show activity for other aliphatic alcohols. The genes ADHI (GI:113358) and ADHII (GI:51704293) are preferentially expressed in glucose-grown cells (Bozzi et al, *Biochim Biophys Acta* 1339:133-142 (1997)). Cytosolic alcohol dehydrogenases are encoded by ADH1 (GI:608690) in *C. albicans*, ADH1 (GI:3810864) in *S. pombe*, ADHI (GI:5802617) in *Y. lipolytica*, ADH1 (GI:2114038) and ADHII (GI:2143328) in *Pichia stipitis* or *Scheffersomyces stipitis* (Passoth et al, *Yeast* 14:1311-23 (1998)). Candidate alcohol dehydrogenases are shown the table below.

| Protein | GenBank ID | GI number | Organism |
| --- | --- | --- | --- |
| SADH | BAA24528.1 | 2815409 | Candida parapsilosis |
| ADH1 | NP_014555.1 | 6324486 | Saccharomyces cerevisiae s288c |
| ADH2 | NP_014032.1 | 6323961 | Saccharomyces cerevisiae s288c |
| ADH3 | NP_013800.1 | 6323729 | Saccharomyces cerevisiae s288c |
| ADH4 | NP_011258.2 | 269970305 | Saccharomyces cerevisiae s288c |
| ADH5 (SFA1) | NP_010113.1 | 6320033 | Saccharomyces cerevisiae s288c |

| Protein | GenBank ID | GI number | Organism |
|---|---|---|---|
| ADH6 | NP_014051.1 | 6323980 | Saccharomyces cerevisiae s288c |
| ADH7 | NP_010030.1 | 6319949 | Saccharomyces cerevisiae s288c |
| adhP | CAA44614.1 | 2810 | Kluyveromyces lactis |
| ADH1 | P20369.1 | 113358 | Kluyveromyces lactis |
| ADH2 | CAA45739.1 | 2833 | Kluyveromyces lactis |
| ADH3 | P49384.2 | 51704294 | Kluyveromyces lactis |
| ADH1 | YP_001126968.1 | 138896515 | Geobacillus thermodenitrificans |
| ADH2 | YP_001125863.1 | 138895410 | Geobacillus thermodenitrificans |

Substrate specificity ranges of selected alcohol dehydrogenase enzymes are show in the table below.

| Chain length | Gene | Organism |
|---|---|---|
| C6-C7 | lsadh | Leifsonia sp. S749 |
| C2-C8 | yqhD | Escherichia coli |
| C3-C10 | Adh | Pseudomonas putida |
| C2-C14 | alrA | Acinetobacter sp. strain M-1 |
| C2-C30 | ADH1 | Geobacillus thermodenitrificans |

Those skilled in the art also can obtain nucleic acids encoding any or all of the malonyl-CoA independent FAS pathway or acyl-reduction pathway enzymes by cloning using known sequences from available sources. For example, any or all of the encoding nucleic acids for the malonyl-CoA independent FAS pathway can be readily obtained using methods well known in the art from E. gracilis as this pathway has been well characterized in this organism. E. gracilis encoding nucleic acids can be isolated from, for example, an E. gracilis cDNA library using probes of known sequence. The probes can be designed with whole or partial DNA sequences from the following EST sequences from the publically available sequence database TBestDB (http://tbestdb.bcm.umontreal.ca). The nucleic acids generated from this process can be inserted into an appropriate expression vector and transformed into E. coli or other microorganisms to generate fatty alcohols, fatty aldehydes or fatty acids production organisms of the invention.

Thiolase (FIG. 1A): ELL00002550, ELL00002493, ELL00000789

3-Hydroxyacyl-CoA dehydrogenase (FIG. 1B): ELL00000206, ELL00002419, ELL00006286, ELL00006656

Enoyl-CoA hydratase (FIG. 1C): ELL00005926, ELL00001952, ELL00002235, ELL00006206

Enoyl-CoA reductase (FIG. 1D): ELL00002199, ELL00002335, ELL00002648

Acyl-CoA reductase (FIG. 1E; 1E/F): ELL00002572, ELL00002581, ELL00000108

Alternatively, the above EST sequences can be used to identify homologue polypeptides in GenBank through BLAST search. The resulting homologue polypeptides and their corresponding gene sequences provide additional encoding nucleic acids for transformation into E. coli or other microorganisms to generate the fatty alcohols, fatty aldehydes or fatty acids producing organisms of the invention. Listed below are exemplary homologue polypeptide and their gene accession numbers in GenBank which are applicable for use in the non-naturally occurring organisms of the invention.

Ketoacyl-CoA Acyltransferase (or Ketoacyl-CoA Thiolase)

| Protein | GenBank ID | GI number | Organism |
|---|---|---|---|
| Dole_2160 | YP_001530041 | 158522171 | Desulfococcus oleovorans Hxd3 |
| DalkDRAFT_1939 | ZP_02133627 | 163726110 | Desulfatibacillum alkenivorans AK-01 |
| BSG1_09488 | ZP_01860900 | 149182424 | Bacillus sp. SG-1 |

3-Hydroxyacyl-CoA Dehydrogenase

| Protein | GenBank ID | GI number | Organism |
|---|---|---|---|
| AaeL_AAEL002841 | XP_001655993 | 157132312 | Aedes aegypti |
| hadh | NP_001011073 | 58331907 | Xenopus tropicalis |
| hadh | NP_001003515 | 51011113 | Danio rerio |

Enoyl-CoA Hydratase

| Protein | GenBank ID | GI number | Organism |
|---|---|---|---|
| Tb927.3.4850 | XP_844077 | 72387305 | Trypanosoma brucei |
| Tc00.1047053509701.10 | XP_802711 | 71399112 | Trypanosoma cruzi strain CL Brener |
| PputGB1_3629 | XP_001669856 | 167034625 | Pseudomonas putida GB-1 |

Enoyl-CoA Reductase

| Protein | GenBank ID | GI number | Organism |
|---|---|---|---|
| mecr | XP_642118 | 66816217 | Dictyostelium discoideum AX4 |
| NEMVEDRAFT_v1g228294 | XP_001639469 | 156402181 | Nematostella vectensis |
| AaeL_AAEL003995 | XP_001648220 | 157104018 | Aedes aegypti |

In addition to the above exemplary encoding nucleic acids, nucleic acids other than those within the MI-FAE cycle and/or termination pathways of the invention also can be introduced into a host organism for further production of fatty alcohols, fatty aldehydes or fatty acids. For example, the *Ralstonia eutropha* BktB and PhbB genes catalyze the condensation of butyryl-CoA and acetyl-CoA to form β-keto-hexanoyl-CoA and the reduction of β-keto-hexanoyl-CoA to 3-hydroxy-hexanoyl-CoA (Fukui et al., *Biomacromolecules* 3:618-624 (2002)). To improve the production of fatty alcohols, exogenous DNA sequences encoding for these specific enzymes can be expressed in the production host of interest. Furthermore, the above described enzymes can be subjected to directed evolution to generate improved versions of these enzymes with high activity and high substrate specificity. A similar approach also can be utilized with any or all other enzymatic steps in the fatty alcohol, fatty aldehyde or fatty acid producing pathways of the invention to, for example, improve enzymatic activity and/or specificity and/or to generate a fatty alcohol, a fatty aldehyde or a fatty acid of a predetermined chain length or lengths.

Example II

Pathways for Producing Cytosolic Acetyl-CoA from Cytosolic Pyruvate

Figure 2:
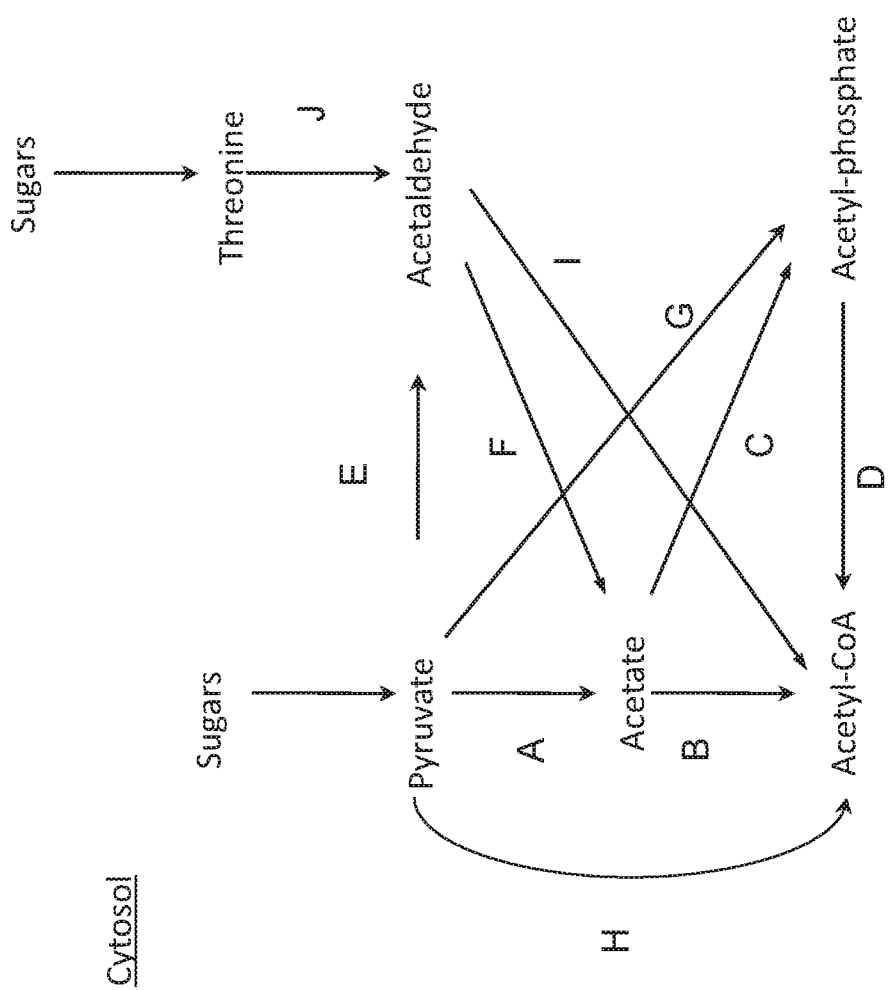
FIG. 2 shows exemplary pathways for production of cytosolic acetyl-CoA from pyruvate or threonine. Enzymes are: A. pyruvate oxidase (acetate-forming); B. acetyl-CoA synthetase, ligase or transferase; C. acetate kinase; D. phosphotransacetylase; E. pyruvate decarboxylase; F. acetaldehyde dehydrogenase; G. pyruvate oxidase (acetyl-phosphate forming); H. pyruvate dehydrogenase, pyruvate:ferredoxin oxidoreductase, pyruvate:NAD(P)H oxidoreductase or pyruvate formate lyase; I. acetaldehyde dehydrogenase (acylating); and J. threonine aldolase.
Figure 3:
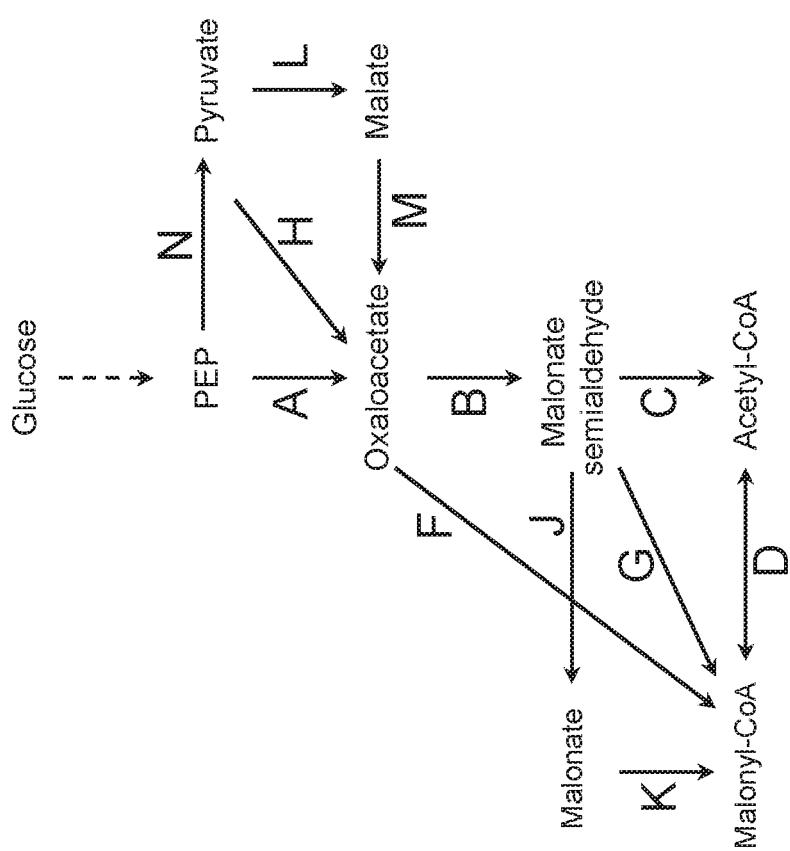
FIG. 3 shows exemplary pathways for production of acetyl-CoA from phosphoenolpyruvate (PEP). Enzymes are: A. PEP carboxylase or PEP carboxykinase; B. oxaloacetate decarboxylase; C. malonate semialdehyde dehydrogenase (acetylating); D. acetyl-CoA carboxylase or malonyl-CoA decarboxylase; F. oxaloacetate dehydrogenase or oxaloacetate oxidoreductase; G. malonate semialdehyde dehydrogenase (acylating); H. pyruvate carboxylase; J. malonate semialdehyde dehydrogenase; K. malonyl-CoA synthetase or transferase; L. malic enzyme; M. malate dehydrogenase or oxidoreductase; and N. pyruvate kinase or PEP phosphatase.

The following example describes exemplary pathways for the conversion of cytosolic pyruvate and threonine to cytosolic acetyl-CoA, as shown in FIG. 2.

Pathways for the conversion of cytosolic pyruvate and threonine to cytosolic acetyl-CoA could enable deployment of a cytosolic fatty alcohol, fatty aldehyde or fatty acid production pathway that originates from acetyl-CoA. Several pathways for converting cytosolic pyruvate to cytosolic acetyl-CoA are shown in FIG. 2. Direct conversion of pyruvate to acetyl-CoA can be catalyzed by pyruvate dehydrogenase, pyruvate formate lyase, pyruvate:NAD(P) oxidoreductase or pyruvate:ferredoxin oxidoreductase. If a pyruvate formate lyase is utilized, the formate byproduct can be further converted to CO2 by formate dehydrogenase or formate hydrogen lyase.

Indirect conversion of pyruvate to acetyl-CoA can proceed through several alternate routes. Pyruvate can be converted to acetaldehyde by a pyruvate decarboxylase. Acetaldehyde can then converted to acetyl-CoA by an acylating (CoA-dependent) acetaldehyde dehydrogenase. Alternately, acetaldehyde generated by pyruvate decarboxylase can be converted to acetyl-CoA by the "PDH bypass" pathway. In this pathway, acetaldehyde is oxidized by acetaldehyde dehydrogenase to acetate, which is then converted to acetyl-CoA by a CoA ligase, synthetase or transferase. In another embodiment, the acetate intermediate is converted by an acetate kinase to acetyl-phosphate that is then converted to acetyl-CoA by a phosphotransacetylase. In yet another embodiment, pyruvate is directly converted to acetyl-phosphate by a pyruvate oxidase (acetyl-phosphate forming). Conversion of pyruvate to acetate is also catalyzed by acetate-forming pyruvate oxidase.

Cytosolic acetyl-CoA can also be synthesized from threonine by expressing a native or heterologous threonine aldolase (FIG. 5J) (van Maris et al, *AEM* 69:2094-9 (2003)). Threonine aldolase converts threonine into acetaldehyde and glycine. The acetaldehyde product is subsequently converted to acetyl-CoA by various pathways described above.

Gene candidates for the acetyl-CoA forming enzymes shown in FIG. 2 are described below.

Pyruvate oxidase (acetate-forming) (FIG. 2A) or pyruvate:quinone oxidoreductase (PQO) can catalyze the oxidative decarboxylation of pyruvate into acetate, using ubiquione (EC 1.2.5.1) or quinone (EC 1.2.2.1) as an electron acceptor. The *E. coli* enzyme, PoxB, is localized on the inner membrane (Abdel-Hamid et al., *Microbiol* 147:1483-98 (2001)). The enzyme has thiamin pyrophosphate and flavin adenine dinucleotide (FAD) cofactors (Koland and Gennis, *Biochemistry* 21:4438-4442 (1982)); O'Brien et al., *Biochemistry* 16:3105-3109 (1977); O'Brien and Gennis, *J. Biol. Chem.* 255:3302-3307 (1980)). PoxB has similarity to pyruvate decarboxylase of *S. cerevisiae* and *Zymomonas mobilis*. The pqo transcript of *Corynebacterium glutamicum* encodes a quinone-dependent and acetate-forming pyruvate oxidoreductase (Schreiner et al., *J Bacteriol* 188:1341-50 (2006)). Similar enzymes can be inferred by sequence homology.

| Protein | GenBank ID | GI Number | Organism |
|---------|------------|-----------|----------|
| poxB | NP_415392.1 | 16128839 | *Escherichia coli* |
| pqo | YP_226851.1 | 62391449 | *Corynebacterium glutamicum* |
| poxB | YP_309835.1 | 74311416 | *Shigella sonnei* |
| poxB | ZP_03065403.1 | 194433121 | *Shigella dysenteriae* |

The acylation of acetate to acetyl-CoA (FIG. 2B) can be catalyzed by enzymes with acetyl-CoA synthetase, ligase or transferase activity. Two enzymes that can catalyze this reaction are AMP-forming acetyl-CoA synthetase or ligase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol.* 102:327-336 (1977)), *Ralstonia eutropha* (Priefert and Steinbuchel, *J. Bacteriol.* 174:6590-6599 (1992)), *Methanothermobacter thermautotrophicus* (Ingram-Smith and Smith, Archaea 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431 (2004)). ADP-forming acetyl-CoA synthetases are reversible enzymes with a generally broad substrate range (Musfeldt and Schonheit, *J. Bacteriol.* 184:636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus*, *H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). The aforementioned proteins are shown below.

| Protein | GenBank ID | GI Number | Organism |
|---|---|---|---|
| acs | AAC77039.1 | 1790505 | Escherichia coli |
| acoE | AAA21945.1 | 141890 | Ralstonia eutropha |
| acs1 | ABC87079.1 | 86169671 | Methanothermobacter thermautotrophicus |
| acs1 | AAL23099.1 | 16422835 | Salmonella enterica |
| ACS1 | Q01574.2 | 257050994 | Saccharomyces cerevisiae |
| AF1211 | NP_070039.1 | 11498810 | Archaeoglobus fulgidus |
| AF1983 | NP_070807.1 | 11499565 | Archaeoglobus fulgidus |
| scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| paaF | AAC24333.2 | 22711873 | Pseudomonas putida |

The acylation of acetate to acetyl-CoA can also be catalyzed by CoA transferase enzymes (FIG. 2B). Numerous enzymes employ acetate as the CoA acceptor, resulting in the formation of acetyl-CoA. An exemplary CoA transferase is acetoacetyl-CoA transferase, encoded by the *E. coli* atoA (alpha subunit) and atoD (beta subunit) genes (Korolev et al., *Acta Crystallogr. D. Biol. Crystallogr.* 58:2116-2121 (2002); Vanderwinkel et al., 33:902-908 (1968)). This enzyme has a broad substrate range (Sramek et al., *Arch Biochem Biophys* 171:14-26 (1975)) and has been shown to transfer the CoA moiety to acetate from a variety of branched and linear acyl-CoA substrates, including isobutyrate (Matthies et al., *Appl Environ. Microbiol* 58:1435-1439 (1992)), valerate (Vanderwinkel et al., *Biochem. Biophys. Res. Commun.* 33:902-908 (1968)) and butanoate (Vanderwinkel et al., *Biochem. Biophys. Res. Commun.* 33:902-908 (1968)). Similar enzymes exist in *Corynebacterium glutamicum* ATCC 13032 (Duncan et al., 68:5186-5190 (2002)), *Clostridium acetobutylicum* (Cary et al., *Appl Environ Microbiol* 56:1576-1583 (1990); Wiesenborn et al., *Appl Environ Microbiol* 55:323-329 (1989)), and *Clostridium saccharoperbutylacetonicum* (Kosaka et al., *Biosci. Biotechnol Biochem.* 71:58-68 (2007)).

| Gene | GI # | Accession No. | Organism |
|---|---|---|---|
| atoA | 2492994 | P76459.1 | Escherichia coli |
| atoD | 2492990 | P76458.1 | Escherichia coli |
| actA | 62391407 | YP_226809.1 | Corynebacterium glutamicum |
| cg0592 | 62389399 | YP_224801.1 | Corynebacterium glutamicum |
| ctfA | 15004866 | NP_149326.1 | Clostridium acetobutylicum |
| ctfB | 15004867 | NP_149327.1 | Clostridium acetobutylicum |
| ctfA | 31075384 | AAP42564.1 | Clostridium saccharoperbutylacetonicum |
| ctfB | 31075385 | AAP42565.1 | Clostridium saccharoperbutylacetonicum |

Acetate kinase (EC 2.7.2.1) can catalyzes the reversible ATP-dependent phosphorylation of acetate to acetylphosphate (FIG. 2C). Exemplary acetate kinase enzymes have been characterized in many organisms including *E. coli*, *Clostridium acetobutylicum* and *Methanosarcina thermophila* (Ingram-Smith et al., *J. Bacteriol.* 187:2386-2394 (2005); Fox and Roseman, *J. Biol. Chem.* 261:13487-13497 (1986); Winzer et al., *Microbioloy* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)). Homologs exist in several other organisms including *Salmonella enterica* and *Chlamydomonas reinhardtii*.

| Protein | GenBank ID | GI Number | Organism |
|---|---|---|---|
| ackA | NP_416799.1 | 16130231 | Escherichia coli |
| Ack | AAB18301.1 | 1491790 | Clostridium acetobutylicum |
| Ack | AAA72042.1 | 349834 | Methanosarcina thermophila |
| purT | AAC74919.1 | 1788155 | Escherichia coli |
| buk1 | NP_349675 | 15896326 | Clostridium acetobutylicum |
| buk2 | Q97II1 | 20137415 | Clostridium acetobutylicum |
| ackA | NP_461279.1 | 16765664 | Salmonella typhimurium |
| ACK1 | XP_001694505.1 | 159472745 | Chlamydomonas reinhardtii |
| ACK2 | XP_001691682.1 | 159466992 | Chlamydomonas reinhardtii |

The formation of acetyl-CoA from acetyl-phosphate can be catalyzed by phosphotransacetylase (EC 2.3.1.8) (FIG. 2D). Thepta gene from *E. coli* encodes an enzyme that reversibly converts acetyl-CoA into acetyl-phosphate (Suzuki, T., *Biochim. Biophys. Acta* 191:559-569 (969)). Additional acetyltransferase enzymes have been characterized in *Bacillus subtilis* (Rado and Hoch, *Biochim. Biophys. Acta* 321:114-125 (1973), *Clostridium kluyveri* (Stadtman, E., *Methods Enzymol.* 1:5896-599 (1955), and *Thermotoga maritima* (Bock et al., *J. Bacteriol.* 181:1861-1867 (1999)). This reaction can also be catalyzed by some phosphotranbutyrylase enzymes (EC 2.3.1.19), including the ptb gene products from *Clostridium acetobutylicum* (Wiesenborn et al., *App. Environ. Microbiol.* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004) and *Bacillus megaterium* (Vazquez et al., *Curr. Microbiol.* 42:345-349 (2001). Homologs to the *E. coli* pta gene exist in several other organisms including *Salmonella enterica* and *Chlamydomonas reinhardtii*.

| Protein | GenBank ID | GI Number | Organism |
|---|---|---|---|
| Pta | NP_416800.1 | 71152910 | Escherichia coli |
| Pta | P39646 | 730415 | Bacillus subtilis |
| Pta | A5N801 | 146346896 | Clostridium kluyveri |
| Pta | Q9X0L4 | 6685776 | Thermotoga maritime |
| Ptb | NP_349676 | 34540484 | Clostridium acetobutylicum |
| Ptb | AAR19757.1 | 38425288 | butyrate-producing bacterium L2-50 |
| Ptb | CAC07932.1 | 10046659 | Bacillus megaterium |
| Pta | NP_461280.1 | 16765665 | Salmonella enterica subsp. enterica serovar Typhimurium str. LT2 |
| PAT2 | XP_001694504.1 | 159472743 | Chlamydomonas reinhardtii |
| PAT1 | XP_001691787.1 | 159467202 | Chlamydomonas reinhardtii |

Pyruvate decarboxylase (PDC) is a key enzyme in alcoholic fermentation, catalyzing the decarboxylation of pyruvate to acetaldehyde (FIG. 2E). The PDC1 enzyme from *Saccharomyces cerevisiae* has been extensively studied (Killenberg-Jabs et al., *Eur. J. Biochem.* 268:1698-1704 (2001); Li et al., *Biochemistry.* 38:10004-10012 (1999); ter Schure et al., *Appl. Environ. Microbiol.* 64:1303-1307 (1998)). Other well-characterized PDC enzymes are found in *Zymomonas mobilus* (Siegert et al., *Protein Eng Des Sel* 18:345-357 (2005)), *Acetobacter pasteurians* (Chandra et al., 176:443-451 (2001)) and *Kluyveromyces lactis* (Krieger et al., 269:3256-3263 (2002)). The PDC1 and PDC5 enzymes of *Saccharomyces cerevisiae* are subject to positive transcriptional regulation by PDC2 (Hohmann et al, *Mol Gen Genet* 241:657-66 (1993)). Pyruvate decarboxylase activity is also possessed by a protein encoded by CTRG_03826 (GI:255729208) in *Candida tropicalis*, PDC1 (GI number: 1226007) in *Kluyveromyces lactis*, YALI0D10131g (GI:50550349) in *Yarrowia lipolytica*, PAS_chr3_0188 (GI:254570575) in *Pichia pastoris*, pyruvate decarboxylase (GI: GI: 159883897) in *Schizosaccharomyces pombe*, ANI_1_1024084 (GI: 145241548), ANI_1_796114 (GI:317034487), ANI_1_936024 (GI: 317026934) and ANI_1_2276014 (GI:317025935) in *Aspergillus niger*.

| Protein | GenBank ID | GI Number | Organism |
| --- | --- | --- | --- |
| pdc | P06672.1 | 118391 | *Zymomonas mobilis* |
| pdc1 | P06169 | 30923172 | *Saccharomyces cerevisiae* |
| Pdc2 | NP_010366.1 | 6320286 | *Saccharomyces cerevisiae* |
| Pdc5 | NP_013235.1 | 6323163 | *Saccharomyces cerevisiae* |
| CTRG_03826 | XP_002549529 | 255729208 | *Candida tropicalis*, |
| CU329670.1:585597.587312 | CAA90807 | 159883897 | *Schizosaccharomyces pombe* |
| YALI0D10131g | XP_502647 | 50550349 | *Yarrowia lipolytica* |
| PAS_chr3_0188 | XP_002492397 | 254570575 | *Pichia pastoris* |
| pdc | Q8L388 | 20385191 | *Acetobacter pasteurians* |
| pdc1 | Q12629 | 52788279 | *Kluyveromyces lactis* |
| ANI_1_1024084 | XP_001393420 | 145241548 | *Aspergillus niger* |
| ANI_1_796114 | XP_001399817 | 317026934 | *Aspergillus niger* |
| ANI_1_936024 | XP_001396467 | 317034487 | *Aspergillus niger* |
| ANI_1_2276014 | XP_001388598 | 317025935 | *Aspergillus niger* |

Aldehyde dehydrogenase enzymes in EC class 1.2.1 catalyze the oxidation of acetaldehyde to acetate (FIG. 2F). Exemplary genes encoding this activity were described above. The oxidation of acetaldehyde to acetate can also be catalyzed by an aldehyde oxidase with acetaldehyde oxidase activity. Such enzymes can convert acetaldehyde, water and 02 to acetate and hydrogen peroxide. Exemplary aldehyde oxidase enzymes that have been shown to catalyze this transformation can be found in *Bos taurus* and *Mus musculus* (Garattini et al., *Cell Mol Life Sci* 65:1019-48 (2008); Cabre et al., *Biochem Soc Trans* 15:882-3 (1987)). Additional aldehyde oxidase gene candidates include the two flavin- and molybdenum-containing aldehyde oxidases of *Zea mays*, encoded by zmAO-1 and zmAO-2 (Sekimoto et al., *J Biol Chem* 272:15280-85 (1997)).

| Gene | GenBank Accession No. | GI No. | Organism |
| --- | --- | --- | --- |
| zmAO-1 | NP_001105308.1 | 162458742 | *Zea mays* |
| zmAO-2 | BAA23227.1 | 2589164 | *Zea mays* |
| Aox1 | O54754.2 | 20978408 | *Mus musculus* |
| XDH | DAA24801.1 | 296482686 | *Bos taurus* |

Pyruvate oxidase (acetyl-phosphate forming) can catalyze the conversion of pyruvate, oxygen and phosphate to acetyl-phosphate and hydrogen peroxide (FIG. 2G). This type of pyruvate oxidase is soluble and requires the cofactors thiamin diphosphate and flavin adenine dinucleotide (FAD). Acetyl-phosphate forming pyruvate oxidase enzymes can be found in lactic acid bacteria *Lactobacillus delbrueckii* and *Lactobacillus plantarum* (Lorquet et al., *J Bacteriol* 186: 3749-3759 (2004); Hager et al., *Fed Proc* 13:734-38 (1954)). A crystal structure of the *L. plantarum* enzyme has been solved (Muller et al., (1994)). In *Streptococcus sanguinis* and *Streptococcus pneumonia*, acetyl-phosphate forming pyruvate oxidase enzymes are encoded by the spxB gene (Spellerberg et al., *Mol Micro* 19:803-13 (1996); Ramos-Montanez et al., *Mol Micro* 67:729-46 (2008)). The SpxR was shown to positively regulate the transcription of spxB in *S. pneumoniae* (Ramos-Montanez et al., supra). A similar regulator in *S. sanguinis* was identified by sequence homology. Introduction or modification of catalase activity can reduce accumulation of the hydrogen peroxide product.

| Gene | GenBank Accession No. | GI No. | Organism |
| --- | --- | --- | --- |
| poxB | NP_786788.1 | 28379896 | *Lactobacillus plantarum* |
| spxB | L39074.1 | 1161269 | *Streptococcus pneumoniae* |
| Spd_0969 (spxR) | YP_816445.1 | 116517139 | *Streptococcus pneumoniae* |
| spxB | ZP_07887723.1 | 315612812 | *Streptococcus sanguinis* |
| spxR | ZP_07887944.1 GI: | 315613033 | *Streptococcus sanguinis* |

The pyruvate dehydrogenase (PDH) complex catalyzes the conversion of pyruvate to acetyl-CoA (FIG. 2H). The *E. coli* PDH complex is encoded by the genes aceEF and lpdA. Enzyme engineering efforts have improved the *E. coli* PDH enzyme activity under anaerobic conditions (Kim et al., *J. Bacteriol.* 190:3851-3858 (2008); Kim et al., *Appl. Environ. Microbiol.* 73:1766-1771 (2007); Zhou et al., *Biotechnol. Lett.* 30:335-342 (2008)). In contrast to the *E. coli* PDH, the *B. subtilis* complex is active and required for growth under anaerobic conditions (Nakano et al., 179:6749-6755 (1997)). The *Klebsiella pneumoniae* PDH, characterized during growth on glycerol, is also active under anaerobic conditions (Menzel et al., 56:135-142 (1997)). Crystal structures of the enzyme complex from bovine kidney (Zhou et al., 98:14802-14807 (2001)) and the E2 catalytic domain from *Azotobacter vinelandii* are available (Mattevi et al., *Science.* 255:1544-1550 (1992)). Some mammalian PDH enzymes complexes can react on alternate substrates such as 2-oxobutanoate. Comparative kinetics of *Rattus norvegicus* PDH and BCKAD indicate that BCKAD has higher activity on 2-oxobutanoate as a substrate (Paxton et al., *Biochem. J.* 234:295-303 (1986)). The *S. cerevisiae* PDH complex can consist of an E2 (LA Ti) core that binds E1 (PDA1, PDB), E3 (LPD1), and Protein X (PDX1) components (Pronk et al., *Yeast* 12:1607-1633 (1996)). The PDH complex of *S. cerevisiae* is regulated by phosphorylation of E1 involving PKP1 (PDH kinase I), PTC5 (PDH phosphatase I), PKP2 and PTC6. Modification of these regulators may also enhance PDH activity. Coexpression of lipoyl ligase (LplA of *E. coli* and AIM22 in *S. cerevisiae*) with PDH in the cytosol may be necessary for activating the PDH enzyme complex. Increasing the supply of cytosolic lipoate, either by modifying a metabolic pathway or media supplementation with lipoate, may also improve PDH activity.

| Gene | Accession No. | GI Number | Organism |
| --- | --- | --- | --- |
| aceE | NP_414656.1 | 16128107 | *Escherichia coli* |
| aceF | NP_414657.1 | 16128108 | *Escherichia coli* |
| lpd | NP_414658.1 | 16128109 | *Escherichia coli* |
| lplA | NP_418803.1 | 16132203 | *Escherichia coli* |
| pdhA | P21881.1 | 3123238 | *Bacillus subtilis* |
| pdhB | P21882.1 | 129068 | *Bacillus subtilis* |
| pdhC | P21883.2 | 129054 | *Bacillus subtilis* |
| pdhD | P21880.1 | 118672 | *Bacillus subtilis* |
| aceE | YP_001333808.1 | 152968699 | *Klebsiella pneumoniae* |
| aceF | YP_001333809.1 | 152968700 | *Klebsiella pneumoniae* |
| lpdA | YP_001333810.1 | 152968701 | *Klebsiella pneumoniae* |
| Pdha1 | NP_001004072.2 | 124430510 | *Rattus norvegicus* |
| Pdha2 | NP_446446.1 | 16758900 | *Rattus norvegicus* |
| Dlat | NP_112287.1 | 78365255 | *Rattus norvegicus* |
| Dld | NP_955417.1 | 40786469 | *Rattus norvegicus* |
| LAT1 | NP_014328 | 6324258 | *Saccharomyces cerevisiae* |
| PDA1 | NP_011105 | 37362644 | *Saccharomyces cerevisiae* |
| PDB1 | NP_009780 | 6319698 | *Saccharomyces cerevisiae* |
| LPD1 | NP_116635 | 14318501 | *Saccharomyces cerevisiae* |
| PDX1 | NP_011709 | 6321632 | *Saccharomyces cerevisiae* |
| AIM22 | NP_012489.2 | 83578101 | *Saccharomyces cerevisiae* |

As an alternative to the large multienzyme PDH complexes described above, some organisms utilize enzymes in the 2-ketoacid oxidoreductase family (OFOR) to catalyze acylating oxidative decarboxylation of 2-keto-acids. Unlike the PDH complexes, PFOR enzymes contain iron-sulfur clusters, utilize different cofactors and use ferredoxin or flavodixin as electron acceptors in lieu of NAD(P)H. Pyruvate ferredoxin oxidoreductase (PFOR) can catalyze the oxidation of pyruvate to form acetyl-CoA (FIG. 2H). The PFOR from *Desulfovibrio africanus* has been cloned and expressed in *E. coli* resulting in an active recombinant enzyme that was stable for several days in the presence of oxygen (Pieulle et al., *J Bacteriol.* 179:5684-5692 (1997)). Oxygen stability is relatively uncommon in PFORs and is believed to be conferred by a 60 residue extension in the polypeptide chain of the *D. africanus* enzyme. The *M. thermoacetica* PFOR is also well characterized (Menon et al., *Biochemistry* 36:8484-8494 (1997)) and was even shown to have high activity in the direction of pyruvate synthesis during autotrophic growth (Furdui et al., *J Biol Chem.* 275:28494-28499 (2000)). Further, *E. coli* possesses an uncharacterized open reading frame, ydbK, that encodes a protein that is 51% identical to the *M. thermoacetica* PFOR. Evidence for pyruvate oxidoreductase activity in *E. coli* has been described (Blaschkowski et al., *Eur. J Biochem.* 123: 563-569 (1982)). Several additional PFOR enzymes are described in Ragsdale, *Chem. Rev.* 103:2333-2346 (2003). Finally, flavodoxin reductases (e.g., fqrB from *Helicobacter pylori* or *Campylobacter jejuni* (St Maurice et al., *J. Bacteriol.* 189:4764-4773 (2007))) or Rnf-type proteins (Seedorf et al., *Proc. Natl. Acad. Sci. U.S.A.* 105:2128-2133 (2008); Herrmann et al., *J. Bacteriol.* 190:784-791 (2008)) provide a means to generate NADH or NADPH from the reduced ferredoxin generated by PFOR. These proteins are identified below.

| Protein | GenBank ID | GI Number | Organism |
| --- | --- | --- | --- |
| Por | CAA70873.1 | 1770208 | *Desulfovibrio africanus* |
| Por | YP_428946.1 | 83588937 | *Moorella thermoacetica* |
| ydbK | NP_415896.1 | 16129339 | *Escherichia coli* |
| fqrB | NP_207955.1 | 15645778 | *Helicobacter pylori* |
| fqrB | YP_001482096.1 | 157414840 | *Campylobacter jejuni* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |

Pyruvate formate-lyase (PFL, EC 2.3.1.54) (FIG. 2H), encoded by pflB in *E. coli*, can convert pyruvate into acetyl-CoA and formate. The activity of PFL can be enhanced by an activating enzyme encoded by pflA (Knappe et al., *Proc. Natl. Acad. Sci U.S.A* 81:1332-1335 (1984); Wong et al., *Biochemistry* 32:14102-14110 (1993)). Keto-acid formate-lyase (EC 2.3.1.-), also known as 2-ketobutyrate formate-lyase (KFL) and pyruvate formate-lyase 4, is the gene product of tdcE in *E. coli*. This enzyme catalyzes the conversion of 2-ketobutyrate to propionyl-CoA and formate during anaerobic threonine degradation, and can also substitute for pyruvate formate-lyase in anaerobic catabolism (Simanshu et al., *J Biosci.* 32:1195-1206 (2007)). The enzyme is oxygen-sensitive and, like PflB, can require post-translational modification by PFL-AE to activate a glycyl radical in the active site (Hesslinger et al., *Mol. Microbiol* 27:477-492 (1998)). A pyruvate formate-lyase from *Archaeoglobus fulgidus* encoded by pflD has been cloned, expressed in *E. coli* and characterized (Lehtio et al., *Protein Eng Des Sel* 17:545-552 (2004)). The crystal structures of the *A. fulgidus* and *E. coli* enzymes have been resolved (Lehtio et al., *J Mol. Biol.* 357:221-235 (2006); Leppanen et al., *Structure.* 7:733-744 (1999)). Additional PFL and PFL-AE candidates are found in *Lactococcus lactis* (Melchiorsen et al., *Appl Microbiol Biotechnol* 58:338-344 (2002)), and *Streptococcus mutans* (Takahashi-Abbe et al., *Oral. Microbiol Immunol.* 18:293-297 (2003)), *Chlamydomonas reinhardtii* (Hemschemeier et al., *Eukaryot. Cell* 7:518-526 (2008b); Atteia et al., *J. Biol. Chem.* 281: 9909-9918 (2006)) and *Clostridium pasteurianum* (Weidner et al., *J Bacteriol.* 178:2440-2444 (1996)).

| Protein | GenBank ID | GI Number | Organism |
| --- | --- | --- | --- |
| pflB | NP_415423 | 16128870 | *Escherichia coli* |
| pflA | NP_415422.1 | 16128869 | *Escherichia coli* |
| tdcE | AAT48170.1 | 48994926 | *Escherichia coli* |
| pflD | NP_070278.1 | 11499044 | *Archaeoglobus fulgidus* |
| pfl | CAA03993 | 2407931 | *Lactococcus lactis* |
| pfl | BAA09085 | 1129082 | *Streptococcus mutans* |
| PFL1 | XP_001689719.1 | 159462978 | *Chlamydomonas reinhardtii* |
| pflA1 | XP_001700657.1 | 159485246 | *Chlamydomonas reinhardtii* |
| pfl | Q46266.1 | 2500058 | *Clostridium pasteurianum* |
| act | CAA63749.1 | 1072362 | *Clostridium pasteurianum* |

If a pyruvate formate lyase is utilized to convert pyruvate to acetyl-CoA, coexpression of a formate dehydrogenase or formate hydrogen lyase enzyme will convert formate to carbon dioxide. Formate dehydrogenase (FDH) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and hydrogenases (EC 1.1.99.33). FDH enzymes have been characterized from *Moorella thermo-* acetica (Andreesen and Ljungdahl, *J Bacteriol* 116:867-873 (1973); Li et al., *J Bacteriol* 92:405-412 (1966); Yamamoto et al., *J Biol Chem.* 258:1826-1832 (1983). The loci, Moth_2312 is responsible for encoding the alpha subunit of formate dehydrogenase while the beta subunit is encoded by Moth_2314 (Pierce et al., *Environ Microbiol* (2008)). Another set of genes encoding formate dehydrogenase activity with a propensity for $CO_2$ reduction is encoded by Sfum_2703 through Sfum_2706 in *Syntrophobacter fumaroxidans* (de Bok et al., *Eur J Biochem.* 270:2476-2485 (2003)); Reda et al., *PNAS* 105:10654-10658 (2008)). A similar set of genes presumed to carry out the same function are encoded by CHY_0731, CHY_0732, and CHY_0733 in *C. hydrogenoformans* (Wu et al., *PLoS Genet* 1:e65 (2005)). Formate dehydrogenases are also found many additional organisms including *C. carboxidivorans* P7, *Bacillus methanolicus, Burkholderia stabilis, Moorella thermoacetica* ATCC 39073, *Candida boidinii, Candida methylica*, and *Saccharomyces cerevisiae* S288c.

| Protein | GenBank ID | GI Number | Organism |
| --- | --- | --- | --- |
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| CHY_0731 | YP_359585.1 | 78044572 | *Carboxydothermus hydrogenoformans* |
| CHY_0732 | YP_359586.1 | 78044500 | *Carboxydothermus hydrogenoformans* |
| CHY_0733 | YP_359587.1 | 78044647 | *Carboxydothermus hydrogenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |
| fdhA, MGA3_06625 | EIJ82879.1 | 387590560 | *Bacillus methanolicus* MGA3 |
| fdhA, PB1_11719 | ZP_10131761.1 | 387929084 | *Bacillus methanolicus* PB1 |
| fdhD, MGA3_06630 | EIJ82880.1 | 387590561 | *Bacillus methanolicus* MGA3 |
| fdhD, PB1_11724 | ZP_10131762.1 | 387929085 | *Bacillus methanolicus* PB1 |
| fdh | ACF35003. | 194220249 | *Burkholderia stabilis* |
| FDH1 | AAC49766.1 | 2276465 | *Candida boidinii* |
| fdh | CAA57036.1 | 1181204 | *Candida methylica* |
| FDH2 | P0CF35.1 | 294956522 | *Saccharomyces cerevisiae* S288c |
| FDH1 | NP_015033.1 | 6324964 | *Saccharomyces cerevisiae* S288c |

Alternately, a formate hydrogen lyase enzyme can be employed to convert formate to carbon dioxide and hydrogen. An exemplary formate hydrogen lyase enzyme can be found in *Escherichia coli*. The *E. coli* formate hydrogen lyase consists of hydrogenase 3 and formate dehydrogenase-H (Maeda et al., *Appl Microbiol Biotechnol* 77:879-890 (2007)). It is activated by the gene product of JhlA. (Maeda et al., *Appl Microbiol Biotechnol* 77:879-890 (2007)). The addition of the trace elements, selenium, nickel and molybdenum, to a fermentation broth has been shown to enhance formate hydrogen lyase activity (Soini et al., *Microb. Cell Fact.* 7:26 (2008)). Various hydrogenase 3, formate dehydrogenase and transcriptional activator genes are shown below. A formate hydrogen lyase enzyme also exists in the hyperthermophilic archaeon, *Thermococcus litoralis* (Takacs et al., *BMC. Microbiol* 8:88 (2008)). Additional formate hydrogen lyase systems have been found in *Salmonella typhimurium, Klebsiella pneumoniae, Rhodospirillum rubrum, Methanobacterium formicicum* (Vardar-Schara et al., Microbial Biotechnology 1:107-125 (2008)).

| Protein | GenBank ID | GI number | Organism |
| --- | --- | --- | --- |
| hycA | NP_417205 | 16130632 | *Escherichia coli* K-12 MG1655 |
| hycB | NP_417204 | 16130631 | *Escherichia coli* K-12 MG1655 |
| hycC | NP_417203 | 16130630 | *Escherichia coli* K-12 MG1655 |
| hycD | NP_417202 | 16130629 | *Escherichia coli* K-12 MG1655 |
| hycE | NP_417201 | 16130628 | *Escherichia coli* K-12 MG1655 |
| hycF | NP_417200 | 16130627 | *Escherichia coli* K-12 MG1655 |
| hycG | NP_417199 | 16130626 | *Escherichia coli* K-12 MG1655 |
| hycH | NP_417198 | 16130625 | *Escherichia coli* K-12 MG1655 |
| hycI | NP_417197 | 16130624 | *Escherichia coli* K-12 MG1655 |
| fdhF | NP_418503 | 16131905 | *Escherichia coli* K-12 MG1655 |
| fhlA | NP_417211 | 16130638 | *Escherichia coli* K-12 MG1655 |
| mhyC | ABW05543 | 157954626 | *Thermococcus litoralis* |
| mhyD | ABW05544 | 157954627 | *Thermococcus litoralis* |
| mhyE | ABW05545 | 157954628 | *Thermococcus litoralis* |
| myhF | ABW05546 | 157954629 | *Thermococcus litoralis* |
| myhG | ABW05547 | 157954630 | *Thermococcus litoralis* |
| myhH | ABW05548 | 157954631 | *Thermococcus litoralis* |
| fdhA | AAB94932 | 2746736 | *Thermococcus litoralis* |
| fdhB | AAB94931 | 157954625 | *Thermococcus litoralis* |

Pyruvate:NADP oxidoreductase (PNO) catalyzes the conversion of pyruvate to acetyl-CoA. This enzyme is encoded by a single gene and the active enzyme is a homodimer, in contrast to the multi-subunit PDH enzyme complexes described above. The enzyme from *Euglena gracilis* is stabilized by its cofactor, thiamin pyrophosphate (Nakazawa et al, *Arch Biochem Biophys* 411:183-8 (2003)). The mitochondrial targeting sequence of this enzyme should be removed for expression in the cytosol. The PNO protein of *E. gracilis* protein and other NADP-dependant pyruvate: NADP+ oxidoreductase enzymes are listed in the table below.

| Protein | GenBank ID | GI Number | Organism |
|---|---|---|---|
| PNO | Q94IN5.1 | 33112418 | *Euglena gracilis* |
| cgd4_690 | XP_625673.1 | 66356990 | *Cryptosporidium parvum* Iowa II |
| TPP_PFOR_PNO | XP_002765111.11 | 294867463 | *Perkinsus marinus* ATCC 50983 |

The NAD(P)$^+$ dependent oxidation of acetaldehyde to acetyl-CoA (FIG. 2I) can be catalyzed by an acylating acetaldehyde dehydrogenase (EC 1.2.1.10). Acylating acetaldehyde dehydrogenase enzymes of *E. coli* are encoded by adhE, eutE, and mhpF (Ferrandez et al, *J Bacteriol* 179: 2573-81 (1997)). The *Pseudomonas* sp. CF600 enzyme, encoded by dmpF, participates in meta-cleavage pathways and forms a complex with 4-hydroxy-2-oxovalerate aldolase (Shingler et al, *J Bacteriol* 174:711-24 (1992)). Solventogenic organisms such as *Clostridium acetobutylicum* encode bifunctional enzymes with alcohol dehydrogenase and acetaldehyde dehydrogenase activities. The bifunctional *C. acetobutylicum* enzymes are encoded by bdh I and adhE2 (Walter, et al., *J. Bacteriol.* 174:7149-7158 (1992); Fontaine et al., *J. Bacteriol.* 184:821-830 (2002)). Yet another candidate for acylating acetaldehyde dehydrogenase is the ald gene from *Clostridium beijerinckii* (Toth, *Appl. Environ. Microbiol.* 65:4973-4980 (1999). This gene is very similar to the eutE acetaldehyde dehydrogenase genes of *Salmonella typhimurium* and *E. coli* (Toth, *Appl. Environ. Microbiol.* 65:4973-4980 (1999).

| Protein | GenBank ID | GI Number | Organism |
|---|---|---|---|
| adhE | NP_415757.1 | 16129202 | *Escherichia coli* |
| mhpF | NP_414885.1 | 16128336 | *Escherichia coli* |
| dmpF | CAA43226.1 | 45683 | *Pseudomonas* sp. CF600 |
| adhE2 | AAK09379.1 | 12958626 | *Clostridium acetobutylicum* |
| bdh I | NP_349892.1 | 15896543 | *Clostridium acetobutylicum* |
| Ald | AAT66436 | 49473535 | *Clostridium beijerinckii* |
| eutE | NP_416950 | 16130380 | *Escherichia coli* |
| eutE | AAA80209 | 687645 | *Salmonella typhimurium* |

Threonine aldolase (EC 4.1.2.5) catalyzes the cleavage of threonine to glycine and acetaldehyde (FIG. 2J). The *Saccharomyces cerevisiae* and *Candida albicans* enzymes are encoded by GLY1 (Liu et al, Eur J Biochem 245:289-93 (1997); McNeil et al, Yeast 16:167-75 (2000)). The ltaE and glyA gene products of *E. coli* also encode enzymes with this activity (Liu et al, Eur J Biochem 255:220-6 (1998)).

| Protein | GenBank ID | GI Number | Organism |
|---|---|---|---|
| GLY1 | NP_010868.1 | 6320789 | *Saccharomyces cerevisiae* |
| GLY1 | AAB64198.1 | 2282060 | *Candida albicans* |
| ltaE | AAC73957.1 | 1787095 | *Escherichia coli* |
| glyA | AAC75604.1 | 1788902 | *Escherichia coli* |

Example III

Pathways for Producing Acetyl-CoA from PEP and Pyruvate

Pathways for the conversion of cytosolic phosphoenolpyruvate (PEP) and pyruvate to cytosolic acetyl-CoA can also enable deployment of a cytosolic fatty alcohol, fatty aldehyde or fatty acid production pathway from acetyl-CoA. FIG. 3 shows numerous pathways for converting PEP and pyruvate to acetyl-CoA.

The conversion of PEP to oxaloacetate is catalyzed in one, two or three enzymatic steps. Oxaloacetate is further converted to acetyl-CoA via malonate semialdehyde or malonyl-CoA intermediates. In one pathway, PEP carboxylase or PEP carboxykinase converts PEP to oxaloacetate (step A); oxaloacetate decarboxylase converts the oxaloacetate to malonate (step B); and malonate semialdehyde dehydrogenase (acetylating) converts the malonate semialdehyde to acetyl-CoA (step C). In another pathway pyruvate kinase or PEP phosphatase converts PEP to pyruvate (step N); pyruvate carboxylase converts the pyruvate to (step H); oxaloacetate decarboxylase converts the oxaloacetate to malonate (step B); and malonate semialdehyde dehydrogenase (acetylating) converts the malonate semialdehyde to acetyl-CoA (step C). In another pathway pyruvate kinase or PEP phosphatase converts PEP to pyruvate (step N); malic enzyme converts the pyruvate to malate (step L); malate dehydrogenase or oxidoreductase converts the malate to oxaloacetate (step M); oxaloacetate decarboxylase converts the oxaloacetate to malonate (step B); and malonate semialdehyde dehydrogenase (acetylating) converts the malonate semialdehyde to acetyl-CoA (step C). In another pathway, PEP carboxylase or PEP carboxykinase converts PEP to oxaloacetate (step A); oxaloacetate decarboxylase converts the oxaloacetate to malonate semialdehyde (step B); malonyl-CoA reductase converts the malonate semialdehyde to malonyl-CoA (step G); and malonyl-CoA decarboxylase converts the malonyl-CoA to acetyl-CoA (step D). In another pathway, pyruvate kinase or PEP phosphatase converts PEP to pyruvate (step N); pyruvate carboxylase converts the pyruvate to oxaloacetate (step H); (oxaloacetate decarboxylase converts the oxaloacetate to malonate semialdehyde (step B); malonyl-CoA reductase converts the malonate semialdehyde to malonyl-CoA (step G); and malonyl-CoA decarboxylase converts the malonyl-CoA to acetyl-CoA (step D). In another pathway, pyruvate kinase or PEP phosphatase converts PEP to pyruvate (step N); malic enzyme converts the pyruvate to malate (step L); malate dehydrogenase or oxidoreductase converts the malate to oxaloacetate (step M); oxaloacetate decarboxylase converts the oxaloacetate to malonate semialdehyde (step B); malonyl-CoA reductase converts the malonate semialdehyde to malonyl-CoA (step G); and malonyl-CoA decarboxylase converts the malonyl-CoA to acetyl-CoA (step D). In another pathway, PEP carboxylase or PEP carboxykinase converts PEP to oxaloacetate (step A); oxaloacetate decarboxylase converts the oxaloacetate to malonate semialdehyde (step B); malonate semialdehyde dehydrogenase converts the malonate semialdehyde to malonate (step J); malonyl-CoA synthetase or transferase converts the malonate to malonyl-CoA (step K); and malonyl-CoA decarboxylase converts the malonyl-CoA to acetyl-CoA (step D). In another pathway, pyruvate kinase or PEP phosphatase converts PEP to pyruvate (step N); pyruvate carboxylase converts the pyruvate to oxaloacetate (step H); oxaloacetate decarboxylase converts the oxaloacetate to malonate semialdehyde (step B); malonate semialdehyde dehydrogenase converts the malonate semialdehyde to malonate (step J); malonyl-CoA synthetase or transferase converts the malonate to malonyl-CoA (step K); and malonyl-CoA decarboxylase converts the malonyl-CoA to acetyl-CoA (step D). In another pathway, pyruvate kinase or PEP phosphatase converts PEP to pyruvate (step N); malic enzyme converts the pyruvate to malate (step L); malate dehydrogenase or oxidoreductase converts the malate to oxaloacetate (step M); oxaloacetate decarboxylase converts the oxaloacetate to malonate semialdehyde (step B); malonate semialdehyde dehydrogenase converts the malonate semialdehyde to malonate (step J); malonyl-CoA synthetase or transferase converts the malonate to malonyl-CoA (step K); and malonyl-CoA decarboxylase converts the malonyl-CoA to acetyl-CoA (step D). In another pathway, PEP carboxylase or PEP carboxykinase converts PEP to oxaloacetate (step A); oxaloacetate dehydrogenase or oxaloacetate oxidoreductase converts the oxaloacetate to malonyl-CoA (step F); and malonyl-CoA decarboxylase converts the malonyl-CoA to acetyl-CoA (step D). In another pathway, pyruvate kinase or PEP phosphatase converts PEP to pyruvate (step N); pyruvate carboxylase converts the pyruvate to oxaloacetate (step H); oxaloacetate dehydrogenase or oxaloacetate oxidoreductase converts the oxaloacetate to malonyl-CoA (step F); and malonyl-CoA decarboxylase converts the malonyl-CoA to acetyl-CoA (step D). In another pathway, pyruvate kinase or PEP phosphatase converts PEP to pyruvate (step N); malic enzyme converts the pyruvate to malate (step L); malate dehydrogenase or oxidoreductase converts the malate to oxaloacetate (step M); oxaloacetate dehydrogenase or oxaloacetate oxidoreductase converts the oxaloacetate to malonyl-CoA (step F); and malonyl-CoA decarboxylase converts the malonyl-CoA to acetyl-CoA (step D).

Enzymes candidates for the reactions shown in FIG. 3 are described below.

| 1.1.n.a | Oxidoreductase (alcohol to oxo) | M |
| 1.1.1.d | Malic enzyme | L |
| 1.2.1.a | Oxidoreductase (aldehyde to acid) | J |
| 1.2.1.b | Oxidoreductase (acyl-CoA to aldehyde) | G |
| 1.2.1.f | Oxidoreductase (decarboxylating acyl-CoA to aldehyde) | C |
| 2.7.2.a | Kinase | N |
| 2.8.3.a | CoA transferase | K |
| 3.1.3.a | Phosphatase | N |
| 4.1.1.a | Decarboxylase | A, B, D |
| 6.2.1.a | CoA synthetase | K |
| 6.4.1.a | Carboxylase | D, H |

Enzyme candidates for several enzymes in FIG. 3 have been described elsewhere herein. These include acetyl-CoA carboxylase, acetoacetyl-CoA synthase, acetoacetyl-CoA thiolase, malonyl-CoA reductase (also called malonate semialdehyde dehydrogenase (acylating), malate dehydrogenase. 1.1.n.a Oxidoreductase (Alcohol to Oxo)

Malate dehydrogenase or oxidoreductase catalyzes the oxidation of malate to oxaloacetate. Different carriers can act as electron acceptors for enzymes in this class. Malate dehydrogenase enzymes utilize NADP or NAD as electron acceptors. Malate dehydrogenase (Step M) enzyme candidates are described above in example 1 (Table 7, 23). Malate:quinone oxidoreductase enzymes (EC 1.1.5.4) are membrane-associated and utilize quinones, flavoproteins or vitamin K as electron acceptors. Malate:quinone oxidoreductase enzymes of *E. coli, Helicobacter pylori* and *Pseudomonas syringae* are encoded by mqo (Kather et al, J Bacteriol 182:3204-9 (2000); Mellgren et al, J Bacteriol 191:3132-42 (2009)). The Cgl2001 gene of *C. gluamicum* also encodes an MQO enzyme (Mitsuhashi et al, Biosci Biotechnol Biochem 70:2803-6 (2006)).

| Protein | GenBank ID | GI Number | Organism |
|---|---|---|---|
| mqo | NP_416714.1 | 16130147 | *Escherichia coli* |
| mqo | NP_206886.1 | 15644716 | *Helicobacter pylori* |
| mqo | NP_790970.1 | 28868351 | *Pseudomonas syringae* |
| Cgl2001 | NP_601207.1 | 19553205 | *Corynebacterium glutamicum* |

1.1.1.d Malic Enzyme

Malic enzyme (malate dehydrogenase) catalyzes the reversible oxidative carboxylation of pyruvate to malate. *E. coli* encodes two malic enzymes, MaeA and MaeB (Takeo, J. Biochem. 66:379-387 (1969)). Although malic enzyme is typically assumed to operate in the direction of pyruvate formation from malate, the NAD-dependent enzyme, encoded by maeA, has been demonstrated to operate in the carbon-fixing direction (Stols and Donnelly, Appl. Environ. Microbiol. 63(7) 2695-2701 (1997)). A similar observation was made upon overexpressing the malic enzyme from *Ascaris suum* in *E. coli* (Stols et al., Appl. Biochem. Biotechnol. 63-65(1), 153-158 (1997)). The second *E. coli* malic enzyme, encoded by maeB, is NADP-dependent and also decarboxylates oxaloacetate and other alpha-keto acids (Iwakura et al., J. Biochem. 85(5):1355-65 (1979)). Another suitable enzyme candidate is me1 from *Zea mays* (Furumoto et al, Plant Cell Physiol 41:1200-1209 (2000)).

| Protein | GenBank ID | GI Number | Organism |
|---|---|---|---|
| maeA | NP_415996 | 90111281 | *Escherichia coli* |
| maeB | NP_416958 | 16130388 | *Escherichia coli* |
| NAD-ME | P27443 | 126732 | *Ascaris suum* |
| Mel | P16243.1 | 126737 | *Zea mays* |

1.2.1.a Oxidoreductase (Aldehyde to Acid)

The oxidation of malonate semialdehyde to malonate is catalyzed by malonate semialdehyde dehydrogenase (EC 1.2.1.15). This enzyme was characterized in *Pseudomonas aeruginosa* (Nakamura et al, Biochim Biophys Acta 50:147-52 (1961)). The NADP and NAD-dependent succinate semialdehyde dehydrogenase enzymes of *Euglena gracilas* accept malonate semialdehyde as substrates (Tokunaga et al, Biochem Biophys Act 429:55-62 (1976)). Genes encoding these enzymes has not been identified to date. Aldehyde dehydrogenase enzymes from eukoryotic organisms such as *S. cerevisiae, C. albicans, Y. lipolytica* and *A. niger* typically have broad substrate specificity and are suitable candidates. These enzymes and other acid forming aldehyde dehydrogenase and aldehyde oxidase enzymes are described earlier and listed in Tables 9 and 30. Additional MSA dehydrogenase enzyme candidates include NAD(P)+-dependent aldehyde dehydrogenase enzymes (EC 1.2.1.3). Two aldehyde dehydrogenases found in human liver, ALDH-1 and ALDH-2, have broad substrate ranges for a variety of aliphatic, aromatic and polycyclic aldehydes (Klyosov, Biochemistry 35:4457-4467 (1996a)). Active ALDH-2 has been efficiently expressed in *E. coli* using the GroEL proteins as chaperonins (Lee et al., Biochem. Biophys. Res. Commun. 298:216-224 (2002)). The rat mitochondrial aldehyde dehydrogenase also has a broad substrate range (Siew et al., Arch. Biochem. Biophys. 176:638-649 (1976)). The *E. coli* genes astD and aldH encode NAD+-dependent aldehyde dehydrogenases. AstD is active on succinic semialdehyde (Kuznetsova et al., FEMS Microbiol Rev 29:263-279 (2005)) and aldH is active on a broad range of aromatic and aliphatic substrates (Jo et al, Appl Microbiol Biotechnol 81:51-60 (2008)).

| Gene | GenBank Accession No. | GI No. | Organism |
| --- | --- | --- | --- |
| astD | P76217.1 | 3913108 | *Escherichia coli* |
| aldH | AAC74382.1 | 1787558 | *Escherichia coli* |
| ALDH-2 | P05091.2 | 118504 | *Homo sapiens* |
| ALDH-2 | NP_115792.1 | 14192933 | *Rattus norvegicus* |

1.2.1.f Oxidoreductase (Decarboxylating Acyl-CoA to Aldehyde)

Malonate semialdehyde dehydrogenase (acetylating) (EC 1.2.1.18) catalyzes the oxidative decarboxylation of malonate semialdehyde to acetyl-CoA. Exemplary enzymes are encoded by ddcC of *Halomonas* sp. HTNK1 (Todd et al, *Environ Microbiol* 12:237-43 (2010)) and IolA of *Lactobacillus casei* (Yebra et al, AEM 73:3850-8 (2007)). The DdcC enzyme has homologs in *A. niger* and *C. albicans*, shown in the table below. The malonate semialdehyde dehydrogenase enzyme in *Rattus norvegicus*, Mmsdh, also converts malonate semialdehyde to acetyl-CoA (U.S. Pat. No. 8,048,624). A malonate semialdehyde dehydrogenase (acetylating) enzyme has also been characterized in *Pseudomonas fluorescens*, although the gene has not been identified to date (Hayaishi et al, *J Biol Chem* 236:781-90 (1961)). Methylmalonate semialdehyde dehydrogenase (acetylating) enzymes (EC 1.2.1.27) are also suitable candidates, as several enzymes in this class accept malonate semialdehyde as a substrate including Msdh of *Bacillus subtilis* (Stines-Chaumeil et al, *Biochem J* 395:107-15 (2006)) and the methylmalonate semialdehyde dehydrogenase of *R. norvegicus* (Kedishvii et al, *Methods Enzymol* 324:207-18 (2000)).

2.8.3.a CoA Transferase

Activation of malonate to malonyl-CoA is catalyzed by a CoA transferase in EC class 2.8.3.a. Malonyl-CoA:acetate CoA transferase (EC 2.8.3.3) enzymes have been characterized in *Pseudomonas* species including *Pseudomonas fluorescens* and *Pseudomonas putida* (Takamura et al, *Biochem Int* 3:483-91 (1981); Hayaishi et al, *J Biol Chem* 215:125-36 (1955)). Genes associated with these enzymes have not been identified to date. A mitochondrial CoA transferase found in *Rattus norvegicus* liver also catalyzes this reaction and is able to utilize a range of CoA donors and acceptors (Deana et al, *Biochem Int* 26:767-73 (1992)). Several CoA transferase enzymes described above can also be applied to catalyze step K of FIG. 10. These enzymes include acetyl-CoA transferase (Table 26), 3-HB CoA transferase (Table 8), acetoacetyl-CoA transferase (table 55), SCOT (table 56) and other CoA transferases (table 57).

3.1.3.a Phosphatase

Phosphoenolpyruvate phosphatase (EC 3.1.3.60, Step 10N) catalyzes the hydrolysis of PEP to pyruvate and phosphate. Numerous phosphatase enzymes catalyze this activity, including alkaline phosphatase (EC 3.1.3.1), acid phosphatase (EC 3.1.3.2), phosphoglycerate phosphatase (EC 3.1.3.20) and PEP phosphatase (EC 3.1.3.60). PEP phosphatase enzymes have been characterized in plants such as Vignia radiate, Bruguiera sexangula and *Brassica nigra*. The phytase from *Aspergillus fumigates*, the acid phosphatase from *Homo sapiens* and the alkaline phosphatase of *E. coli* also catalyze the hydrolysis of PEP to pyruvate (Brugger et al, *Appl Microbiol Biotech* 63:383-9 (2004);

| Protein | GenBank ID | GI Number | Organism |
| --- | --- | --- | --- |
| ddcC | ACV84070.1 | 258618587 | *Halomonas* sp. HTNK1 |
| ANI_1_1120014 | XP_001389265.1 | 145229913 | *Aspergillus niger* |
| ALD6 | XP_710976.1 | 68490403 | *Candida albicans* |
| YALI0C01859g | XP_501343.1 | 50547747 | *Yarrowia lipolytica* |
| mmsA_1 | YP_257876.1 | 70734236 | *Pseudomonas fluorescens* |
| mmsA_2 | YP_257884.1 | 70734244 | *Pseudomonas fluorescens* |
| PA0130 | NP_248820.1 | 15595328 | *Pseudomonas aeruginosa* |
| Mmsdh | Q02253.1 | 400269 | *Rattus norvegicus* |
| msdh | NP_391855.1 | 16081027 | *Bacillus subtilis* |
| IolA | ABP57762.1 | 145309085 | *Lactobacillus casei* |

2.7.2.a Kinase

Pyruvate kinase (Step 10N), also known as phosphoenolpyruvate synthase (EC 2.7.9.2), converts pyruvate and ATP to PEP and AMP. This enzyme is encoded by the PYK1 (Burke et al., *J. Biol. Chem.* 258:2193-2201 (1983)) and PYK2 (Boles et al., *J. Bacteriol.* 179:2987-2993 (1997)) genes in *S. cerevisiae*. In *E. coli*, this activity is catalyzed by the gene products of pykF and pykA. Selected homologs of the *S. cerevisiae* enzymes are also shown in the table below.

Hayman et al, *Biochem J* 261:601-9 (1989); et al, *The Enzymes* 3$^{rd}$ Ed. 4:373-415 (1971))). Similar enzymes have been characterized in *Campylobacter jejuni* (van Mourik et al., *Microbiol.* 154:584-92 (2008)), *Saccharomyces cerevisiae* (Oshima et al., *Gene* 179:171-7 (1996)) and *Staphylococcus aureus* (Shah and Blobel, *J. Bacteriol.* 94:780-1 (1967)). Enzyme engineering and/or removal of targeting sequences may be required for alkaline phosphatase enzymes to function in the cytoplasm.

| Protein | GenBank ID | GI Number | Organism |
| --- | --- | --- | --- |
| PYK1 | NP_009362 | 6319279 | *Saccharomyces cerevisiae* |
| PYK2 | NP_014992 | 6324923 | *Saccharomyces cerevisiae* |
| pykF | NP_416191.1 | 16129632 | *Escherichia coli* |
| pykA | NP_416368.1 | 16129807 | *Escherichia coli* |
| KLLA0F23397g | XP_456122.1 | 50312181 | *Kluyveromyces lactis* |
| CaO19.3575 | XP_714934.1 | 68482353 | *Candida albicans* |
| CaO19.11059 | XP_714997.1 | 68482226 | *Candida albicans* |
| YALI0F09185p | XP_505195 | 210075987 | *Yarrowia lipolytica* |
| ANI_1_1126064 | XP_001391973 | 145238652 | *Aspergillus niger* |

| Protein | GenBank ID | GI Number | Organism |
| --- | --- | --- | --- |
| phyA | O00092.1 | 41017447 | Aspergillus fumigatus |
| Acp5 | P13686.3 | 56757583 | Homo sapiens |
| phoA | NP_414917.2 | 49176017 | Escherichia coli |
| phoX | ZP_01072054.1 | 86153851 | Campylobacter jejuni |
| PHO8 | AAA34871.1 | 172164 | Saccharomyces cerevisiae |
| SaurJH1_2706 | YP_001317815.1 | 150395140 | Staphylococcus aureus |

4.1.1.a Decarboxylase

Several reactions in FIG. 10 are catalyzed by decarboxylase enzymes in EC class 4.1.1, including oxaloacetate decarboxylase (Step B), malonyl-CoA decarboxylase (step D) and pyruvate carboxylase or carboxykinase (step A).

Carboxylation of phosphoenolpyruvate to oxaloacetate is catalyzed by phosphoenolpyruvate carboxylase (EC 4.1.1.31). Exemplary PEP carboxylase enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
| --- | --- | --- | --- |
| Ppc | NP_418391 | 16131794 | Escherichia coli |
| ppcA | AAB58883 | 28572162 | Methylobacterium extorquens |
| Ppc | ABB53270 | 80973080 | Corynebacterium glutamicum |

An alternative enzyme for carboxylating phosphoenolpyruvate to oxaloacetate is PEP carboxykinase (EC 4.1.1.32, 4.1.1.49), which simultaneously forms an ATP or GTP. In most organisms PEP carboxykinase serves a gluconeogenic function and converts oxaloacetate to PEP at the expense of one ATP. *S. cerevisiae* is one such organism whose native PEP carboxykinase, PCK1, serves a gluconeogenic role (Valdes-Hevia et al., *FEBS Lett.* 258:313-316 (1989). *E. coli* is another such organism, as the role of PEP carboxykinase in producing oxaloacetate is believed to be minor when compared to PEP carboxylase (Kim et al., *Appl. Environ. Microbiol.* 70:1238-1241 (2004)). Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high $NaHCO_3$ concentrations. Mutant strains of *E. coli* can adopt Pck as the dominant $CO_2$-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee et al., *Biotechnol. Bioprocess Eng.* 7:95-99 (2002)), *Anaerobiospirillum succiniciproducens* (Laivenieks et al., *Appl. Environ. Microbiol.* 63:2273-2280 (1997), and *Actinobacillus succinogenes* (Kim et al. supra). The PEP carboxykinase enzyme encoded by *Haemophilus influenza* is effective at forming oxaloacetate from PEP. Another suitable candidate is the PEPCK enzyme from *Megathyrsus maximus*, which has a low Km for $CO_2$, a substrate thought to be rate-limiting in the *E. coli* enzyme (Chen et al., *Plant Physiol* 128:160-164 (2002); Cotelesage et al., *Int. J Biochem. Cell Biol.* 39:1204-1210 (2007)). The kinetics of the GTP-dependentpepck gene product from *Cupriavidus necator* favor oxaloacetate formation (U.S. Pat. No. 8,048,624 and Lea et al, *Amino Acids* 20:225-41 (2001)).

| Protein | GenBank ID | GI Number | Organism |
| --- | --- | --- | --- |
| PCK1 | NP_013023 | 6322950 | Saccharomyces cerevisiae |
| pck | NP_417862.1 | 16131280 | Escherichia coli |
| pckA | YP_089485.1 | 52426348 | Mannheimia succiniciproducens |
| pckA | O09460.1 | 3122621 | Anaerobiospirillum succiniciproducens |
| pckA | Q6W6X5 | 75440571 | Actinobacillus succinogenes |
| pckA | P43923.1 | 1172573 | Haemophilus influenza |
| AF532733.1:1..1929 | AAQ10076.1 | 33329363 | Megathyrsus maximus |
| pepck | YP_728135.1 | 113869646 | Cupriavidus necator |

Oxaloacetate decarboxylase catalyzes the decarboxylation of oxaloacetate to malonate semialdehyde. Enzymes catalyzing this reaction include kgd of *Mycobacterium tuberculosis* (GenBank ID: 050463.4, GI: 160395583). Enzymes evolved from kgd with improved activity and/or substrate specificity for oxaloacetate have also been described (U.S. Pat. No. 8,048,624). Additional enzymes useful for catalyzing this reaction include keto-acid decarboxylases shown in the table below.

| EC number | Name |
| --- | --- |
| 4.1.1.1 | Pyruvate decarboxylase |
| 4.1.1.7 | Benzoylformate decarboxylase |
| 4.1.1.40 | Hydroxypyruvate decarboxylase |
| 4.1.1.43 | Ketophenylpyruvate decarboxylase |
| 4.1.1.71 | Alpha-ketoglutarate decarboxylase |
| 4.1.1.72 | Branched chain keto-acid decarboxylase |
| 4.1.1.74 | Indolepyruvate decarboxylase |
| 4.1.1.75 | 2-Ketoarginine decarboxylase |
| 4.1.1.79 | Sulfopyruvate decarboxylase |
| 4.1.1.80 | Hydroxyphenylpyruvate decarboxylase |
| 4.1.1.82 | Phosphonopyruvate decarboxylase |

The decarboxylation of keto-acids is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase. Pyruvate decarboxylase (PDC), also termed keto-acid decarboxylase, is a key enzyme in alcoholic fermentation, catalyzing the decarboxylation of pyruvate to acetaldehyde. The PDC1 enzyme from Saccharomyces cerevisiae has a broad substrate range for aliphatic 2-keto acids including 2-ketobutyrate, 2-ketovalerate, 3-hydroxypyruvate and 2-phenylpyruvate (22). This enzyme has been extensively studied, engineered for altered activity, and functionally expressed in E. coli (Killenberg-Jabs et al., Eur. J. Biochem. 268:1698-1704 (2001); Li et al., Biochemistry. 38:10004-10012 (1999); ter Schure et al., Appl. Environ. Microbiol. 64:1303-1307 (1998)). The PDC from Zymomonas mobilis, encoded by pdc, also has a broad substrate range and has been a subject of directed engineering studies to alter the affinity for different substrates (Siegert et al., Protein Eng Des Sel 18:345-357 (2005)). The crystal structure of this enzyme is available (Killenberg-Jabs et al., Eur. J. Biochem. 268:1698-1704 (2001)). Other well-characterized PDC candidates include the enzymes from Acetobacter pasteurians (Chandra et al., 176:443-451 (2001)) and Kluyveromyces lactis (Krieger et al., 269:3256-3263 (2002)).

| Protein | GenBank ID | GI Number | Organism |
|---|---|---|---|
| pdc | P06672.1 | 118391 | Zymomonas mobilis |
| pdc1 | P06169 | 30923172 | Saccharomyces cerevisiae |
| pdc | Q8L388 | 20385191 | Acetobacter pasteurians |
| pdc1 | Q12629 | 52788279 | Kluyveromyces lactis |

Like PDC, benzoylformate decarboxylase (EC 4.1.1.7) has a broad substrate range and has been the target of enzyme engineering studies. The enzyme from Pseudomonas putida has been extensively studied and crystal structures of this enzyme are available (Polovnikova et al., 42:1820-1830 (2003); Hasson et al., 37:9918-9930 (1998)). Site-directed mutagenesis of two residues in the active site of the Pseudomonas putida enzyme altered the affinity (Km) of naturally and non-naturally occurring substrates (Siegert et al., Protein Eng Des Sel 18:345-357 (2005)). The properties of this enzyme have been further modified by directed engineering (Lingen et al., Chembiochem. 4:721-726 (2003); Lingen et al., Protein Eng 15:585-593 (2002)). The enzyme from Pseudomonas aeruginosa, encoded by mdlC, has also been characterized experimentally (Barrowman et al., 34:57-60 (1986)). Additional gene candidates from Pseudomonas stutzeri, Pseudomonas fluorescens and other organisms can be inferred by sequence homology or identified using a growth selection system developed in Pseudomonas putida (Henning et al., Appl. Environ. Microbiol. 72:7510-7517 (2006)).

| Protein | GenBank ID | GI Number | Organism |
|---|---|---|---|
| mdlC | P20906.2 | 3915757 | Pseudomonas putida |
| mdlC | Q9HUR2.1 | 81539678 | Pseudomonas aeruginosa |
| dpgB | ABN80423.1 | 126202187 | Pseudomonas stutzeri |
| ilvB-1 | YP_260581.1 | 70730840 | Pseudomonas fluorescens |

A third enzyme capable of decarboxylating 2-oxoacids is alpha-ketoglutarate decarboxylase (KGD, EC 4.1.1.71). The substrate range of this class of enzymes has not been studied to date. An exemplarly KDC is encoded by kad in Mycobacterium tuberculosis (Tian et al., PNAS 102:10670-10675 (2005)). KDC enzyme activity has also been detected in several species of rhizobia including Bradyrhizobium japonicum and Mesorhizobium loti (Green et al., J Bacteriol 182:2838-2844 (2000)). Although the KDC-encoding gene(s) have not been isolated in these organisms, the genome sequences are available and several genes in each genome are annotated as putative KDCs. A KDC from Euglena gracilis has also been characterized but the gene associated with this activity has not been identified to date (Shigeoka et al., Arch. Biochem. Biophys. 288:22-28 (1991)). The first twenty amino acids starting from the N-terminus were sequenced MTYKAPVKDVKFLLDKVFKV (SEQ ID NO: 8) (Shigeoka and Nakano, Arch. Biochem. Biophys. 288:22-28 (1991)). The gene could be identified by testing candidate genes containing this N-terminal sequence for KDC activity. A novel class of AKG decarboxylase enzymes has recently been identified in cyanobacteria such as Synechococcus sp. PCC 7002 and homologs (Zhang and Bryant, Science 334:1551-3 (2011)).

| Protein | GenBank ID | GI Number | Organism |
|---|---|---|---|
| kgd | O50463.4 | 160395583 | Mycobacterium tuberculosis |
| kgd | NP_767092.1 | 27375563 | Bradyrhizobium japonicum USDA 110 |
| kgd | NP_105204.1 | 13473636 | Mesorhizobium loti |
| ilvB | ACB00744.1 | 169887030 | Synechococcus sp. PCC 7002 |

A fourth candidate enzyme for catalyzing this reaction is branched chain alpha-ketoacid decarboxylase (BCKA). This class of enzyme has been shown to act on a variety of compounds varying in chain length from 3 to 6 carbons (Oku et al., J Biol Chem. 263:18386-18396 (1988); Smit et al., Appl Environ Microbiol 71:303-311 (2005)). The enzyme in Lactococcus lactis has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., Appl Environ Microbiol 71:303-311 (2005)). The enzyme has been structurally characterized (Berg et al., Science. 318:1782-1786 (2007)). Sequence alignments between the Lactococcus lactis enzyme and the pyruvate decarboxylase of Zymomonas mobilis indicate that the catalytic and substrate recognition residues are nearly identical (Siegert et al., Protein Eng Des Sel 18:345-357 (2005)), so this enzyme would be a promising candidate for directed engineering. Several ketoacid decarboxylases of Saccharomyces cerevisiae catalyze the decarboxylation of branched substrates, including ARO10, PDC6, PDC5, PDC1 and THI3 (Dickenson et al, J Biol Chem 275:10937-42 (2000)). Yet another BCKAD enzyme is encoded by rv0853c of Mycobacterium tuberculosis (Werther et al, J Biol Chem 283:5344-54 (2008)). This enzyme is subject to allosteric activation by alpha-ketoacid substrates. Decarboxylation of alpha-ketoglutarate by a BCKA was detected in *Bacillus subtilis*; however, this activity was low (5%) relative to activity on other branched-chain substrates (Oku and Kaneda, *J Biol Chem.* 263:18386-18396 (1988)) and the gene encoding this enzyme has not been identified to date. Additional BCKA gene candidates can be identified by homology to the *Lactococcus lactis* protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria. Recombinant branched chain alpha-keto acid decarboxylase enzymes derived from the E1 subunits of the mitochondrial branched-chain keto acid dehydrogenase complex from *Homo sapiens* and *Bos taurus* have been cloned and functionally expressed in *E. coli* (Davie et al., *J. Biol. Chem.* 267:16601-16606 (1992); Wynn et al., *J. Biol. Chem.* 267:12400-12403 (1992); Wynn et al., *J. Biol. Chem.* 267:1881-1887 (1992)). In these studies, the authors found that co-expression of chaperonins GroEL and GroES enhanced the specific activity of the decarboxylase by 500-fold (Wynn et al., *J. Biol. Chem.* 267:12400-12403 (1992)). These enzymes are composed of two alpha and two beta subunits.

| Protein | GenBank ID | GI Number | Organism |
| --- | --- | --- | --- |
| kdcA | AAS49166.1 | 44921617 | *Lactococcus lactis* |
| PDC6 | NP_010366.1 | 6320286 | *Saccharomyces cerevisiae* |
| PDC5 | NP_013235.1 | 6323163 | *Saccharomyces cerevisiae* |
| PDC1 | P06169 | 30923172 | *Saccharomyces cerevisiae* |
| ARO10 | NP_010668.1 | 6320588 | *Saccharomyces cerevisiae* |
| THI3 | NP_010203.1 | 6320123 | *Saccharomyces cerevisiae* |
| rv0853c | O53865.1 | 81343167 | *Mycobacterium tuberculosis* |
| BCKDHB | NP_898871.1 | 34101272 | *Homo sapiens* |
| BCKDHA | NP_000700.1 | 11386135 | *Homo sapiens* |
| BCKDHB | P21839 | 115502434 | *Bos taurus* |
| BCKDHA | P11178 | 129030 | *Bos taurus* |

3-Phosphonopyruvate decarboxylase (EC 4.1.1.82) catalyzes the decarboxylation of 3-phosphonopyruvate to 2-phosphonoacetaldehyde. Exemplary phosphonopyruvate decarboxylase enzymes are encoded by dhpF of *Streptomyces luridus*, ppd of *Streptomyces viridochromogenes*, fom2 of *Streptomyces wedmorensis* and bcpC of *Streptomyces hygroscopius* (Circello et al, *Chem Biol* 17:402-11 (2010); Blodgett et al, *FEMS Microbiol Lett* 163:149-57 (2005); Hidaka et al, *Mol Gen Genet* 249:274-80 (1995); Nakashita et al, *Biochim Biophys Acta* 1490:159-62 (2000)). The *Bacteroides fragilis* enzyme, encoded by aepY, also decarboxylates pyruvate and sulfopyruvate (Zhang et al, *J Biol Chem* 278:41302-8 (2003)).

| Protein | GenBank ID | GI Number | Organism |
| --- | --- | --- | --- |
| dhpF | ACZ13457.1 | 268628095 | *Streptomyces luridus* |
| Ppd | CAJ14045.1 | 68697716 | *Streptomyces viridochromogenes* |
| Fom2 | BAA32496.1 | 1061008 | *Streptomyces wedmorensis* |
| aepY | AAG26466.1 | 11023509 | *Bacteroides fragilis* |

Many oxaloacetate decarboxylase enzymes such as the eda gene product in *E. coli* (EC 4.1.1.3), act on the terminal acid of oxaloacetate to form pyruvate. Because decarboxylation at the 3-keto acid position competes with the malonate semialdehyde forming decarboxylation at the 2-keto-acid position, this enzyme activity can be knocked out in a host strain with a pathway proceeding through a malonate semialdehyde intermediate.

Malonyl-CoA decarboxylase (EC 4.1.1.9) catalyzes the decarboxylation of malonyl-CoA to acetyl-CoA. Enzymes have been characterized in *Rhizobium leguminosarum* and *Acinetobacter calcoaceticus* (An et al, *Eur J Biochem* 257: 395-402 (1998); Koo et al, *Eur J Biochem* 266:683-90 (1999)). Similar enzymes have been characterized in *Streptomyces erythreus* (Hunaiti et al, *Arch Biochem Biophys* 229:426-39 (1984)). A recombinant human malonyl-CoA decarboxylase was overexpressed in *E. coli* (Zhou et al, *Prot Expr Pur* 34:261-9 (2004)). Methylmalonyl-CoA decarboxylase enzymes that decarboxylate malonyl-CoA are also suitable candidates. For example, the *Veillonella parvula* enzyme accepts malonyl-CoA as a substrate (Hilpert et al, *Nature* 296:584-5 (1982)). The *E. coli* enzyme is encoded by ygfG (Benning et al., *Biochemistry.* 39:4630-4639 (2000); Haller et al., *Biochemistry.* 39:4622-4629 (2000)). The stereo specificity of the *E. coli* enzyme was not reported, but the enzyme in *Propionigenium modestum* (Bott et al., *Eur. J. Biochem.* 250:590-599 (1997)) and *Veillonella parvula* (Huder et al., *J. Biol. Chem.* 268:24564-24571 (1993)) catalyzes the decarboxylation of the (S)-stereoisomer of methylmalonyl-CoA (Hoffmann et al., *FEBS. Lett.* 220:121-125 (1987)). The enzymes from *P. modestum* and *V. parvula* are comprised of multiple subunits that not only decarboxylate (S)-methylmalonyl-CoA, but also create a pump that transports sodium ions across the cell membrane as a means to generate energy.

| Protein | GenBank ID | GI Number | Organism |
| --- | --- | --- | --- |
| YgfG | NP_417394 | 90111512 | *Escherichia coli* |
| matA | Q9ZIP6 | 75424899 | *Rhizobium leguminosarum* |
| mdcD | AAB97628.1 | 2804622 | *Acinetobacter calcoaceticus* |
| mdcE | AAF20287.1 | 6642782 | *Acinetobacter calcoaceticus* |
| mdcA | AAB97627.1 | 2804621 | *Acinetobacter calcoaceticus* |
| mdcC | AAB97630.1 | 2804624 | *Acinetobacter calcoaceticus* |
| mcd | NP_036345.2 | 110349750 | *Homo sapiens* |
| mmdA | CAA05137 | 2706398 | *Propionigenium modestum* |
| mmdD | CAA05138 | 2706399 | *Propionigenium modestum* |
| mmdC | CAA05139 | 2706400 | *Propionigenium modestum* |
| mmdB | CAA05140 | 2706401 | *Propionigenium modestum* |
| mmdA | CAA80872 | 415915 | *Veillonella parvula* |
| mmdC | CAA80873 | 415916 | *Veillonella parvula* |
| mmdE | CAA80874 | 415917 | *Veillonella parvula* |
| mmdD | CAA80875 | 415918 | *Veillonella parvula* |
| mmdB | CAA80876 | 415919 | *Veillonella parvula* |

6.2.1.a CoA Synthetase

Activation of malonate to malonyl-CoA is catalyzed by a CoA synthetase in EC class 6.2.1.a. CoA synthetase enzymes that catalyze this reaction have not been described in the literature to date. Several CoA synthetase enzymes described above can also be applied to catalyze step K of FIG. 10. These enzymes include acetyl-CoA synthetase (Table 16, 25) and ADP forming CoA synthetases (Table 17).

6.4.1.a Carboxylase

Pyruvate carboxylase (EC 6.4.1.1) converts pyruvate to oxaloacetate at the cost of one ATP (step H). Exemplary pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

| Protein | GenBank ID | GI Number | Organism |
|---|---|---|---|
| PYC1 | NP_011453 | 6321376 | Saccharomyces cerevisiae |
| PYC2 | NP_009777 | 6319695 | Saccharomyces cerevisiae |
| Pyc | YP_890857.1 | 118470447 | Mycobacterium smegmatis |

Example IV

Pathways for Producing Cytosolic Acetyl-CoA from Mitochondrial Acetyl-CoA

A mechanism for transporting acetyl-CoA from the mitochondrion to the cytosol can facilitate deployment of a cytosolic fatty alcohol, fatty aldehyde or fatty acid production pathway that originates from acetyl-CoA. Exemplary mechanisms for exporting acetyl-CoA include those depicted in FIGS. 4 and 5, which can involve forming citrate from acetyl-CoA and oxaloacetate in the mitochondrion, exporting the citrate from the mitochondrion to the cytosol, and converting the citrate to oxaloacetate and either acetate or acetyl-CoA. In certain embodiments, provided herein are methods for engineering a eukaryotic organism to increase its availability of cytosolic acetyl-CoA by introducing enzymes capable of carrying out the transformations depicted in any one of FIGS. 4 and 5. Exemplary enzymes capable of carrying out the required transformations are also disclosed herein.

The production of cytosolic acetyl-CoA from mitochondrial acetyl-CoA can be accomplished by a number of pathways, for example, in three to five enzymatic steps. In one exemplary pathway, mitochondrial acetyl-CoA and oxaloacetate are combined into citrate by a citrate synthase and the citrate is exported out of the mitochondrion by a citrate or citrate/oxaloacetate transporter. Enzymatic conversion of the citrate in the cytosol results in cytosolic acetyl-CoA and oxaloacetate. The cytosolic oxaloacetate can then optionally be transported back into the mitochondrion by an oxaloacetate transporter and/or a citrate/oxaloacetate transporter. In another exemplary pathway, the cytosolic oxaloacetate is first enzymatically converted into malate in the cytosol and then optionally transferred into the mitochondrion by a malate transporter and/or a malate/citrate transporter. Mitochondrial malate can then be converted into oxaloacetate with a mitochondrial malate dehydrogenase.

In yet another exemplary pathway, mitochondrial acetyl-CoA can be converted to cytosolic acetyl-CoA via a citramalate intermediate. For example, mitochondrial acetyl-CoA and pyruvate are converted to citramalate by citramalate synthase. Citramalate can then be transported into the cytosol by a citramalate or dicarboxylic acid transporter. Cytosolic acetyl-CoA and pyruvate are then regenerated from citramalate, directly or indirectly, and the pyruvate can re-enter the mitochondria.

Figure 4:
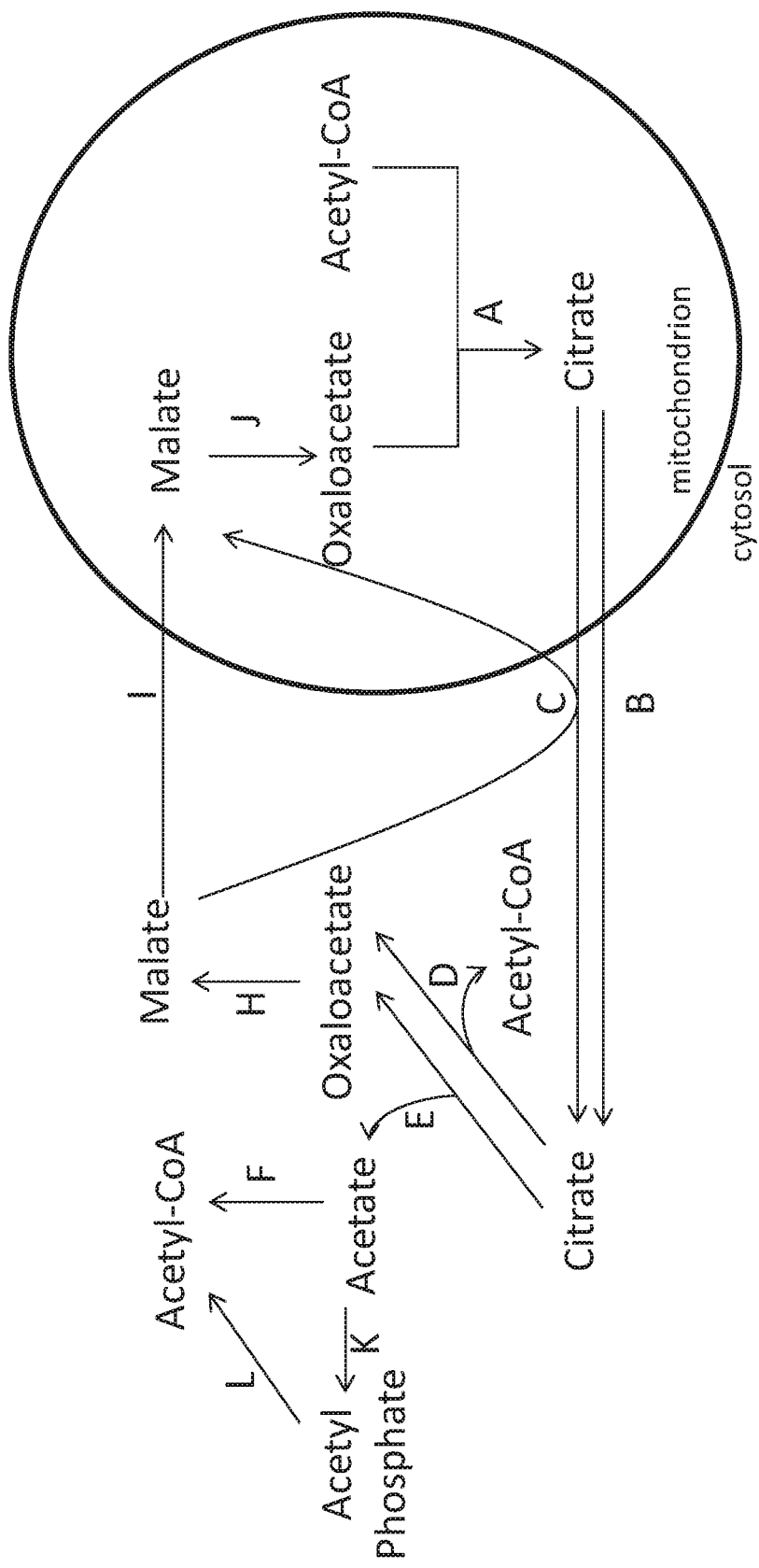
FIG. 4 shows exemplary pathways for production of cytosolic acetyl-CoA from mitochondrial acetyl-CoA using citrate and malate transporters. Enzymes are: A. citrate synthase; B. citrate transporter; C. citrate/malate transporter; D. ATP citrate lyase; E. citrate lyase; F. acetyl-CoA synthetase or transferase; H. cytosolic malate dehydrogenase; I. malate transporter; J. mitochondrial malate dehydrogenase; K. acetate kinase; and L. phosphotransacetylase.
Figure 5:
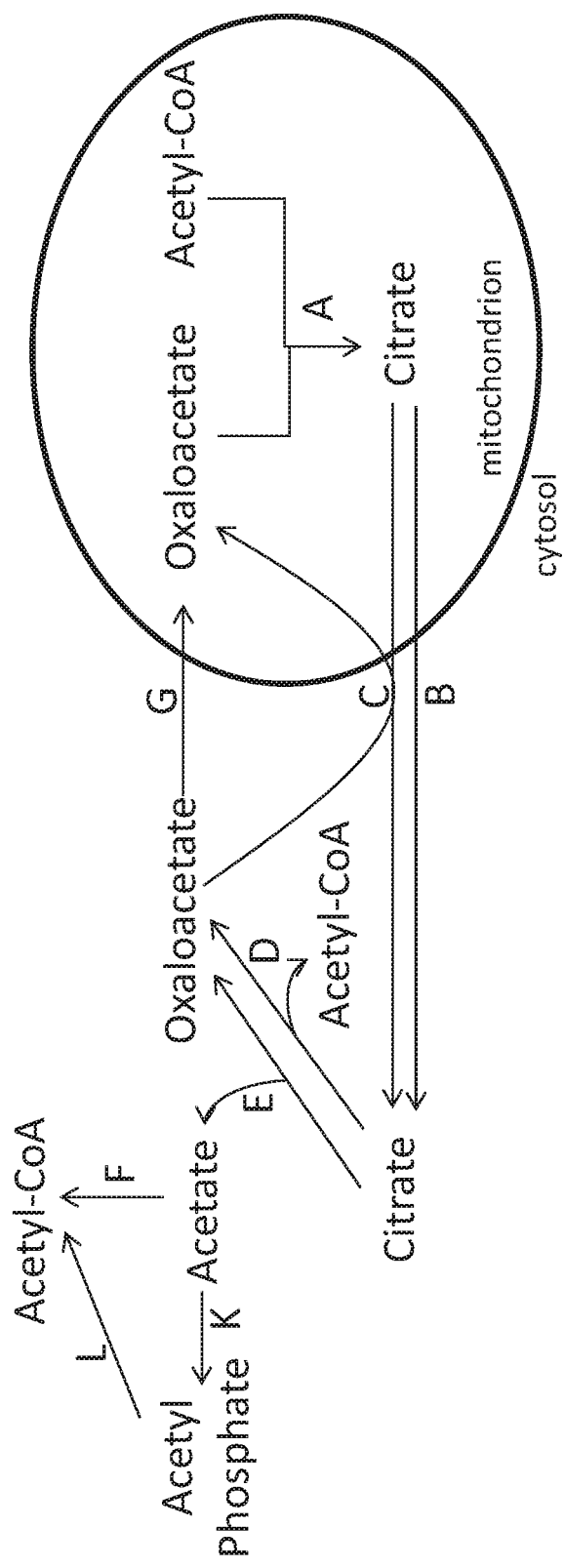
FIG. 5 shows exemplary pathways for production of cytosolic acetyl-CoA from mitochondrial acetyl-CoA using citrate and oxaloacetate transporters. Enzymes are: A. citrate synthase; B. citrate transporter; C. citrate/oxaloacetate transporter; D. ATP citrate lyase; E. citrate lyase; F. acetyl-CoA synthetase or transferase; G) oxaloacetate transporter; K) acetate kinase; and L) phosphotransacetylase.

Along these lines, several exemplary acetyl-CoA pathways for the production of cytosolic acetyl-CoA from mitochondrial acetyl-CoA are shown in FIGS. 4 and 5. In one embodiment, mitochondrial oxaloacetate is combined with mitochondrial acetyl-CoA to form citrate by a citrate synthase. The citrate is transported outside of the mitochondrion by a citrate transporter, a citrate/oxaloacetate transporter or a citrate/malate transporter. Cytosolic citrate is converted into cytosolic acetyl-CoA and oxaloacetate by an ATP citrate lyase. In another pathway, cytosolic citrate is converted into acetate and oxaloacetate by a citrate lyase. Acetate can then be converted into cytosolic acetyl-CoA by an acetyl-CoA synthetase or transferase. Alternatively, acetate can be converted by an acetate kinase to acetyl phosphate, and the acetyl phosphate can be converted to cytosolic acetyl-CoA by a phosphotransacetylase. Exemplary enzyme candidates for acetyl-CoA pathway enzymes are described below.

The conversion of oxaloacetate and mitochondrial acetyl-CoA is catalyzed by a citrate synthase (FIGS. 4 and 5, step A). In certain embodiments, the citrate synthase is expressed in a mitochondrion of a non-naturally occurring eukaryotic organism provided herein.

| Protein | GenBank ID | GI number | Organism |
|---|---|---|---|
| CIT1 | NP_014398.1 | 6324328 | Saccharomyces cerevisiae S288c |
| CIT2 | NP_009931.1 | 6319850 | Saccharomyces cerevisiae S288c |
| CIT3 | NP_015325.1 | 6325257 | Saccharomyces cerevisiae S288c |
| YALI0E02684p | XP_503469.1 | 50551989 | Yarrowia lipolytica |
| YALI0E00638p | XP_503380.1 | 50551811 | Yarrowia lipolytica |
| ANI_1_876084 | XP_001393983.1 | 145242820 | Aspergillus niger CBS 513.88 |
| ANI_1_1474074 | XP_001393195.2 | 317030721 | Aspergillus niger CBS 513.88 |
| ANI_1_2950014 | XP_001389414.2 | 317026339 | Aspergillus niger CBS 513.88 |
| ANI_1_1226134 | XP_001396731.1 | 145250435 | Aspergillus niger CBS 513.88 |
| gltA | NP_415248.1 | 16128695 | Escherichia coli K-12 MG1655 |

Transport of citrate from the mitochondrion to the cytosol can be carried out by several transport proteins. Such proteins either export citrate directly (i.e., citrate transporter, FIGS. 4 and 5, step B) to the cytosol or export citrate to the cytosol while simultaneously transporting a molecule such as malate (i.e., citrate/malate transporter, FIG. 4, step C) or oxaloacetate (i.e., citrate/oxaloacetate transporter FIG. 5, step C) from the cytosol into the mitochondrion as shown in FIGS. 4 and 5. Exemplary transport enzymes that carry out these transformations are provided in the table below.

| Protein | GenBank ID | GI number | Organism |
|---|---|---|---|
| CTP1 | NP_009850.1 | 6319768 | Saccharomyces cerevisiae S288c |
| YALI0F26323p | XP_505902.1 | 50556988 | Yarrowia lipolytica |
| ATEG_09970 | EAU29419.1 | 114187719 | Aspergillus terreus NIH2624 |
| KLLA0E18723g | XP_454797.1 | 50309571 | Kluyveromyces lactis NRRL Y-1140 |
| CTRG_02320 | XP_002548023.1 | 255726194 | Candida tropicalis MYA-3404 |
| ANI_1_1474094 | XP_001395080.1 | 145245625 | Aspergillus niger CBS 513.88 |
| YHM2 | NP_013968.1 | 6323897 | Saccharomyces cerevisiae S288c |
| DTC | CAC84549.1 | 19913113 | Arabidopsis thaliana |
| DTC1 | CAC84545.1 | 19913105 | Nicotiana tabacum |
| DTC2 | CAC84546.1 | 19913107 | Nicotiana tabacum |
| DTC3 | CAC84547.1 | 19913109 | Nicotiana tabacum |
| DTC4 | CAC84548.1 | 19913111 | Nicotiana tabacum |
| DTC | AAR06239.1 | 37964368 | Citrus junos |

ATP citrate lyase (ACL, EC 2.3.3.8, FIGS. 4 and 5, step D), also called ATP citrate synthase, catalyzes the ATP-dependent cleavage of citrate to oxaloacetate and acetyl-CoA. In certain embodiments, ATP citrate lyase is expressed in the cytosol of a eukaryotic organism. ACL is an enzyme of the RTCA cycle that has been studied in green sulfur bacteria *Chlorobium limicola* and *Chlorobium tepidum*. The alpha(4)beta(4) heteromeric enzyme from *Chlorobium limicola* was cloned and characterized in *E. coli* (Kanao et al., *Eur. J. Biochem.* 269:3409-3416 (2002). The *C. limicola* enzyme, encoded by aclAB, is irreversible and activity of the enzyme is regulated by the ratio of ADP/ATP. The *Chlorobium tepidum* a recombinant ACL from *Chlorobium tepidum* was also expressed in *E. coli* and the holoenzyme was reconstituted in vitro, in a study elucidating the role of the alpha and beta subunits in the catalytic mechanism (Kim and Tabita, *J. Bacteriol.* 188:6544-6552 (2006). ACL enzymes have also been identified in *Balnearium lithotrophicum*, *Sulfurihydrogenibium subterraneum* and other members of the bacterial phylum Aquificae (Hugler et al., *Environ. Microbiol.* 9:81-92 (2007)). This activity has been reported in some fungi as well. Exemplary organisms include *Sordaria macrospora* (Nowrousian et al., *Curr. Genet.* 37:189-93 (2000)), *Aspergillus nidulans* and *Yarrowia lipolytica* (Hynes and Murray, Eukaryotic Cell, July: 1039-1048, (2010), and *Aspergillus niger* (Meijer et al. *J. Ind. Microbiol. Biotechnol.* 36:1275-1280 (2009). Other candidates can be found based on sequence homology. Information related to these enzymes is tabulated below.

| Protein | GenBank ID | GI Number | Organism |
|---|---|---|---|
| aclA | BAB21376.1 | 12407237 | Chlorobium limicola |
| aclB | BAB21375.1 | 12407235 | Chlorobium limicola |
| aclA | AAM72321.1 | 21647054 | Chlorobium tepidum |
| aclB | AAM72322.1 | 21647055 | Chlorobium tepidum |
| aclB | ABI50084.1 | 114055039 | Sulfurihydrogenibium subterraneum |
| aclA | AAX76834.1 | 62199504 | Sulfurimonas denitrificans |
| aclB | AAX76835.1 | 62199506 | Sulfurimonas denitrificans |
| acl1 | XP_504787.1 | 50554757 | Yarrowia lipolytica |
| acl2 | XP_503231.1 | 50551515 | Yarrowia lipolytica |
| SPBC1703.07 | NP_596202.1 | 19112994 | Schizosaccharomyces pombe |
| SPAC22A12.16 | NP_593246.1 | 19114158 | Schizosaccharomyces pombe |
| acl1 | CAB76165.1 | 7160185 | Sordaria macrospora |
| acl2 | CAB76164.1 | 7160184 | Sordaria macrospora |
| aclA | CBF86850.1 | 259487849 | Aspergillus nidulans |
| aclB | CBF86848 | 259487848 | Aspergillus nidulans |

In some organisms the conversion of citrate to oxaloacetate and acetyl-CoA proceeds through a citryl-CoA intermediate and is catalyzed by two separate enzymes, citryl-CoA synthetase (EC 6.2.1.18) and citryl-CoA lyase (EC 4.1.3.34) (Aoshima, M., Appl. Microbiol. Biotechnol. 75:249-255 (2007). Citryl-CoA synthetase catalyzes the activation of citrate to citryl-CoA. The *Hydrogenobacter thermophilus* enzyme is composed of large and small subunits encoded by ccsA and ccsB, respectively (Aoshima et al., Mol. Micrbiol. 52:751-761 (2004)). The citryl-CoA synthetase of *Aquifex aeolicus* is composed of alpha and beta subunits encoded by sucC1 and sucD1 (Hugler et al., Environ. Microbiol. 9:81-92 (2007)). Citryl-CoA lyase splits citryl-CoA into oxaloacetate and acetyl-CoA. This enzyme is a homotrimer encoded by ccl in *Hydrogenobacter thermophilus* (Aoshima et al., Mol. Microbiol. 52:763-770 (2004)) and aq 150 in *Aquifex aeolicus* (Hugler et al., supra (2007)). The genes for this mechanism of converting citrate to oxaloacetate and citryl-CoA have also been reported recently in *Chlorobium tepidum* (Eisen et al., PNAS 99(14): 9509-14 (2002)).

| Protein | GenBank ID | GI Number | Organism |
| --- | --- | --- | --- |
| ccsA | BAD17844.1 | 46849514 | *Hydrogenobacter thermophilus* |
| ccsB | BAD17846.1 | 46849517 | *Hydrogenobacter thermophilus* |
| sucC1 | AAC07285 | 2983723 | *Aquifex aeolicus* |
| sucD1 | AAC07686 | 2984152 | *Aquifex aeolicus* |
| ccl | BAD17841.1 | 46849510 | *Hydrogenobacter thermophilus* |
| aq_150 | AAC06486 | 2982866 | *Aquifex aeolicus* |
| CT0380 | NP_661284 | 21673219 | *Chlorobium tepidum* |
| CT0269 | NP_661173.1 | 21673108 | *Chlorobium tepidum* |
| CT1834 | AAM73055.1 | 21647851 | *Chlorobium tepidum* |

Citrate lyase (EC 4.1.3.6, FIGS. 4 and 5, step E) catalyzes a series of reactions resulting in the cleavage of citrate to acetate and oxaloacetate. In certain embodiments, citrate lyase is expressed in the cytosol of a eukaryotic organism. The enzyme is active under anaerobic conditions and is composed of three subunits: an acyl-carrier protein (ACP, gamma), an ACP transferase (alpha), and an acyl lyase (beta). Enzyme activation uses covalent binding and acetylation of an unusual prosthetic group, 2'-(5"-phosphoribosyl)-3'-dephospho-CoA, which is similar in structure to acetyl-CoA. Acylation is catalyzed by CitC, a citrate lyase synthetase. Two additional proteins, CitG and CitX, are used to convert the apo enzyme into the active holo enzyme (Schneider et al., Biochemistry 39:9438-9450 (2000)). Wild type *E. coli* does not have citrate lyase activity; however, mutants deficient in molybdenum cofactor synthesis have an active citrate lyase (Clark, FEMS Microbiol. Lett. 55:245-249 (1990)). The *E. coli* enzyme is encoded by citEFD and the citrate lyase synthetase is encoded by citC (Nilekani and SivaRaman, Biochemistry 22:4657-4663 (1983)). The *Leuconostoc mesenteroides* citrate lyase has been cloned, characterized and expressed in *E. coli* (Bekal et al., J. Bacteriol. 180:647-654 (1998)). Citrate lyase enzymes have also been identified in enterobacteria that utilize citrate as a carbon and energy source, including *Salmonella typhimurium* and *Klebsiella pneumoniae* (Bott, Arch. Microbiol. 167: 78-88 (1997); Bott and Dimroth, Mol. Microbiol. 14:347-356 (1994)). The aforementioned proteins are tabulated below.

| Protein | GenBank ID | GI Number | Organism |
| --- | --- | --- | --- |
| citF | AAC73716.1 | 1786832 | *Escherichia coli* |
| cite | AAC73717.2 | 87081764 | *Escherichia coli* |
| citD | AAC73718.1 | 1786834 | *Escherichia coli* |
| citC | AAC73719.2 | 87081765 | *Escherichia coli* |
| citG | AAC73714.1 | 1786830 | *Escherichia coli* |
| citX | AAC73715.1 | 1786831 | *Escherichia coli* |
| citF | CAA71633.1 | 2842397 | *Leuconostoc mesenteroides* |
| citE | CAA71632.1 | 2842396 | *Leuconostoc mesenteroides* |
| citD | CAA71635.1 | 2842395 | *Leuconostoc mesenteroides* |
| citC | CAA71636.1 | 3413797 | *Leuconostoc mesenteroides* |
| citG | CAA71634.1 | 2842398 | *Leuconostoc mesenteroides* |
| citX | CAA71634.1 | 2842398 | *Leuconostoc mesenteroides* |
| citF | NP_459613.1 | 16763998 | *Salmonella typhimurium* |
| citE | AAL19573.1 | 16419133 | *Salmonella typhimurium* |
| citD | NP_459064.1 | 16763449 | *Salmonella typhimurium* |
| citC | NP_459616.1 | 16764001 | *Salmonella typhimurium* |
| citG | NP_459611.1 | 16763996 | *Salmonella typhimurium* |
| citX | NP_459612.1 | 16763997 | *Salmonella typhimurium* |
| citF | CAA56217.1 | 565619 | *Klebsiella pneumoniae* |
| citE | CAA56216.1 | 565618 | *Klebsiella pneumoniae* |
| citD | CAA56215.1 | 565617 | *Klebsiella pneumoniae* |
| citC | BAH66541.1 | 238774045 | *Klebsiella pneumoniae* |
| citG | CAA56218.1 | 565620 | *Klebsiella pneumoniae* |
| citX | AAL60463.1 | 18140907 | *Klebsiella pneumoniae* |

The acylation of acetate to acetyl-CoA is catalyzed by enzymes with acetyl-CoA synthetase activity (FIGS. 4 and 5, step F). In certain embodiments, acetyl-CoA synthetase is expressed in the cytosol of a eukaryotic organism. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., J. Gen. Microbiol. 102:327-336 (1977)), *Ralstonia eutropha* (Priefert and Steinbuchel, J. Bacteriol. 174:6590-6599 (1992)), *Methanothermobacter thermautotrophicus* (Ingram-Smith and Smith, Archaea 2:95-107 (2007)), *Salmonella enterica* (Gulick et al., Biochemistry 42:2866-2873 (2003)) and *Saccharomyces cerevisiae* (Jogl and Tong, Biochemistry 43:1425-1431 (2004)).

| Protein | GenBank ID | GI Number | Organism |
| --- | --- | --- | --- |
| acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |
| ACS1 | Q01574.2 | 257050994 | *Saccharomyces cerevisiae* |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF 1211, was shown to operate on a variety of linear and branched-chain substrates including acetyl-CoA, propionyl-CoA, butyryl- CoA, acetate, propionate, butyrate, isobutyryate, isovalerate, succinate, fumarate, phenylacetate, indoleacetate (Musfeldt et al., *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus*, *H. marismortui* and *P. aerophilum* have all been cloned, functionally expressed, and characterized in *E. coli* (Musfeldt et al., supra; Brasen et al., supra (2004)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). Information related to these proteins and genes is shown below.

| Protein | GenBank ID | GI number | Organism |
| --- | --- | --- | --- |
| AF1211 | NP_070039.1 | 11498810 | *Archaeoglobus fulgidus* DSM 4304 |
| AF1983 | NP_070807.1 | 11499565 | *Archaeoglobus fulgidus* DSM 4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |

An alternative method for adding the CoA moiety to acetate is to apply a pair of enzymes such as a phosphate-transferring acyltransferase and an acetate kinase (FIGS. 4 and 5, Step F). This activity enables the net formation of acetyl-CoA with the simultaneous consumption of ATP. In certain embodiments, phosphotransacetylase is expressed in the cytosol of a eukaryotic organism. An exemplary phosphate-transferring acyltransferase is phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Homologs exist in several other organisms including *Salmonella enterica* and *Chlamydomonas reinhardtii*.

| Protein | GenBank ID | GI number | Organism |
| --- | --- | --- | --- |
| Pta | NP_416800.1 | 16130232 | *Escherichia coli* |
| Pta | NP_461280.1 | 16765665 | *Salmonella enterica* subsp. *enterica* serovar *Typhimurium* str. LT2 |
| PAT2 | XP_001694504.1 | 159472743 | *Chlamydomonas reinhardtii* |
| PAT1 | XP_001691787.1 | 159467202 | *Chlamydomonas reinhardtii* |

An exemplary acetate kinase is the *E. coli* acetate kinase, encoded by ackA (Skarstedt and Silverstein *J. Biol. Chem.* 251:6775-6783 (1976)). Homologs exist in several other organisms including *Salmonella enterica* and *Chlamydomonas reinhardtii*. Information related to these proteins and genes is shown below:

| Protein | GenBank ID | GI number | Organism |
| --- | --- | --- | --- |
| AckA | NP_416799.1 | 16130231 | *Escherichia coli* |
| AckA | NP_461279.1 | 16765664 | *Salmonella enterica* subsp. *enterica* serovar *Typhimurium* str. LT2 |
| ACK1 | XP_001694505.1 | 159472745 | *Chlamydomonas reinhardtii* |
| ACK2 | XP_001691682.1 | 159466992 | *Chlamydomonas reinhardtii* |

In some embodiments, cytosolic oxaloacetate is transported back into a mitochondrion by an oxaloacetate transporter. Oxaloacetate transported back into a mitochondrion can then be used in the acetyl-CoA pathways described herein. Transport of oxaloacetate from the cytosol to the mitochondrion can be carried out by several transport proteins. Such proteins either import oxaloacetate directly (i.e., oxaloacetate transporter) to the mitochondrion or import oxaloacetate to the cytosol while simultaneously transporting a molecule such as citrate (i.e., citrate/oxaloacetate transporter) from the mitochondrion into the cytosol as shown in FIG. 5. Exemplary transport enzymes that carry out these transformations are provided in the table below.

| Protein | GenBank ID | GI number | Organism |
| --- | --- | --- | --- |
| OAC1 | NP_012802.1 | 6322729 | Saccharomyces cerevisiae S288c |
| KLLA0B12826g | XP_452102.1 | 50304305 | Kluyveromyces lactis NRRL Y-1140 |
| YALI0E04048g | XP_503525.1 | 50552101 | Yarrowia lipolytica |
| CTRG_02239 | XP_002547942.1 | 255726032 | Candida tropicalis MYA-3404 |
| DIC1 | NP_013452.1 | 6323381 | Saccharomyces cerevisiae S288c |
| YALI0B03344g | XP_500457.1 | 50545838 | Yarrowia lipolytica |
| CTRG_02122 | XP_002547815.1 | 255725772 | Candida tropicalis MYA-3404 |
| PAS_chr4_0877 | XP_002494326.1 | 254574434 | Pichia pastoris GS115 |
| DTC | CAC84549.1 | 19913113 | Arabidopsis thaliana |
| DTC1 | CAC84545.1 | 19913105 | Nicotiana tabacum |
| DTC2 | CAC84546.1 | 19913107 | Nicotiana tabacum |
| DTC3 | CAC84547.1 | 19913109 | Nicotiana tabacum |
| DTC4 | CAC84548.1 | 19913111 | Nicotiana tabacum |
| DTC | AAR06239.1 | 37964368 | Citrus junos |

In some embodiments, cytosolic oxaloacetate is first converted to malate by a cytosolic malate dehydrogenase (FIG. 4, step H). Cytosolic malate is transported into a mitochondrion by a malate transporter or a citrate/malate transporter (FIG. 4, step I). Mitochondrial malate is then converted to oxaloacetate by a mitochondrial malate dehydrogenase (FIG. 4, step J). Mitochondrial oxaloacetate can then be used in the acetyl-CoA pathways described herein. Exemplary examples of each of these enzymes are provided below.

Oxaloacetate is converted into malate by malate dehydrogenase (EC 1.1.1.37, FIG. 4, step H). When malate is the dicarboxylate transported from the cytosol to mitochondrion, expression of both a cytosolic and mitochondrial version of malate dehydrogenase, e.g., as shown in FIG. 3, can be used. S. cerevisiae possesses three copies of malate dehydrogenase, MDH1 (McAlister-Henn and Thompson, J. Bacteriol. 169:5157-5166 (1987), MDH2 (Minard and McAlister-Henn, Mol. Cell. Biol. 11:370-380 (1991); Gibson and McAlister-Henn, J. Biol. Chem. 278:25628-25636 (2003)), and MDH3 (Steffan and McAlister-Henn, J. Biol. Chem. 267:24708-24715 (1992)), which localize to the mitochondrion, cytosol, and peroxisome, respectively. Close homologs to the cytosolic malate dehydrogenase, MDH2, from S. cerevisiae are found in several organisms including Kluyveromyces lactis and Candida tropicalis. E. coli is also known to have an active malate dehydrogenase encoded by mdh.

| Protein | GenBank ID | GI Number | Organism |
| --- | --- | --- | --- |
| MDH1 | NP_012838 | 6322765 | Saccharomyces cerevisiae |
| MDH2 | NP_014515 | 116006499 | Saccharomyces cerevisiae |
| MDH3 | NP_010205 | 6320125 | Saccharomyces cerevisiae |
| Mdh | NP_417703.1 | 16131126 | Escherichia coli |
| KLLA0E07525p | XP_454288.1 | 50308571 | Kluyveromyces lactis NRRL Y-1140 |
| YALI0D16753g | XP_502909.1 | 50550873 | Yarrowia lipolytica |
| CTRG_01021 | XP_002546239.1 | 255722609 | Candida tropicalis MYA-3404 |

Transport of malate from the cytosol to the mitochondrion can be carried out by several transport proteins. Such proteins either import malate directly (i.e., malate transporter) to the mitochondrion or import malate to the cytosol while simultaneously transporting a molecule such as citrate (i.e., citrate/malate transporter) from the mitochondrion into the cytosol as shown in FIG. 4. Exemplary transport enzymes that carry out these transformations are provided in the table below.

| Protein | GenBank ID | GI number | Organism |
|---|---|---|---|
| OAC1 | NP_012802.1 | 6322729 | Saccharomyces cerevisiae S288c |
| KLLA0B12826g | XP_452102.1 | 50304305 | Kluyveromyces lactis NRRL Y-1140 |
| YALI0E04048g | XP_503525.1 | 50552101 | Yarrowia lipolytica |
| CTRG_02239 | XP_002547942.1 | 255726032 | Candida tropicalis MYA-3404 |
| DIC1 | NP_013452.1 | 6323381 | Saccharomyces cerevisiae S288c |
| YALI0B03344g | XP_500457.1 | 50545838 | Yarrowia lipolytica |
| CTRG_02122 | XP_002547815.1 | 255725772 | Candida tropicalis MYA-3404 |
| PAS_chr4_0877 | XP_002494326.1 | 254574434 | Pichia pastoris GS115 |
| DTC | CAC84549.1 | 19913113 | Arabidopsis thaliana |
| DTC1 | CAC84545.1 | 19913105 | Nicotiana tabacum |
| DTC2 | CAC84546.1 | 19913107 | Nicotiana tabacum |
| DTC3 | CAC84547.1 | 19913109 | Nicotiana tabacum |
| DTC4 | CAC84548.1 | 19913111 | Nicotiana tabacum |
| DTC | AAR06239.1 | 37964368 | Citrus junos |

Malate can be converted into oxaloacetate by malate dehydrogenase (EC 1.1.1.37, FIG. 4, step J). When malate is the dicarboxylate transported from the cytosol to mitochondrion, in certain embodiments, both a cytosolic and mitochondrial version of malate dehydrogenase is expressed, as shown in FIGS. 3 and 4. S. cerevisiae possesses three copies of malate dehydrogenase, MDH1 (McAlister-Henn and Thompson, J. Bacteriol. 169:5157-5166 (1987), MDH2 (Minard and McAlister-Henn, Mol. Cell. Biol. 11:370-380 (1991); Gibson and McAlister-Henn, J. Biol. Chem. 278: 25628-25636 (2003)), and MDH3 (Steffan and McAlister-Henn, J. Biol. Chem. 267:24708-24715 (1992)), which localize to the mitochondrion, cytosol, and peroxisome, respectively. Close homologs to the mitochondrial malate dehydrogenase, MDH1, from S. cerevisiae are found in several organisms including Kluyveromyces lactis, Yarrowia lipolytica, Candida tropicalis. E. coli is also known to have an active malate dehydrogenase encoded by mdh.

| Protein | GenBankID | GI Number | Organism |
|---|---|---|---|
| MDH1 | NP_012838 | 6322765 | Saccharomyces cerevisiae |
| MDH2 | NP_014515 | 116006499 | Saccharomyces cerevisiae |
| MDH3 | NP_010205 | 6320125 | Saccharomyces cerevisiae |
| Mdh | NP_417703.1 | 16131126 | Escherichia coli |
| KLLA0F25960g | XP_456236.1 | 50312405 | Kluyveromyces lactis NRRL Y-1140 |
| YALI0D16753g | XP_502909.1 | 50550873 | Yarrowia lipolytica |
| CTRG_00226 | XP_002545445.1 | 255721021 | Candida tropicalis MYA-3404 |

Example V

Utilization of Pathway Enzymes with a Preference for NADH

The production of acetyl-CoA from glucose can generate at most four reducing equivalents in the form of NADH. A straightforward and energy efficient mode of maximizing the yield of reducing equivalents is to employ the Embden-Meyerhof-Parnas glycolysis pathway (EMP pathway). In many carbohydrate utilizing organisms, one NADH molecule is generated per oxidation of each glyceraldehyde-3-phosphate molecule by means of glyceraldehyde-3-phosphate dehydrogenase. Given that two molecules of glyceraldehyde-3-phosphate are generated per molecule of glucose metabolized via the EMP pathway, two NADH molecules can be obtained from the conversion of glucose to pyruvate.

Two additional molecules of NADH can be generated from conversion of pyruvate to acetyl-CoA given that two molecules of pyruvate are generated per molecule of glucose metabolized via the EMP pathway. This could be done by employing any of the following enzymes or enzyme sets to convert pyruvate to acetyl-CoA:

I. NAD-dependant pyruvate dehydrogenase;
  II. Pyruvate formate lyase and NAD-dependant formate dehydrogenase;

III. Pyruvate:ferredoxin oxidoreductase and NADH:ferredoxin oxidoreductase;
IV. Pyruvate decarboxylase and an NAD-dependant acylating acetylaldehyde dehydrogenase;
V. Pyruvate decarboxylase, NAD-dependant acylating acetaldehyde dehydrogenase, acetate kinase, and phosphotransacetylase; and
VI. Pyruvate decarboxylase, NAD-dependant acylating acetaldehyde dehydrogenase, and acetyl-CoA synthetase.

Overall, four molecules of NADH can be attained per glucose molecule metabolized. In one aspect, the fatty alcohol pathway requires three reduction steps from acetyl-CoA. Therefore, it can be possible that each of these three reduction steps will utilize NADPH or NADH as the reducing agents, in turn converting these molecules to NADP or NAD, respectively. Therefore, in some aspects, it can be desireable that all reduction steps are NADH-dependant in order to maximize the yield of fatty alcohols, fatty aldehydes or fatty acis. High yields of fatty alcohols, fatty aldehydes and fatty acids can thus be accomplished by:

Identifying and implementing endogenous or exogenous fatty alcohol, fatty aldehyde or fatty acid pathway enzymes with a stronger preference for NADH than other reducing equivalents such as NADPH,
  I. Attenuating one or more endogenous fatty alcohol, fatty aldehyde or fatty acid pathway enzymes that contribute NADPH-dependant reduction activity,
  II. Altering the cofactor specificity of endogenous or exogenous fatty alcohol, fatty aldehyde or fatty acid pathway enzymes so that they have a stronger preference for NADH than their natural versions, or
  III. Altering the cofactor specificity of endogenous or exogenous fatty alcohol, fatty aldehyde or fatty acid pathway enzymes so that they have a weaker preference for NADPH than their natural versions.

The individual enzyme or protein activities from the endogenous or exogenous DNA sequences can be assayed using methods well known in the art. For example, the genes can be expressed in *E. coli* and the activity of their encoded proteins can be measured using cell extracts. Alternatively, the enzymes can be purified using standard procedures well known in the art and assayed for activity. Spectrophotometric based assays are particularly effective.

Several examples and methods of altering the cofactor specificity of enzymes are known in the art. For example, Khoury et al. (Protein Sci. 2009 October; 18(10): 2125-2138) created several xylose reductase enzymes with an increased affinity for NADH and decreased affinity for NADPH. Ehsani et al (Biotechnology and Bioengineering, Volume 104, Issue 2, pages 381-389, 1 Oct. 2009) drastically decreased activity of 2,3-butanediol dehydrogenase on NADH while increasing activity on NADPH. Machielsen et al (Engineering in Life Sciences, Volume 9, Issue 1, pages 38-44, February 2009) dramatically increased activity of alcohol dehydrogenase on NADH. Khoury et al (Protein Sci. 2009 October; 18(10): 2125-2138) list in Table I several previous examples of successfully changing the cofactor preference of over 25 other enzymes. Additional descriptions can be found in Lutz et al, Protein Engineering Handbook, Volume 1 and Volume 2, 2009, Wiley-VCH Verlag GmbH & Co. KGaA, in particular, Chapter 31: Altering Enzyme Substrate and Cofactor Specificity via Protein Engineering.

Example VI

Determining Cofactor Preference of Pathway Enzymes

This example describes an experimental method for determining the cofactor preference of an enzyme.

Cofactor preference of enzymes for each of the pathway steps can be determined by cloning the individual genes on a plasmid behind a constitutive or inducible promoter and transforming into a host organism such as *Escherichia coli*. For example, genes encoding enzymes that catalyze pathway steps from: 1) acetoacetyl-CoA to 3-hydroxybutyryl-CoA, 2) 3-hydroxybutyryl-CoA to 3-hydroxybutyraldehyde, 3) 3-hydroxybutyraldehyde to 1,3-butanediol (wherein $R_1$ is $C_1$; $R_3$ is OH) can be assembled onto the pZ-based expression vectors as described below.

Replacement of the Stuffer Fragment in the pZ-based Expression Vectors. Vector backbones were obtained from Dr. Rolf Lutz of Expressys (www.expressys.de/). The vectors and strains are based on the pZ Expression System developed by Lutz and Bujard (*Nucleic Acids Res* 25, 1203-1210 (1997)). The pZE13luc, pZA33luc, pZS*13luc and pZE22luc contain the luciferase gene as a stuffer fragment. To replace the luciferase stuffer fragment with a lacZ-alpha fragment flanked by appropriate restriction enzyme sites, the luciferase stuffer fragment is removed from each vector by digestion with EcoRI and XbaI. The lacZ-alpha fragment is PCR amplified from pUC19 with the following primers:

```
lacZalpha-R1
                                        (SEQ ID NO: 1)
5'GACGAATTCGCTAGCAAGAGGAGAAGTCGACATGTCCAATTCACTGGC
CGTCGTTTTAC3' lacZalpha 3'BB
                                        (SEQ ID NO: 2)
5'-GACCCTAGGAAGCTTTCTAGAGTCGACCTATGCGGCATCAGAGCAG
A-3'
```

This generates a fragment with a 5' end of EcoRI site, NheI, a Ribosomal Binding Site, a SalI site and the start codon. On the 3' end of the fragment are the stop codon, XbaI, HindIII, and AvrII sites. The PCR product is digested with EcoRI and AvrII and ligated into the base vectors digested with EcoRI and XbaI (XbaI and AvrII have compatible ends and generate a non-site). Because NheI and XbaI restriction enzyme sites generate compatible ends that can be ligated together (but generate a site after ligation that is not digested by either enzyme), the genes cloned into the vectors can be "Biobricked" together (openwetware.org/wiki/Synthetic_Biology:BioBricks). Briefly, this method enables joining an unlimited number of genes into the vector using the same 2 restriction sites (as long as the sites do not appear internal to the genes), because the sites between the genes are destroyed after each addition. These vectors can be subsequently modified using the Phusion® Site-Directed Mutagenesis Kit (NEB, Ipswich, Mass., USA) to insert the spacer sequence AATTAA between the EcoRI and NheI sites. This eliminates a putative stem loop structure in the RNA that bound the RBS and start codon.

All vectors have the pZ designation followed by letters and numbers indicating the origin of replication, antibiotic resistance marker and promoter/regulatory unit. The origin of replication is the second letter and is denoted by E for ColE1, A for p15A and S for pSC101 (as well as a lower copy number version of pSC101 designated S*)-based origins. The first number represents the antibiotic resistance marker (1 for Ampicillin, 2 for Kanamycin, 3 for Chloramphenicol). The final number defines the promoter that regulated the gene of interest (1 for PLtetO-1, 2 for PLlacO-1 and 3 for PA1lacO-1). For the work discussed here we employed three base vectors, pZS*13S, pZA33S and pZE13S, modified for the biobricks insertions as discussed above.

Plasmids containing genes encoding pathway enzymes can then transformed into host strains containing lacIQ, which allow inducible expression by addition of isopropyl 3-D-1-thiogalactopyranoside (IPTG). Activities of the heterologous enzymes are tested in in vitro assays, using strain E. coli MG1655 lacIQ as the host for the plasmid constructs containing the pathway genes. Cells can be grown aerobically in LB media (Difco) containing the appropriate antibiotics for each construct, and induced by addition of IPTG at 1 mM when the optical density (OD600) reached approximately 0.5. Cells can be harvested after 6 hours, and enzyme assays conducted as discussed below.

In Vitro Enzyme Assays. To obtain crude extracts for activity assays, cells can be harvested by centrifugation at 4,500 rpm (Beckman-Coulter, Allegera X-15R) for 10 min. The pellets are resuspended in 0.3 mL BugBuster (Novagen) reagent with benzonase and lysozyme, and lysis proceeds for about 15 minutes at room temperature with gentle shaking. Cell-free lysate is obtained by centrifugation at 14,000 rpm (Eppendorf centrifuge 5402) for 30 min at 4° C. Cell protein in the sample is determined using the method of Bradford et al., Anal. Biochem. 72:248-254 (1976), and specific enzyme assays conducted as described below. Activities are reported in Units/mg protein, where a unit of activity is defined as the amount of enzyme required to convert 1 micromol of substrate in 1 minute at room temperature.

Pathway steps can be assayed in the reductive direction using a procedure adapted from several literature sources (Durre et al., FEMS Microbiol. Rev. 17:251-262 (1995); Palosaari and Rogers, Bacteriol. 170:2971-2976 (1988) and Welch et al., Arch. Biochem. Biophys. 273:309-318 (1989). The oxidation of NADH or NADPH can be followed by reading absorbance at 340 nM every four seconds for a total of 240 seconds at room temperature. The reductive assays can be performed in 100 mM MOPS (adjusted to pH 7.5 with KOH), 0.4 mM NADH or 0.4 mM NADPH, and from 1 to 50 μmol of cell extract. For carboxylic acid reductase-like enzymes, ATP can also be added at saturating concentrations. The reaction can be started by adding the following reagents: 100 μmol of 100 mM acetoacetyl-CoA, 3-hydroxybutyryl-CoA, 3-hydroxybutyrate, or 3-hydroxybutyraldehyde. The spectrophotometer is quickly blanked and then the kinetic read is started. The resulting slope of the reduction in absorbance at 340 nM per minute, along with the molar extinction coefficient of NAD(P)H at 340 nM (6000) and the protein concentration of the extract, can be used to determine the specific activity.

Example VII

Methods for Increasing NADPH Availability

In some aspects of the invention, it can be advantageous to employ pathway enzymes that have activity using NADPH as the reducing agent. For example, NADPH-dependant pathway enzymes can be highly specific for MI-FAE cycle and/or termination pathway intermediates or can possess favorable kinetic properties using NADPH as a substrate. If one or more pathway steps is NADPH dependant, several alternative approaches to increase NADPH availability can be employed. These include:

1) Increasing flux relative to wild-type through the oxidative branch of the pentose phosphate pathway comprising glucose-6-phosphate dehydrogenase, 6-phosphogluconolactonase, and 6-phosphogluconate dehydrogenase (decarboxylating). This will generate 2 NADPH molecules per glucose-6-phosphate metabolized. However, the decarboxylation step will reduce the maximum theoretical yield of 1,3-butanediol.
2) Increasing flux relative to wild-type through the Entner Doudoroff pathway comprising glucose-6-phosphate dehydrogenase, 6-phosphogluconolactonase, phosphogluconate dehydratase, and 2-keto-3-deoxygluconate 6-phosphate aldolase.
3) Introducing a soluble transhydrogenase to convert NADH to NADPH.
4) Introducing a membrane-bound transhydrogenase to convert NADH to NADPH.
5) Employing an NADP-dependant glyceraldehyde-3-phosphate dehydrogenase.
6) Employing any of the following enzymes or enzyme sets to convert pyruvate to acetyl-CoA
   a) NADP-dependant pyruvate dehydrogenase;
   b) Pyruvate formate lyase and NADP-dependant formate dehydrogenase;
   c) Pyruvate:ferredoxin oxidoreductase and NADPH: ferredoxin oxidoreductase;
   d) Pyruvate decarboxylase and an NADP-dependant acylating acetylaldehyde dehydrogenase;
   e) Pyruvate decarboxylase, NADP-dependant acetaldehyde dehydrogenase, acetate kinase, and phosphotransacetylase; and
   f) Pyruvate decarboxylase, NADP-dependant acetaldehyde dehydrogenase, and acetyl-CoA synthetase; and optionally attenuating NAD-dependant versions of these enzymes.
7) Altering the cofactor specificity of a native glyceraldehyde-3-phosphate dehydrogenase, pyruvate dehydrogenase, formate dehydrogenase, or acylating acetylaldehyde dehydrogenase to have a stronger preference for NADPH than their natural versions.
8) Altering the cofactor specificity of a native glyceraldehyde-3-phosphate dehydrogenase, pyruvate dehydrogenase, formate dehydrogenase, or acylating acetylaldehyde dehydrogenase to have a weaker preference for NADH than their natural versions.

The individual enzyme or protein activities from the endogenous or exogenous DNA sequences can be assayed using methods well known in the art. For example, the genes can be expressed in E. coli and the activity of their encoded proteins can be measured using cell extracts as described in the previous example. Alternatively, the enzymes can be purified using standard procedures well known in the art and assayed for activity. Spectrophotometric based assays are particularly effective.

Several examples and methods of altering the cofactor specificity of enzymes are known in the art. For example, Khoury et al (Protein Sci. 2009 October; 18(10): 2125-2138) created several xylose reductase enzymes with an increased affinity for NADH and decreased affinity for NADPH. Ehsani et al (Biotechnology and Bioengineering, Volume 104, Issue 2, pages 381-389, 1 Oct. 2009) drastically decreased activity of 2,3-butanediol dehydrogenase on NADH while increasing activity on NADPH. Machielsen et al (Engineering in Life Sciences, Volume 9, Issue 1, pages 38-44, February 2009) dramatically increased activity of alcohol dehydrogenase on NADH. Khoury et al (Protein Sci. 2009 October; 18(10): 2125-2138) list in Table I several previous examples of successfully changing the cofactor preference of over 25 other enzymes. Additional descriptions can be found in Lutz et al, Protein Engineering Handbook, Volume 1 and Volume 2, 2009, Wiley-VCH Verlag GmbH & Co. KGaA, in particular, Chapter 31: Altering Enzyme Substrate and Cofactor Specificity via Protein Engineering.

Enzyme candidates for these steps are provided below.

Glucose-6-Phosphate Dehydrogenase

| Protein | GenBank ID | GI Number | Organism |
|---|---|---|---|
| ZWF1 | NP_014158.1 | 6324088 | *Saccharomyces cerevisiae* S288c |
| ZWF1 | XP_504275.1 | 50553728 | *Yarrowia lipolytica* |
| Zwf | XP_002548953.1 | 255728055 | *Candida tropicalis* MYA-3404 |
| Zwf | XP_001400342.1 | 145233939 | *Aspergillus niger* CBS 513.88 |
| KLLA0D19855g | XP_453944.1 | 50307901 | *Kluyveromyces lactis* NRRL Y-1140 |

6-Phosphogluconolactonase

| Protein | GenBank ID | GI Number | Organism |
|---|---|---|---|
| SOL3 | NP_012033.2 | 82795254 | *Saccharomyces cerevisiae* S288c |
| SOL4 | NP_011764.1 | 6321687 | *Saccharomyces cerevisiae* S288c |
| YALI0E11671g | XP_503830.1 | 50552840 | *Yarrowia lipolytica* |
| YALI0C19085g | XP_501998.1 | 50549055 | *Yarrowia lipolytica* |
| ANI_1_656014 | XP_001388941.1 | 145229265 | *Aspergillus niger* CBS 513.88 |
| CTRG_00665 | XP_002545884.1 | 255721899 | *Candida tropicalis* MYA-3404 |
| CTRG_02095 | XP_002547788.1 | 255725718 | *Candida tropicalis* MYA-3404 |
| KLLA0A05390g | XP_451238.1 | 50302605 | *Kluyveromyces lactis* NRRL Y-1140 |
| KLLA0C08415g | XP_452574.1 | 50305231 | *Kluyveromyces lactis* NRRL Y-1140 |

6-Phosphogluconate Dehydrogenase (Decarboxylating)

| Protein | GenBank ID | GI Number | Organism |
|---|---|---|---|
| GND1 | NP_012053.1 | 6321977 | *Saccharomyces cerevisiae* S288c |
| GND2 | NP_011772.1 | 6321695 | *Saccharomyces cerevisiae* S288c |
| ANI_1_282094 | XP_001394208.2 | 317032184 | *Aspergillus niger* CBS 513.88 |
| ANI_1_2126094 | XP_001394596.2 | 317032939 | *Aspergillus niger* CBS 513.88 |
| YALI0B15598g | XP_500938.1 | 50546937 | *Yarrowia lipolytica* |
| CTRG_03660 | XP_002549363.1 | 255728875 | *Candida tropicalis* MYA-3404 |
| KLLA0A09339g | XP_451408.1 | 50302941 | *Kluyveromyces lactis* NRRL Y-1140 |

Phosphogluconate Dehydratase

| Protein | GenBank ID | GI Number | Organism |
|---|---|---|---|
| Edd | AAC74921.1 | 1788157 | *Escherichia coli* K-12 MG1655 |
| Edd | AAG29866.1 | 11095426 | *Zymomonas mobilis* subsp. *mobilis* ZM4 |
| Edd | YP_350103.1 | 77460596 | *Pseudomonas fluorescens* Pf0-1 |
| ANI_1_2126094 | XP_001394596.2 | 317032939 | *Aspergillus niger* CBS 513.88 |
| YALI0B15598g | XP_500938.1 | 50546937 | *Yarrowia lipolytica* |
| CTRG_03660 | XP_002549363.1 | 255728875 | *Candida tropicalis* MYA-3404 |
| KLLA0A09339g | XP_451408.1 | 50302941 | *Kluyveromyces lactis* NRRL Y-1140 |

2-Keto-3-Deoxygluconate 6-Phosphate Aldolase

| Protein | GenBank ID | GI Number | Organism |
|---|---|---|---|
| Eda | NP_416364.1 | 16129803 | Escherichia coli K-12 MG 1655 |
| Eda | Q00384.2 | 59802878 | Zymomonas mobilis subsp. mobilis ZM4 |
| Eda | ABA76098.1 | 77384585 | Pseudomonas fluorescens Pf0-1 |

Soluble Transhydrogenase

| Protein | GenBank ID | GI Number | Organism |
|---|---|---|---|
| SthA | NP_418397.2 | 90111670 | Escherichia coli K-12 MG1655 |
| SthA | YP_002798658.1 | 226943585 | Azotobacter vinelandii DJ |
| SthA | O05139.3 | 11135075 | Pseudomonas fluorescens |

Membrane-Bound Transhydrogenase

| Protein | GenBank ID | GI Number | Organism |
|---|---|---|---|
| ANI_1_29100 | XP_001400109.2 | 317027842 | Aspergillus niger CBS 513.88 |
| Pc21g18800 | XP_002568871.1 | 226943585 | Penicillium chrysogenum Wisconsin 54-1255 |
| SthA | O05139.3 | 11135075 | Pseudomonas fluorescens |
| NCU01140 | XP_961047.2 | 164426165 | Neurospora crassa OR74A |

NADP-Dependant Glyceraldehyde-3-Phosphate Dehydrogenase

| Protein | GenBank ID | GI Number | Organism |
|---|---|---|---|
| gapN | AAA91091.1 | 642667 | Streptococcus mutans |
| NP-GAPDH | AEC07555.1 | 330252461 | Arabidopsis thaliana |
| GAPN | AAM77679.2 | 82469904 | Triticum aestivum |
| gapN | CAI56300.1 | 87298962 | Clostridium acetobutylicum |
| NADP-GAPDH | 2D2I_A | 112490271 | Synechococcus elongatus PCC 7942 |
| NADP-GAPDH | CAA62619.1 | 4741714 | Synechococcus elongatus PCC 7942 |
| GDP1 | XP_455496.1 | 50310947 | Kluyveromyces lactis NRRL Y-1140 |
| HP1346 | NP_208138.1 | 15645959 | Helicobacter pylori 26695 |

NAD-dependant glyceraldehyde-3-phosphate dehydrogenase

| Protein | GenBank ID | GI Number | Organism |
|---|---|---|---|
| TDH1 | NP_012483.1 | 6322409 | Saccharomyces cerevisiae s288c |
| TDH2 | NP_012542.1 | 6322468 | Saccharomyces cerevisiae s288c |
| TDH3 | NP_011708.1 | 632163 | Saccharomyces cerevisiae s288c |
| KLLA0A11858g | XP_451516.1 | 50303157 | Kluyveromyces lactis NRRL Y-1140 |
| KLLA0F20988g | XP_456022.1 | 50311981 | Kluyveromyces lactis NRRL Y-1140 |
| ANI_1_256144 | XP_001397496.1 | 145251966 | Aspergillus niger CBS 513.88 |
| YALI0C06369g | XP_501515.1 | 50548091 | Yarrowia lipolytica |
| CTRG_05666 | XP_002551368.1 | 255732890 | Candida tropicalis MYA-3404 |

Mutated LpdA from *E. coli* K-12 MG1655 described in Biochemistry, 1993, 32 (11), pp 2737-2740:

(SEQ ID NO: 3)
MSTEIKTQVVVLGAGPAGYSAAFRCADLGLETVIVERYNTLGGVCLNVGC

IPSKALLHVAKVIEEAKALAEHGIVFGEPKTDIDKIRTWKEKVINQLTGG

LAGMAKGRKVKVVNGLGKFTGANTLEVEGENGKTVINFDNAIIAAGSRPI

QLPFIPHEDPRIWDSTDALELKEVPERLLVMGGGIIGLEMGTVYHALGSQ

IDVVVRKHQVIRAADKDIVKVFTKRISKKFNLMLETKVTAVEAKEDGIYV

TMEGKKAPAEPQRYDAVLVAIGRVPNGKNLDAGKAGVEVDDRGFIRVDKQ

LRTNVPHIFAIGDIVGQPMLAHKGVHEGHVAAEVIAGKKHYFDPKVIPSI

AYTEPEVAWVGLTEKEAKEKGISYETATFPWAASGRAIASDCADGMTKLI

FDKESHRVIGGAIVGTNGGELLGEIGLAIEMGCDAEDIALTIHAHPTLHE

SVGLAAEVFEGSITDLPNPKAKKK

Mutated LpdA from *E. coli* K-12 MG1655 described in Biochemistry, 1993, 32 (11), pp 2737-2740:

(SEQ ID NO: 4)
MSTEIKTQVVVLGAGPAGYSAAFRCADLGLETVIVERYNTLGGVCLNVGC

IPSKALLHVAKVIEEAKALAEHGIVFGEPKTDIDKIRTWKEKVINQLTGG

LAGMAKGRKVKVVNGLGKFTGANTLEVEGENGKTVINFDNAIIAAGSRPI

QLPFIPHEDPRIWDSTDALELKEVPERLLVMGGGIIALEMATVYHALGSQ

IDVVVRKHQVIRAADKDIVKVFTKRISKKFNLMLETKVTAVEAKEDGIYV

TMEGKKAPAEPQRYDAVLVAIGRVPNGKNLDAGKAGVEVDDRGFIRVDKQ

LRTNVPHIFAIGDIVGQPMLAHKGVHEGHVAAEVIAGKKHYFDPKVIPSI

AYTEPEVAWVGLTEKEAKEKGISYETATFPWAASGRAIASDCADGMTKLI

FDKESHRVIGGAIVGTNGGELLGEIGLAIEMGCDAEDIALTIHAHPTLHE

SVGLAAEVFEGSITDLPNPKAKKK

NADP-dependant formate dehydrogenase

| Protein | GenBank ID | GI Number | Organism |
|---|---|---|---|
| fdh | ACF35003. | 194220249 | *Burkholderia stabilis* |
| fdh | ABC20599.2 | 146386149 | *Moorella thermoacetica* ATCC 39073 |

Mutant *Candida bodinii* enzyme described in Journal of Molecular Catalysis B: Enzymatic, Volume 61, Issues 3-4, December 2009, Pages 157-161:

(SEQ ID NO: 5)
MKIVLVLYDAGKHAADEEKLYGCTENKLGIANWLKDQGHELITTSDKEGE

TSELDKHIPDADIIITTPFHPAYITKERLDKAKNLKLVVVAGVGSDHIDL

DYINQTGKKISVLEVTGSNVVSVAEHVVMTMLVLVRNEVPAHEQIINHDW

EVAAIAKDAYDIEGKTIATIGAGRIGYRVLERLLPFNPKELLYYQRQALP

KEAEEKVGARRVENIEELVAQADIVTVNAPLHAGTKGLINKELLSKFKKG

AWLVNTARGAICVAEDVAAALESGQLRGYGGDVWFPQPAPKDHPWRDMRN

KYGAGNAMTPHYSGTTLDAQTRYAEGTKNILESFFTGKFDYRPQDIILLN

GEYVTKAYGKHDKK

Mutant *Candida bodinii* enzyme described in Journal of Molecular Catalysis B: Enzymatic, Volume 61, Issues 3-4, December 2009, Pages 157-161:

(SEQ ID NO: 6)
MKIVLVLYDAGKHAADEEKLYGCTENKLGIANWLKDQGHELITTSDKEGE

TSELDKHIPDADIIITTPFHPAYITKERLDKAKNLKLVVVAGVGSDHIDL

DYINQTGKKISVLEVTGSNVVSVAEHVVMTMLVLVRNFVPAHEQIINHDW

EVAAIAKDAYDIEGKTIATIGAGRIGYRVLERLLPFNPKELLYYSPQALP

KEAEEKVGARRVENIEELVAQADIVTVNAPLHAGTKGLINKELLSKFKKG

AWLVNTARGAICVAEDVAAALESGQLRGYGGDVWFPQPAPKDHPWRDMRN

KYGAGNAMTPHYSGTTLDAQTRYAEGTKNILESFFTGKFDYRPQDIILLN

GEYVTKAYGKHDKK

Mutant *Saccharomyces cerevisiae* enzyme described in Biochem J. 2002 November 1:367(Pt. 3):841-847:

(SEQ ID NO: 7)
MSKGKVLLVLYEGGKHAEEQEKLLGCIENELGIRNFIEEQGYELVTTIDK

DPEPTSTVDRELKDAEIVITTPFFPAYISRNRIAEAPNLKLCVTAGVGSD

HVDLEAANERKITVTEVTGSNVVSVAEHVMATILVLIRNYNGGHQQAING

EWDIAGVAKNEYDLEDKIISTVGAGRIGYRVLERLVAFNPKKLLYYARQE

LPAEAINRLNEASKLFNGRGDIVQRVEKLEDMVAQSDVVTINCPLHKDSR

GLFNKKLISHMKDGAYLVNTARGAICVAEDVAEAVKSGKLAGYGGDVWDK

QPAPKDHPWRTMDNKDHVGNAMTVHISGTSLDAQKRYAQGVKNILNSYFS

KKFDYRPQDIIVQNGSYATRAYGQKK.

NADPH:Ferredoxin Oxidoreductase

| Protein | GenBank ID | GI Number | Organism |
|---|---|---|---|
| petH | YP_171276.1 | 56750575 | *Synechococcus elongatus* PCC 6301 |
| fpr | NP_457968.1 | 16762351 | *Salmonella enterica* |
| fnr1 | XP_001697352.1 | 159478523 | *Chlamydomonas reinhardtii* |
| rfnr1 | NP_567293.1 | 18412939 | *Arabidopsis thaliana* |
| aceF | NP_414657.1 | 6128108 | *Escherichia coli* K-12 MG1655 |

NADP-dependant acylating acetylaldehyde dehydrogenase

| Protein | GenBank ID | GI Number | Organism |
|---|---|---|---|
| adhB | AAB06720.1 | 1513071 | *Thermoanaerobacter pseudethanolicus* ATCC 33223 |
| TheetDRAFT_0840 | ZP_08211603. | 326390041 | *Thermoanaerobacter ethanolicus* JW 200 |
| Cbei_3832 | YP_001310903.1 | 150018649 | *Clostridium beijerinckii* NCIMB 8052 |
| Cbei_4054 | YP_001311120.1 | 150018866 | *Clostridium beijerinckii* NCIMB 8052 |
| Cbei_4045 | YP_001311111.1 | 150018857 | *Clostridium beijerinckii* NCIMB 8052 |

Exemplary genes encoding pyruvate dehydrogenase, pyruvate:ferredoxin oxidoreductase, pyruvate formate lyase, pyruvate decarboxylase, acetate kinase, phosphotransacetylase and acetyl-CoA synthetase are described above in Example II.

Example VIII

Engineering *Saccharomyces cerevisiae* for Chemical Production

Eukaryotic hosts have several advantages over prokaryotic systems. They are able to support post-translational modifications and host membrane-anchored and organelle-specific enzymes. Genes in eukaryotes typically have introns, which can impact the timing of gene expression and protein structure.

An exemplary eukaryotic organism well suited for industrial chemical production is *Saccharomyces cerevisiae*. This organism is well characterized, genetically tractable and industrially robust. Genes can be readily inserted, deleted, replaced, overexpressed or underexpressed using methods known in the art. Some methods are plasmid-based whereas others modify the chromosome (Guthrie and Fink. *Guide to Yeast Genetics and Molecular and Cell Biology*, Part B, Volume 350, Academic Press (2002); Guthrie and Fink, *Guide to Yeast Genetics and Molecular and Cell Biology*, Part C, Volume 351, Academic Press (2002)).

Plasmid-mediated gene expression is enabled by yeast episomal plasmids (YEps). YEps allow for high levels of expression; however they are not very stable and they require cultivation in selective media. They also have a high maintenance cost to the host metabolism. High copy number plasmids using auxotrophic (e.g., URA3, TRP1, HIS3, LEU2) or antibiotic selectable markers (e.g., $Zeo^R$ or $Kan^R$) can be used, often with strong, constitutive promoters such as PGK1 or ACT1 and a transcription terminator-polyadenylation region such as those from CYC1 or AOX. Many examples are available for one well-versed in the art. These include pVV214 (a 2 micron plasmid with URA3 selectable marker) and pVV200 (2 micron plasmid with TRP1 selectable marker) (Van et al., *Yeast* 20:739-746 (2003)). Alternatively, low copy plasmids such as centromeric or CEN plamids can be used. Again, many examples are available for one well-versed in the art. These include pRS313 and pRS315 (Sikorski and Hieter, *Genetics* 122:19-27 (1989) both of which require that a promoter (e.g., PGK1 or ACT1) and a terminator (e.g., CYC1, AOX) are added.

For industrial applications, chromosomal overexpression of genes is preferable to plasmid-mediated overexpression. Mikkelsen and coworkers have identified 11 integration sites on highly expressed regions of the *S. cerevisiae* genome on chromosomes X, XI and XII (Mikkelsen et al, *Met Eng* 14:104-11 (2012)). The sites are separated by essential genes, minimizing the possibility of recombination between sites.

Tools for inserting genes into eukaryotic organisms such as *S. cerevisiae* are known in the art. Particularly useful tools include yeast integrative plasmids (YIps), yeast artificial chromosomes (YACS) and gene targeting/homologous recombination. Note that these tools can also be used to insert, delete, replace, underexpress or otherwise alter the genome of the host.

Yeast integrative plasmids (YIps) utilize the native yeast homologous recombination system to efficiently integrate DNA into the chromosome. These plasmids do not contain an origin of replication and can therefore only be maintained after chromosomal integration. An exemplary construct includes a promoter, the gene of interest, a terminator, and a selectable marker with a promoter, flanked by FRT sites, loxP sites, or direct repeats enabling the removal and recycling of the resistance marker. The method entails the synthesis and amplification of the gene of interest with suitable primers, followed by the digestion of the gene at a unique restriction site, such as that created by the EcoRI and XhoI enzymes (Vellanki et al., *Biotechnol Lett.* 29:313-318 (2007)). The gene of interest is inserted at the EcoRI and XhoI sites into a suitable expression vector, downstream of the promoter. The gene insertion is verified by PCR and DNA sequence analysis. The recombinant plasmid is then linearized and integrated at a desired site into the chromosomal DNA of *S. cerevisiae* using an appropriate transformation method. The cells are plated on the YPD medium with an appropriate selection marker and incubated for 2-3 days. The transformants are analyzed for the requisite gene insert by colony PCR. To remove the antibiotic marker from a construct flanked by loxP sites, a plasmid containing the Cre recombinase is introduced. Cre recombinase promotes the excision of sequences flanked by loxP sites. (Gueldener et al., *Nucleic Acids Res* 30:e23 (2002)). The resulting strain is cured of the Cre plasmid by successive culturing on media without any antibiotic present. Alternately, the Cre recombinase plasmid has a URA selection marker and the plasmid is efficiently removed by growing cells on 5-FOA which acts as a counter-selection for URA. This method can also be employed for a scarless integration instead of using loxP. One skilled in the art can integrate using URA as a marker, select for integration by growing on URA-minus plates, and then select for URA mutants by growing on 5-FOA plates. 5-FOA is converted to the toxic 5-fluoruracil by the URA gene product. Alternatively, the FLP-FRT system can be used to integrate genes into the chromosome. This system involves the recombination of sequences between short Flipase Recognition Target (FRT) sites by the Flipase recombination enzyme (FLP) derived from the 2 plasmid of the yeast *Saccharomyces cerevisiae* (Sadowski, P. D., *Prog. Nucleic. Acid. Res. Mol. Biol.* 51:53-91 (1995); Zhu and Sadowski *J. Biol. Chem.* 270:23044-23054 (1995)). Similarly, gene deletion methodologies will be carried out as described in refs. Baudin et al. *Nucleic. Acids Res.* 21:3329-3330 (1993); Brachmann et al., *Yeast* 14:115-132 (1998);

Giaever et al., *Nature* 418:387-391 (2002); Longtine et al., *Yeast* 14:953-961 (1998) Winzeler et al., *Science* 285:901-906 (1999).

Another approach for manipulating the yeast chromosome is gene targeting. This approach takes advantage of the fact that double stranded DNA breaks in yeast are repaired by homologous recombination. Linear DNA fragments flanked by targeting sequences can thus be efficiently integrated into the yeast genome using the native homologous recombination machinery. In addition to the application of inserting genes, gene targeting approaches are useful for genomic DNA manipulations such as deleting genes, introducing mutations in a gene, its promoter or other regulatory elements, or adding a tag to a gene.

Yeast artificial chromosomes (YACs) are artificial chromosomes useful for pathway construction and assembly. YACs enable the expression of large sequences of DNA (100-3000 kB) containing multiple genes. The use of YACs was recently applied to engineer flavenoid biosynthesis in yeast (Naesby et al, *Microb Cell Fact* 8:49-56 (2009)). In this approach, YACs were used to rapidly test randomly assembled pathway genes to find the best combination.

The expression level of a gene can be modulated by altering the sequence of a gene and/or its regulatory regions. Such gene regulatory regions include, for example, promoters, enhancers, introns, and terminators. Functional disruption of negative regulatory elements such as repressors and/or silencers also can be employed to enhance gene expression. RNA based tools can also be employed to regulate gene expression. Such tools include RNA aptamers, riboswitches, antisense RNA, ribozymes and riboswitches.

For altering a gene's expression by its promoter, libraries of constitutive and inducible promoters of varying strengths are available. Strong constitutive promoters include pTEF1, pADH1 and promoters derived from glycolytic pathway genes. The pGAL promoters are well-studied inducible promoters activated by galactose and repressed by glucose. Another commonly used inducible promoter is the copper inducible promoter pCUP1 (Farhi et al, *Met Eng* 13:474-81 (2011)). Further variation of promoter strengths can be introduced by mutagenesis or shuffling methods. For example, error prone PCR can be applied to generate synthetic promoter libraries as shown by Alper and colleagues (Alper et al, *PNAS* 102:12678-83 (2005)). Promoter strength can be characterized by reporter proteins such as beta-galactosidase, fluorescent proteins and luciferase.

The placement of an inserted gene in the genome can alter its expression level. For example, overexpression of an integrated gene can be achieved by integrating the gene into repeating DNA elements such as ribosomal DNA or long terminal repeats.

For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Genetic modifications can also be made to enhance polypeptide synthesis. For example, translation efficiency is enhanced by substituting ribosome binding sites with an optimal or consensus sequence and/or altering the sequence of a gene to add or remove secondary structures. The rate of translation can also be increased by substituting one coding sequence with another to better match the codon preference of the host.

Example IX

Termination Pathways for Making Fatty Alcohols, Aldehydes and Acids

This example describes enzymes for converting intermediates of the MI-FAE cycle to products of interest such as fatty alcohols, fatty aldehydes, and fatty acids. Pathways are shown in FIGS. 1 and 7. Enzymes for catalyzing steps A-G are disclosed in Example I. This example describes enzymes suitable for catalyzing steps H-N.

Enzymes include: A. Thiolase, B. 3-Ketoacyl-CoA reductase, C. 3-Hydroxyl-ACP dehydratase, D. Enoyl-CoA reductase, E. Acyl-CoA reductase (aldehyde forming), F. Alcohol dehydrogenase, G. Acyl-CoA reductase (alcohol forming), H. acyl-CoA hydrolase, transferase or synthetase, J. Acyl-ACP reductase, K. Acyl-CoA:ACP acyltransferase, L. Thioesterase, N. Aldehyde dehydrogenase (acid forming) or carboxylic acid reductase.

Pathways for converting an MI-FAE cycle intermediate to an fatty alcohol, fatty aldehyde or fatty acid product are shown in the table below. These pathways are also referred to herein as "termination pathways".

| Product | Termination pathway enzymes from FIG. 1 |
|---|---|
| Acid | H |
|  | K/L |
|  | E/N |
|  | K/J/N |
| Aldehyde | E |
|  | K/J |
|  | H/N |
|  | K/L/N |
| Alcohol | E/F |
|  | K/J/F |
|  | H/N/F |
|  | K/L/N/F |
|  | G |

Product specificity can be fine-tuned using one or more enzymes shown in FIGS. 1 and 6. Chain length is controlled by one or more enzymes of the elongation pathway in conjunction with one more enzymes of the termination pathway as described above. The structure of the product is controlled by one or more enzymes of the termination pathway. Examples of selected termination pathway enzymes reacting with various pathway intermediates are shown in the table below. Additional examples are described herein.

| Enzyme | Substrate | Example |
|---|---|---|
| Acyl-CoA reductase | Acyl-CoA | Acr1 of *A. baylyi* (GenBank AAC45217) |
|  | 3-Hydroxy-acyl-CoA | PduP of *L. reuteri* (GenBank CCC03595.1) |
|  | 3-Oxoacyl-CoA | Mcr of *S. tokodaii* (GenBank NP_378167) |
| Acyl-CoA hydrolase, transferase or synthetase | Acyl-CoA | tesB of *E. coli* (GenBank NP_414986) |
|  | 3-Hydroxyacyl-CoA | hibch of *R. norvegicus* (GenBank Q5XIE6.2) |
|  | 3-Oxoacyl-CoA | MKS2 of *S. lycopersicum* (GenBank ACG69783) |

| Enzyme | Substrate | Example |
|---|---|---|
| | Enoyl-CoA | gctAB of *Acidaminococcus fermentans* (GenBank CAA57199, CAA57200) |
| Acyl-ACP acyltransferase | Acyl-CoA | fabH of *E. coli* (GenBank AAC74175.1) |

Step H. Acyl-CoA Hydrolase, Transferase or Synthase

Acyl-CoA hydrolase, transferase and synthase enzymes convert acyl-CoA moieties to their corresponding acids. Such an enzyme can be utilized to convert, for example, a fatty acyl-CoA to a fatty acid, a 3-hydroxyacyl-CoA to a 3-hydroxyacid, a 3-oxoacyl-CoA to a 3-oxoacid, or an enoyl-CoA to an enoic acid.

CoA hydrolase or thioesterase enzymes in the 3.1.2 family hydrolyze acyl-CoA molecules to their corresponding acids. Several CoA hydrolases with different substrate ranges are suitable for hydrolyzing acyl-CoA, 3-hydroxyacyl-CoA, 3-oxoacyl-CoA and enoyl-CoA substrates to their corresponding acids. For example, the enzyme encoded by acot12 from *Rattus norvegicus* brain (Robinson et al., *Biochem. Biophys. Res. Commun.* 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)). The closest *E. coli* homolog to this enzyme, tesB, can also hydrolyze a range of CoA thiolesters (Naggert et al., *J Biol Chem* 266:11044-11050 (1991)). A similar enzyme has also been characterized in the rat liver (Deana R., *Biochem Int* 26:767-773 (1992)). Additional enzymes with hydrolase activity in *E. coli* include ybgC, paaI, and ybdB (Kuznetsova, et al., *FEMS Microbiol Rev,* 2005, 29(2):263-279; Song et al., *J Biol Chem,* 2006, 281(16):11028-38). Though its sequence has not been reported, the enzyme from the mitochondrion of the pea leaf has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)) The acetyl-CoA hydrolase, ACH1, from *S. cerevisiae* represents another candidate hydrolase (Buu et al., *J. Biol. Chem.* 278:17203-17209 (2003)). Additional enzymes with aryl-CoA hydrolase activity include the palmitoyl-CoA hydrolase of *Mycobacterium tuberculosis* (Wang et al., *Chem. Biol.* 14:543-551 (2007)) and the acyl-CoA hydrolase of *E. coli* encoded by entH (Guo et al., *Biochemistry* 48:1712-1722 (2009)). Additional CoA hydrolase enzymes are described above.

| Gene name | GenBank Accession # | GI# | Organism |
|---|---|---|---|
| acot12 | NP_570103.1 | 18543355 | *Rattus norvegicus* |
| tesB | NP_414986 | 16128437 | *Escherichia coli* |
| acot8 | CAA15502 | 3191970 | *Homo sapiens* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |
| ACH1 | NP_009538 | 6319456 | *Saccharomyces cerevisiae* |
| Rv0098 | NP_214612.1 | 15607240 | *Mycobacterium tuberculosis* |
| entH | AAC73698.1 | 1786813 | *Escherichia coli* |

CoA hydrolase enzymes active on 3-hydroxyacyl-CoA, 3-oxoacyl-CoA and enoyl-CoA intermediates are also well known in the art. For example, an enzyme for converting enoyl-CoA substrates to their corresponding acids is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). Another suitable enzyme is the fadM thioesterase III of *E. coli*. This enzyme is involved in oleate beta-oxidation and the preferred substrate is 3,5-tetradecadienoyl-CoA (Nie et al, *Biochem* 47:7744-51 (2008)).

| Protein | GenBank ID | GI Number | Organism |
|---|---|---|---|
| gctA | CAA57199.1 | 559392 | *Acidaminococcus fermentans* |
| gctB | CAA57200.1 | 559393 | *Acidaminococcus fermentans* |
| gctA | ACJ24333.1 | 212292816 | *Clostridium symbiosum* |
| gctB | ACJ24326.1 | 212292808 | *Clostridium symbiosum* |
| gctA | NP_603109.1 | 19703547 | *Fusobacterium nucleatum* |
| gctB | NP_603110.1 | 19703548 | *Fusobacterium nucleatum* |
| fadM | NP_414977.1 | 16128428 | *Escherichia coli* |

3-Hydroxyisobutyryl-CoA hydrolase is active on 3-hydroxyacyl-CoA substrates (Shimomura et al., *J Biol Chem.* 269:14248-14253 (1994)). Genes encoding this enzyme include hibch of *Rattus norvegicus* (Shimomura et al., *Methods Enzymol.* 324:229-240 (2000)) and *Homo sapiens* (Shimomura et al., supra). Similar gene candidates can also be identified by sequence homology, including hibch of *Saccharomyces cerevisiae* and BC 2292 of *Bacillus cereus*. An exemplary 3-oxoacyl-CoA hydrolase is MKS2 of *Solanum lycopersicum* (Yu et al, *Plant Physiol* 154:67-77 (2010)). The native substrate of this enzyme is 3-oxomyristoyl-CoA, which produces a C14 chain length product.

| Gene name | GenBank Accession # | GI# | Organism |
|---|---|---|---|
| fadM | NP_414977.1 | 16128428 | *Escherichia coli* |
| hibch | Q5X1E6.2 | 146324906 | *Rattus norvegicus* |
| hibch | Q6NVY1.2 | 146324905 | *Homo sapiens* |
| hibch | P28817.2 | 2506374 | *Saccharomyces cerevisiae* |
| BC_2292 | AP09256 | 29895975 | *Bacillus cereus* |
| MKS2 | ACG69783.1 | 196122243 | *Solanum lycopersicum* |

CoA transferases catalyze the reversible transfer of a CoA moiety from one molecule to another. Several transformations require a CoA transferase to activate carboxylic acids to their corresponding acyl-CoA derivatives. CoA transferase enzymes have been described in the open literature and represent suitable candidates for these steps. These are described below.

The gene products of cat1, cat2, and cat3 of *Clostridium kluyveri* have been shown to exhibit succinyl-CoA, 4-hydroxybutyryl-CoA, and butyryl-CoA transferase activity, respectively (Seedorf et al., *Proc. Natl. Acad. Sci U.S.A* 105:2128-2133 (2008); Sohling et al., *J Bacteriol.* 178:871-

880 (1996)). Similar CoA transferase activities are also present in *Trichomonas vaginalis, Trypanosoma brucei, Clostridium aminobutyricum* and *Porphyromonas gingivalis* (Riviere et al., *J. Biol. Chem.* 279:45337-45346 (2004); van Grinsven et al., *J. Biol. Chem.* 283:1411-1418 (2008)).

25667 (1997)), *Bacillus subtilis* (Stols et al., *Protein Expr. Purif* 53:396-403 (2007)) and *Homo sapiens* (Fukao, T., et al., *Genomics* 68:144-151 (2000); Tanaka, H., et al., *Mol Hum Reprod* 8:16-23 (2002)). Genbank information related to these genes is summarized below.

| Protein | GenBank ID | GI Number | Organism |
|---|---|---|---|
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| cat2 | CAB60036.1 | 6249316 | *Clostridium aminobutyricum* |
| cat2 | NP_906037.1 | 34541558 | *Porphyromonas gingivalis* W83 |

A fatty acyl-CoA transferase that utilizes acetyl-CoA as the CoA donor is acetoacetyl-CoA transferase, encoded by the *E. coli* atoA (alpha subunit) and atoD (beta subunit) genes (Korolev et al., *Acta Crystallogr. D. Biol. Crystallogr.* 58:2116-2121 (2002); Vanderwinkel et al., 33:902-908 (1968)). This enzyme has a broad substrate range on substrates of chain length C3-C6 (Sramek et al., *Arch Biochem Biophys* 171:14-26 (1975)) and has been shown to transfer the CoA moiety to acetate from a variety of branched and linear 3-oxo and acyl-CoA substrates, including isobutyrate (Matthies et al., *Appl Environ. Microbiol* 58:1435-1439 (1992)), valerate (Vanderwinkel et al., *Biochem. Biophys. Res. Commun.* 33:902-908 (1968)) and butanoate (Vanderwinkel et al., *Biochem. Biophys. Res. Commun.* 33:902-908 (1968)). This enzyme is induced at the transcriptional level by acetoacetate, so modification of regulatory control may be necessary for engineering this enzyme into a pathway (Pauli et al., *Eur. J Biochem.* 29:553-562 (1972)). Similar enzymes exist in *Corynebacterium glutamicum* ATCC 13032 (Duncan et al., 68:5186-5190 (2002)), *Clostridium acetobutylicum* (Cary et al., *Appl Environ Microbiol* 56:1576-1583 (1990); Wiesenborn et al., *Appl Environ Microbiol* 55:323-329 (1989)), and *Clostridium saccharoperbutylacetonicum* (Kosaka et al., *Biosci. Biotechnol Biochem.* 71:58-68 (2007)).

| Gene | GI # | Accession No. | Organism |
|---|---|---|---|
| atoA | 2492994 | P76459.1 | *Escherichia coli* |
| atoD | 2492990 | P76458.1 | *Escherichia coli* |
| actA | 62391407 | YP_226809.1 | *Corynebacterium glutamicum* |
| cg0592 | 62389399 | YP_224801.1 | *Corynebacterium glutamicum* |
| ctfA | 15004866 | NP_149326.1 | *Clostridium acetobutylicum* |
| ctfB | 15004867 | NP_149327.1 | *Clostridium acetobutylicum* |
| ctfA | 31075384 | AAP42564.1 | *Clostridium saccharoperbutylacetonicum* |
| ctfB | 31075385 | AAP42565.1 | *Clostridium saccharoperbutylacetonicum* |

Beta-ketoadipyl-CoA transferase, also known as succinyl-CoA:3: oxoacid-CoA transferase, is active on 3-oxoacyl-CoA substrates. This enzyme is encoded by pcaI and pcaJ in *Pseudomonas putida* (Kaschabek et al., *J Bacteriol.* 184: 207-215 (2002)). Similar enzymes are found in *Acinetobacter* sp. ADP1 (Kowalchuk et al., *Gene* 146:23-30 (1994)), *Streptomyces coelicolor* and *Pseudomonas knackmussii* (formerly sp. B13) (Gobel et al., *J Bacteriol.* 184: 216-223 (2002); Kaschabek et al., *J Bacteriol.* 184:207-215 (2002)). Additional exemplary succinyl-CoA:3:oxoacid-CoA transferases have been characterized in in *Helicobacterpylori* (Corthesy-Theulaz et al., *J Biol. Chem.* 272:25659-

| Gene | GI # | Accession No. | Organism |
|---|---|---|---|
| pcaI | 24985644 | AAN69545.1 | *Pseudomonas putida* |
| pcaJ | 26990657 | NP_746082.1 | *Pseudomonas putida* |
| pcaI | 50084858 | YP_046368.1 | *Acinetobacter* sp. ADP1 |
| pcaJ | 141776 | AAC37147.1 | *Acinetobacter* sp. ADP1 |
| pcaI | 21224997 | NP_630776.1 | *Streptomyces coelicolor* |
| pcaJ | 21224996 | NP_630775.1 | *Streptomyces coelicolor* |
| catI | 75404583 | Q8VPF3 | *Pseudomonas knackmussii* |
| catJ | 75404582 | Q8VPF2 | *Pseudomonas knackmussii* |
| HPAG1_0676 | 108563101 | YP_627417 | *Helicobacter pylori* |
| HPAG1_0677 | 108563102 | YP_627418 | *Helicobacter pylori* |
| ScoA | 16080950 | NP_391778 | *Bacillus subtilis* |
| ScoB | 16080949 | NP_391777 | *Bacillus subtilis* |
| OXCT1 | NP_000427 | 4557817 | *Homo sapiens* |
| OXCT2 | NP_071403 | 11545841 | *Homo sapiens* |

The conversion of acyl-CoA substrates to their acid products can be catalyzed by a CoA acid-thiol ligase or CoA synthetase in the 6.2.1 family of enzymes. CoA synthases that convert ATP to ADP (ADP-forming) are reversible and react in the direction of acid formation, whereas AMP forming enzymes only catalyze the activation of an acid to an acyl-CoA. For fatty acid formation, deletion or attenuation of AMP forming enzymes will reduce backflux. ADP-forming acetyl-CoA synthetase (ACD, EC 6.2.1.13) is an enzyme that couples the conversion of acyl-CoA esters to their corresponding acids with the concomitant synthesis of ATP. ACD I from *Archaeoglobus fulgidus*, encoded by AF1211, was shown to operate on a variety of linear and branched-chain substrates including isobutyrate, isopentanoate, and fumarate (Musfeldt et al., *J Bacteriol.* 184:636-644 (2002)). A second reversible ACD in *Archaeoglobus fulgidus*, encoded by AF1983, was also shown to have a broad substrate range (Musfeldt and Schonheit, *J Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al, supra). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra; Musfeldt and Schonheit, *J Bacteriol.* 184:636-644 (2002)). An additional candidate is succinyl-CoA synthetase, encoded by sucCD of *E. coli* and LSC1 and LSC2 genes of *Saccharomyces cerevisiae*. These enzymes catalyze the formation of succinyl-CoA from succinate with the concomitant consumption of one ATP in a reaction which is reversible in vivo (Buck et al., *Biochemistry* 24:6245-6252 (1985)). The acyl CoA ligase from *Pseudomonas putida* has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Appl. Environ. Microbiol.* 59:1149-1154 (1993)). A related enzyme, malonyl CoA synthetase (6.3.4.9) from *Rhizobium leguminosarum* could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., *J. Am. Chem. Soc.* 123:5822-5823 (2001)).

| Protein | GenBank ID | GI Number | Organism |
|---|---|---|---|
| AF1211 | NP_070039.1 | 11498810 | *Archaeoglobus fulgidus* |
| AF1983 | NP_070807.1 | 11499565 | *Archaeoglobus fulgidus* |
| scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |
| paaF | AAC24333.2 | 22711873 | *Pseudomonas putida* |
| matB | AAC83455.1 | 3982573 | *Rhizobium leguminosarum* |

Step J. Acyl-ACP Reductase

The reduction of an acyl-ACP to its corresponding aldehyde is catalyzed by an acyl-ACP reductase (AAR). Such a transformation is depicted in step J of FIGS. 1 and 7. Suitable enzyme candidates include the orf1594 gene product of *Synechococcus elongatus* PCC7942 and homologs thereof (Schirmer et al, *Science,* 329: 559-62 (2010)). The *S. elongates* PCC7942 acyl-ACP reductase is coexpressed with an aldehyde decarbonylase in an operon that appears to be conserved in a majority of cyanobacterial organisms. This enzyme, expressed in *E. coli* together with the aldehyde decarbonylase, conferred the ability to produce alkanes. The *P. marinus* AAR was also cloned into *E. coli* and, together with a decarbonylase, demonstrated to produce alkanes (US Application 2011/0207203).

Step K. Acyl-CoA:ACP Acyltransferase

The transfer of an acyl-CoA to an acyl-ACP is catalyzed by acyltransferase enzymes in EC class 2.3.1. Enzymes with this activity are described above.

Step L. Thioesterase

Acyl-ACP thioesterase enzymes convert an acyl-ACP to its corresponding acid. Such a transformation is required in step L of FIG. 1. Exemplary enzymes include the FatA and FatB isoforms of *Arabidopsis thaliana* (Salas et al, Arch Biochem Biophys 403:25-34 (2002)). The activities of these two proteins vary with carbon chain length, with FatA preferring oleyl-ACP and FatB preferring palmitoyl-ACP. A number of thioesterases with different chain length specificities are listed in WO 2008/113041 and are included in the table below. For example, it has been shown previously that expression of medium chain plant thioesterases like FatB from *Umbellularia californica* in *E. coli* results in accumulation of high levels of medium chain fatty acids, primarily laurate (C12:0). Similarly, expression of *Cuphea palustris* FatB 1 thioesterase in *E. coli* led to accumulation of $C_8$-10:0 products (Dehesh et al, *Plant Physiol* 110:203-10 (1996)). Similarly, *Carthamus tinctorius* thioesterase expressed in *E. coli* leads to >50 fold elevation in C 18:1 chain termination and release as free fatty acid (Knutzon et al, *Plant Physiol* 100:1751-58 (1992)). Methods for altering the substrate specificity of thioesterases are also known in the art (for example, EP1605048).

| Protein | GenBank ID | GI Number | Organism |
|---|---|---|---|
| fatA | AEE76980.1 | 332643459 | *Arabidopsis thaliana* |
| fatB | AEE28300.1 | 332190179 | *Arabidopsis thaliana* |
| fatB2 | AAC49269.1 | 1292906 | *Cuphea hookeriana* |
| fatB3 | AAC72881.1 | 3859828 | *Cuphea hookeriana* |
| fatB1 | AAC49179.1 | 1215718 | *Cuphea palustris* |
| M96568.1: 94 . . . 1251 | AAA33019.1 | 404026 | *Carthamus tinctorius* |
| fatB1 | Q41635.1 | 8469218 | *Umbellularia californica* |
| tesA | AAC73596.1 | 1786702 | *Escherichia coli* |

Step N. Aldehyde Dehydrogenase (Acid Forming) or Carboxylic Acid Reductase

The conversion of an aldehyde to an acid is catalyzed by an acid-forming aldehyde dehydrogenase. Several *Saccharomyces cerevisiae* enzymes catalyze the oxidation of aldehydes to acids including ALD1 (ALD6), ALD2 and ALD3 (Navarro-Avino et al, *Yeast* 15:829-42 (1999); Quash et al, *Biochem Pharmacol* 64:1279-92 (2002)). The mitochondrial proteins ALD4 and ALD5 catalyze similar transformations (Wang et al, *J Bacteriol* 180:822-30 (1998); Boubekeur et al, *Eur J Biochem* 268:5057-65 (2001)). HFD1 encodes a hexadecanal dehydrogenase. Exemplary acid-forming aldehyde dehydrogenase enzymes are listed in the table below.

| Protein | GenBank ID | GI Number | Organism |
|---|---|---|---|
| orf1594 | YP_400611.1 | 81300403 | *Synechococcus elongatus* PCC7942 |
| PMT9312_0533 | YP_397030.1 | 78778918 | *Prochlorococcus marinus* MIT 9312 |
| syc0051_d | YP_170761.1 | 56750060 | *Synechococcus elongatus* PCC 6301 |
| Ava_2534 | YP_323044.1 | 75908748 | *Anabaena variabilis* ATCC 29413 |
| alr5284 | NP_489324.1 | 17232776 | *Nostoc* sp. PCC 7120 |
| Aazo_3370 | YP_003722151.1 | 298491974 | *Nostoc azollae* |
| Cyan7425_0399 | YP_002481152.1 | 220905841 | *Cyanothece* sp. PCC 7425 |
| N9414_21225 | ZP_01628095.1 | 119508943 | *Nodularia spumigena* CCY9414 |
| L8106_07064 | ZP_01619574.1 | 119485189 | *Lyngbya* sp. PCC 8106 |

| Protein | GenBank ID | GI number | Organism |
|---|---|---|---|
| ALD2 | NP_013893.1 | 6323822 | Saccharomyces cerevisiae s288c |
| ALD3 | NP_013892.1 | 6323821 | Saccharomyces cerevisiae s288c |
| ALD4 | NP_015019.1 | 6324950 | Saccharomyces cerevisiae s288c |
| ALD5 | NP_010996.2 | 330443526 | Saccharomyces cerevisiae s288c |
| ALD6 | NP_015264.1 | 6325196 | Saccharomyces cerevisiae s288c |
| HFD1 | NP_013828.1 | 6323757 | Saccharomyces cerevisiae s288c |
| CaO19.8361 | XP_710976.1 | 68490403 | Candida albicans |
| CaO19.742 | XP_710989.1 | 68490378 | Candida albicans |
| YALI0C03025 | CAG81682.1 | 49647250 | Yarrowia lipolytica |
| ANI_1_1334164 | XP_001398871.1 | 145255133 | Aspergillus niger |
| ANI_1_2234074 | XP_001392964.2 | 317031176 | Aspergillus niger |
| ANI_1_226174 | XP_001402476.1 | 145256256 | Aspergillus niger |
| ALDH | P41751.1 | 1169291 | Aspergillus niger |
| KLLA0D09999 | CAH00602.1 | 49642640 | Kluyveromyces lactis |

The conversion of an acid to an aldehyde is thermodynamically unfavorable and typically requires energy-rich cofactors and multiple enzymatic steps. For example, in butanol biosynthesis conversion of butyrate to butyraldehyde is catalyzed by activation of butyrate to its corresponding acyl-CoA by a CoA transferase or ligase, followed by reduction to butyraldehyde by a CoA-dependent aldehyde dehydrogenase. Alternately, an acid can be activated to an acyl-phosphate and subsequently reduced by a phosphate reductase. Direct conversion of the acid to aldehyde by a single enzyme is catalyzed by a bifunctional carboxylic acid reductase enzyme in the 1.2.1 family. Exemplary enzymes that catalyze these transformations include carboxylic acid reductase, alpha-aminoadipate reductase and retinoic acid reductase.

Carboxylic acid reductase (CAR), found in *Nocardia iowensis*, catalyzes the magnesium, ATP and NADPH-dependent reduction of carboxylic acids to their corresponding aldehydes (Venkitasubramanian et al., *J Biol. Chem.* 282: 478-485 (2007)). The natural substrate of this enzyme is benzoic acid and the enzyme exhibits broad acceptance of aromatic and aliphatic substrates including fatty acids of length $C_{12}$-$C_{18}$ (Venkitasubramanian et al., *Biocatalysis in Pharmaceutical and Biotechnology Industries*. CRC press (2006); WO 2010/135624). CAR requires post-translational activation by a phosphopantetheine transferase (PPTase) that converts the inactive apo-enzyme to the active holo-enzyme (Hansen et al., *Appl. Environ. Microbiol* 75:2765-2774 (2009)). The *Nocardia* CAR enzyme was cloned and functionally expressed in *E. coli* (Venkitasubramanian et al., *J Biol. Chem.* 282:478-485 (2007)). Co-expression of the npt gene, encoding a specific PPTase, improved activity of the enzyme. A related enzyme from *Mycobacterium* sp. strain JLS catalyzes the reduction of fatty acids of length C12-C16. Variants of this enzyme with enhanced activity on fatty acids are described in WO 2010/135624. Alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269: 271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J Biol. Chem.* 278:8250-8256 (2003)). The gene encoding the *P. chrysogenum* PPTase has not been identified to date and no high-confidence hits were identified by sequence comparison homology searching.

| Protein | GenBank ID | GI Number | Organism |
|---|---|---|---|
| car | AAR91681.1 | 40796035 | Nocardia iowensis |
| npt | ABI83656.1 | 114848891 | Nocardia iowensis |
| car | YP_001070587.1 | 126434896 | Mycobacterium sp. strain JLS |
| npt | YP_001070355.1 | 126434664 | Mycobacterium sp. strain JLS |
| LYS2 | AAA34747.1 | 171867 | Saccharomyces cerevisiae |
| LYSS | P50113.1 | 1708896 | Saccharomyces cerevisiae |
| LYS2 | AAC02241.1 | 2853226 | Candida albicans |
| LYS5 | AAO26020.1 | 28136195 | Candida albicans |
| Lys1p | P40976.3 | 13124791 | Schizosaccharomyces pombe |
| Lys7p | Q10474.1 | 1723561 | Schizosaccharomyces pombe |
| Lys2 | CAA74300.1 | 3282044 | Penicillium chrysogenum |

Additional car and npt genes can be identified based on sequence homology.

| Gene name | GI No. | GenBank Accession No. | Organism |
|---|---|---|---|
| fadD9 | 121638475 | YP_978699.1 | Mycobacterium bovis BCG |
| BCG_2812c | 121638674 | YP_978898.1 | Mycobacterium bovis BCG |
| nfa20150 | 54023983 | YP_118225.1 | Nocardia farcinica IFM 10152 |
| nfa40540 | 54026024 | YP_120266.1 | Nocardia farcinica IFM 10152 |
| SGR_6790 | YP_001828302.1 | 182440583 | Streptomyces griseus subsp. griseus NBRC 13350 |
| SGR_665 | YP_001822177.1 | 182434458 | Streptomyces griseus subsp. griseus NBRC 13350 |
| MSMEG_2956 | YP_887275.1 | 118473501 | Mycobacterium smegmatis MC2 155 |
| MSMEG_5739 | YP_889972.1 | 118469671 | Mycobacterium smegmatis MC2 155 |
| MSMEG_2648 | YP_886985.1 | 118471293 | Mycobacterium smegmatis MC2 155 |
| MAP1040c | NP_959974.1 | 41407138 | Mycobacterium avium subsp. paratuberculosis K-10 |
| MAP2899C | NP_961833.1 | 41408997 | Mycobacterium avium subsp. paratuberculosis K-10 |
| MMAR_2117 | YP_001850422.1 | 183982131 | Mycobacterium marinum M |
| MMAR_2936 | YP_001851230.1 | 183982939 | Mycobacterium marinum M |
| MMAR_1916 | YP_001850220.1 | 183981929 | Mycobacterium marinum M |
| Tpau_1373 | YP_003646340.1 | 296139097 | Tsukamurella paurometabola DSM 20162 |
| Tpau_1726 | YP_003646683.1 | 296139440 | Tsukamurella paurometabola DSM 20162 |

| Gene name | GI No. | GenBank Accession No. | Organism |
|---|---|---|---|
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR_665, an enzyme similar in sequence to the *Nocardia iowensis* npt, can be beneficial.

| Gene name | GI No. | GenBank Accession No. | Organism |
|---|---|---|---|
| griC | YP_001825755.1 | 182438036 | *Streptomyces griseus* subsp. *griseus* NBRC 13350 |
| griD | YP_001825756.1 | 182438037 | *Streptomyces griseus* subsp. *griseus* NBRC 13350 |

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism for production of a compound of Formula (VI), (X) or (XIV):

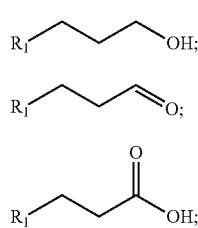

wherein at least 80% of the compound produced by the microbial organism is $C_6$ linear alkyl at $R_1$, wherein the microbial organism comprises a malonyl-CoA independent fatty acyl-CoA elongation (MI-FAE) cycle and a termination pathway, wherein said MI-FAE cycle comprises one or more thiolase, one or more 3-oxoacyl-CoA reductase, one or more 3-hydroxyacyl-CoA dehydratase, and one or more enoyl-CoA reductase, wherein said termination pathway comprises a pathway selected from:

(1) 1H;
(2) 1K and 1L;
(3) 1E and 1N;
(4) 1K, 1J, and 1N;
(5) 1E;
(6) 1K and 1J;
(7) 1H and 1N;
(8) 1K, 1L, and 1N;
(9) 1E and 1F;
(10) 1K, 1J, and 1F;
(11) 1H, 1N, and 1F;
(12) 1K, 1L, 1N, and 1F; and
(13) 1G, wherein 1E is an acyl-CoA reductase (aldehyde forming), wherein 1F is an alcohol dehydrogenase, wherein 1G is an acyl-CoA reductase (alcohol forming), wherein 1H is an acyl-CoA hydrolase, acyl-CoA transferase or acyl-CoA synthase, wherein 1J is an acyl-ACP reductase, wherein 1K is an acyl-CoA:ACP acyltransferase, wherein 1L is a thioesterase, wherein 1N is an aldehyde dehydrogenase (acid forming) or a carboxylic acid reductase, wherein an enzyme of the MI-FAE cycle or termination pathway is encoded by at least one exogenous nucleic acid and is expressed in a sufficient amount to produce the compound of Formula (VI), (X) or (XIV), wherein one or more enzymes of the MI-FAE cycle are each independently selective for a compound of Formula (II) as a substrate:

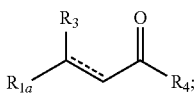 (II)

wherein $R_{1a}$ is no greater than $C_6$ linear alkyl; $R_3$ is H, OH, or oxo (=O); $R_4$ is S-CoA; and ===== represents a single or double bond with the proviso that the valency of the carbon atom to which $R_3$ is attached is four;

wherein the compound of Formula (II) is derived from an acetyl-CoA substrate combined with a propionyl-CoA substrate; and wherein one or more enzymes of the termination pathway are each independently selective for the compound of Formula (II) as a substrate wherein: $R_{1a}$ is no less than $C_6$ linear alkyl; $R_3$ is H; and $R_4$ is S-CoA, ACP, OH or H.

2. The non-naturally occurring microbial organism of claim 1, wherein said microbial organism comprises:
 (a) two, three, or four exogenous nucleic acids each encoding an enzyme of said MI-FAE cycle;
 (b) two, three, or four exogenous nucleic acids each encoding an enzyme of said termination pathway; or
 (c) exogenous nucleic acids encoding each of the enzymes of at least one of the pathways selected from (1)-(13).

3. The non-naturally occurring microbial organism of claim 1, wherein said at least one exogenous nucleic acid is a heterologous nucleic acid.

4. The non-naturally occurring microbial organism of claim 1, wherein said microbial organism further comprises an acetyl-CoA pathway and at least one exogenous nucleic acid encoding an acetyl-CoA pathway enzyme expressed in a sufficient amount to produce acetyl-CoA, wherein said acetyl-CoA pathway comprises a pathway selected from:
 (1) 2A and 2B;
 (2) 2A, 2C, and 2D;
 (3) 2H;
 (4) 2G and 2D;
 (5) 2E, 2F and 2B;
 (6) 2E and 2I;
 (7) 2J, 2F and 2B;
 (8) 2J and 2I;
 (9) 3A, 3B, and 3C;
 (10) 3A, 3B, 3J, 3K, and 3D;
 (11) 3A, 3B, 3G, and 3D;
 (12) 3A, 3F, and 3D;
 (13) 3N, 3H, 3B and 3C;
 (14) 3N, 3H, 3B, 3J, 3K, and 3D;
 (15) 3N, 3H, 3B, 3G, and 3D;
 (16) 3N, 3H, 3F, and 3D;
 (17) 3L, 3M, 3B and 3C;
 (18) 3L, 3M, 3B, 3J, 3K, and 3D;
 (19) 3L, 3M, 3B, 3G, and 3D;
 (20) 3L, 3M, 3F, and 3D;
 (21) 4A, 4B, 4D, 4H, 4I, and 4J;
 (22) 4A, 4B, 4E, 4F, 4H, 4I, and 4J;
 (23) 4A, 4B, 4E, 4K, 4L, 4H, 4I, and 4J;
 (24) 4A, 4C, 4D, 4H, and 4J;
 (25) 4A, 4C, 4E, 4F, 4H, and 4J;
 (26) 4A, 4C, 4E, 4K, 4L, 4H, and 4J;
 (27) 5A, 5B, 5D, and 5G;
 (28) 5A, 5B, 5E, 5F, and 5G;
 (29) 5A, 5B, 5E, 5K, 5L, and 5G;
 (30) 5A, 5C, and 5D;
 (31) 5A, 5C, 5E, and 5F; and
 (32) 5A, 5C, 5E, 5K, and 5L, wherein 2A is a pyruvate oxidase (acetate-forming), wherein 2B is an acetyl-CoA synthetase, an acetyl-CoA ligase or an acetyl-CoA transferase, wherein 2C is an acetate kinase, wherein 2D is a phosphotransacetylase, wherein 2E is a pyruvate decarboxylase, wherein 2F is an acetaldehyde dehydrogenase, wherein 2G is a pyruvate oxidase (acetyl-phosphate forming), wherein 2H is a pyruvate dehydrogenase, a pyruvate:ferredoxin oxidoreductase, a pyruvate:NAD(P)H oxidoreductase or a pyruvate formate lyase, wherein 2I is an acetaldehyde dehydrogenase (acylating), wherein 2J is a threonine aldolase, wherein 3A is a phosphoenolpyruvate (PEP) carboxylase or a PEP carboxykinase, wherein 3B is an oxaloacetate decarboxylase, wherein 3C is a malonate semialdehyde dehydrogenase (acetylating), wherein 3D is an acetyl-CoA carboxylase or a malonyl-CoA decarboxylase, wherein 3F is an oxaloacetate dehydrogenase or an oxaloacetate oxidoreductase, wherein 3G is a malonate semialdehyde dehydrogenase (acylating), wherein 3H is a pyruvate carboxylase, wherein 3J is a malonate semialdehyde dehydrogenase, wherein 3K is a malonyl-CoA synthetase or a malonyl-CoA transferase, wherein 3L is a malic enzyme, wherein 3M is a malate dehydrogenase or a malate oxidoreductase, wherein 3N is a pyruvate kinase or a PEP phosphatase, wherein 4A is a citrate synthase, wherein 4B is a citrate transporter, wherein 4C is a citrate/malate transporter, wherein 4D is an ATP citrate lyase, wherein 4E is a citrate lyase, wherein 4F is an acetyl-CoA synthetase or an acetyl-CoA transferase, wherein 4H is a cytosolic malate dehydrogenase, wherein 4I is a malate transporter, wherein 4J is a mitochondrial malate dehydrogenase, wherein 4K is an acetate kinase, wherein 4L is a phosphotransacetylase, wherein 5A is a citrate synthase, wherein 5B is a citrate transporter, wherein 5C is a citrate/oxaloacetate transporter, wherein 5D is an ATP citrate lyase, wherein 5E is a citrate lyase, wherein 5F is an acetyl-CoA synthetase or an acetyl-CoA transferase, wherein 5G is an oxaloacetate transporter, wherein 5K is an acetate kinase, and wherein 5L is a phosphotransacetylase.

5. The non-naturally occurring microbial organism of claim 1, wherein the microbial organism further comprises:
 (a) one or more gene disruptions, said one or more gene disruptions occurring in endogenous genes encoding proteins or enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, wherein said one or more gene disruptions confer increased production of the compound of Formula (VI), (X) or (XIV) in said microbial organism;
 (b) one or more gene disruptions occurring in genes encoding proteins or enzymes that result in an increased ratio of NAD(P)H to NAD(P) present in the cytosol of said microbial organism following said disruptions;
 (c) one or more endogenous enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, has attenuated enzyme activity or expression levels;

(d) one or more endogenous enzymes involved in the oxidation of NAD(P)H or NADH, has attenuated enzyme activity or expression levels;

(e) one or more enzymes of the MI-FAE cycle or the termination pathway preferentially react with an NADH cofactor or have reduced preference for reacting with an NAD(P)H cofactor, wherein said one or more enzymes of the MI-FAE cycle are a 3-ketoacyl-CoA reductase or an enoyl-CoA reductase, and wherein said one or more enzymes of the termination pathway are selected from an acyl-CoA reductase (aldehyde forming), an alcohol dehydrogenase, an acyl-CoA reductase (alcohol forming), an aldehyde decarbonylase, an acyl-ACP reductase, an aldehyde dehydrogenase (acid forming) and a carboxylic acid reductase; or (f) at least one exogenous nucleic acid encoding an extracellular transporter or an extracellular transport system for the compound of Formula (VI), (X) or (XIV).

6. The non-naturally occurring microbial organism of claim 1, wherein said microbial organism is Crabtree positive and is in culture medium comprising excess glucose, thereby increasing the ratio of NAD(P)H to NAD(P) present in the cytosol of said microbial organism.

7. The non-naturally occurring microbial organism of claim 1, wherein at least 85%, 90%, or 95% of the compound produced by the microbial organism is $C_6$ linear alkyl at $R_1$.

8. A method for producing the compound of Formula (VI), (X) or (XIV) comprising culturing the non-naturally occurring microbial organism of claim 1 under conditions and for a sufficient period of time to produce said compound of Formula (VI), (X) or (XIV).

9. A non-naturally occurring microbial organism for production of a compound of Formula (VI), (X) or (XIV):

wherein at least 80% of the compound produced by the microbial organism is $C_8$ linear alkyl at $R_1$,
wherein the microbial organism comprises a malonyl-CoA independent fatty acyl-CoA elongation (MI-FAE) cycle and a termination pathway,
wherein said MI-FAE cycle comprises one or more thiolase, one or more 3-oxoacyl-CoA reductase, one or more 3-hydroxyacyl-CoA dehydratase, and one or more enoyl-CoA reductase,
wherein said termination pathway comprises a pathway selected from:
(1) 1H;
(2) 1K and 1L;
(3) 1E and 1N;
(4) 1K, 1J, and 1N;
(5) 1E;
(6) 1K and 1J;
(7) 1H and 1N;
(8) 1K, 1L, and 1N;
(9) 1E and 1F;
(10) 1K, 1J, and 1F;
(11) 1H, 1N, and 1F;
(12) 1K, 1L, 1N, and 1F; and
(13) 1G,
wherein 1E is an acyl-CoA reductase (aldehyde forming), wherein 1F is an alcohol dehydrogenase, wherein 1G is an acyl-CoA reductase (alcohol forming), wherein 1H is an acyl-CoA hydrolase, acyl-CoA transferase or acyl-CoA synthase, wherein 1J is an acyl-ACP reductase, wherein 1K is an acyl-CoA:ACP acyltransferase, wherein 1L is a thioesterase, wherein 1N is an aldehyde dehydrogenase (acid forming) or a carboxylic acid reductase,
wherein an enzyme of the MI-FAE cycle or termination pathway is encoded by at least one exogenous nucleic acid and is expressed in a sufficient amount to produce the compound of Formula (VI), (X) or (XIV),
wherein one or more enzymes of the MI-FAE cycle are each independently selective for a compound of Formula (II) as a substrate:

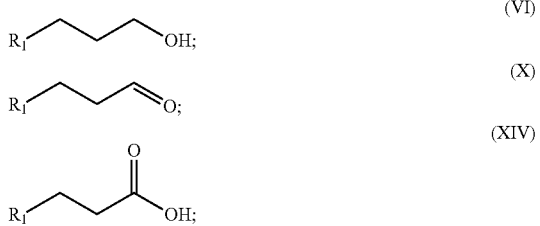

wherein $R_{1a}$ is no greater than $C_8$ linear alkyl; $R_3$ is H, OH, or oxo (=O); $R_4$ is S-CoA; and ===== represents a single or double bond with the proviso that the valency of the carbon atom to which $R_3$ is attached is four;
wherein the compound of Formula (II) is derived from an acetyl-CoA substrate combined with a propionyl-CoA substrate; and
wherein one or more enzymes of the termination pathway are each independently selective for the compound of Formula (II) as a substrate wherein: $R_{1a}$ is no less than $C_8$ linear alkyl; $R_3$ is H; and $R_4$ is S-CoA, ACP, OH or H.

10. The non-naturally occurring microbial organism of claim 9, wherein said microbial organism comprises:
(a) two, three, or four exogenous nucleic acids each encoding an enzyme of said MI-FAE cycle;
(b) two, three, or four exogenous nucleic acids each encoding an enzyme of said termination pathway; or
(c) exogenous nucleic acids encoding each of the enzymes of at least one of the pathways selected from (1)-(13).

11. The non-naturally occurring microbial organism of claim 9, wherein said at least one exogenous nucleic acid is a heterologous nucleic acid.

12. The non-naturally occurring microbial organism of claim 9, wherein said microbial organism further comprises an acetyl-CoA pathway and at least one exogenous nucleic acid encoding an acetyl-CoA pathway enzyme expressed in a sufficient amount to produce acetyl-CoA, wherein said acetyl-CoA pathway comprises a pathway selected from:
(1) 2A and 2B;
(2) 2A, 2C, and 2D;
(3) 2H;

(4) 2G and 2D;
(5) 2E, 2F and 2B;
(6) 2E and 2I;
(7) 2J, 2F and 2B;
(8) 2J and 2I;
(9) 3A, 3B, and 3C;
(10) 3A, 3B, 3J, 3K, and 3D;
(11) 3A, 3B, 3G, and 3D;
(12) 3A, 3F, and 3D;
(13) 3N, 3H, 3B and 3C;
(14) 3N, 3H, 3B, 3J, 3K, and 3D;
(15) 3N, 3H, 3B, 3G, and 3D;
(16) 3N, 3H, 3F, and 3D;
(17) 3L, 3M, 3B and 3C;
(18) 3L, 3M, 3B, 3J, 3K, and 3D;
(19) 3L, 3M, 3B, 3G, and 3D;
(20) 3L, 3M, 3F, and 3D;
(21) 4A, 4B, 4D, 4H, 4I, and 4J;
(22) 4A, 4B, 4E, 4F, 4H, 4I, and 4J;
(23) 4A, 4B, 4E, 4K, 4L, 4H, 4I, and 4J;
(24) 4A, 4C, 4D, 4H, and 4J;
(25) 4A, 4C, 4E, 4F, 4H, and 4J;
(26) 4A, 4C, 4E, 4K, 4L, 4H, and 4J;
(27) 5A, 5B, 5D, and 5G;
(28) 5A, 5B, 5E, 5F, and 5G;
(29) 5A, 5B, 5E, 5K, 5L, and 5G;
(30) 5A, 5C, and 5D;
(31) 5A, 5C, 5E, and 5F; and
(32) 5A, 5C, 5E, 5K, and 5L,
wherein 2A is a pyruvate oxidase (acetate-forming), wherein 2B is an acetyl-CoA synthetase, an acetyl-CoA ligase or an acetyl-CoA transferase, wherein 2C is an acetate kinase, wherein 2D is a phosphotransacetylase, wherein 2E is a pyruvate decarboxylase, wherein 2F is an acetaldehyde dehydrogenase, wherein 2G is a pyruvate oxidase (acetyl-phosphate forming), wherein 2H is a pyruvate dehydrogenase, a pyruvate:ferredoxin oxidoreductase, a pyruvate:NAD(P)H oxidoreductase or a pyruvate formate lyase, wherein 2I is an acetaldehyde dehydrogenase (acylating), wherein 2J is a threonine aldolase, wherein 3A is a phosphoenolpyruvate (PEP) carboxylase or a PEP carboxykinase, wherein 3B is an oxaloacetate decarboxylase, wherein 3C is a malonate semialdehyde dehydrogenase (acetylating), wherein 3D is an acetyl-CoA carboxylase or a malonyl-CoA decarboxylase, wherein 3F is an oxaloacetate dehydrogenase or an oxaloacetate oxidoreductase, wherein 3G is a malonate semialdehyde dehydrogenase (acylating), wherein 3H is a pyruvate carboxylase, wherein 3J is a malonate semialdehyde dehydrogenase, wherein 3K is a malonyl-CoA synthetase or a malonyl-CoA transferase, wherein 3L is a malic enzyme, wherein 3M is a malate dehydrogenase or a malate oxidoreductase, wherein 3N is a pyruvate kinase or a PEP phosphatase, wherein 4A is a citrate synthase, wherein 4B is a citrate transporter, wherein 4C is a citrate/malate transporter, wherein 4D is an ATP citrate lyase, wherein 4E is a citrate lyase, wherein 4F is an acetyl-CoA synthetase or an acetyl-CoA transferase, wherein 4H is a cytosolic malate dehydrogenase, wherein 4I is a malate transporter, wherein 4J is a mitochondrial malate dehydrogenase, wherein 4K is an acetate kinase, wherein 4L is a phosphotransacetylase, wherein 5A is a citrate synthase, wherein 5B is a citrate transporter, wherein 5C is a citrate/oxaloacetate transporter, wherein 5D is an ATP citrate lyase, wherein 5E is a citrate lyase, wherein 5F is an acetyl-CoA synthetase or an acetyl-CoA transferase, wherein 5G is an oxaloacetate transporter, wherein 5K is an acetate kinase, and wherein 5L is a phosphotransacetylase.

13. The non-naturally occurring microbial organism of claim 9, wherein the microbial organism further comprises:
(a) one or more gene disruptions, said one or more gene disruptions occurring in endogenous genes encoding proteins or enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, wherein said one or more gene disruptions confer increased production of the compound of Formula (VI), (X) or (XIV) in said microbial organism;
(b) one or more gene disruptions occurring in genes encoding proteins or enzymes that result in an increased ratio of NAD(P)H to NAD(P) present in the cytosol of said microbial organism following said disruptions;
(c) one or more endogenous enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, has attenuated enzyme activity or expression levels;
(d) one or more endogenous enzymes involved in the oxidation of NAD(P)H or NADH, has attenuated enzyme activity or expression levels;
(e) one or more enzymes of the MI-FAE cycle or the termination pathway preferentially react with an NADH cofactor or have reduced preference for reacting with an NAD(P)H cofactor, wherein said one or more enzymes of the MI-FAE cycle are a 3-ketoacyl-CoA reductase or an enoyl-CoA reductase, and wherein said one or more enzymes of the termination pathway are selected from an acyl-CoA reductase (aldehyde forming), an alcohol dehydrogenase, an acyl-CoA reductase (alcohol forming), an aldehyde decarbonylase, an acyl-ACP reductase, an aldehyde dehydrogenase (acid forming) and a carboxylic acid reductase; or
(f) at least one exogenous nucleic acid encoding an extracellular transporter or an extracellular transport system for the compound of Formula (VI), (X) or (XIV).

14. The non-naturally occurring microbial organism of claim 9, wherein said microbial organism is Crabtree positive and is in culture medium comprising excess glucose, thereby increasing the ratio of NAD(P)H to NAD(P) present in the cytosol of said microbial organism.

15. The non-naturally occurring microbial organism of claim 9, wherein at least 85%, 90%, or 95% of the compound produced by the microbial organism is $C_8$ linear alkyl at $R_1$.

16. A method for producing the compound of Formula (VI), (X) or (XIV) comprising culturing the non-naturally occurring microbial organism of claim 9, under conditions and for a sufficient period of time to produce said compound of Formula (VI), (X) or (XIV).

17. A non-naturally occurring microbial organism for production of a compound of Formula (VI), (X) or (XIV):

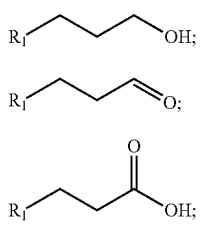

(VI)

(X)

(XIV)

wherein at least 80% of the compound produced by the microbial organism is $C_{10}$ linear alkyl at $R_1$, wherein the microbial organism comprises a malonyl-CoA independent fatty acyl-CoA elongation (MI-FAE) cycle and a termination pathway, wherein said MI-FAE cycle comprises one or more thiolase, one or more 3-oxoacyl-CoA reductase, one or more 3-hydroxyacyl-CoA dehydratase, and one or more enoyl-CoA reductase, wherein said termination pathway comprises a pathway selected from:
(1) 1H;
(2) 1K and 1L;
(3) 1E and 1N;
(4) 1K, 1J, and 1N;
(5) 1E;
(6) 1K and 1J;
(7) 1H and 1N;
(8) 1K, 1L, and 1N;
(9) 1E and 1F;
(10) 1K, 1J, and 1F;
(11) 1H, 1N, and 1F;
(12) 1K, 1L, 1N, and 1F; and
(13) 1G, wherein 1E is an acyl-CoA reductase (aldehyde forming), wherein 1F is an alcohol dehydrogenase, wherein 1G is an acyl-CoA reductase (alcohol forming), wherein 1H is an acyl-CoA hydrolase, acyl-CoA transferase or acyl-CoA synthase, wherein 1J is an acyl-ACP reductase, wherein 1K is an acyl-CoA:ACP acyltransferase, wherein 1L is a thioesterase, wherein 1N is an aldehyde dehydrogenase (acid forming) or a carboxylic acid reductase, wherein an enzyme of the MI-FAE cycle or termination pathway is encoded by at least one exogenous nucleic acid and is expressed in a sufficient amount to produce the compound of Formula (VI), (X) or (XIV), wherein one or more enzymes of the MI-FAE cycle are each independently selective for a compound of Formula (II) as a substrate:

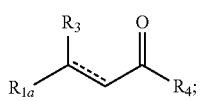

(II)

wherein $R_{1a}$ is no greater than $C_{10}$ linear alkyl; $R_3$ is H, OH, or oxo (=O); $R_4$ is S-CoA; and ----- represents a single or double bond with the proviso that the valency of the carbon atom to which $R_3$ is attached is four;

wherein the compound of Formula (II) is derived from an acetyl-CoA substrate combined with a propionyl-CoA substrate; and wherein one or more enzymes of the termination pathway are each independently selective for the compound of Formula (II) as a substrate wherein: $R_{1a}$ is no less than $C_{10}$ linear alkyl; $R_3$ is H; and $R_4$ is S-CoA, ACP, OH or H.

18. The non-naturally occurring microbial organism of claim 17, wherein said microbial organism comprises:
(a) two, three, or four exogenous nucleic acids each encoding an enzyme of said MI-FAE cycle;
(b) two, three, or four exogenous nucleic acids each encoding an enzyme of said termination pathway; or
(c) exogenous nucleic acids encoding each of the enzymes of at least one of the pathways selected from (1)-(13).

19. The non-naturally occurring microbial organism of claim 17, wherein said at least one exogenous nucleic acid is a heterologous nucleic acid.

20. The non-naturally occurring microbial organism of claim 17, wherein said microbial organism further comprises an acetyl-CoA pathway and at least one exogenous nucleic acid encoding an acetyl-CoA pathway enzyme expressed in a sufficient amount to produce acetyl-CoA, wherein said acetyl-CoA pathway comprises a pathway selected from:
(1) 2A and 2B;
(2) 2A, 2C, and 2D;
(3) 2H;
(4) 2G and 2D;
(5) 2E, 2F and 2B;
(6) 2E and 2I;
(7) 2J, 2F and 2B;
(8) 2J and 2I;
(9) 3A, 3B, and 3C;
(10) 3A, 3B, 3J, 3K, and 3D;
(11) 3A, 3B, 3G, and 3D;
(12) 3A, 3F, and 3D;
(13) 3N, 3H, 3B and 3C;
(14) 3N, 3H, 3B, 3J, 3K, and 3D;
(15) 3N, 3H, 3B, 3G, and 3D;
(16) 3N, 3H, 3F, and 3D;
(17) 3L, 3M, 3B and 3C;
(18) 3L, 3M, 3B, 3J, 3K, and 3D;
(19) 3L, 3M, 3B, 3G, and 3D;
(20) 3L, 3M, 3F, and 3D;
(21) 4A, 4B, 4D, 4H, 4I, and 4J;
(22) 4A, 4B, 4E, 4F, 4H, 4I, and 4J;
(23) 4A, 4B, 4E, 4K, 4L, 4H, 4I, and 4J;
(24) 4A, 4C, 4D, 4H, and 4J;
(25) 4A, 4C, 4E, 4F, 4H, and 4J;
(26) 4A, 4C, 4E, 4K, 4L, 4H, and 4J;
(27) 5A, 5B, 5D, and 5G;
(28) 5A, 5B, 5E, 5F, and 5G;
(29) 5A, 5B, 5E, 5K, 5L, and 5G;
(30) 5A, 5C, and 5D;
(31) 5A, 5C, 5E, and 5F; and
(32) 5A, 5C, 5E, 5K, and 5L, wherein 2A is a pyruvate oxidase (acetate-forming), wherein 2B is an acetyl-CoA synthetase, an acetyl-CoA ligase or an acetyl-CoA transferase, wherein 2C is an acetate kinase, wherein 2D is a phosphotransacetylase, wherein 2E is a pyruvate decarboxylase, wherein 2F is an acetaldehyde dehydrogenase, wherein 2G is a pyruvate oxidase (acetyl-phosphate forming), wherein 2H is a pyruvate dehydrogenase, a pyruvate:ferredoxin oxidoreductase, a pyruvate:NAD(P)H oxidoreductase or a pyruvate formate lyase, wherein 2I is an acetaldehyde dehydrogenase (acylating), wherein 2J is a threonine aldolase, wherein 3A is a phosphoenolpyruvate (PEP)

carboxylase or a PEP carboxykinase, wherein 3B is an oxaloacetate decarboxylase, wherein 3C is a malonate semialdehyde dehydrogenase (acetylating), wherein 3D is an acetyl-CoA carboxylase or a malonyl-CoA decarboxylase, wherein 3F is an oxaloacetate dehydrogenase or an oxaloacetate oxidoreductase, wherein 3G is a malonate semialdehyde dehydrogenase (acylating), wherein 3H is a pyruvate carboxylase, wherein 3J is a malonate semialdehyde dehydrogenase, wherein 3K is a malonyl-CoA synthetase or a malonyl-CoA transferase, wherein 3L is a malic enzyme, wherein 3M is a malate dehydrogenase or a malate oxidoreductase, wherein 3N is a pyruvate kinase or a PEP phosphatase, wherein 4A is a citrate synthase, wherein 4B is a citrate transporter, wherein 4C is a citrate/malate transporter, wherein 4D is an ATP citrate lyase, wherein 4E is a citrate lyase, wherein 4F is an acetyl-CoA synthetase or an acetyl-CoA transferase, wherein 4H is a cytosolic malate dehydrogenase, wherein 4I is a malate transporter, wherein 4J is a mitochondrial malate dehydrogenase, wherein 4K is an acetate kinase, wherein 4L is a phosphotransacetylase, wherein 5A is a citrate synthase, wherein 5B is a citrate transporter, wherein 5C is a citrate/oxaloacetate transporter, wherein 5D is an ATP citrate lyase, wherein 5E is a citrate lyase, wherein 5F is an acetyl-CoA synthetase or an acetyl-CoA transferase, wherein 5G is an oxaloacetate transporter, wherein 5K is an acetate kinase, and wherein 5L is a phosphotransacetylase.

21. The non-naturally occurring microbial organism of claim 17, wherein the microbial organism further comprises:
(a) one or more gene disruptions, said one or more gene disruptions occurring in endogenous genes encoding proteins or enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, wherein said one or more gene disruptions confer increased production of the compound of Formula (VI), (X) or (XIV) in said microbial organism;
(b) one or more gene disruptions occurring in genes encoding proteins or enzymes that result in an increased ratio of NAD(P)H to NAD(P) present in the cytosol of said microbial organism following said disruptions;
(c) one or more endogenous enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, has attenuated enzyme activity or expression levels;
(d) one or more endogenous enzymes involved in the oxidation of NAD(P)H or NADH, has attenuated enzyme activity or expression levels;
(e) one or more enzymes of the MI-FAE cycle or the termination pathway preferentially react with an NADH cofactor or have reduced preference for reacting with an NAD(P)H cofactor, wherein said one or more enzymes of the MI-FAE cycle are a 3-ketoacyl-CoA reductase or an enoyl-CoA reductase, and wherein said one or more enzymes of the termination pathway are selected from an acyl-CoA reductase (aldehyde forming), an alcohol dehydrogenase, an acyl-CoA reductase (alcohol forming), an aldehyde decarbonylase, an acyl-ACP reductase, an aldehyde dehydrogenase (acid forming) and a carboxylic acid reductase; or
(f) at least one exogenous nucleic acid encoding an extracellular transporter or an extracellular transport system for the compound of Formula (VI), (X) or (XIV).

22. The non-naturally occurring microbial organism of claim 17, wherein said microbial organism is Crabtree positive and is in culture medium comprising excess glucose, thereby increasing the ratio of NAD(P)H to NAD(P) present in the cytosol of said microbial organism.

23. The non-naturally occurring microbial organism of claim 17, wherein at least 85%, 90%, or 95% of the compound produced by the microbial organism is $C_{10}$ linear alkyl at $R_1$.

24. A method for producing the compound of Formula (VI), (X) or (XIV) comprising culturing the non-naturally occurring microbial organism of claim 17, under conditions and for a sufficient period of time to produce said compound of Formula (VI), (X) or (XIV).

25. A non-naturally occurring microbial organism for production of a compound of Formula (VI), (X) or (XIV):

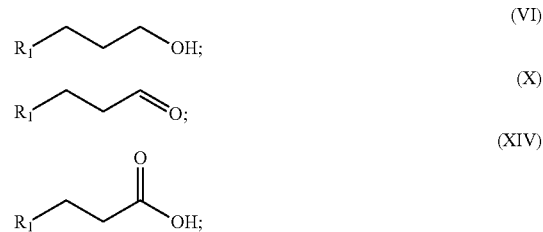

wherein at least 80% of the compound produced by the microbial organism is $C_{12}$ linear alkyl at $R_1$,
wherein the microbial organism comprises a malonyl-CoA independent fatty acyl-CoA elongation (MI-FAE) cycle and a termination pathway,
wherein said MI-FAE cycle comprises one or more thiolase, one or more 3-oxoacyl-CoA reductase, one or more 3-hydroxyacyl-CoA dehydratase, and one or more enoyl-CoA reductase,
wherein said termination pathway comprises a pathway selected from:
(1) 1H;
(2) 1K and 1L;
(3) 1E and 1N;
(4) 1K, 1J, and 1N;
(5) 1E;
(6) 1K and 1J;
(7) 1H and 1N;
(8) 1K, 1L, and 1N;
(9) 1E and 1F;
(10) 1K, 1J, and 1F;
(11) 1H, 1N, and 1F;
(12) 1K, 1L, 1N, and 1F; and
(13) 1G,
wherein 1E is an acyl-CoA reductase (aldehyde forming), wherein 1F is an alcohol dehydrogenase, wherein 1G is an acyl-CoA reductase (alcohol forming), wherein 1H is an acyl-CoA hydrolase, acyl-CoA transferase or acyl-CoA synthase, wherein 1J is an acyl-ACP reductase, wherein 1K is an acyl-CoA:ACP acyltransferase, wherein 1L is a thioesterase, wherein 1N is an aldehyde dehydrogenase (acid forming) or a carboxylic acid reductase, wherein an enzyme of the MI-FAE cycle or termination pathway is encoded by at least one exogenous nucleic acid and is expressed in a sufficient amount to produce the compound of Formula (VI), (X) or (XIV), wherein one or more enzymes of the MI-FAE cycle are each independently selective for a compound of Formula (II) as a substrate:

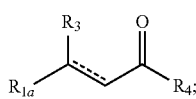

(II)

wherein $R_{1a}$ is no greater than $C_{12}$ linear alkyl; $R_3$ is H, OH, or oxo (=O); $R_4$ is S-CoA; and ===== represents a single or double bond with the proviso that the valency of the carbon atom to which $R_3$ is attached is four;

wherein the compound of Formula (II) is derived from an acetyl-CoA substrate combined with a propionyl-CoA substrate; and wherein one or more enzymes of the termination pathway are each independently selective for the compound of Formula (II) as a substrate wherein: $R_{1a}$ is no less than $C_{12}$ linear alkyl; $R_3$ is H; and $R_4$ is S-CoA, ACP, OH or H.

26. The non-naturally occurring microbial organism of claim 25, wherein said microbial organism comprises:
(a) two, three, or four exogenous nucleic acids each encoding an enzyme of said MI-FAE cycle;
(b) two, three, or four exogenous nucleic acids each encoding an enzyme of said termination pathway; or
(c) exogenous nucleic acids encoding each of the enzymes of at least one of the pathways selected from (1)-(13).

27. The non-naturally occurring microbial organism of claim 25, wherein said at least one exogenous nucleic acid is a heterologous nucleic acid.

28. The non-naturally occurring microbial organism of claim 25, wherein said microbial organism further comprises an acetyl-CoA pathway and at least one exogenous nucleic acid encoding an acetyl-CoA pathway enzyme expressed in a sufficient amount to produce acetyl-CoA, wherein said acetyl-CoA pathway comprises a pathway selected from:
(1) 2A and 2B;
(2) 2A, 2C, and 2D;
(3) 2H;
(4) 2G and 2D;
(5) 2E, 2F and 2B;
(6) 2E and 2I;
(7) 2J, 2F and 2B;
(8) 2J and 2I;
(9) 3A, 3B, and 3C;
(10) 3A, 3B, 3J, 3K, and 3D;
(11) 3A, 3B, 3G, and 3D;
(12) 3A, 3F, and 3D;
(13) 3N, 3H, 3B and 3C;
(14) 3N, 3H, 3B, 3J, 3K, and 3D;
(15) 3N, 3H, 3B, 3G, and 3D;
(16) 3N, 3H, 3F, and 3D;
(17) 3L, 3M, 3B and 3C;
(18) 3L, 3M, 3B, 3J, 3K, and 3D;
(19) 3L, 3M, 3B, 3G, and 3D;
(20) 3L, 3M, 3F, and 3D;
(21) 4A, 4B, 4D, 4H, 4I, and 4J;
(22) 4A, 4B, 4E, 4F, 4H, 4I, and 4J;
(23) 4A, 4B, 4E, 4K, 4L, 4H, 4I, and 4J;
(24) 4A, 4C, 4D, 4H, and 4J;
(25) 4A, 4C, 4E, 4F, 4H, and 4J;
(26) 4A, 4C, 4E, 4K, 4L, 4H, and 4J;
(27) 5A, 5B, 5D, and 5G;
(28) 5A, 5B, 5E, 5F, and 5G;
(29) 5A, 5B, 5E, 5K, 5L, and 5G;
(30) 5A, 5C, and 5D;
(31) 5A, 5C, 5E, and 5F; and
(32) 5A, 5C, 5E, 5K, and 5L, wherein 2A is a pyruvate oxidase (acetate-forming), wherein 2B is an acetyl-CoA synthetase, an acetyl-CoA ligase or an acetyl-CoA transferase, wherein 2C is an acetate kinase, wherein 2D is a phosphotransacetylase, wherein 2E is a pyruvate decarboxylase, wherein 2F is an acetaldehyde dehydrogenase, wherein 2G is a pyruvate oxidase (acetyl-phosphate forming), wherein 2H is a pyruvate dehydrogenase, a pyruvate:ferredoxin oxidoreductase, a pyruvate:NAD(P)H oxidoreductase or a pyruvate formate lyase, wherein 2I is an acetaldehyde dehydrogenase (acylating), wherein 2J is a threonine aldolase, wherein 3A is a phosphoenolpyruvate (PEP) carboxylase or a PEP carboxykinase, wherein 3B is an oxaloacetate decarboxylase, wherein 3C is a malonate semialdehyde dehydrogenase (acetylating), wherein 3D is an acetyl-CoA carboxylase or a malonyl-CoA decarboxylase, wherein 3F is an oxaloacetate dehydrogenase or an oxaloacetate oxidoreductase, wherein 3G is a malonate semialdehyde dehydrogenase (acylating), wherein 3H is a pyruvate carboxylase, wherein 3J is a malonate semialdehyde dehydrogenase, wherein 3K is a malonyl-CoA synthetase or a malonyl-CoA transferase, wherein 3L is a malic enzyme, wherein 3M is a malate dehydrogenase or a malate oxidoreductase, wherein 3N is a pyruvate kinase or a PEP phosphatase, wherein 4A is a citrate synthase, wherein 4B is a citrate transporter, wherein 4C is a citrate/malate transporter, wherein 4D is an ATP citrate lyase, wherein 4E is a citrate lyase, wherein 4F is an acetyl-CoA synthetase or an acetyl-CoA transferase, wherein 4H is a cytosolic malate dehydrogenase, wherein 4I is a malate transporter, wherein 4J is a mitochondrial malate dehydrogenase, wherein 4K is an acetate kinase, wherein 4L is a phosphotransacetylase, wherein 5A is a citrate synthase, wherein 5B is a citrate transporter, wherein 5C is a citrate/oxaloacetate transporter, wherein 5D is an ATP citrate lyase, wherein 5E is a citrate lyase, wherein 5F is an acetyl-CoA synthetase or an acetyl-CoA transferase, wherein 5G is an oxaloacetate transporter, wherein 5K is an acetate kinase, and wherein 5L is a phosphotransacetylase.

29. The non-naturally occurring microbial organism of claim 25, wherein the microbial organism further comprises:
(a) one or more gene disruptions, said one or more gene disruptions occurring in endogenous genes encoding proteins or enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, wherein said one or more gene disruptions confer increased production of the compound of Formula (VI), (X) or (XIV) in said microbial organism;

(b) one or more gene disruptions occurring in genes encoding proteins or enzymes that result in an increased ratio of NAD(P)H to NAD(P) present in the cytosol of said microbial organism following said disruptions;

(c) one or more endogenous enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate or a termination pathway intermediate by said microbial organism, has attenuated enzyme activity or expression levels;

(d) one or more endogenous enzymes involved in the oxidation of NAD(P)H or NADH, has attenuated enzyme activity or expression levels;

(e) one or more enzymes of the MI-FAE cycle or the termination pathway preferentially react with an NADH cofactor or have reduced preference for reacting with an NAD(P)H cofactor, wherein said one or more enzymes of the MI-FAE cycle are a 3-ketoacyl-CoA reductase or an enoyl-CoA reductase, and wherein said one or more enzymes of the termination pathway are selected from an acyl-CoA reductase (aldehyde forming), an alcohol dehydrogenase, an acyl-CoA reductase (alcohol forming), an aldehyde decarbonylase, an acyl-ACP reductase, an aldehyde dehydrogenase (acid forming) and a carboxylic acid reductase; or (f) at least one exogenous nucleic acid encoding an extracellular transporter or an extracellular transport system for the compound of Formula (VI), (X) or (XIV).

30. The non-naturally occurring microbial organism of claim 25, wherein said microbial organism is Crabtree positive and is in culture medium comprising excess glucose, thereby increasing the ratio of NAD(P)H to NAD(P) present in the cytosol of said microbial organism.

31. The non-naturally occurring microbial organism of claim 25, wherein at least 85%, 90%, or 95% of the compound produced by the microbial organism is $C_{12}$ linear alkyl at $R_1$.

32. A method for producing the compound of Formula (VI), (X) or (XIV) comprising culturing the non-naturally occurring microbial organism of claim 25, under conditions and for a sufficient period of time to produce said compound of Formula (VI), (X) or (XIV).

* * * * *

SEQUENCE LISTING

```
<160> NUMBER OF SEQ ID NOS: 8

<210> SEQ ID NO 1
<211> LENGTH: 59
<212> TYPE: DNA
<213> ORGANISM: Artificial Sequence
<220> FEATURE:
<223> OTHER INFORMATION: lacZalpha-RI primer

<400> SEQUENCE: 1
gacgaattcg ctagcaagag gagaagtcga catgtccaat tcactggccg tcgttttac      59

<210> SEQ ID NO 2
<211> LENGTH: 47
<212> TYPE: DNA
<213> ORGANISM: Artificial Sequence
<220> FEATURE:
<223> OTHER INFORMATION: lacZalpha 3prime-BB primer

<400> SEQUENCE: 2
gaccctagga agctttctag agtcgaccta tgcggcatca gagcaga                   47

<210> SEQ ID NO 3
<211> LENGTH: 474
<212> TYPE: PRT
<213> ORGANISM: Artificial Sequence
<220> FEATURE:
<223> OTHER INFORMATION: Mutated LpdA from E. coli K-12 MG1655

<400> SEQUENCE: 3

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
                20                  25                  30

Val Ile Val Glu Arg Tyr Asn Thr Leu Gly Gly Val Cys Leu Asn Val
            35                  40                  45
```

Gly Cys Ile Pro Ser Lys Ala Leu Leu His Val Ala Lys Val Ile Glu
 50                  55                  60

Glu Ala Lys Ala Leu Ala Glu His Gly Ile Val Phe Gly Glu Pro Lys
 65                  70                  75                  80

Thr Asp Ile Asp Lys Ile Arg Thr Trp Lys Glu Lys Val Ile Asn Gln
                 85                  90                  95

Leu Thr Gly Gly Leu Ala Gly Met Ala Lys Gly Arg Lys Val Lys Val
                100                 105                 110

Val Asn Gly Leu Gly Lys Phe Thr Gly Ala Asn Thr Leu Glu Val Glu
            115                 120                 125

Gly Glu Asn Gly Lys Thr Val Ile Asn Phe Asp Asn Ala Ile Ile Ala
            130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
                180                 185                 190

Val Tyr His Ala Leu Gly Ser Gln Ile Asp Val Val Arg Lys His
            195                 200                 205

Gln Val Ile Arg Ala Ala Asp Lys Asp Ile Val Lys Val Phe Thr Lys
210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
            290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
            435                 440                 445

His Glu Ser Val Gly Leu Ala Ala Glu Val Phe Glu Gly Ser Ile Thr
450                 455                 460

Asp Leu Pro Asn Pro Lys Ala Lys Lys Lys

<210> SEQ ID NO 4
<211> LENGTH: 474
<212> TYPE: PRT
<213> ORGANISM: Artificial Sequence
<220> FEATURE:
<223> OTHER INFORMATION: Mutated LpdA from E. coli K-12 MG1655

<400> SEQUENCE: 4

```
Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Ala Leu Glu Met Ala Thr
            180                 185                 190

Val Tyr His Ala Leu Gly Ser Gln Ile Asp Val Val Arg Lys His
        195                 200                 205

Gln Val Ile Arg Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
```

```
                355                 360                 365
Glu Lys Gly Ile Ser Tyr Glu Thr Ala Thr Phe Pro Trp Ala Ala Ser
370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Ala Ile Val Gly Thr
                405                 410                 415

Asn Gly Gly Glu Leu Leu Gly Glu Ile Gly Leu Ala Ile Glu Met Gly
                420                 425                 430

Cys Asp Ala Glu Asp Ile Ala Leu Thr Ile His Ala His Pro Thr Leu
                435                 440                 445

His Glu Ser Val Gly Leu Ala Ala Glu Val Phe Glu Gly Ser Ile Thr
        450                 455                 460

Asp Leu Pro Asn Pro Lys Ala Lys Lys Lys
465                 470

<210> SEQ ID NO 5
<211> LENGTH: 364
<212> TYPE: PRT
<213> ORGANISM: Artificial Sequence
<220> FEATURE:
<223> OTHER INFORMATION: Mutant Candida bodinii enzyme

<400> SEQUENCE: 5

Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
                20                  25                  30

Trp Leu Lys Asp Gln Gly His Glu Leu Ile Thr Thr Ser Asp Lys Glu
            35                  40                  45

Gly Glu Thr Ser Glu Leu Asp Lys His Ile Pro Asp Ala Asp Ile Ile
        50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
                100                 105                 110

Leu Glu Val Thr Gly Ser Asn Val Val Ser Val Ala Glu His Val Val
            115                 120                 125

Met Thr Met Leu Val Leu Val Arg Asn Phe Val Pro Ala His Glu Gln
        130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
                180                 185                 190

Tyr Tyr Gln Arg Gln Ala Leu Pro Lys Glu Ala Glu Lys Val Gly
            195                 200                 205

Ala Arg Arg Val Glu Asn Ile Glu Glu Leu Val Ala Gln Ala Asp Ile
        210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
```

-continued

```
                245                 250                 255
Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360
```

<210> SEQ ID NO 6
<211> LENGTH: 364
<212> TYPE: PRT
<213> ORGANISM: Artificial Sequence
<220> FEATURE:
<223> OTHER INFORMATION: Mutant Candida bodinii enzyme

<400> SEQUENCE: 6

```
Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Ser Pro Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
```

```
                245                 250                 255
Ala Arg Gly Ala Ile Cys Val Ala Glu Asp Val Ala Ala Leu Glu
            260                 265                 270

Ser Gly Gln Leu Arg Gly Tyr Gly Gly Asp Val Trp Phe Pro Gln Pro
            275                 280                 285

Ala Pro Lys Asp His Pro Trp Arg Asp Met Arg Asn Lys Tyr Gly Ala
            290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360
```

<210> SEQ ID NO 7
<211> LENGTH: 376
<212> TYPE: PRT
<213> ORGANISM: Artificial Sequence
<220> FEATURE:
<223> OTHER INFORMATION: Mutant Saccharomyces cerevisiae

<400> SEQUENCE: 7

```
Met Ser Lys Gly Lys Val Leu Leu Val Leu Tyr Glu Gly Gly Lys His
1               5                   10                  15

Ala Glu Glu Gln Glu Lys Leu Leu Gly Cys Ile Glu Asn Glu Leu Gly
            20                  25                  30

Ile Arg Asn Phe Ile Glu Glu Gln Gly Tyr Glu Leu Val Thr Thr Ile
        35                  40                  45

Asp Lys Asp Pro Glu Pro Thr Ser Thr Val Asp Arg Glu Leu Lys Asp
    50                  55                  60

Ala Glu Ile Val Ile Thr Thr Pro Phe Phe Pro Ala Tyr Ile Ser Arg
65                  70                  75                  80

Asn Arg Ile Ala Glu Ala Pro Asn Leu Lys Leu Cys Val Thr Ala Gly
                85                  90                  95

Val Gly Ser Asp His Val Asp Leu Glu Ala Ala Asn Glu Arg Lys Ile
            100                 105                 110

Thr Val Thr Glu Val Thr Gly Ser Asn Val Val Ser Val Ala Glu His
        115                 120                 125

Val Met Ala Thr Ile Leu Val Leu Ile Arg Asn Tyr Asn Gly Gly His
    130                 135                 140

Gln Gln Ala Ile Asn Gly Glu Trp Asp Ile Ala Gly Val Ala Lys Asn
145                 150                 155                 160

Glu Tyr Asp Leu Glu Asp Lys Ile Ile Ser Thr Val Gly Ala Gly Arg
                165                 170                 175

Ile Gly Tyr Arg Val Leu Glu Arg Leu Val Ala Phe Asn Pro Lys Lys
            180                 185                 190

Leu Leu Tyr Tyr Ala Arg Gln Glu Leu Pro Ala Glu Ala Ile Asn Arg
        195                 200                 205

Leu Asn Glu Ala Ser Lys Leu Phe Asn Gly Arg Gly Asp Ile Val Gln
    210                 215                 220

Arg Val Glu Lys Leu Glu Asp Met Val Ala Gln Ser Asp Val Val Thr
225                 230                 235                 240

Ile Asn Cys Pro Leu His Lys Asp Ser Arg Gly Leu Phe Asn Lys Lys
```

```
                       245                 250                 255
Leu Ile Ser His Met Lys Asp Gly Ala Tyr Leu Val Asn Thr Ala Arg
            260                 265                 270

Gly Ala Ile Cys Val Ala Glu Asp Val Ala Glu Ala Val Lys Ser Gly
            275                 280                 285

Lys Leu Ala Gly Tyr Gly Gly Asp Val Trp Asp Lys Gln Pro Ala Pro
            290                 295                 300

Lys Asp His Pro Trp Arg Thr Met Asp Asn Lys Asp His Val Gly Asn
305                 310                 315                 320

Ala Met Thr Val His Ile Ser Gly Thr Ser Leu Asp Ala Gln Lys Arg
            325                 330                 335

Tyr Ala Gln Gly Val Lys Asn Ile Leu Asn Ser Tyr Phe Ser Lys Lys
            340                 345                 350

Phe Asp Tyr Arg Pro Gln Asp Ile Ile Val Gln Asn Gly Ser Tyr Ala
            355                 360                 365

Thr Arg Ala Tyr Gly Gln Lys Lys
            370                 375

<210> SEQ ID NO 8
<211> LENGTH: 20
<212> TYPE: PRT
<213> ORGANISM: Artificial Sequence
<220> FEATURE:
<223> OTHER INFORMATION: first 20 aa of N-terminus of putative KDCs

<400> SEQUENCE: 8

Met Thr Tyr Lys Ala Pro Val Lys Asp Val Lys Phe Leu Leu Asp Lys
1               5                   10                  15

Val Phe Lys Val
            20
```